(12) United States Patent
Bozung

(10) Patent No.: US 11,135,014 B2
(45) Date of Patent: *Oct. 5, 2021

(54) SURGICAL INSTRUMENT INCLUDING HOUSING, A CUTTING ACCESSORY THAT EXTENDS FROM THE HOUSING AND ACTUATORS THAT ESTABLISH THE POSITION OF THE CUTTING ACCESSORY RELATIVE TO THE HOUSING

(71) Applicant: Stryker Corporation, Kalamazoo, MI (US)

(72) Inventor: Timothy J. Bozung, Scotts, MI (US)

(73) Assignee: Stryker Corporation, Kalamazoo, MI (US)

( * ) Notice: Subject to any disclaimer, the term of this patent is extended or adjusted under 35 U.S.C. 154(b) by 540 days.

This patent is subject to a terminal disclaimer.

(21) Appl. No.: 15/440,819

(22) Filed: Feb. 23, 2017

(65) Prior Publication Data
US 2017/0156799 A1  Jun. 8, 2017

Related U.S. Application Data

(62) Division of application No. 13/600,888, filed on Aug. 31, 2012, now Pat. No. 9,707,043.
(Continued)

(51) Int. Cl.
*A61B 34/10* (2016.01)
*A61B 34/00* (2016.01)
(Continued)

(52) U.S. Cl.
CPC ........ *A61B 34/10* (2016.02); *A61B 17/00234* (2013.01); *A61B 17/0218* (2013.01);
(Continued)

(58) Field of Classification Search
CPC . A61B 17/16; A61B 17/1624; A61B 17/1626; A61B 17/1666; A61B 17/1675;
(Continued)

(56) References Cited

U.S. PATENT DOCUMENTS

| 649,046 A | 5/1900 | Fiske |
|---|---|---|
| 4,660,573 A | 4/1987 | Brumbach |

(Continued)

FOREIGN PATENT DOCUMENTS

| DE | 103 53 700 A1 | 6/2005 |
|---|---|---|
| DE | 103 53 700 B4 | 4/2008 |

(Continued)

OTHER PUBLICATIONS

Machine-Assisted English Translation of JP2010207252; downloaded from espacenet.com on Jan. 8, 2018; 45 pages.
(Continued)

*Primary Examiner* — Thomas McEvoy
(74) *Attorney, Agent, or Firm* — Howard & Howard Attorneys PLLC

(57) ABSTRACT

An instrument for treating tissue during a medical procedure includes a hand-held portion and a working portion. The hand-held portion is manually supported and moved by a user and the working portion is movably coupled to the hand-held portion. A tracking device is attached to the hand-held portion for tracking the instrument. The tracking device is in communication with a control system, which is used to keep the working portion within or outside of a boundary. A plurality of actuators are operatively coupled to the working portion. The control system instructs the actuators to move the working portion relative to the hand-held portion during the medical procedure in order to maintain a desired relationship between the working portion and the boundary.

20 Claims, 84 Drawing Sheets

Related U.S. Application Data

(60) Provisional application No. 61/662,070, filed on Jun. 20, 2012, provisional application No. 61/530,614, filed on Sep. 2, 2011.

(51) Int. Cl.

| | |
|---|---|
| *A61B 90/11* | (2016.01) |
| *A61B 17/32* | (2006.01) |
| *A61F 2/08* | (2006.01) |
| *A61B 17/16* | (2006.01) |
| *A61F 2/44* | (2006.01) |
| *A61F 2/46* | (2006.01) |
| *A61B 17/00* | (2006.01) |
| *A61B 17/02* | (2006.01) |
| *A61B 17/17* | (2006.01) |
| *A61B 17/34* | (2006.01) |
| *A61F 2/28* | (2006.01) |
| *A61F 2/30* | (2006.01) |
| *A61B 34/20* | (2016.01) |
| *A61F 11/00* | (2006.01) |
| *A61N 1/05* | (2006.01) |
| *A61B 90/00* | (2016.01) |

(52) U.S. Cl.
CPC .......... *A61B 17/16* (2013.01); *A61B 17/1615* (2013.01); *A61B 17/1622* (2013.01); *A61B 17/1626* (2013.01); *A61B 17/1666* (2013.01); *A61B 17/1675* (2013.01); *A61B 17/1703* (2013.01); *A61B 17/1746* (2013.01); *A61B 17/32002* (2013.01); *A61B 17/3403* (2013.01); *A61B 17/3423* (2013.01); *A61B 34/20* (2016.02); *A61B 34/25* (2016.02); *A61B 34/70* (2016.02); *A61B 34/75* (2016.02); *A61B 90/11* (2016.02); *A61F 2/08* (2013.01); *A61F 2/28* (2013.01); *A61F 2/30756* (2013.01); *A61F 2/4455* (2013.01); *A61F 2/4611* (2013.01); *A61F 11/00* (2013.01); *A61N 1/0541* (2013.01); *A61B 17/162* (2013.01); *A61B 17/1624* (2013.01); *A61B 2017/0042* (2013.01); *A61B 2017/00199* (2013.01); *A61B 2017/00398* (2013.01); *A61B 2017/00455* (2013.01); *A61B 2017/00694* (2013.01); *A61B 2017/00991* (2013.01); *A61B 2017/1602* (2013.01); *A61B 2034/107* (2016.02); *A61B 2034/2055* (2016.02); *A61B 2034/2072* (2016.02); *A61B 2090/372* (2016.02); *A61B 2090/374* (2016.02); *A61B 2090/3762* (2016.02); *A61F 2002/2839* (2013.01)

(58) Field of Classification Search
CPC ............ A61B 17/1703; A61B 17/1746; A61B 17/32002; A61B 17/3403; A61B 2017/00199; A61B 2017/00398; A61B 2017/00455; A61B 2017/00694; A61B 2034/105; A61B 2034/107; A61B 2034/2055; A61B 2034/2059; A61B 2034/2068; A61B 2034/2072; A61B 2090/372; A61B 2090/376; A61B 2090/3762; A61B 34/10; A61B 34/20; A61B 34/75
See application file for complete search history.

(56) References Cited

U.S. PATENT DOCUMENTS

| | | |
|---|---|---|
| 4,711,238 A | 12/1987 | Cunningham |
| 4,736,742 A | 4/1988 | Alexson et al. |
| 4,834,092 A | 5/1989 | Alexson et al. |
| 5,154,717 A | 10/1992 | Matsen, III et al. |
| 5,279,309 A | 1/1994 | Taylor et al. |
| 5,299,288 A | 3/1994 | Glassman et al. |
| 5,343,391 A | 8/1994 | Mushabac |
| 5,405,344 A | 4/1995 | Williamson et al. |
| 5,408,409 A | 4/1995 | Glassman et al. |
| 5,454,827 A | 10/1995 | Aust et al. |
| 5,458,206 A | 10/1995 | Bourner et al. |
| 5,464,144 A | 11/1995 | Guy et al. |
| 5,497,934 A | 3/1996 | Brady et al. |
| 5,562,448 A | 10/1996 | Mushabac |
| 5,569,578 A | 10/1996 | Mushabac |
| 5,577,502 A | 11/1996 | Darrow et al. |
| 5,591,170 A | 1/1997 | Spievack et al. |
| 5,618,294 A | 4/1997 | Aust et al. |
| 5,630,431 A | 5/1997 | Taylor |
| 5,638,819 A | 6/1997 | Manwaring et al. |
| 5,662,111 A | 9/1997 | Cosman |
| 5,676,673 A | 10/1997 | Ferre et al. |
| 5,682,886 A | 11/1997 | Delp et al. |
| 5,695,500 A | 12/1997 | Taylor et al. |
| 5,711,299 A | 1/1998 | Manwaring et al. |
| 5,748,767 A | 5/1998 | Raab |
| 5,810,828 A | 9/1998 | Lightman et al. |
| 5,817,105 A | 10/1998 | Van Der Brug |
| 5,823,066 A | 10/1998 | Huitema et al. |
| 5,824,085 A | 10/1998 | Sahay et al. |
| 5,848,967 A | 12/1998 | Cosman |
| 5,871,018 A | 2/1999 | Delp et al. |
| 5,880,976 A | 3/1999 | DiGioia et al. |
| 5,882,206 A | 3/1999 | Gillio |
| 5,888,200 A | 3/1999 | Walen |
| 5,891,157 A | 4/1999 | Day et al. |
| 5,899,914 A | 5/1999 | Zirps et al. |
| 5,902,239 A | 5/1999 | Buurman |
| 5,906,591 A | 5/1999 | Dario et al. |
| 5,921,992 A | 7/1999 | Costales et al. |
| 5,931,832 A | 8/1999 | Jensen |
| 5,938,678 A | 8/1999 | Zirps et al. |
| 5,941,891 A | 8/1999 | Walen |
| 5,950,629 A | 9/1999 | Taylor et al. |
| 5,952,796 A | 9/1999 | Colgate et al. |
| 5,954,648 A | 9/1999 | Van Der Brug |
| 5,976,156 A | 11/1999 | Taylor et al. |
| 5,995,738 A | 11/1999 | DiGioia, III et al. |
| 6,002,859 A | 12/1999 | DiGioia, III et al. |
| 6,006,127 A | 12/1999 | Van Der Brug et al. |
| 6,021,343 A | 2/2000 | Foley et al. |
| 6,026,315 A | 2/2000 | Lenz et al. |
| 6,033,415 A | 3/2000 | Mittlelstadt et al. |
| 6,038,467 A | 3/2000 | De Bliek et al. |
| 6,045,564 A | 4/2000 | Walen |
| 6,063,095 A | 5/2000 | Wang et al. |
| 6,097,168 A | 8/2000 | Katoh et al. |
| 6,102,850 A | 8/2000 | Wang et al. |
| 6,106,464 A | 8/2000 | Bass et al. |
| 6,112,113 A | 8/2000 | Van Der Brug et al. |
| 6,122,538 A | 9/2000 | Sliwa, Jr. et al. |
| 6,126,633 A | 10/2000 | Kaji et al. |
| 6,126,667 A | 10/2000 | Barry et al. |
| 6,200,321 B1 | 3/2001 | Orbay et al. |
| 6,205,411 B1 | 3/2001 | DiGioia, III et al. |
| 6,228,089 B1 | 5/2001 | Wahrburg |
| 6,235,038 B1 | 5/2001 | Hunter et al. |
| 6,236,875 B1 | 5/2001 | Bucholz et al. |
| 6,238,384 B1 | 5/2001 | Peer |
| 6,273,896 B1 | 8/2001 | Franck et al. |
| 6,285,902 B1 | 9/2001 | Kienzle, III et al. |
| 6,322,567 B1 | 11/2001 | Mittlelstadt et al. |
| 6,329,778 B1 | 12/2001 | Culp et al. |
| 6,330,837 B1 | 12/2001 | Charles et al. |
| 6,336,931 B1 | 1/2002 | Hsu et al. |
| 6,423,077 B2 | 7/2002 | Carol et al. |
| 6,436,107 B1 | 8/2002 | Wang et al. |
| 6,450,978 B1 | 9/2002 | Brosseau et al. |
| 6,466,815 B1 | 10/2002 | Saito et al. |
| 6,494,882 B1 | 12/2002 | Lebouitz et al. |
| 6,533,737 B1 | 3/2003 | Brosseau et al. |

(56) References Cited

U.S. PATENT DOCUMENTS

| | | |
|---|---|---|
| 6,535,756 B1 | 3/2003 | Simon et al. |
| 6,697,664 B2 | 2/2004 | Kienzle, III et al. |
| 6,757,582 B2 | 6/2004 | Brisson et al. |
| 6,827,723 B2 | 12/2004 | Carson |
| 6,837,892 B2 | 1/2005 | Shoham |
| 6,887,245 B2 | 5/2005 | Kienzle, III et al. |
| 6,917,827 B2 | 7/2005 | Kienzle, III |
| 6,923,817 B2 | 8/2005 | Carson et al. |
| 6,929,481 B1 | 8/2005 | Alexander et al. |
| 6,999,852 B2 | 2/2006 | Green |
| 7,001,391 B2 | 2/2006 | Estes et al. |
| 7,006,895 B2 | 2/2006 | Green |
| 7,008,430 B2 | 3/2006 | Dong et al. |
| 7,022,123 B2 | 4/2006 | Heldreth |
| 7,035,716 B2 | 4/2006 | Harris et al. |
| 7,056,123 B2 | 6/2006 | Gregorio et al. |
| 7,090,637 B2 | 8/2006 | Danitz et al. |
| 7,090,677 B2 | 8/2006 | Fallin et al. |
| 7,104,996 B2 | 9/2006 | Bonutti |
| 7,118,574 B2 | 10/2006 | Patel et al. |
| 7,155,316 B2 | 12/2006 | Sutherland et al. |
| 7,166,114 B2 | 1/2007 | Moctezuma De La Barrera et al. |
| 7,206,626 B2 | 4/2007 | Quaid, III |
| 7,213,598 B2 | 5/2007 | Zeiss et al. |
| 7,215,326 B2 | 5/2007 | Rosenberg |
| 7,226,456 B2 | 6/2007 | O'Neil et al. |
| 7,226,465 B1 | 6/2007 | Farin |
| 7,237,708 B1 | 7/2007 | Guy et al. |
| 7,241,289 B2 | 7/2007 | Braun |
| 7,249,951 B2 | 7/2007 | Bevirt et al. |
| 7,252,660 B2 | 8/2007 | Kunz |
| 7,302,288 B1 | 11/2007 | Schellenberg |
| 7,346,417 B2 | 3/2008 | Lüth et al. |
| 7,454,268 B2 | 11/2008 | Jinno |
| 7,465,309 B2 | 12/2008 | Wallen |
| 7,540,867 B2 | 6/2009 | Jinno et al. |
| 7,540,875 B2 | 6/2009 | Jessen |
| 7,559,927 B2 | 7/2009 | Shores et al. |
| 7,582,058 B1 | 9/2009 | Miles et al. |
| 7,608,083 B2 | 10/2009 | Lee et al. |
| 7,618,428 B2 | 11/2009 | O'Quinn et al. |
| 7,654,431 B2 | 2/2010 | Hueil et al. |
| 7,658,740 B2 | 2/2010 | Shores et al. |
| 7,660,623 B2 | 2/2010 | Hunter et al. |
| 7,674,255 B2 | 3/2010 | Braun |
| 7,725,162 B2 | 5/2010 | Malackowski et al. |
| 7,727,185 B2 | 6/2010 | Weitzner et al. |
| 7,747,311 B2 | 6/2010 | Quaid, III |
| 7,763,035 B2 | 6/2010 | Melkent et al. |
| 7,766,894 B2 | 8/2010 | Weitzner et al. |
| 7,780,054 B2 | 8/2010 | Wales |
| 7,784,662 B2 | 8/2010 | Wales et al. |
| 7,810,693 B2 | 10/2010 | Broehi et al. |
| 7,819,884 B2 | 10/2010 | Lee et al. |
| 7,824,328 B2 | 11/2010 | Gattani et al. |
| 7,831,292 B2 | 11/2010 | Quaid, III |
| 7,854,738 B2 | 12/2010 | Lee et al. |
| 7,949,386 B2 | 5/2011 | Buly et al. |
| 8,010,180 B2 | 8/2011 | Quaid et al. |
| 8,066,708 B2 | 11/2011 | Lang et al. |
| 8,296,094 B2 | 10/2012 | Harrison et al. |
| 8,361,163 B2 | 1/2013 | Quaid |
| 8,442,677 B2 | 5/2013 | Shoham |
| 8,560,047 B2 | 10/2013 | Haider et al. |
| 8,679,125 B2 | 3/2014 | Smith et al. |
| 8,696,675 B2 | 4/2014 | Boutin et al. |
| 8,709,016 B2 | 4/2014 | Park et al. |
| 8,834,490 B2 | 9/2014 | Bonutti |
| 8,888,782 B2 | 11/2014 | Smith et al. |
| 8,961,536 B2 | 2/2015 | Nikon et al. |
| 9,020,577 B2 | 4/2015 | Reach, Jr. |
| 9,060,794 B2 | 6/2015 | Kang et al. |
| 9,084,613 B2 | 7/2015 | Qutub |
| 9,113,971 B2 | 8/2015 | Metzger et al. |
| 9,119,638 B2 | 9/2015 | Schwarz et al. |
| 9,342,632 B2 | 5/2016 | Zoran et al. |
| 9,463,031 B2 | 10/2016 | Radermacher et al. |
| 9,561,082 B2 | 2/2017 | Yen et al. |
| 9,563,186 B2 | 2/2017 | Steinle et al. |
| 9,622,823 B2 | 4/2017 | Bozung et al. |
| 9,649,164 B2 | 5/2017 | Kim et al. |
| 9,757,859 B1 | 9/2017 | Kolb et al. |
| 9,901,356 B2 | 2/2018 | Shen et al. |
| 10,005,312 B2 | 6/2018 | Zoran et al. |
| 10,028,789 B2 | 7/2018 | Quaid et al. |
| 10,080,617 B2 | 9/2018 | Haider et al. |
| 10,092,365 B2 | 10/2018 | Seeber |
| 10,136,950 B2 | 11/2018 | Schoenefeld |
| 10,182,875 B2 | 1/2019 | Yates et al. |
| 10,265,854 B2 | 4/2019 | Chen et al. |
| 10,350,014 B2 | 7/2019 | Beelen et al. |
| 10,368,878 B2 | 8/2019 | Lavallee et al. |
| 10,441,294 B2 | 10/2019 | Lavallee et al. |
| 10,441,434 B2 | 10/2019 | Miller et al. |
| 10,492,870 B2 | 12/2019 | Shalayev et al. |
| 10,660,712 B2 | 5/2020 | Kostrzewski et al. |
| 2001/0012932 A1 | 8/2001 | Peer |
| 2002/0077543 A1 | 6/2002 | Grzeszczuk et al. |
| 2002/0156497 A1 | 10/2002 | Nagase et al. |
| 2003/0208296 A1 | 11/2003 | Brisson et al. |
| 2004/0147934 A1 | 7/2004 | Kiester |
| 2004/0152972 A1 | 8/2004 | Hunter |
| 2004/0157188 A1 | 8/2004 | Luth et al. |
| 2004/0171929 A1 | 9/2004 | Leitner |
| 2005/0015005 A1 | 1/2005 | Kockro |
| 2005/0020909 A1 | 1/2005 | Moctezuma De La Barrera et al. |
| 2005/0049580 A1 | 3/2005 | Brock et al. |
| 2005/0059883 A1 | 3/2005 | Peterson |
| 2005/0154296 A1 | 7/2005 | Lechner et al. |
| 2005/0171553 A1 | 8/2005 | Schwarz et al. |
| 2006/0036162 A1 | 2/2006 | Shahidi et al. |
| 2006/0142656 A1 | 6/2006 | Malackowski et al. |
| 2006/0155262 A1 | 7/2006 | Kishi et al. |
| 2006/0229624 A1 | 10/2006 | May et al. |
| 2007/0100462 A1 | 5/2007 | Lang et al. |
| 2007/0198022 A1 | 8/2007 | Lang et al. |
| 2007/0233053 A1 | 10/2007 | Shelton, IV |
| 2007/0249899 A1 | 10/2007 | Seifert |
| 2007/0276391 A1 | 11/2007 | Graves et al. |
| 2007/0282345 A1 | 12/2007 | Graves et al. |
| 2008/0009697 A1* | 1/2008 | Haider ............... A61B 90/11 600/407 |
| 2008/0027448 A1 | 1/2008 | Raus et al. |
| 2008/0077158 A1 | 3/2008 | Haider et al. |
| 2008/0161829 A1 | 7/2008 | Kang |
| 2008/0208041 A1 | 8/2008 | Gilboa |
| 2008/0208195 A1 | 8/2008 | Shores et al. |
| 2008/0300579 A1 | 12/2008 | Broehl et al. |
| 2009/0012532 A1* | 1/2009 | Quaid ............... G06F 19/00 606/130 |
| 2009/0023988 A1 | 1/2009 | Korner et al. |
| 2009/0177202 A1 | 7/2009 | May et al. |
| 2009/0228145 A1 | 9/2009 | Hodgson et al. |
| 2009/0326537 A1 | 12/2009 | Anderson |
| 2010/0041004 A1 | 2/2010 | Meglan |
| 2010/0057087 A1 | 3/2010 | Cha |
| 2010/0133317 A1 | 6/2010 | Shelton, IV |
| 2010/0168722 A1 | 7/2010 | Lee et al. |
| 2010/0168747 A1 | 7/2010 | Lynch et al. |
| 2010/0228235 A1 | 10/2010 | Schmied et al. |
| 2010/0298832 A1 | 11/2010 | Lau et al. |
| 2010/0305552 A1 | 12/2010 | Shelton, IV et al. |
| 2010/0312103 A1 | 12/2010 | Gorek et al. |
| 2011/0082468 A1 | 4/2011 | Hagag et al. |
| 2011/0130761 A1 | 6/2011 | Plaskos et al. |
| 2011/0245833 A1 | 10/2011 | Anderson |
| 2011/0263971 A1 | 10/2011 | Nikou et al. |
| 2011/0264107 A1 | 10/2011 | Nikou et al. |
| 2011/0275957 A1 | 11/2011 | Bhandari |
| 2012/0059378 A1* | 3/2012 | Farrell ............... A61B 17/1626 606/80 |
| 2012/0078236 A1 | 3/2012 | Schoepp |
| 2012/0143084 A1* | 6/2012 | Shoham ............... B25J 17/0216 600/567 |

(56) References Cited

U.S. PATENT DOCUMENTS

| | | | |
|---|---|---|---|
| 2013/0060278 | A1 | 3/2013 | Bozung et al. |
| 2013/0096574 | A1* | 4/2013 | Kang .................... A61B 17/16 606/130 |
| 2013/0172902 | A1 | 7/2013 | Lightcap et al. |
| 2014/0039520 | A1 | 2/2014 | Haider et al. |
| 2014/0107471 | A1 | 4/2014 | Haider et al. |
| 2014/0135791 | A1 | 5/2014 | Nikou et al. |
| 2014/0148808 | A1 | 5/2014 | Inkpen et al. |
| 2014/0236159 | A1 | 8/2014 | Haider et al. |
| 2014/0316412 | A1 | 10/2014 | Janik et al. |
| 2015/0182285 | A1 | 7/2015 | Yen et al. |
| 2015/0182295 | A1 | 7/2015 | Bozung et al. |
| 2015/0272686 | A1 | 10/2015 | Kang et al. |
| 2018/0228501 | A1 | 8/2018 | Shen et al. |
| 2018/0280159 | A1 | 10/2018 | Hunter et al. |
| 2019/0336139 | A1 | 11/2019 | Guzman et al. |
| 2019/0365391 | A1 | 12/2019 | Nikou et al. |
| 2019/0388099 | A1 | 12/2019 | Zuhars et al. |
| 2020/0008884 | A1 | 1/2020 | Lavallee et al. |
| 2020/0008889 | A1 | 1/2020 | Ho et al. |
| 2020/0038108 | A1 | 2/2020 | Chou et al. |
| 2020/0046438 | A1 | 2/2020 | Shalayev et al. |
| 2020/0069373 | A1 | 3/2020 | Yu et al. |
| 2020/0069377 | A1 | 3/2020 | Finley et al. |
| 2020/0093500 | A1 | 3/2020 | Lavallee et al. |

FOREIGN PATENT DOCUMENTS

| | | |
|---|---|---|
| DE | 10 2008 024 261 A1 | 11/2009 |
| EP | 1 422 729 A1 | 3/2006 |
| JP | 2009537231 A | 10/2009 |
| JP | 2010207252 A | 9/2010 |
| JP | 2011505980 A | 3/2011 |
| WO | WO 1996 11624 A2 | 4/1996 |
| WO | WO 2000 059397 A1 | 10/2000 |
| WO | WO 2000 060571 A1 | 10/2000 |
| WO | WO 2002 00131 A1 | 1/2002 |
| WO | WO 2003 094108 A2 | 11/2003 |
| WO | WO 2004 014244 A2 | 2/2004 |
| WO | WO2004028343 A2 | 4/2004 |
| WO | WO 2004069036 A2 | 8/2004 |
| WO | WO 2005 048852 A1 | 6/2005 |
| WO | WO 2006 063156 A1 | 6/2006 |
| WO | WO 2007 017642 A1 | 2/2007 |
| WO | WO 2009 059330 A2 | 5/2009 |
| WO | WO 2011 021192 A1 | 2/2011 |
| WO | WO 2011 088541 A1 | 7/2011 |
| WO | WO 2011 128766 A2 | 10/2011 |
| WO | WO 2011 133927 A2 | 10/2011 |
| WO | 2012131660 A1 | 10/2012 |
| WO | 2018103945 A1 | 6/2018 |
| WO | 2018104439 A1 | 6/2018 |
| WO | 2018104523 A1 | 6/2018 |
| WO | 2019050829 A1 | 3/2019 |
| WO | 2019050878 A2 | 3/2019 |
| WO | 2019219348 A1 | 11/2019 |
| WO | 2020028356 A1 | 2/2020 |

OTHER PUBLICATIONS

Abstract not available for JP2006500993 (A); Abstract of corresponding document WO2004028343 (A2) of JP2006500993 downloaded from espacenet.com on Jan. 8, 2018; 20 pages.
Japanese Office Action for Application No. JP 2017-007627; dated Sep. 26, 2017; 2 pages.
J.L. Moctezuma, F. Gosse and H.J. Schulz, A Computer and Robotic Aided Surgery System for Accomplishing Osteotomies, First International Symposium on Medial Robotics and Computer Assisted Surgery, Sep. 22-24, 1994, Pittsburgh, Pennsylvania, US; 6 pages.
B. Allotta, Giuseppe Giacalone and L. Rinaldi, A Hand-Held Drilling Tool for Orthopedic Surgery, Medhatronics, IEEE/ASME Transactions, vol. 2 Issue 4, Dec. 1997, pp. 218-229, IEEE; 12 pages.
M.L. Schwarz, A Wagner, A El-Shenawy, R. Gundling, A Kopfle, H. Handel, E. Badreddin R. Manner, H.P. Scharf, M. Gotz, M Schill and P.P. Pott, A Handheld Robot for Orthopedic Surgery—ITD, IFMBE Proceedings 25/VI, 2009, pp. 99-102, WWW.SpringerLink.com, 4 pages.
B. Preising, CA Davis; T.C. Hsia and B. Mittelstadt, A Literature Review Robots in Medicine, Engineering in Medicine and Biology Magazine, IEEE (vol. 10, Issue: 2), Jun. 1991, pp. 13-22, IEEE; 10 pages.
P. Dario, C. Paggetti; N. Troisfontaine; E. Papa; T. Ciucci; M.C. Carrozza and M. Marcacci, A Miniature Steerable End-Effector for Application in an Integrated System for Computer-Assisted Arthroscopy, Robotics and Automation, 1997. Proceedings., 1997 IEEE International Conference on (vol. 2), Apr. 20-25, 1997, pp. 1573-1579, IEEE; 7 pages.
L.P. Nolte, L. Zamorano, S. Jiang, Q. Wang, F. Longlotz, E. Arm and H. Visarius, A Novel Approach to Computer Assisted Spine Surgery, Proc. First International Symposium on Medical Robotics and Computer Assisted Surgery, Pittsburgh, 1994, pp. 323-328; 7 pages.
P. Dario, M.C. Carrozza, M. Marcacci, S. D'Attanasio, B. Magnani, O. Tonet and G. Megali, A Novel Mechatronic Tool for Computer-Assisted Arthroscopy, IEEE Trans. on Information Technology in Biomedicine, 2000, pp. 15-28, vol. 4, No. 1, IEEE; 13 pages.
W. Zhang and Yan Pan, A Novel Robotic Assistant for Reducing Hand-held Surgical Tool Tremor in Surgical Navigation, Bioinformatics and Biomedical Engineering, 2009. ICBBE 2009. 3rd International Conference on, 2009, pp. 1-4, Beijing, IEEE; 4 pages.
B. Davies, A review of robotics in surgery, Proceedings of the Institution of Mechanical Engineers, Part H: Journal of Engineering in Medicine Jan. 1, 2000, vol. 214, No. 1, pp. 129-140, Sage Publications; 13 pages.
D. Engel, J. Raczkowsky and H. Worn, a Safe Robot System for Craniofacial Surgery, Robotics and Automation, 2001. Proceedings 2001 ICRA. IEEE International Conference on (vol. 2), pp. 2020-2024, [Volume-Issue Nos.]. IEEE; 5 pages.
S. D'Attanasio, O. Tonet, G. Megali, M.C. Carrozza and P. Dario, A Semi-Automatic Handheld Mechatronic Endoscope with Collision-Avoidance Capabilities, Robotics and Automation, 2000. Proceedings, ICRA 00. IEEE International Conference on (vol. 2), Apr. 2000, pp. 1586-1591, IEEE, San Francisco, CA, US; 6 pages.
R. Taylor, P. Jensen, L. Whitcomb, A Barnes, R. Kumar, D. Stoianovici, P. Gupta, Z Wang, E. Dejuan and L. Kavoussi, A Steady-Hand Robotic System for Microsurgical Augementation, MICCA199: the Second International Conference on Medical Image Computing and Computer-Assisted Intervention, Cambridge, England, Sep. 19-22, 1999. MICCA199 Submission #1361999, pp. 1031-1041, Springer-Verlag Berlin Heidelberg; 11 pages.
W. T. Ang, Active Tremor Compensation in Handheld Instrument for Microsurgery, The Robotics Institute, Carnegie Mellon University, Pittsburgh, Pennsylvania 15213. May 2004; 168 pages.
C.N. Riviere, R.S. Rader and N.V. Thakor, Adaptive Canceling of Physiological Tremor for Improved Precision in Microsurgery, Biomedical Engineering, IEEE Transactions on (vol. 45, Issue No. 7), Jul. 1998, pp. 839-846, IEEE; 8 pages.
H. Rivaz and R. Rohling, An Active Dynamic Vibration Absorber for a Hand-Held Vibro-Elastography Probe, Journal of Vibration and Acoustics, Feb. 2007, pp. 101-112, vol. 129, American Society of Mechanical Engineers; 12 pages.
A. Digioia, III, B. Jaramaz and B. Colgan, Computer Assisted Orthopaedic Surgery Image Guided and Robotic Assistive Technologies, Clinical Orthopaedics and Related Research, 1998, pp. 8-16, No. 354, Lippincott Williams & Wilkins; 9 pages.
M. Fadda, D. Bertelli, S. Martelli, M. Marcacci, P. Dario, C. Paggetti, D. Caramella and D. Trippi, Computer Assisted Planning for Total Knee Arthoplasty, pp. 619-628; 10 pages.
S. Lavallee, P. Sautot, J. Troccaz P. Cinquin and P. Merloz, Computer Assisted Spine Surgery a technique for accurate transpedicular screw fixation using CT data and a 3-D optical localizer, Journal of Image Guided Surgery, 1995, pp. 65-73; 9 pages.
B. Davies, Computer-assisted and robotics surgery, International Congress and Symposium Series 223, 1997, pp. 71-82, Royal Society of Medicine Press Limited; 12 pages.

(56) References Cited

OTHER PUBLICATIONS

M. Fadda, T. Wang, M. Marcacci, S. Martelli, P. Dario, G. Marcenaro, M. Nanetti, C. Paggetti, A. Visani and S. Zaffagnini, Computer-Assisted Knee Arthroplasty at Rizzoli Institutes, First International Symposium on Medical Robotics and Computer Assisted Surgery, Sep. 22-24, 1994, pp. 26-30, Pittsburgh, Pennsylvania US; 6 pages.
F. Leitner, F. Picard, R. Minfelde, H. J. Schulz, P. Cinquin and Saragaglia, Computer-Assisted Knee Surgical Total Replacement, CVRMed-MRCAS'97, Lecture Notes in Computer Science vol. 1205, 1997, pp. 629-638, Springer Berlin Heidelberg, Jan. 1, 1997; 10 pages.
E. Bainville, I. Bricault, P. Cinquin and S. Lavall'ee, Concepts and Methods of Registration for Computer-Integrated Surgery, Computer Assisted Orthopedic Surgery (CAOS), 1999, pp. 15-34, Hogrefe & Huber Publishers, Bern; 22 pages.
A. Wagner, P.P. Pott, M.L. Schwarz, H.P. Scharf, P. Weiser, A Kopfle, R. Manner and E. Badreddin, Control of a Handheld Robot for Orthopedic Surgery, Mechatronic Systems 2004, vol. 1, A Proceedings Volume from the 3rd IFAC Symposium, Sydney, Australia, Sep. 6-8, 2004, vol. 2, Gulf Professional Publishing, 2005; 6 pages.
G. Brandt, A. Zimolong, L. Carrat, P. Merloz, H. W. Staudte, S. Lavallee, K. Radermacher, G. Rau, "CRIGOS: A Compact Robot for Image-Guided Orthopedic Surgery," Information Technology in Biomedicine, IEEE Transactions on, vol. 3, No. 4, pp. 252-260, Dec. 1999; 9 pages.
L.S. Mattos, D.G. Caldwell, M. Dellepiane and E. Grant, Design and control of a robotic system for assistive laser phonomicrosurgery, Engineering in Medicine and Biology Society (EMBC), 2010 Annual International Conference of the IEEE, Aug. 31-Sep. 4, 2010, pp. 5411-5415, IEEE, Buenos Aires, 5 pages.
W.T. Ang, C.N. Riviere and P.K. Khosla, Design and Implementation of Active Error Canceling in Hand-held Microsurgical Instrument, Intelligent Robots and Systems, 2001. Proceedings of the 2001 IEEE/RSJ, International Conference on (vol. 2), Oct. 29-Nov. 3, 2001, pp. 1106-1111, vol. 2, IEEE, Maui, Hawaii, US; 6 pages.
W.T. Ang, C.N. Riviere and P.K. Khosla, Design of All-Accelerometer Inertial Measurement Unit for Tremor Sensing in Hand-held Microsurgical Instrument, Robotics and Automation, 2003. Proceedings. ICRA '03. IEEE International Conference on Sep. 14-19, 2003, pp. 1781-1786, vol. 2, IEEE, Pittsburgh, Pennsylvania, US; 6 pages.
D. Y. Choi and C.N. Riviere, Flexure-based Manipulator for Active Handheld Microsurgical Instrument, Engineering in Medicine and Biology Society, 2005. Proceedings of the 2005 IEEE Engineering in Medicine and Biology 27th Annual Conference of the Digital Object Identifier, 2005, pp. 5085-5088, IEEE, Shanghai, China, Sep. 1-4, 2005; 4 pages.
J. Troccaz, M. Peshkin and B. Davies, Guiding systems for computer-assisted surgery introducing synergistic devices and discussing the different approaches, Medical Image Analysis, Jun. 1998, vol. 2, No. 2, pp. 101-119, Elsevier B.V., 19 pages.
B. Allotta, G. Giacalone and L. Rinaldi, Handheld Drilling Tool for Orthopedic Surgery, Mechatronics, IEEE/ASME Transactions on, vol. 2, Issue 4, Dec. 1997, pp. 218-229, IEEE; 12 pages.
H. Haider, O.A. Barrera and K.L. Garvin, Minimally Invasive Total Knee Arthroplasty Surgery Through Navigated Freehand Bone Cutting, Journal of Arthroplasty, Jun. 2007, vol. 22, No. 4, pp. 535-542, Elsevier B.V.; 8 pages.
C.N. Riviere and N.V. Thakor, Modeling and Canceling Tremor in Human-Machine Interfaces, Engineering in Medicine and Biology Magazine, IEEE, vol. 15, Issue 3, May/Jun. 1996, pp. 29-36, IEEE; 8 pages.
G. Brisson, T. Kanade, A. Digioia and B. Jaramaz, Precision Freehand Sculpting of Bone, Medical Image Computing and Computer-Assisted Intervention—MICCAI 2004, Lecture Notes in Computer Science, vol. 3217, Jan. 1, 2004, pp. 105-112, Springer-Verlag Berlin Heidelberg 2004; 8 pages.
J. Seibold, B. Kubler, and G. Hirzinger, Prototype of Instrument for Minimally Invasive Surgery with 6-Axis Force Sensing Capability, Robotics and Automation, 2005. ICRA 2005. Proceedings of the 2005 IEEE International Conference on Apr. 18-22, 2005, pp. 498-503, IEEE, Barcelona, Spain; 6 pages.
J.T. Lea, D. Watkins, A. Mills, M.A. Peshkin, T.C. Kienzle, III and S.D. Stulberg, Registration and immobilization in robot-assisted surgery, Journal of Image Guided Surgery, Computer Aided Surgery, 1995, vol. 1, No. 2, pp. 80-87; 11 pages.
J.T. Lea, Registration Graphs A Language for Modeling and Analyzing Registration in Image-Guided Surgery, Dec. 1998, Evanston, Illinois, US; 49 pages.
H.A. Paul, W.L. Bargar, B. Mittlestadt, P. Kazanzides, B. Musits, J. Zuhars, P.W. Cain, B. Williamson and F.G. Smith, Robotic Execution of a Surgical Plan, Systems, Man and Cybernetics, 1992, IEEE International Conference on Oct. 18-21, 1992, pp. 1621-1623, IEEE, Sacramento, California, US; 3 pages.
C. Doignon, F. Nageotte and M. De Mathelin, Segmentation and guidance of multiple rigid objects for intra-operative endoscopic vision, Proceeding WDV'05/WDV'06/ICCV'05/ECCV'06 Proceedings of the 2005/2006 international conference on Dynamical vision, pp. 314-327, Springer-Verlag Berlin, Heidelberg; 14 pages.
T.J. Levison, J.E. Moody, B. Jaramaz, C. Nikou, A.M. Digioia, Surgical Navigation for THR A Report on clinical Trial Utilizing HipNav, MICCAI 2000, LNCS 1935, pp. 1185-1187, 2000, Springer-Verlag Berlin Heidelberg; 3 pages.
U. Rembold and C.R. Burghart, Surgical Robotics: An Introduction, Journal of Intelligent and Robotic Systems vol. 30, No. 1, pp. 1-28, 2001, Kluwer Academic Publishers; 28 pages.
C.N. Riviere, W. T. Ang and P.K, Khosla, Toward Active Tremor Canceling in Handheld Microsurgical Instruments, Robotics and Automation, IEEE Transactions, on vol. 19, Issue 5, pp. 793-800, Oct. 2003, IEEE; 8 pages.
B. Bose, A. K. Kalra, S. Thukral, A. Sood, S.K. Guha and S. Anand, Tremor Compensation for Robotics Assisted Microsurgery, Engineering in Medicine and Biology Society, 1992 14th Annual International Conference of the IEEE, vol. 3, Oct. 29, 1992-Nov. 1, 1992, pp. 1067-1068, IEEE, Paris, FR; 2 pages.
Y. Koseki, K. Chinzei, N. Koyachi and T. Arai, Robotic Assist for MR-Guided Surgery Using Leverage and Parallelepiped Mechanism, Medical Image Computing and Computer-Assisted Intervention—MICCAI 2000 Lecture Notes in Computer Science, vol. 1935, 2000, pp. 940-948, Springer Berlin Heidelberg, 9 pages.
English language abstract for JP 2009-537231 extracted from espacenet.com database on May 22, 2019, 2 pages.
English language abstract for JP 2011-505980 extracted from espacenet.com database on Jan. 2, 2019, 2 pages.

* cited by examiner

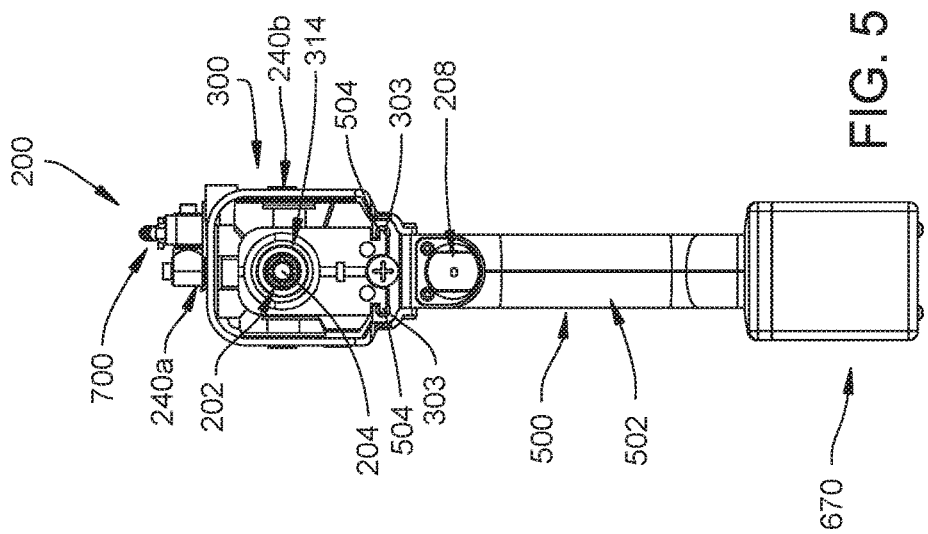
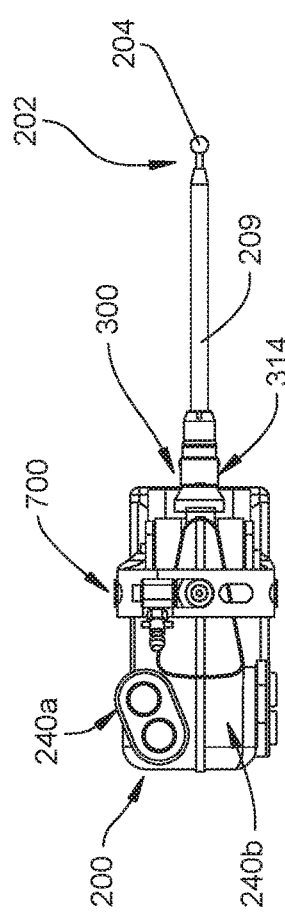
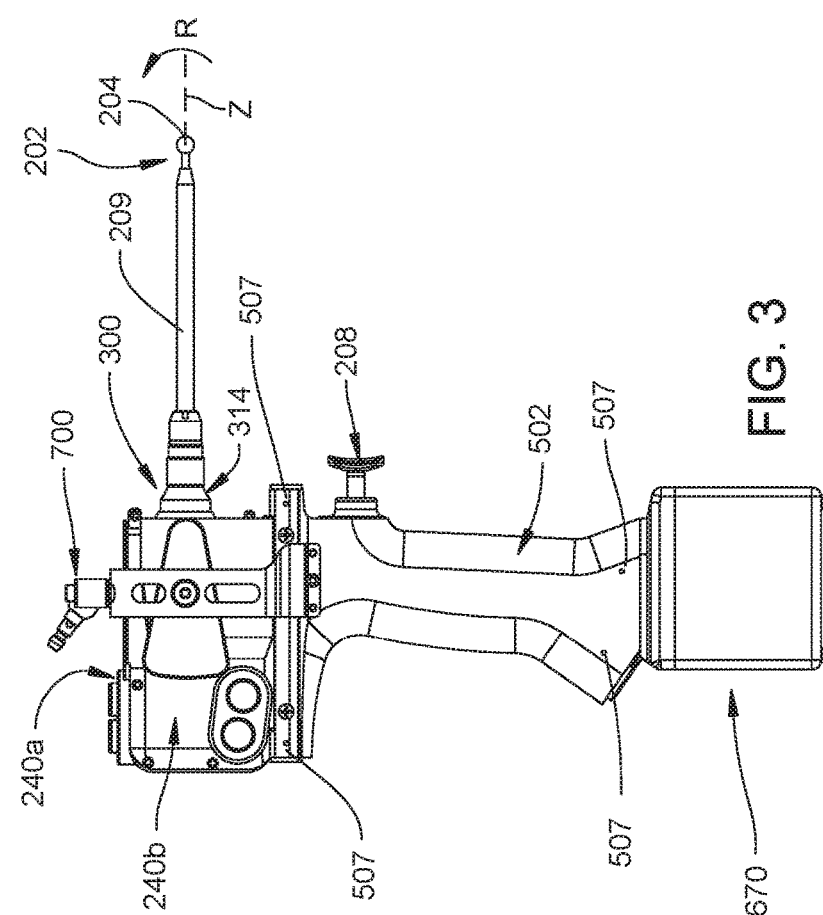

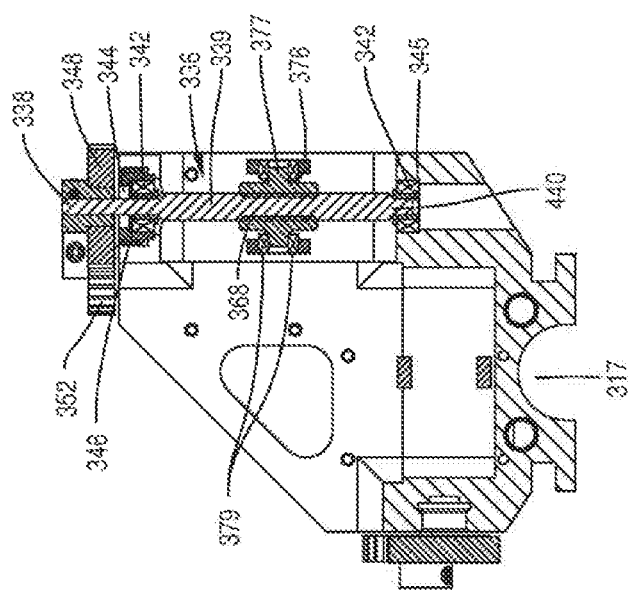

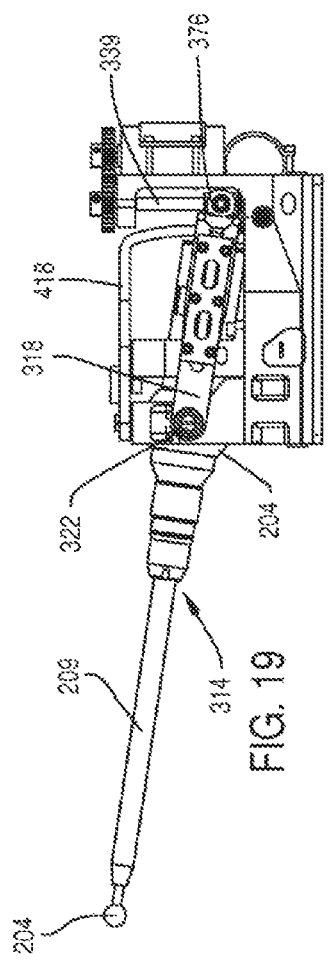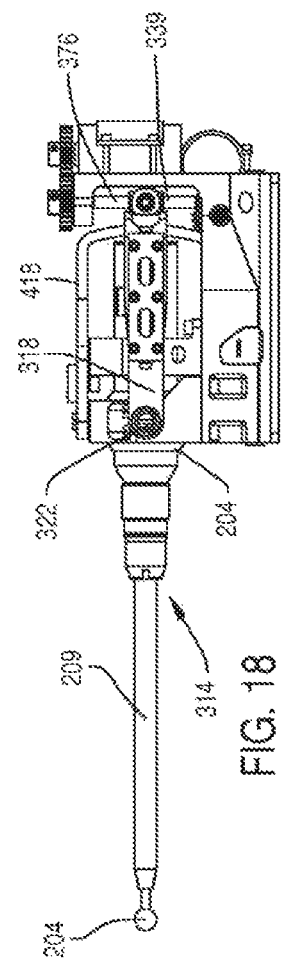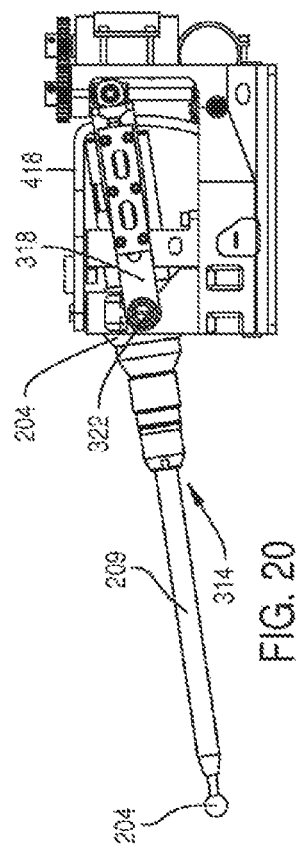

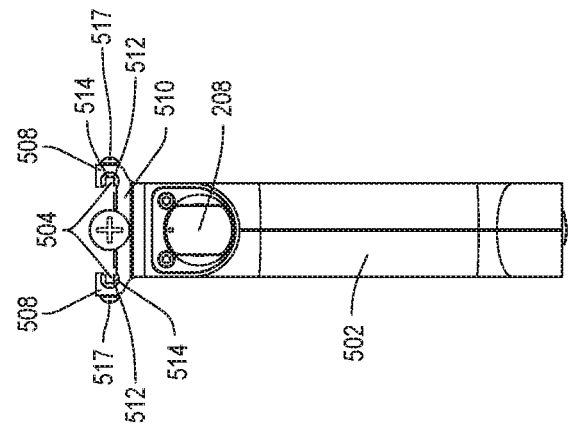
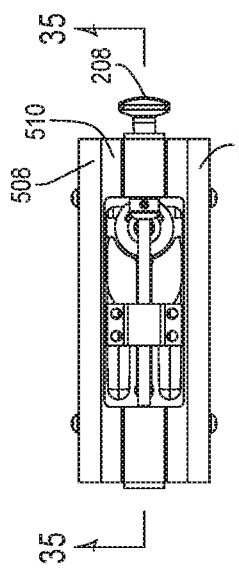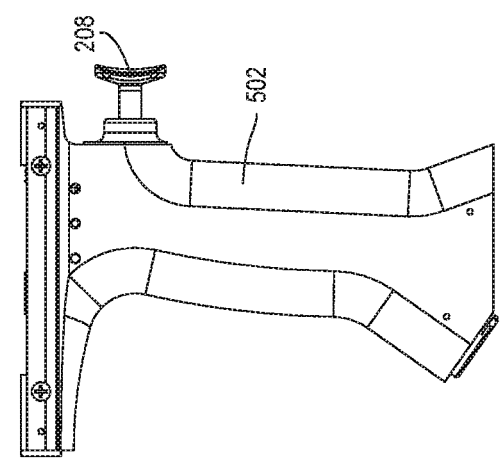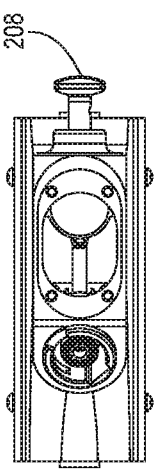
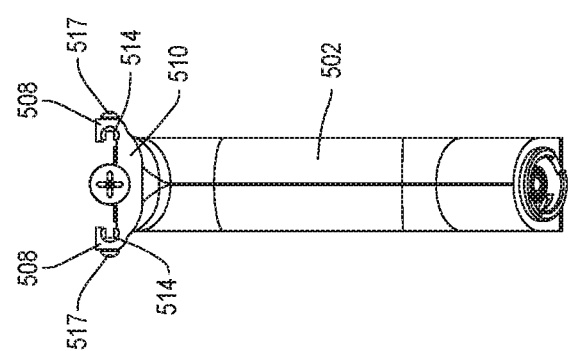

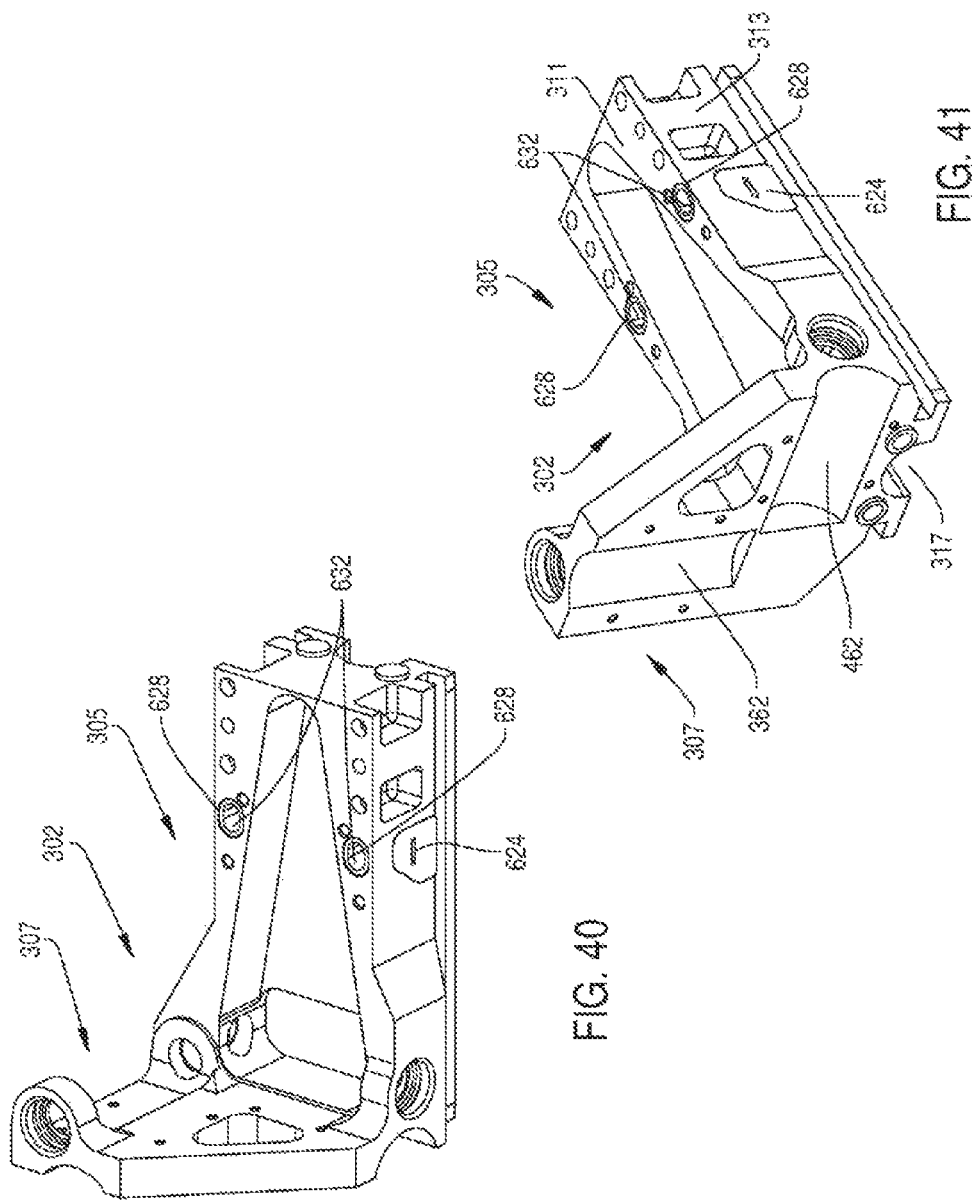

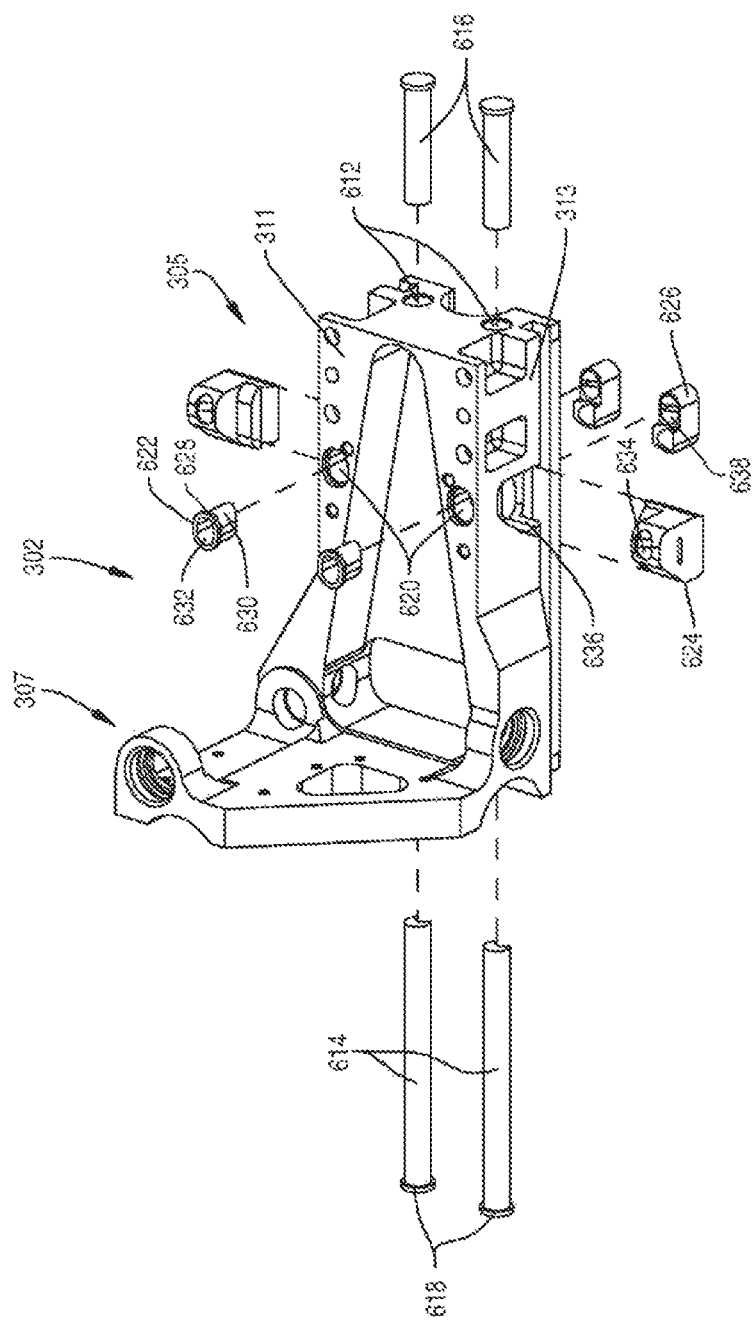

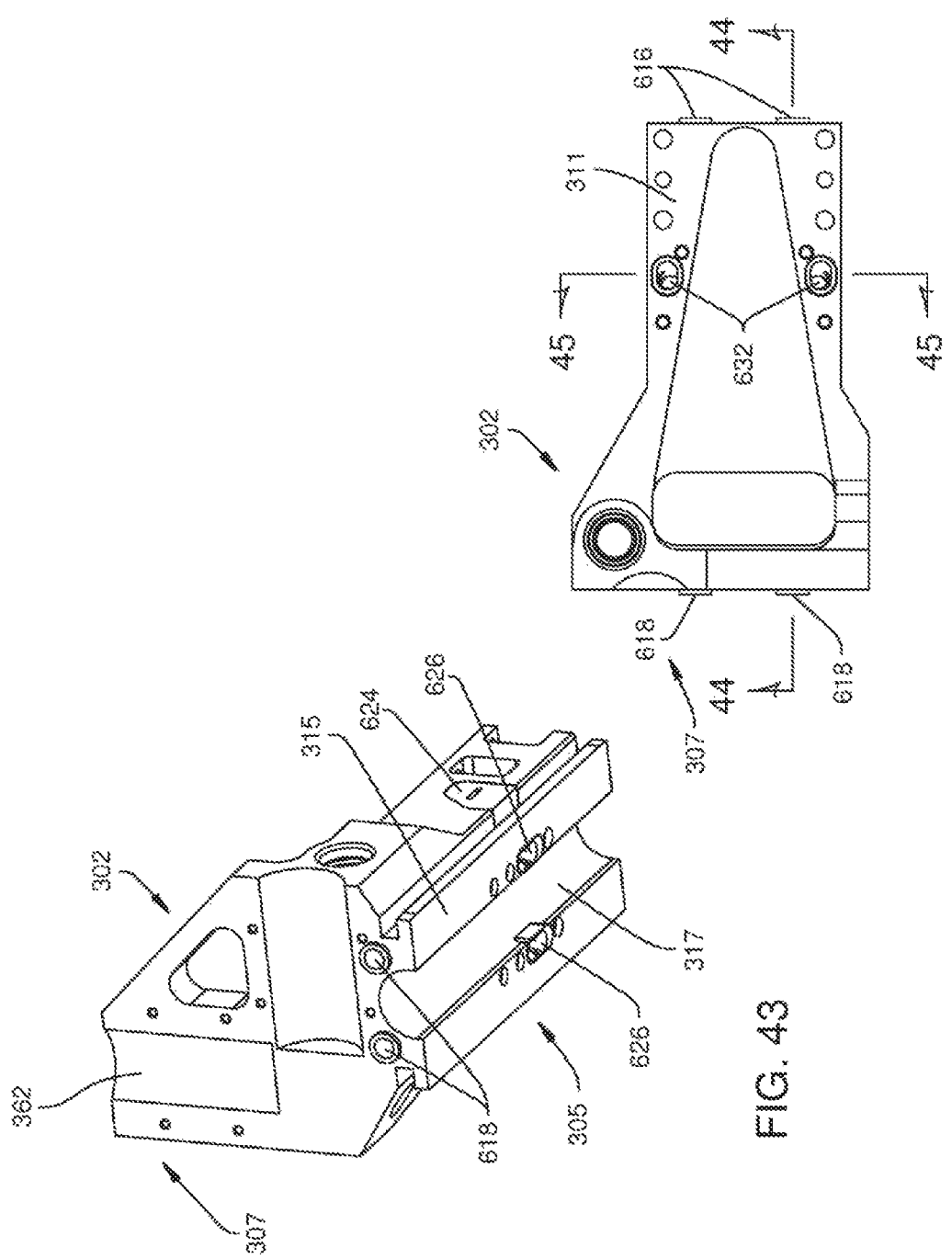

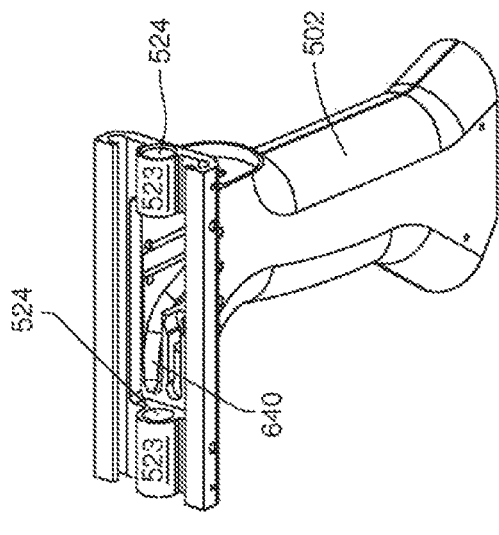
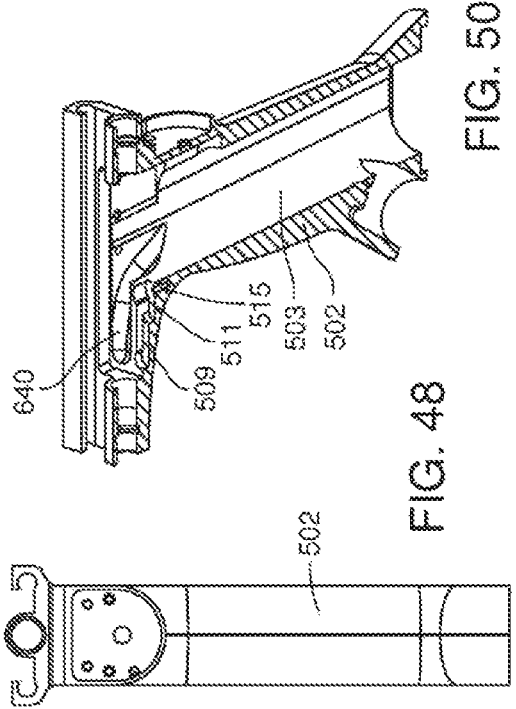
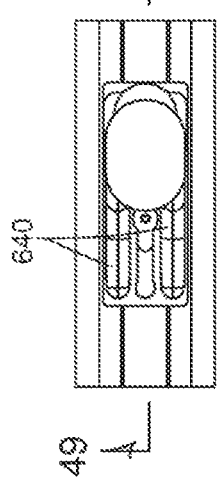
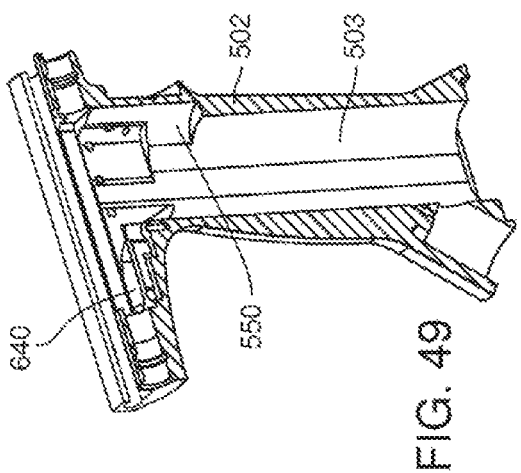
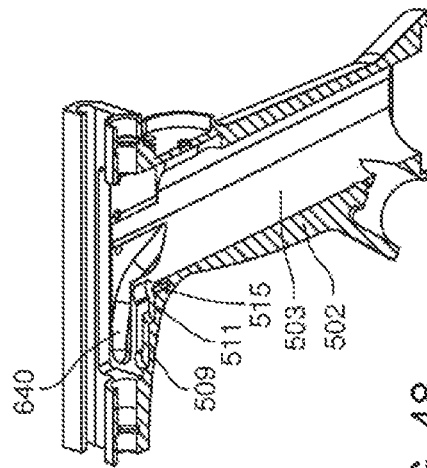
FIG. 46
FIG. 47
FIG. 48
FIG. 49
FIG. 50

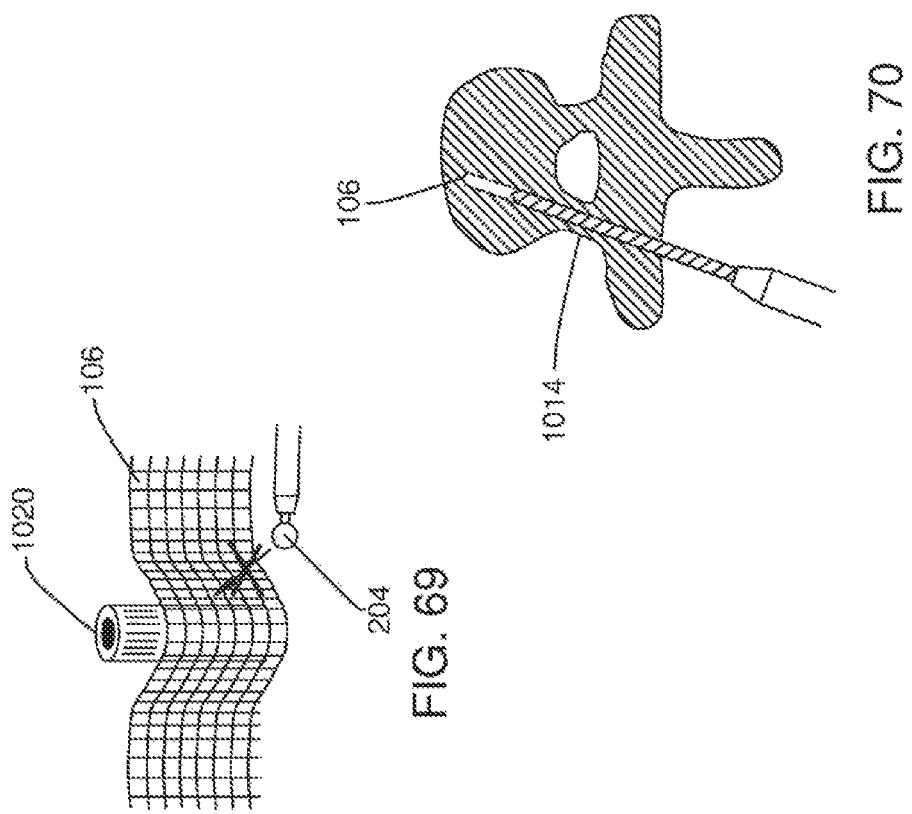

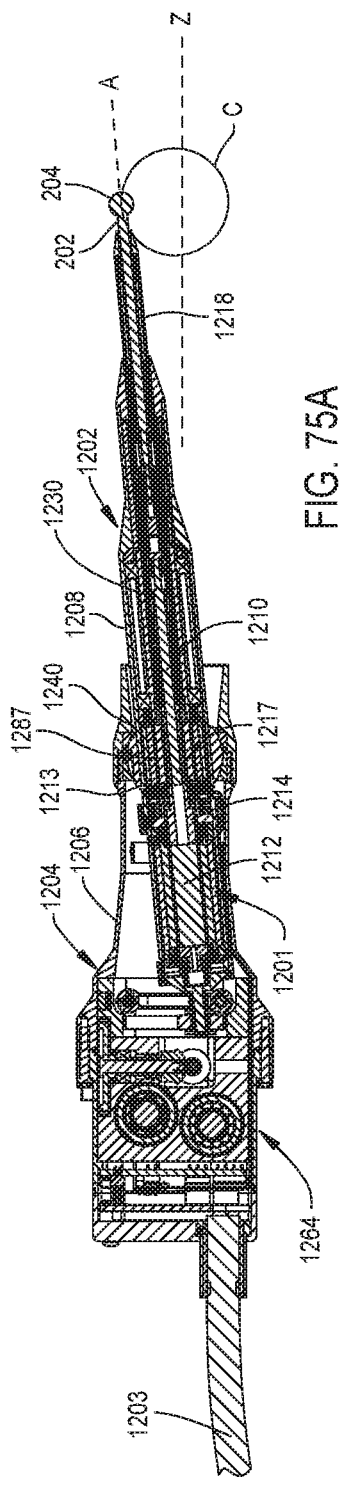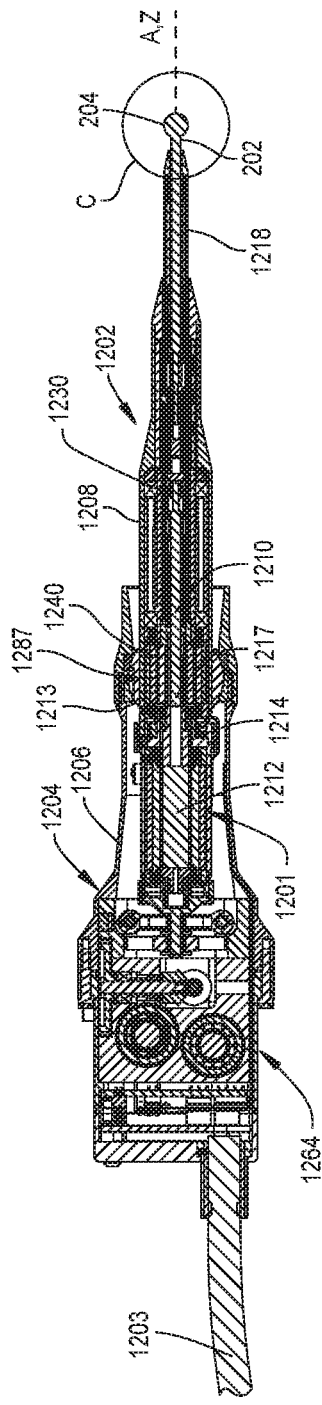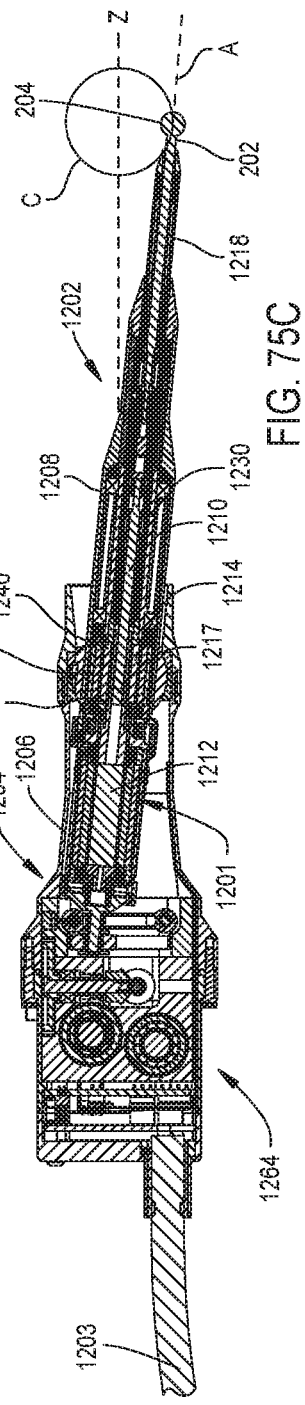

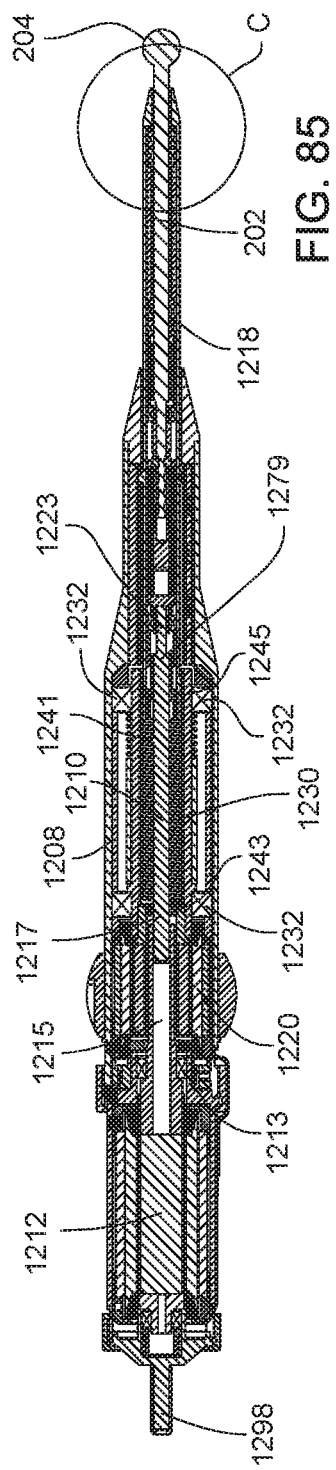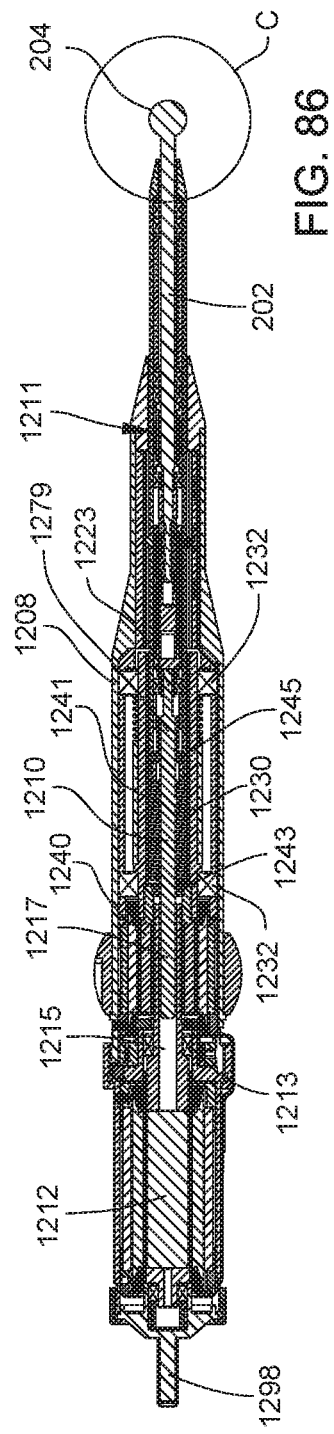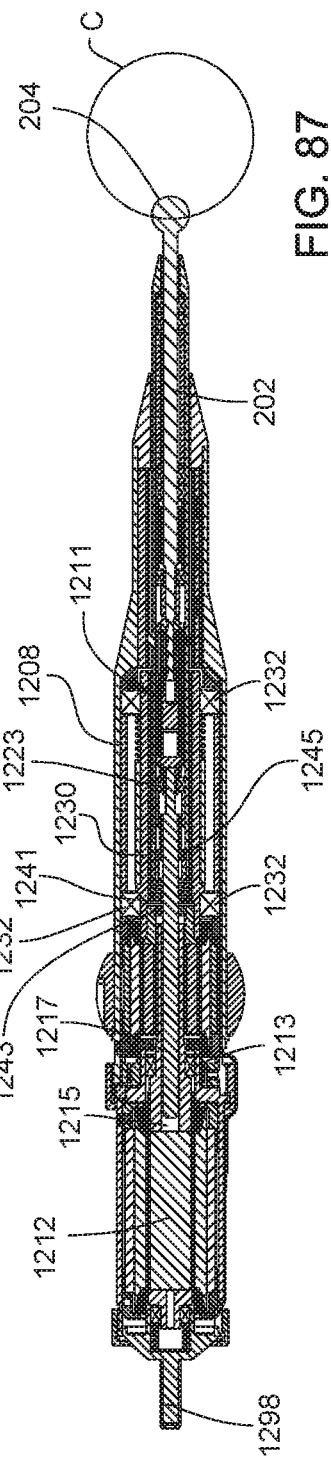

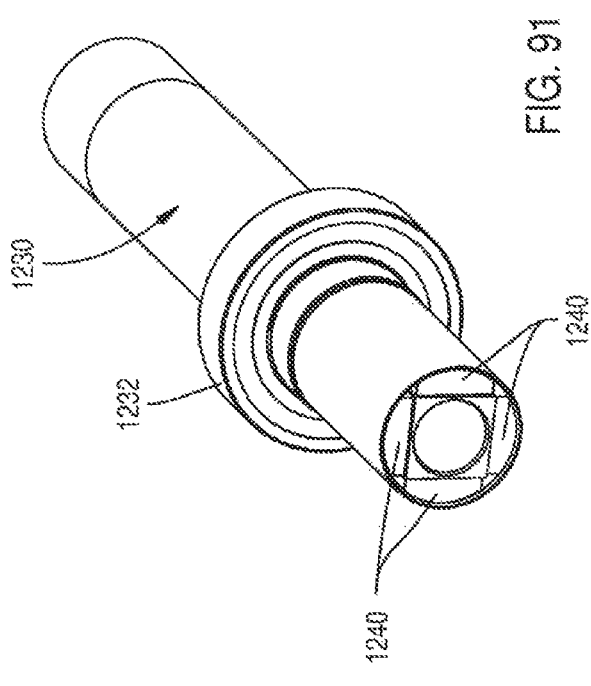
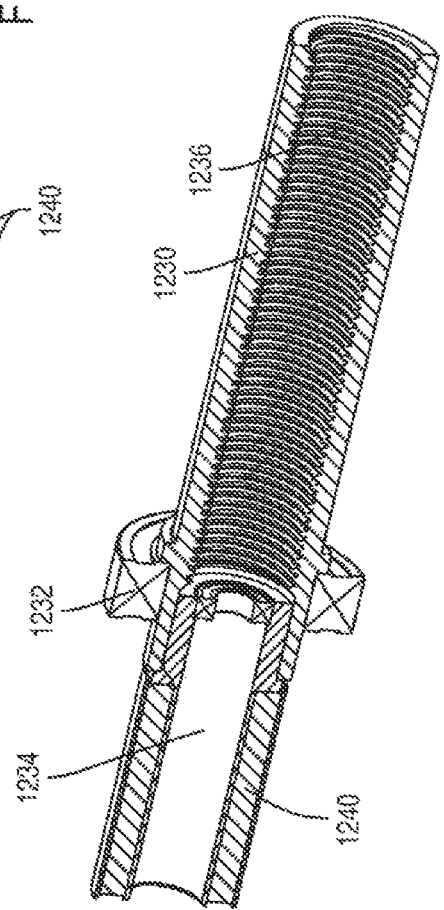

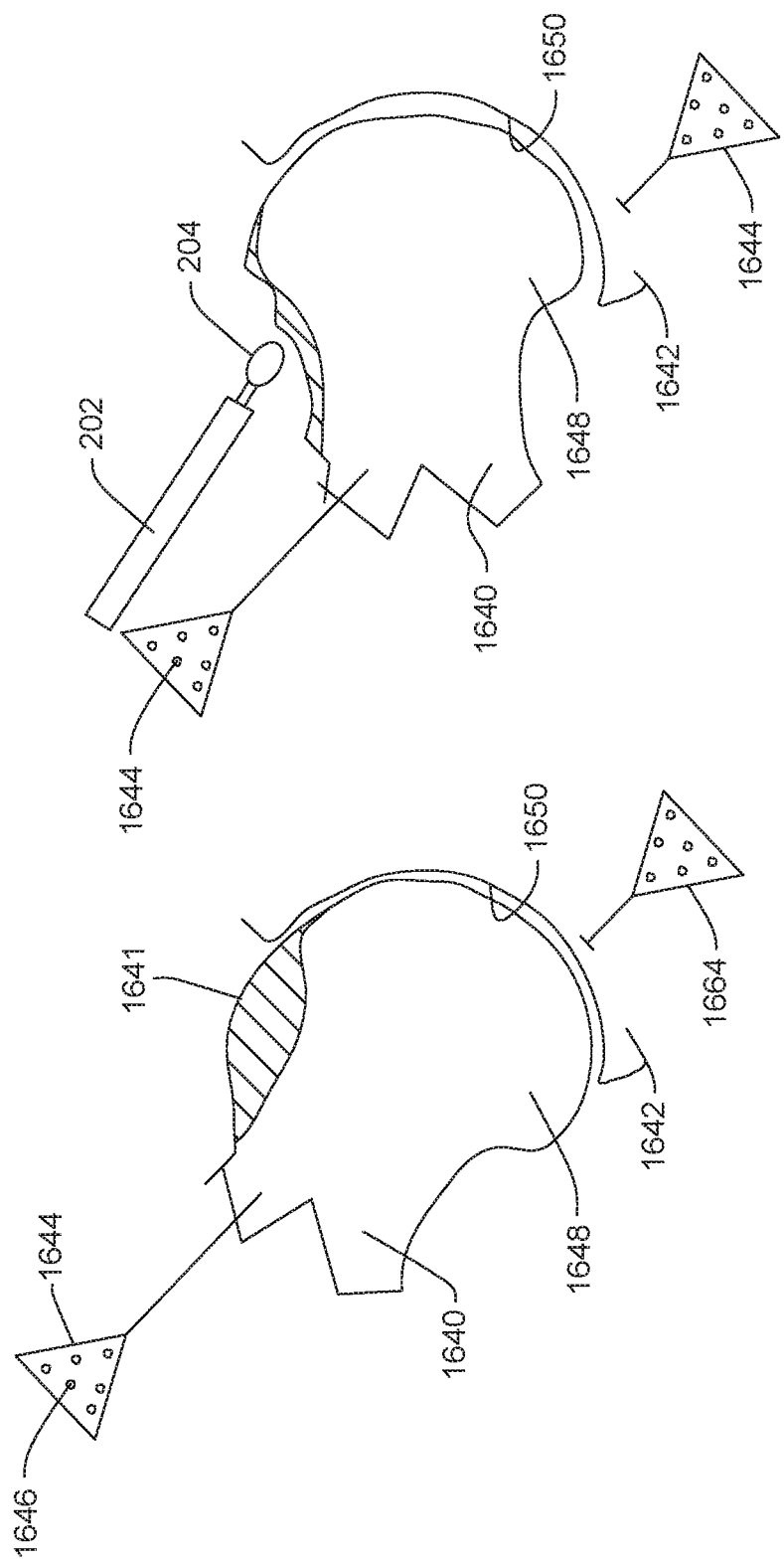

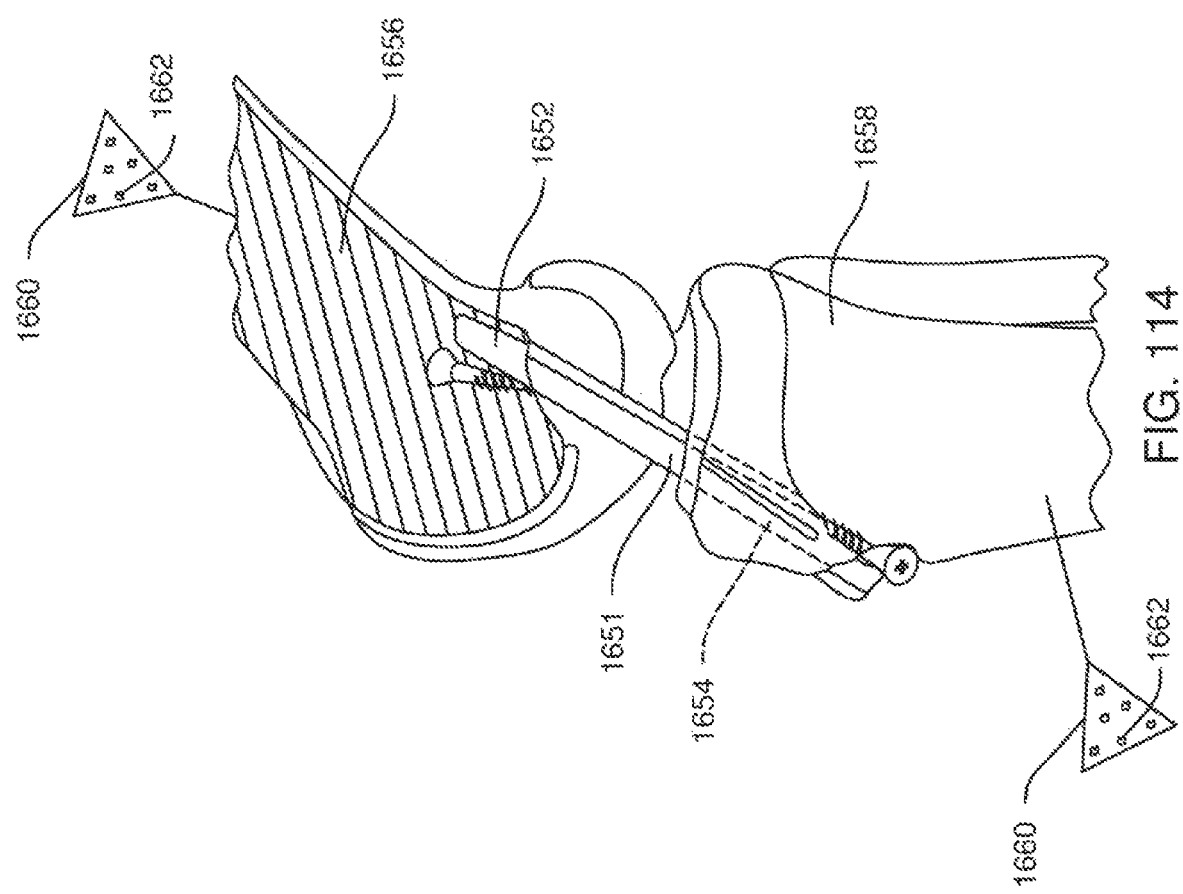

SURGICAL INSTRUMENT INCLUDING HOUSING, A CUTTING ACCESSORY THAT EXTENDS FROM THE HOUSING AND ACTUATORS THAT ESTABLISH THE POSITION OF THE CUTTING ACCESSORY RELATIVE TO THE HOUSING

CROSS-REFERENCE TO RELATED APPLICATIONS

The subject patent application is a divisional of U.S. Nonprovisional patent application Ser. No. 13/600,888, filed on Aug. 31, 2012, which claims the benefit of Provisional Patent Application No. 61/530,614 filed on Sep. 2, 2011 and U.S. Provisional Patent Application No. 61/662,070 filed on Jun. 20, 2012, the contents of each being incorporated herein by reference in their entirety.

FIELD OF THE INVENTION

The present invention relates generally to hand-held surgical instruments, systems for tracking and controlling hand-held surgical instruments, and methods of use. The tracking and control system is used to keep a working part of the instrument in a desired relationship to a boundary. The system controls the position of a cutting accessory integral with the instrument when the accessory is applied to tissue during a medical/surgical procedure.

BACKGROUND OF THE INVENTION

Tracking systems (also known as navigation systems) assist surgeons during surgeries that require the precise locating of instruments. Such surgeries include neurosurgery and orthopedic surgery. The tracking system tracks the position and orientation of an instrument during the procedure and often displays the position and/or orientation of the instrument on a monitor in conjunction with a preoperative image or an intraoperative image of the patient (preoperative images are typically prepared by MRI or CT scans, while intraoperative images may be prepared using a fluoroscope, low level x-ray or any similar device). Alternatively, some systems are image-less in which the patient's anatomy is instead registered and mathematically fitted with an anatomical model.

Prior art tracking systems typically employ a camera that detects a tracking device located on the instrument. The tracking device has a plurality of optical markers such as light emitting diodes (LEDs) to determine the position and orientation of the instrument. The position of the instrument usually correlates to the coordinates of a working end of the instrument in three-dimensional space, the x, y, z or Cartesian coordinates, relative to the camera. The orientation of the instrument means the pitch, roll, and yaw of the instrument. When both the position and the orientation of the instrument are defined, the relative position of that instrument is known to the tracking system.

Orthopedic surgeons have been using tracking systems for some time to assist in properly locating and positioning cutting jigs. Cutting jigs are used to resect bone for the purpose of preparing joints to accept replacement implants. The time required to position and secure a cutting jig can appreciably add to the overall time required to perform a joint replacement surgical procedure. It should be appreciated that the cutting jig must be accurately positioned. Imprecise positioning of a cutting jig can contribute to a less than ideal surgical outcome. As a result, there has been a movement to eliminate the use of cutting jigs. Instead, surgeons would rely solely on tracking the instrument to ensure that the cutting portion of the instrument does not stray beyond a predefined boundary.

In such tracking systems both the instrument and the material being cut are outfitted with trackers such that the tracking system can track both the position and orientation of the instrument and the material being cut such as a bone. The instrument is held by a robot or other articulation mechanism that provides some form of mechanical constraint to movement. This constraint limits the movement of the instrument to within a predefined boundary. If the instrument strays beyond the predefined boundary, a control is sent to the instrument to stop cutting. Such systems are shown in U.S. Pat. No. 5,408,409 to Glassman et al.

It has also been proposed in the prior art that the instrument be used free hand without the aid of cutting jig, guide arm or other constraining mechanism to establish the location to which the cutting implement at the end of the instrument is applied. See, for example, U.S. Pat. No. 6,757,582 to Brisson et al.

SUMMARY AND ADVANTAGES

The present invention provides an instrument for treating tissue during a medical procedure. The instrument comprises a hand-held portion for being manually supported and moved by a user. A working portion is movably coupled to the hand-held portion. A plurality of actuators are operatively coupled to the working portion for moving the working portion in a plurality of degrees of freedom relative to the hand-held portion. A tracking device is attached to the hand-held portion for tracking the instrument. A drive mechanism is coupled to the working portion for rotating the working portion about a rotational axis. The drive mechanism moves in at least one degree of freedom relative to the hand-held portion.

The present invention also provides an instrument for treating tissue during a medical procedure, as described in this paragraph. The instrument comprises a hand-held portion for being manually supported and moved by a user. A working portion is movably coupled to the hand-held portion and includes a distal tip. A plurality of actuators are operatively coupled to the working portion for moving the working portion in a plurality of degrees of freedom relative to the hand-held portion. A tracking device is attached to the hand-held portion for tracking the instrument. The distal tip of the working portion is capable of a total displacement of at least 0.2 inches (0.508 cm) in each of the plurality of degrees of freedom.

The present invention also provides a method for treating tissue during a medical procedure using an instrument having a hand-held portion, a working portion, a plurality of actuators for moving the working portion in a plurality of degrees of freedom relative to the hand-held portion, a plurality of sensors for sensing positions of the working portion relative to the hand-held portion, and a control system for controlling the instrument. The method comprises the steps of: manually supporting and moving the hand-held portion during the medical procedure to treat the tissue of a patient with the working portion; and operating the control system so that the control system establishes a home position of the working portion relative to the hand-held portion and tracks deviation of the working portion from the home position as the working portion moves in one or more of the plurality of degrees of freedom relative to the hand-held portion in order to maintain a desired relationship to a virtual boundary associated with the tissue during the medical procedure.

The present invention also provides a method for treating tissue during a medical procedure using an instrument, as described in this paragraph. The instrument has a hand-held portion, a working portion, a plurality of actuators for moving the working portion in a plurality of degrees of freedom relative to the hand-held portion, a plurality of sensors for sensing positions of the working portion relative to the hand-held portion, and a control system for controlling the instrument. The method comprises the steps of: manually grasping and moving the hand-held portion during the medical procedure to treat the tissue of a patient with the working portion; and operating the control system so that the control system establishes a home position of the working portion relative to the hand-held portion and tracks deviation of the working portion from the home position as the working portion moves in one or more of the plurality of degrees of freedom relative to the hand-held portion in order to maintain a desired relationship to a virtual boundary associated with the tissue during the medical procedure. The control system controls a cutting speed of the working portion based on the deviation.

The present invention also provides an instrument for treating tissue during a medical procedure, as described in this paragraph. The instrument comprises a hand-held portion for being manually supported and moved by a user. A drive assembly is movably coupled to the hand-held portion and supports a working portion. A plurality of actuators are operatively coupled to the working portion for moving the working portion in a plurality of degrees of freedom relative to the hand-held portion. A tracking device is mounted to the hand-held portion for tracking the instrument during the medical procedure. The drive assembly supports one of the actuators and is movable by at least another of the actuators in at least one degree of freedom relative to the hand-held portion.

The present invention also provides an instrument for treating tissue during a medical procedure, as described in this paragraph. The instrument comprises a hand-held portion for being manually supported and moved by a user. A working portion is movably coupled to the hand-held portion. A plurality of actuators are operatively coupled to the working portion for moving the working portion in a plurality of degrees of freedom relative to the hand-held portion. A tracking device is attached to the hand-held portion for tracking the instrument. At least adjustment one mechanism is disposed between the actuators and the working portion for transmitting movement from the actuators to the working portion.

The present invention also provides an instrument for treating tissue during a medical procedure, as described in this paragraph. The instrument comprises a hand-held portion for being manually supported and moved by a user. A working portion is movably coupled to the hand-held portion. A plurality of actuators are operatively coupled to the working portion for moving the working portion in a plurality of degrees of freedom relative to the hand-held portion. A tracking device is mounted to the hand-held portion for tracking the instrument during the medical procedure. A gimbal supports movement of the working portion in at least two of the degrees of freedom relative to the hand-held portion.

The present invention also provides an instrument for treating tissue during a medical procedure, as described in this paragraph. The instrument comprises a hand-held portion for being manually supported and moved by a user. A working portion is movably coupled to the hand-held portion. A plurality of actuators are operatively coupled to the working portion for moving the working portion in a plurality of degrees of freedom relative to the hand-held portion. A drive motor is supported by the hand-held portion and includes a drive shaft coupled to the working portion for rotating the working portion about a cutting axis. A tracking device is mounted to the hand-held portion for tracking the instrument during the medical procedure. One of the actuators includes a motor having a hollow rotor that rotatably receives the drive shaft therein such that the drive shaft of the drive motor rotates within the hollow rotor and relative to the hollow rotor so as to rotatably drive the working portion.

The present invention also provides an instrument for treating tissue during a medical procedure, as described in this paragraph. The instrument comprises a hand-held portion for being manually supported and moved by a user; a cutting accessory movably coupled to the hand-held portion; a plurality of actuators operatively coupled to the cutting accessory for moving the cutting accessory in a plurality of degrees of freedom relative to the hand-held portion, the plurality of actuators including an axial actuator for translating the cutting accessory along an axis; a drive motor including a drive shaft for rotating the cutting accessory about a cutting axis; a tracking device mounted to the hand-held portion for tracking the instrument during the medical procedure; and a collet assembly rotatably coupling the drive shaft to the cutting accessory so that the cutting accessory rotates about the cutting axis upon rotation of the drive shaft, the collet assembly configured to release the cutting accessory in response to actuation of the axial actuator beyond a predefined limit of actuation.

The present invention also provides an instrument for treating tissue during a medical procedure, as described in this paragraph. The instrument comprises a hand-held portion for being manually supported and moved by a user. A rotating cutting accessory is movably coupled to the hand-held portion. A plurality of actuators are operatively coupled to the cutting accessory for moving the rotating cutting accessory in a plurality of degrees of freedom relative to the hand-held portion. A tracking device is attached to the hand-held portion for tracking the instrument. A sleeve at least partially covers the cutting accessory and moves with the cutting accessory in each of the plurality of degrees of freedom. The cutting accessory is configured to rotate within the sleeve during the medical procedure.

The present invention also provides a system for treating tissue during a medical procedure. The system comprises an instrument adapted to be manually supported and moved by a user. The instrument includes a hand-held portion. The working portion is movably coupled to the hand-held portion. A plurality of actuators are operatively coupled to the working portion for moving the working portion in a plurality of degrees of freedom relative to the hand-held portion. A tracking device is attached to the hand-held portion for tracking the instrument. The system includes a navigation system for determining a position of the working portion relative to a virtual boundary associated with the tissue being treated. A control system is in communication with the actuators and is configured to control the actuators to actively position the working portion at the boundary while the user moves the hand-held portion relative to the boundary such that the working portion is substantially maintained at the boundary independent of the movement of the hand-held portion.

The present invention also provides a system for treating tissue during a medical procedure, as described in this paragraph. An instrument is adapted to be manually supported and moved by a user. The instrument includes a hand-held portion. A working portion is movably coupled to the hand-held portion. A plurality of actuators are operatively coupled to the working portion for moving the working portion in a plurality of degrees of freedom relative to the hand-held portion. A tracking device is attached to the hand-held portion for tracking the instrument. The system includes a navigation system for determining a position of the working portion relative to a target volume of the tissue to be removed. A control system is in communication with the actuators and is configured to control the actuators to move the working portion relative to the hand-held portion such that the working portion autonomously follows a path defined in the control system to remove the target volume of material while the user substantially maintains the hand-held portion in a gross position relative to the target volume during the medical procedure.

The present invention also provides a system for treating tissue during a medical procedure, as described in this paragraph. The system comprises an instrument adapted to be manually supported and moved by a user. The instrument includes a hand-held portion, a working portion movably coupled to the hand-held portion, a plurality of actuators operatively coupled to the working portion for moving the working portion in a plurality of degrees of freedom relative to the hand-held portion, and a tracking device attached to the hand-held portion for tracking the instrument. The system includes a navigation system for determining a position of the working portion relative to a virtual boundary associated with the tissue being treated. A display is in communication with the navigation system for indicating the position of the working portion relative to the virtual boundary. A control system is in communication with the actuators to control the actuators to move the working portion relative to the hand-held portion. The control system is configured to establish a home position of the working portion relative to the hand-held portion and track deviation of the working portion from the home position as the working portion moves in one or more of the plurality of degrees of freedom relative to the hand-held portion in order to maintain a desired relationship to the virtual boundary during the medical procedure. The display indicates the deviation of the working portion relative to the home position.

The present invention also provides a system for treating tissue during a medical procedure, as described in this paragraph. The system comprises an instrument adapted to be manually supported and moved by a user. The instrument includes a hand-held portion, a working portion movably coupled to the hand-held portion, a plurality of actuators operatively coupled to the working portion for moving the working portion in a plurality of degrees of freedom relative to the hand-held portion, and a tracking device attached to the hand-held portion for tracking the instrument. The system includes a navigation system for determining a position of the working portion relative to a virtual boundary associated with the tissue being treated. A display is in communication with the navigation system for indicating the position of the working portion relative to the virtual boundary. A control system is in communication with the actuators to control the actuators to move the working portion relative to the hand-held portion. The control system is configured to control the display to change a resolution of the display as the working portion approaches the virtual boundary.

The present invention also provides a method for performing a spinal fusion procedure on a patient's spine. The method comprises: establishing a virtual boundary associated with the patient's spine; providing access through skin to the patient's spine; manually holding an instrument having a hand-held portion, a cutting accessory, a plurality of actuators for moving the cutting accessory in a plurality of degrees of freedom relative to the hand-held portion, and a tracking device; operating a tracking and control system for the instrument to track movement of the cutting accessory relative to the virtual boundary; moving the cutting accessory through the incision in the skin; cutting away material from the patient's spine wherein the tracking and control system controls the actuators to move the cutting accessory relative to the hand-held portion so that the cutting accessory is substantially maintained in a desired relationship to the boundary during cutting; and fitting an implant into the patient's spine after cutting away material from the patient's spine.

The present invention also provides a method for performing a procedure on a patient's hip. The method comprises: establishing a virtual boundary associated with a femoral head of the patient wherein the virtual boundary defines a volume of material that creates a cam impingement between the femoral head and an acetabulum of the patient; providing access through skin to the femoral head of the patient; manually holding an instrument having a hand-held portion, a cutting accessory, a plurality of actuators for moving the cutting accessory in a plurality of degrees of freedom relative to the hand-held portion, and a tracking device; operating a tracking and control system for the instrument so that the tracking and control system tracks movement of the cutting accessory relative to the virtual boundary; moving the cutting accessory through the incision in the skin to the femoral head; and cutting away the volume of material from the femoral head that creates the cam impingement with the acetabulum to relieve the impingement. The tracking and control system controls the actuators to move the cutting accessory relative to the hand-held portion so that the cutting accessory is substantially maintained in a desired relationship to the virtual boundary during cutting to remove the defined volume of material.

The present invention also provides a method for performing a procedure on a patient's knee. The method comprises: establishing a virtual boundary associated with the femur and tibia of the patient wherein the virtual boundaries define a volume of material to be removed from the femur and tibia to receive a graft; creating an access path through skin of the patient to provide access to the femur or tibia of the patient; manually holding an instrument having a hand-held portion, a cutting accessory, a plurality of actuators for moving the cutting accessory in a plurality of degrees of freedom relative to the hand-held portion, and a tracking device; operating a tracking and control system for the instrument so that the tracking and control system tracks movement of the cutting accessory relative to the virtual boundaries; moving the cutting accessory through the access path to the femur or tibia; cutting away the volume of material from the femur and the tibia wherein the cutting occurs first through one or the femur or tibia to create a femur or tibia passage and with the cutting accessory positioned in the femur or tibia passage cutting then occurs in the other of the femur or tibia to form the other of the femur or tibia passage wherein the tracking and control system controls the actuators to move the cutting accessory relative to the hand-held portion so that the cutting accessory is substantially maintained in a desired relationship to the virtual boundaries during cutting in the tibia and the femur to remove the defined volume of material; and placing a graft in the tibia passage and the femur passage.

The present invention also provides a method for repairing a focal defect in cartilage of a patient. The method comprises: establishing a virtual boundary associated with the focal defect in the cartilage of the patient wherein the virtual boundary defines a volume of material to be removed around the focal defect; creating an access path through skin of the patient to provide access to the focal defect; manually holding an instrument having a hand-held portion, a cutting accessory, a plurality of actuators for moving the cutting accessory in a plurality of degrees of freedom relative to the hand-held portion, and a tracking device; operating a tracking and control system for the instrument so that the tracking and control system tracks movement of the cutting accessory relative to the virtual boundary; moving the cutting accessory through the access path to the focal defect; and cutting away the volume of material surrounding the focal defect. The control system controls the actuators to move the cutting accessory relative to the hand-held portion so that the cutting accessory is substantially maintained in a desired relationship to the virtual boundary during cutting to remove the defined volume of material.

The present invention also provides a method for preparing bone to receive an implant. The method comprises: establishing a virtual boundary associated with the bone of the patient wherein the virtual boundary defines a volume of bone to be removed to form an implant pocket shaped to receive an implant; providing access to the volume of bone to be removed; manually holding an instrument having a hand-held portion, a cutting accessory, a plurality of actuators for moving the cutting accessory in a plurality of degrees of freedom relative to the hand-held portion, and a tracking device; operating a tracking and control system for the instrument so that the tracking and control system tracks movement of the cutting accessory relative to the virtual boundary; moving the cutting accessory to the volume of bone to be removed; and cutting away the volume of bone to form the implant pocket. The tracking and control system controls the actuators to move the cutting accessory relative to the hand-held portion so that the cutting accessory is substantially maintained in a desired relationship to the virtual boundary during cutting so to remove the defined volume of bone. The method includes placing the implant in the implant pocket and securing the implant in position in the implant pocket.

Advantageously, the present invention provides for a compact design of the instrument, which beneficially allows the operator to easily manipulate the instrument, while actuators of the instrument position the working portion in a plurality of degrees of freedom relative to the hand-held portion. This compact design also reduces visual interference with the tissue being operated upon. The compact design allows for the hand-held portion to be sized and shaped to be held and supported in the hand of a user.

The present invention also advantageously provides feedback to the operator indicating relative position of the working portion of the instrument to the virtual boundary. The operator can determine the location of the working portion relative to the virtual boundary by observing deviation from the home position and/or speed attenuation of the working portion. The speed attenuation of the working portion can provide visual and/or aural indication of position of the working portion relative to the virtual boundary. Displays also provide feedback regarding the position of the working portion.

The control system provides the ability to operate the instrument in a variety of modes and to perform a variety of procedures. For example, the instrument can be operated in an active mode, a passive mode, or an autonomous mode. The control system, for example, controls the actuators to position the working portion in the plurality of degrees of freedom relative to the hand-held portion to maintain a desired relationship to the virtual boundaries.

The variety of procedures that can be performed with the instrument include, for example, sculpting, shaving, coring, boring, or any other method of removing tissue such as bone. The instrument can be used to remove tissue in spine, knee, hip, and other procedures. These procedures may be open procedures or minimally invasive procedures.

BRIEF DESCRIPTION OF THE DRAWINGS

Advantages of the present invention will be readily appreciated as the same becomes better understood by reference to the following detailed description when considered in connection with the accompanying drawings wherein:

FIGS. 3-5 are, respectively, front, top, and right views of the surgical instrument;

FIG. 17A is a cross-sectional view of the upper assembly taken generally along the line 17A-17A in FIG. 12;

FIGS. 18-20 are back views of the upper assembly illustrating different pitch positions of an end effector of the upper assembly;

FIGS. 30-34 are front, top, bottom, left-side, and right-side views of the handle assembly;

FIG. 40 is a top perspective view of a slider subassembly of the upper assembly;

FIG. 41 is a rear perspective view of the slider subassembly;

FIG. 42 is an exploded view of the slider subassembly;

FIG. 43 is a bottom perspective view of the slider subassembly;

FIG. 43A is a top view of the slider subassembly;

FIG. 46 is a top perspective view of the handle assembly with portions removed to illustrate a path for wires;

FIG. 47 is a top view of the handle assembly with portions removed;

FIG. 48 is a right view of the handle assembly with portions removed;

FIGS. 49 and 50 are perspective cross-sectional views taken along the lines 49-49 in FIG. 47 and illustrating additional paths for wires;

FIG. 69 is an illustration of an application of the invention for use in avoiding tissues or nerves;

FIG. 70 is an illustration of an application of the invention for use in depth control;

FIGS. 75A-C are cross-sectional views of the instrument of FIG. 72 in various pitch positions;

FIGS. 85-87 are cross-sectional views of the instrument in various positions along a z-axis;

FIG. 91 is a perspective view of the lead screw

FIG. 92 is a cross-sectional view of the lead screw;

FIGS. 113A and 113B illustrate steps of alleviating impingement between a femoral head and an acetabulum;

FIG. 114 illustrates an anterior cruciate ligament repair using a graft placed through passages formed in the femur and tibia;

DETAILED DESCRIPTION

I. Overview

Figure 1:
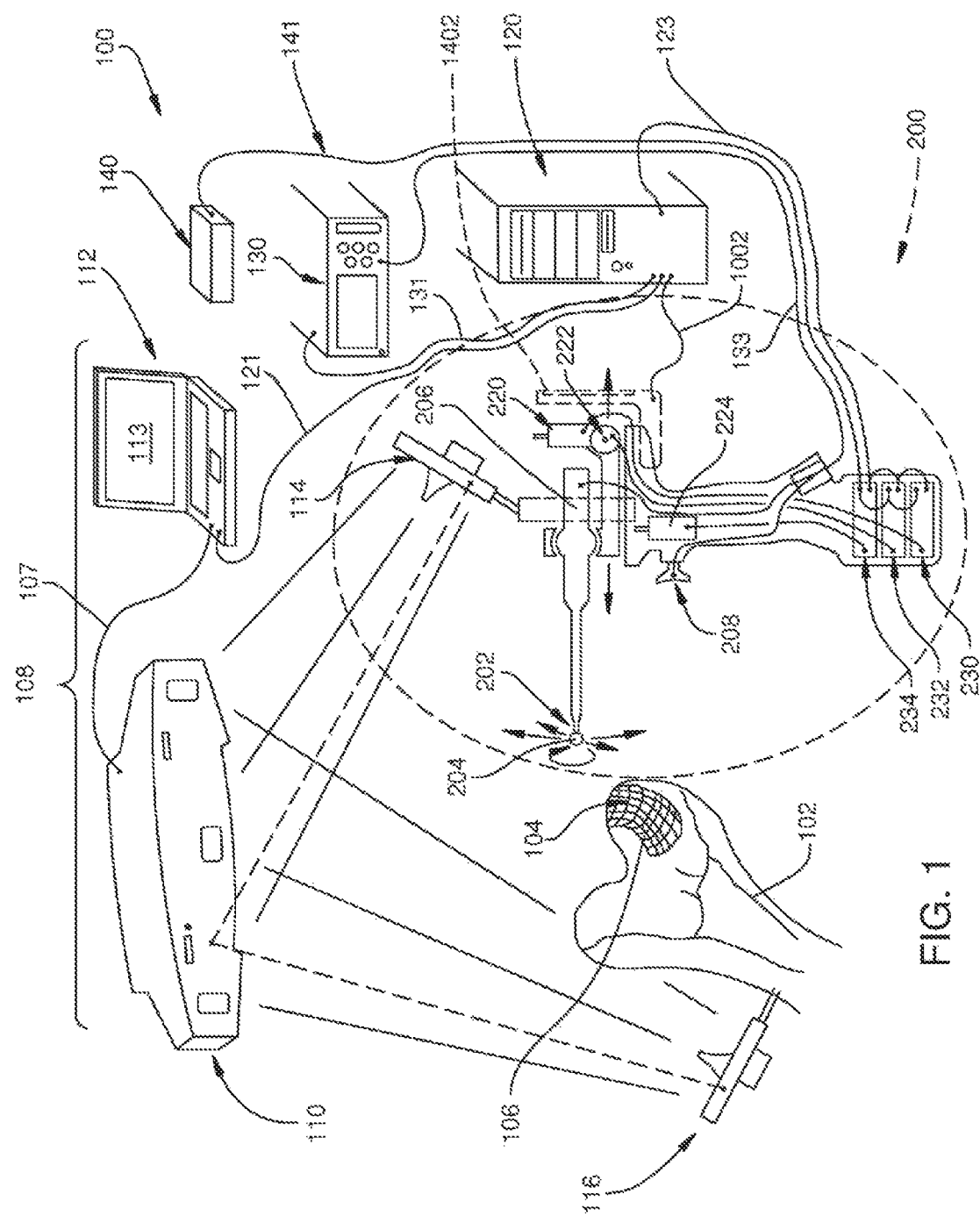
FIG. 1 is a schematic view of a tracking and control system of the present invention.

Referring to FIG. 1, a tracking and control system 100 is shown. Tracking and control system 100 tracks instrument 200 to keep a distal end tip 204 of a cutting accessory 202 that is attached to instrument 200 in a desired relationship to a predefined boundary. (Here "distal" means away from the practitioner holding the instrument 200 and towards the tissue to which the instrument is applied. "Proximal" means towards the practitioner and away from the tissue to which the instrument is applied.) The tracking and control system 100 controls the position of the cutting accessory tip 204 relative to a reference point on the instrument 200. This control prevents the cutting accessory tip 204 from colliding with or breaching a boundary at the surgical site to which the cutting accessory 202 is applied.

Tracking and control system 100 can be used to keep the accessory distal end tip 204 outside of a predefined boundary. For example, it may be desirable to keep an active tip of an ablation instrument away from certain regions inside the body or away from certain body parts. It may also be desirable to control a depth of cutting. In this respect, the system 100 controls the position of the accessory distal end tip 204 to avoid those regions or body parts.

Figure 57:
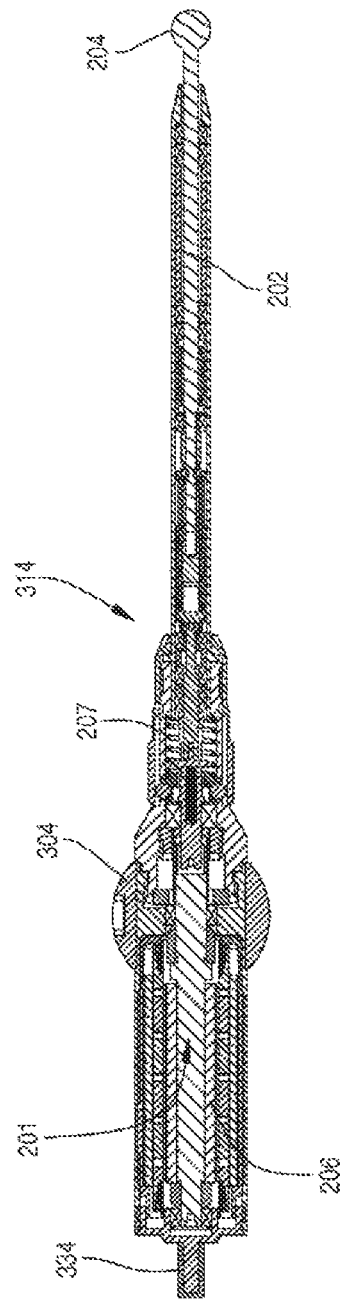
FIG. 57 is a cross-sectional view of the end effector.

The depicted surgical instrument 200 is a motorized surgical handpiece. The instrument 200 includes a drive mechanism 201, for example, referenced in FIGS. 8, 16, and 57, coupled to a working portion, e.g., cutting accessory 202. In some embodiments where the cutting accessory 202 rotates, e.g., a bur, a drill bit, etc., the drive mechanism 201 rotates the working portion about a rotational axis R. As set forth further below, with respect to the instrument 200, the rotational axis R moves relative to a hand-held portion, e.g., handle assembly 500, in pitch, yaw, and along an axis Z. The drive mechanism 201 includes a motor 206 and can include other bearings, rods, etc., to transfer rotation from the motor 206 to the working portion, i.e., cutting accessory 202.

Figure 16:
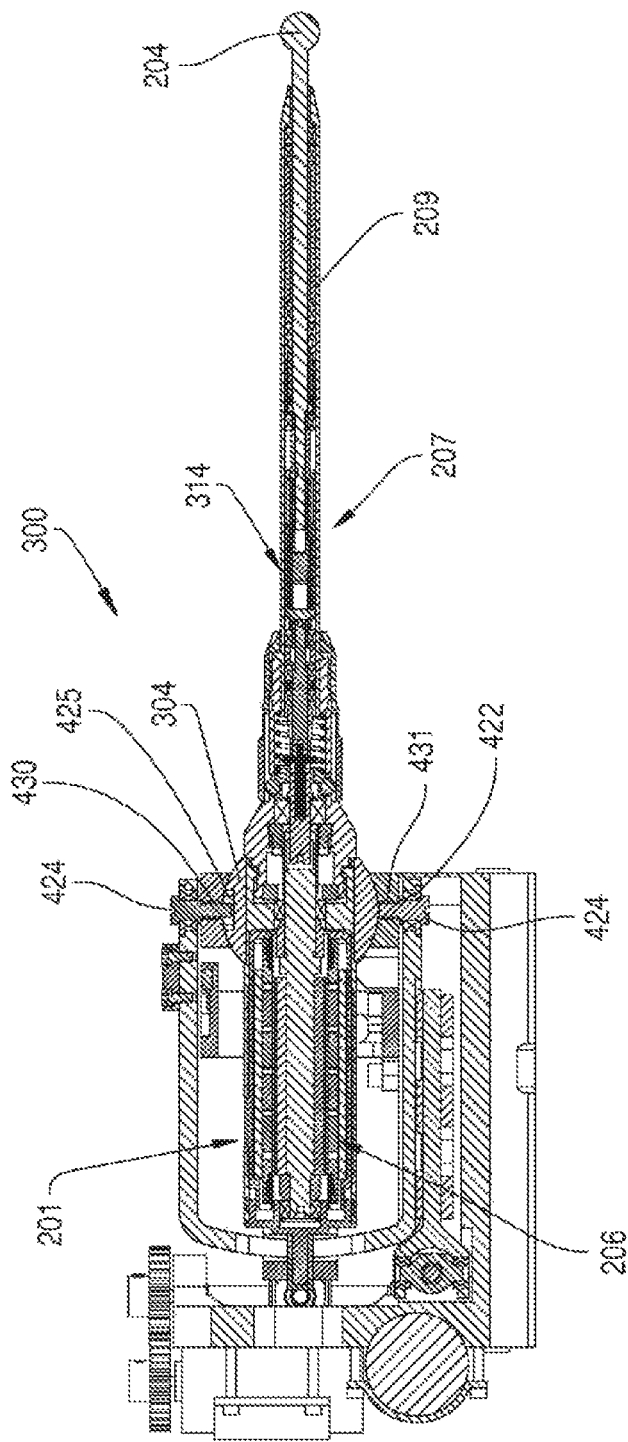
FIG. 16 is a cross-sectional view taken along the line 16-16 in FIG. 12.

A coupling assembly 207, seen in cross section in FIG. 16, is located forward of motor 206. Coupling assembly 207 releasably holds different cutting accessories 202 to the instrument 200. The coupling assembly 207 also provides a mechanical linkage between the motor 206 and accessory 202 so the accessory 202 can be actuated by the motor 206. The cutting accessory 202 is the component that performs a medical/surgical task on the tissue of a patient. The types of cutting accessories that can be driven by instrument 200 include, saw blades, shavers, drill bits and burs. In FIG. 1, the depicted cutting accessory 202 is a bur that has at its distal end a spherical bur head 204 for removing bone.

Figure 17:
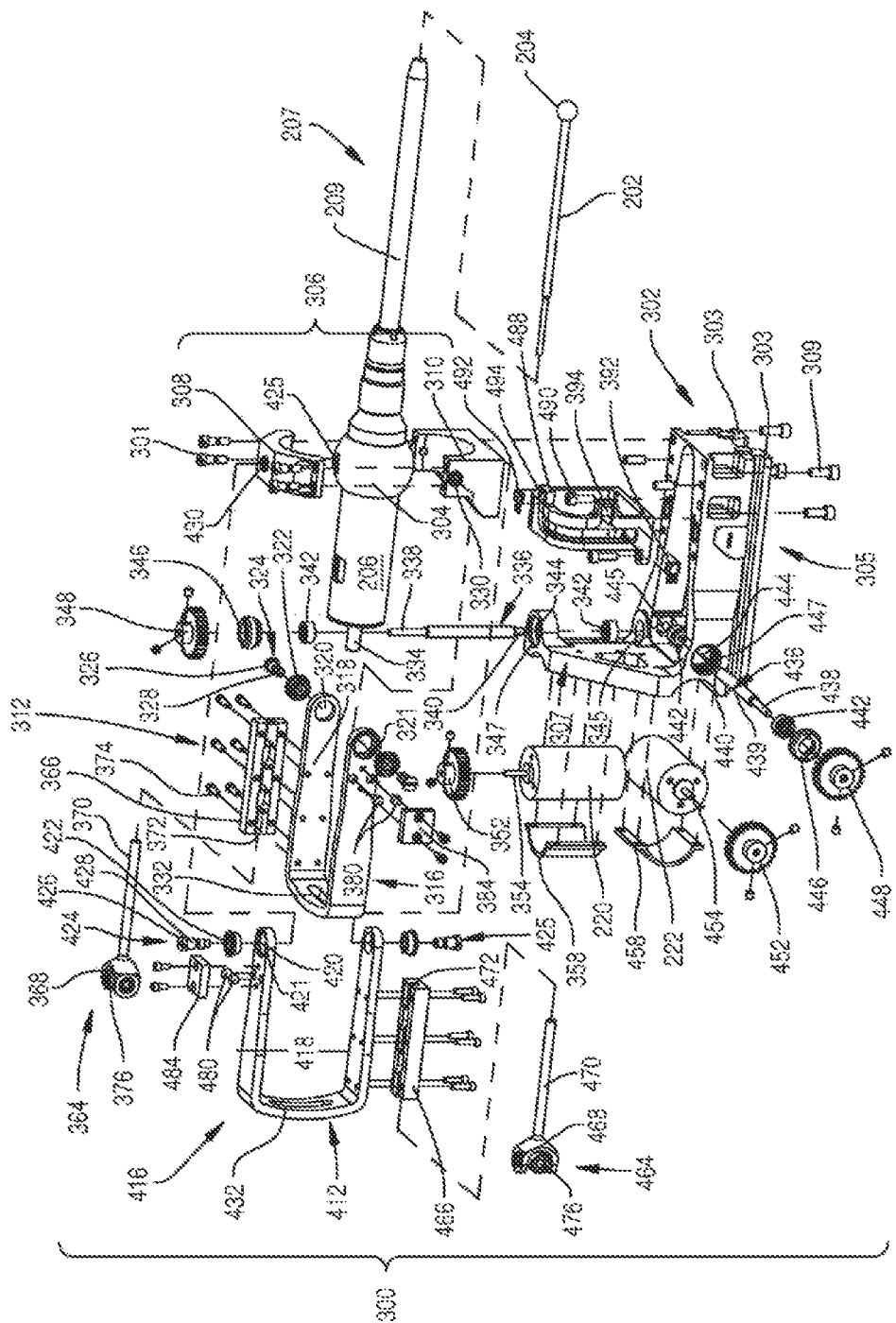
FIG. 17 is an exploded view of the upper assembly.

With reference to FIGS. 16 and 17, a sleeve 209, also referred to as a nose tube, at least partially covers the cutting accessory 202. Cutting accessory 202 moves with sleeve 209 as the cutting accessory 202 moves about a plurality of degrees of freedom, e.g., pitch, yaw, and translation along axis Z, as discussed further below. The axis Z is also referred to as a z-axis. The sleeve 209 remains stationary about rotational axis R, i.e., the cutting accessory 202 is configured to rotate within the sleeve 209 during the medical procedure.

Tracking and control system 100 can track and control other types of surgical instruments 200. These instruments include powered surgical instruments that output energy other than mechanical energy such as: electrical energy; photonic energy (light); RF energy; thermal energy; and that vibrate (emit mechanical energy in the form of vibrations). A surgical instrument 200 of this invention may not even have a power emitting component. The instrument 200 may include as a cutting accessory 202. Alternatively, the cutting accessory 202 may be manually actuated. Examples of manually actuated cutting accessories include forceps and snares.

Figure 1A:
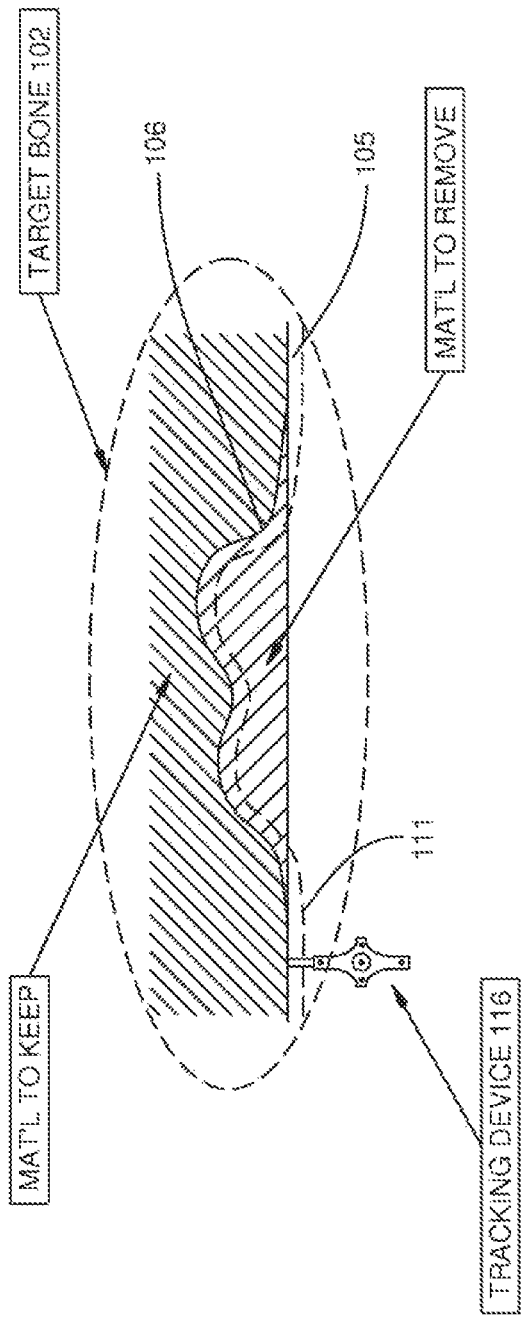
FIG. 1A is an illustration of a work boundary.

The illustrated instrument in FIGS. 1 and 1A with bur as the cutting accessory 202 is shown being used to shape a portion of a femur 102. The instrument 200 can be used to remove other types of tissue, including soft tissue.

With continued reference to FIG. 1, the embodiment shown, the femur 102 has a target volume 104 of material that is to be removed by the bur head 204. The target volume 104 is defined by a boundary 106 called the work boundary. This work boundary 106 defines the surface of the bone that should remain after the procedure. System 100 tracks and controls instrument 200 to ensure that bur head 204 only removes the target volume 104 of material and does not extend beyond the work boundary 106. It should be appreciated that the work boundary in other embodiments may be defined by any shape or size and may include 2-D or 3-D shapes, lines, trajectories, surfaces, linear paths, non-linear paths, volumes, planes, bore holes, contours, and the like. In some embodiments, the work boundary can define a 2-D or 3-D boundary across which the instrument should not cross. In other embodiments, the work boundary may define a line, path, trajectory or course along which the working portion of the instrument should travel. In these cases, the work boundary is also referred to as a work path, work trajectory or work course.

II. Tracking and Control System

Referring to FIG. 1, the tracking and control system 100 includes a navigation unit 108. The navigation unit 108 tracks the positions and orientations of the femur 102 and surgical instrument 200. The navigation unit 108 includes a camera 110. A navigation computer 112 receives and processes signals from the camera 110. The camera 110 is connected to the navigation computer 112 by data connection 107. Data connection 107 may be an IEEE 1394 interface, which is a serial bus interface standard for high-speed communications and isochronous real-time data transfer. Data connection 107 could also use a company specific protocol.

One camera 110 that can be incorporated into system 100 is the FlashPoint® 6000 Camera sold by Stryker Corporation of Kalamazoo, Mich. The camera 110 includes three separate high resolution CCD cameras (not shown). The CCD cameras detect infrared (IR) signals. Camera 110 is mounted to a stand (not shown) to position the camera 110 above the zone in which the procedure is to take place to provide the camera 110 with a field of view of the below discussed trackers 114 and 116 that, ideally, is free from obstructions. Trackers 114 and 116 are also referred to as tracking devices 114 and 116, respectively.

The navigation computer 112 can be a personal computer such as a laptop computer. Navigation computer 112 has a display 113, central processing unit (not shown), memory (not shown), and storage (not shown).

The navigation computer 112 is loaded with software. The software converts the signals received from the camera 110 into data representative of the position and orientation of the objects to which trackers 114 and 116 are attached. Also associated with the navigation computer 112 is a mouse or other suitable pointer-input device and keyboard.

The camera 110 communicates with the navigation computer 112 via data connection 107. The navigation computer 112 initially sets up and registers the navigation unit 108. The software provides a graphical user interface (GUI). The software also provides the geometry and positioning of the work boundary 106. The navigation computer 112 interprets the data received from the camera 110 and generates corresponding position and orientation data that is transmitted to an instrument controller 120.

With reference to FIG. 1, for example, trackers 114 and 116 are affixed to the instrument 200 and the femur 102, respectively. Specifically, the tracker 114, i.e., the tracking device 114, is attached to a hand-held portion of the instrument 200, as discussed below, for tracking the instrument 200. Each tracker 114 and 116 has a plurality of optical markers in the form of light emitting diodes, such as three LEDs (not shown), that transmit infrared light to the camera 110. In some cases, the optical markers are three or more light reflectors (not shown) for use with a camera unit (not shown) that transmits light that reflects off the light reflectors. In other procedures, additional trackers may be affixed to other bones, tissue, or other parts of the body, tools, or equipment.

Based on the light captured signals forwarded from the camera 110, the navigation computer 112 determines the position of each optical marker and thus the position and orientation of the objects to which they are attached relative to the camera 110. An example of the camera 110, navigation computer 112, and trackers 114, 116 are shown in U.S. Pat. No. 7,725,162 to Malackowski et al., hereby incorporated by reference, including the camera, navigation computer and trackers and associated methods of operation and use disclosed therein.

The instrument controller 120 is in communication with the navigation computer 112 via a data connection 121. Data connection 121 may be an IEEE 1394 interface, which is a serial bus interface standard for high-speed communications and isochronous real-time data transfer. Data connection 121 could use a company specific protocol. It should be appreciated that in some versions of this invention navigation computer 112 and instrument controller 120 may be single unit. Instrument controller 120 communicates with the instrument 200 by a data connection 123.

Based on the position and orientation data and other below described data, the instrument controller 120 determines the position and orientation of the cutting accessory 202 relative to the femur 102. By extension, the instrument controller 120, determines the relative location of the accessory tip such as the bur head 204 to the working boundary 106. Based on this determination, the controller 120, if necessary, repositions the cutting accessory and attenuates the speed of the instrument motor 206 as discussed further below. Instrument controller 120 typically performs these operations in a single control loop. In many versions of the invention, the controller 120 repeatedly executes these control loops at a frequency of at least 1 kHz. In some versions of the invention, controller 120 includes plural CPUs. Depending on the structure of the controller 120 these CPU's operate in series and/or parallel. In FIG. 1, instrument controller 120 is represented as a personal computer.

System 100 further includes an instrument driver 130. Instrument driver 130 provides power to instrument motor 206 to control the motor 206. The power supply and control components internal to driver 130 may be similar those in the surgical instrument control console described in U.S. Pat. No. 7,422,582, CONTROL CONSOLE TO WHICH POWERED SURGICAL HANDPIECES ARE CONNECTED, THE CONSOLE CONFIGURED TO SIMULTANEOUSLY ENERGIZE MORE THAN ONE AND LESS THAT ALL OF THE HANDPIECES hereby incorporated by reference, including the power supply and control components of the control console disclosed therein and associated methods of operation and use. Instrument driver 130 is in communication with the instrument controller 120 via a data connection 131. Data connection 131 may be an IEEE 1394 interface, which is a serial bus interface standard for high-speed communications and isochronous real-time data transfer. Data connection 131 could use a company specific protocol. It should be appreciated that in other embodiments the instrument driver 130 could be integrated into or part of the instrument controller 120.

With reference to FIGS. 1-8, for example, a manually actuated trigger 208 mounted to the instrument 200 is selectively depressed to regulate actuation of the instrument motor 206. A sensor (not identified) disposed inside the instrument 200 generates a signal as a function of the extent to which the trigger 208 is actuated. The output signals from the sensor are forwarded by a data connection 133 to the instrument driver 130. Based on the state of this sensor signal and other inputs described below, the instrument driver 130 applies energization signals to the instrument motor 206.

Figure 68:
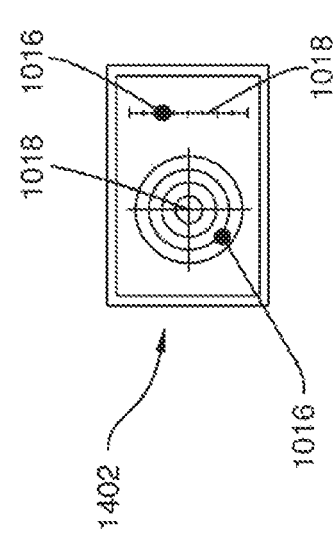
FIG. 68 is an illustration of a potential display located on the instrument.

Display 113 shows a virtual representation (or 3-D model) of the femur 102 and cutting accessory 202. The representation of the femur 102 is based on preoperative images taken of the femur 102. Such images are typically based on MRI or CT scans. Alternatively intraoperative images using a fluoroscope, low level x-ray or any similar device could also be used. These images are registered to the tracking device 116 for tracking purposes. Once registered, movement of the femur 102 results in corresponding movement of the images on the display 113. This can also be displayed on the display 1402 (see below). Screen shots of display 1402 are shown in FIG. 68 and in FIGS. 107-111. It should be appreciated that the various features shown on the screen shots in FIGS. 68 and 107-111 can be used in any combination.

The instrument 200 and the femur 102 are registered to the navigation unit 108 to ensure that the position and orientation data corresponds to their true relative positions within an acceptable level of accuracy.

The display 113 (and/or 1402) also shows the work boundary 106 using color coding, or other visual method of distinguishing the target volume 104 of material to be removed from material that is to remain in the femur 102.

Referring to FIG. 1A, the instrument controller 120 defines a constraint boundary 111 that is located a predetermined distance from the work boundary 106 to define a buffer 105. In one implementation of the system, the instrument controller 120 determines the position of the center of the bur head 204, relative to the constraint boundary 111 to control the instrument 200. The relative distance between the working boundary 106 and the constraint boundary 111 is a function, in part, of the geometry of the cutting accessory 202. For example, if the cutting accessory 202 includes a spherical bur head 204, the constraint boundary is one-half the diameter of the bur head 204. Thus, when the centroid of the bur head 204 is on the constraint boundary 111, the bur's outer cutting surface is at the work boundary 106.

III. Surgical Instrument

A. Overview

Referring to FIG. 1, surgical instrument 200 communicates with the instrument controller 120 via the data connection 123. The data connection 123 provides the path for the input and output required to control the instrument 200 based on the position and orientation data generated by the navigation computer 112 and transmitted to the instrument controller 120.

The instrument 200 includes a hand-held portion, e.g., a handle assembly 500 as discussed further below, and a working portion, e.g., the cutting accessory 202. The working portion is movably coupled to the hand-held portion. The hand-held portion is manually supported and moved by a user during the medical procedure to treat the tissue of a patient with the working portion. The user operates the instrument 200 by grasping and supporting hand-held portion, and the instrument 200 is unsupported by other mechanical arms, frames, etc.

The instrument 200 has a plurality of actuators, e.g., motors 220, 222 and 224. The motors 220, 222, and 224 are coupled to the working portion, e.g., the cutting accessory 202, for moving the working portion in a plurality of degrees of freedom relative to the hand-held portion, e.g., the handle assembly 500. Each motor 220, 222 and, 224 is controlled by a separate controller 230, 232, 234, respectively. Controllers 230-234 can be those provided by Technosoft U.S., Inc. of Canton, Mich., part number IBL2401-CAN. In some embodiments, the motors 220, 222, 224 can be controlled by a single controller. Controllers 230, 232 and 234 are wired separately to the motors 220, 222 and 224, respectively to individually direct each motor to a given target position. In some versions of the invention, controllers 230, 232 and 234 are proportional integral derivative controllers. The data connection 123 may be a CAN-bus interface between the instrument controller 120 and the controllers 230, 232, 234 or any other high speed interface. In other embodiments, the controllers 230, 232, 234 can be integrated with or form part of the instrument controller 120.

A power source 140 provides, for example, 24 VDC power signals to the motors 220, 222 and 224. The 24 VDC signal is applied to the motors 220, 222, and 224 through the controllers 230, 232 and 234. Each controller 230, 232 and 234 selectively provides the power signal to the complementary motor 220, 222 and 224, respectively, to selectively activate the motor. This selective activation of the motors 220, 222 and 224 is what positions the cutting accessory 202. Power source 140 also supplies power to the controllers 230, 232 and 234 to energize the components internal to the controllers. It should be appreciated that the power source 140 can provide other types of power signals such as, for example, 12 VDC, 40 VDC, etc.

The motors 220, 222, 224 move the cutting accessory 202 and, by extension the bur head 204, when the bur head 204 approaches, meets, or exceeds the constraint boundary 111. For example, the instrument controller 120 may determine that the bur head 204 is crossing the constraint boundary 111 as the bur head 204 removes bone. In response, the instrument controller 120 transmits a signal to at least one of the controllers 230, 232 or 234 that causes the deflection of the cutting accessory 202 that moves the bur head 204 away from the constraint boundary 111.

In one version of the invention, motors 220, 222 and 224 are brushless DC servomotors. One servomotor is available from MICROMO of Clearwater, Fla., Part No. 1628T024B K1155. Each servomotor includes three integrated linear Hall-effect sensors (not shown) that transmit signals back to the instrument controller 120. The levels of these signals vary as a function of the rotational position of the associated motor rotor. These Hall-effect sensors output analog signals based on the sensed magnet fields from the rotor. In the above-described motor, the sensors are spaced 120° apart from each other around the rotor. A low voltage signal, typically, 5 VDC, for energizing the motor Hall effect sensors is supplied from the controller 230, 232 or 234 associated with the motor 220, 222 or 224 in which the Hall-effect sensors are located.

The output signals from the Hall-effect sensors internal to each motor 220, 222 and 224 are applied to the associated controller 230, 232 and 234, respectively. Each controller 230, 232 and 234, monitors the received signals for changes in their levels. Based on these signals the controller 230, 232 or 234 determines the rotor position. Here "rotor position" is understood to be the degrees of rotation of the rotor from an initial or home position. A motor rotor can undergo plural 360° rotations. A rotor position can therefore exceed 360°. Each motor controller 230, 232 and 234 maintains a scalar value referred to as a "count" representative of rotor position from the home position. The motor rotors rotate in both clockwise and counterclockwise directions. Each time the signal levels of the plural analog signals undergo a defined state change, the controller 230, 232 and 234 increments or decrements the count to indicate an arcuate change in rotor position. For every complete 360° rotation of the motor rotor, the associated motor controller 230, 232 and 234 increments or decrements the value of the count by a fixed number of counts. In some versions of the invention, the count is incremented or decremented between 1500 and 2500 per 360° revolution of the rotor.

Internal to each controller 230, 232 and 234 is a counter (not illustrated). The counter stores a value equal to the cumulative number of counts incremented or decremented by the controller 230, 232 or 234. The count value can be positive, zero or negative.

Figure 6:
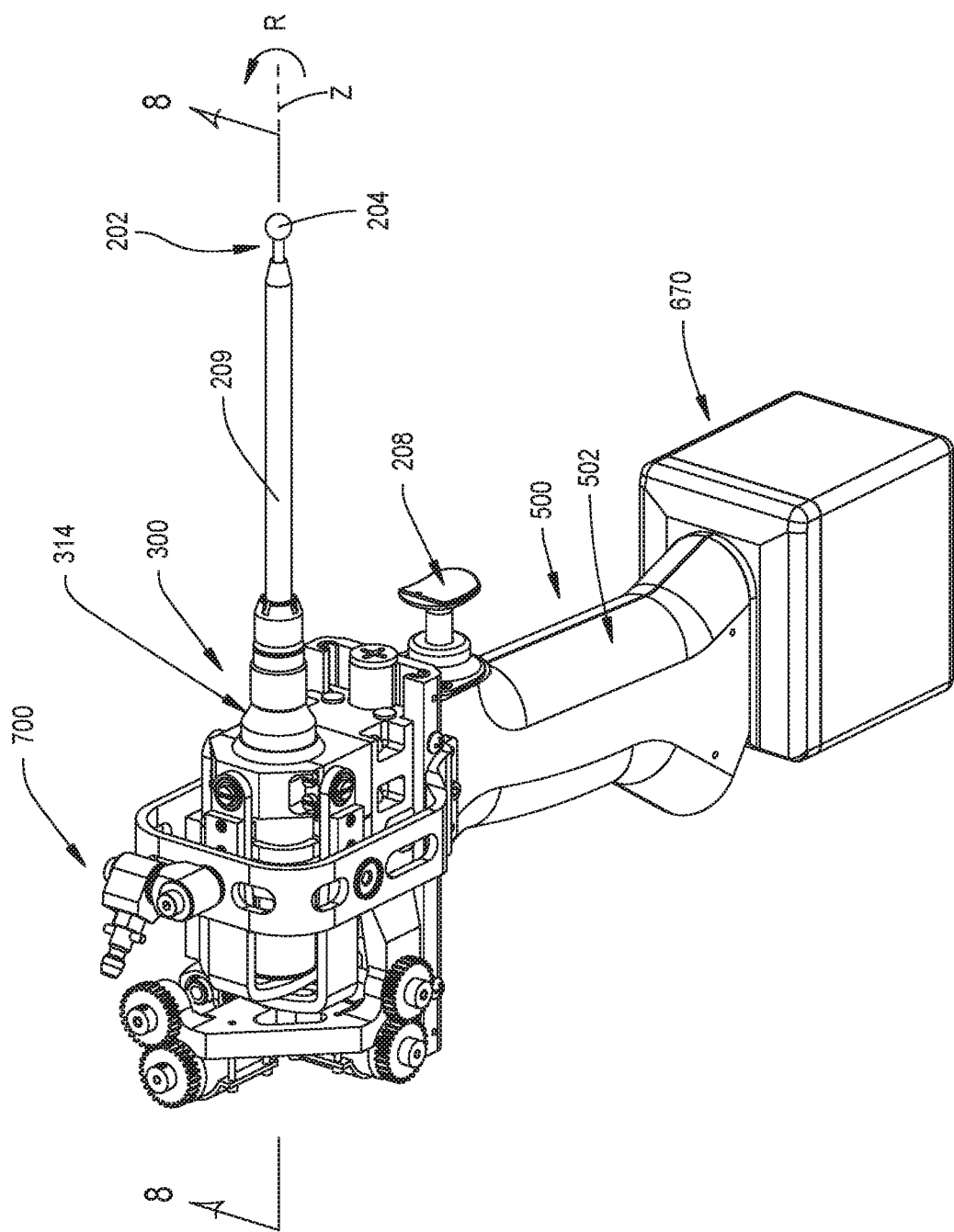
FIG. 6 is a top perspective view of the surgical instrument of FIG. 2 with protective covers, display, and covers removed.
Figure 7:
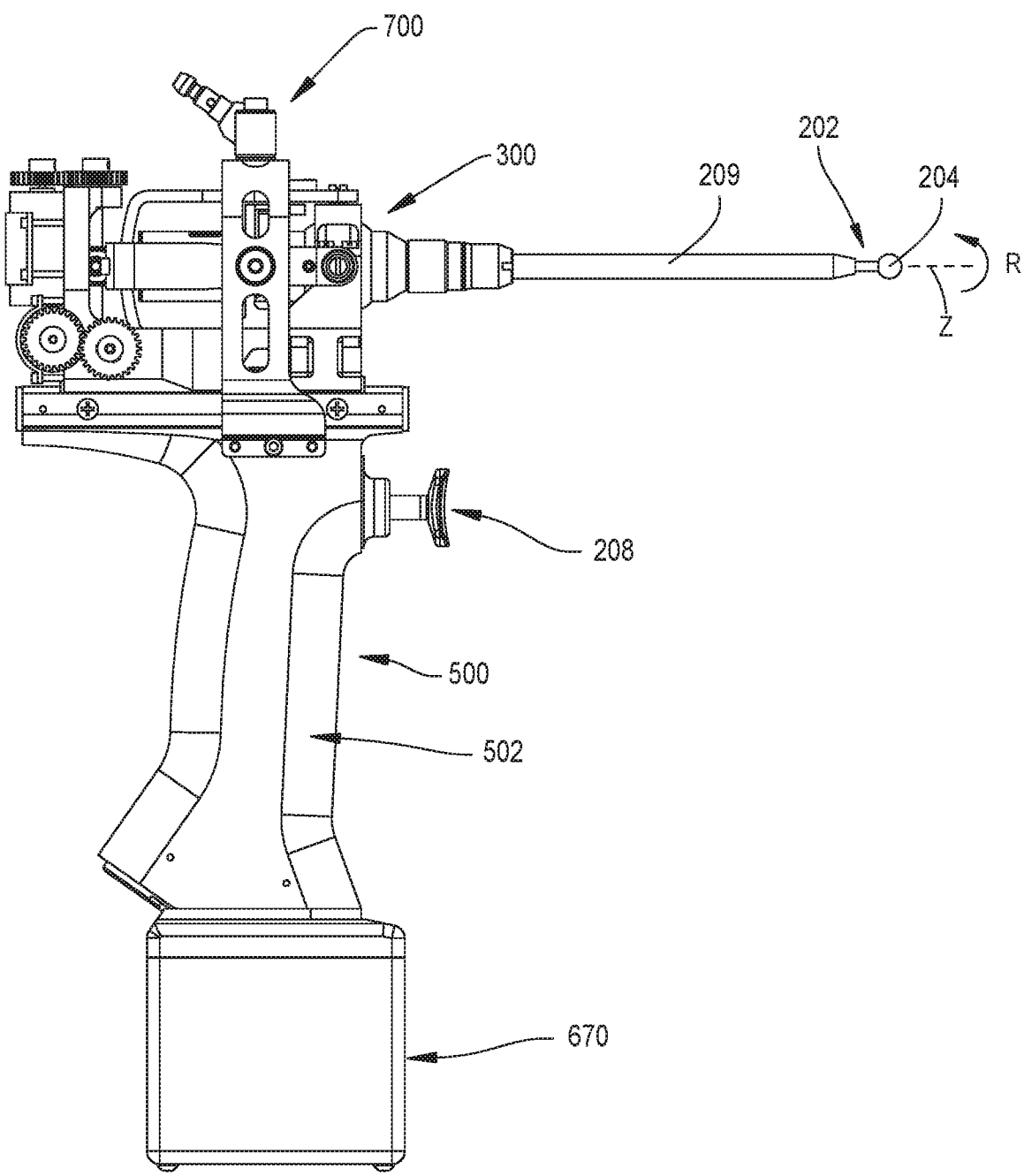
FIG. 7 is a front view of the surgical instrument from FIG. 6.
Figure 8:
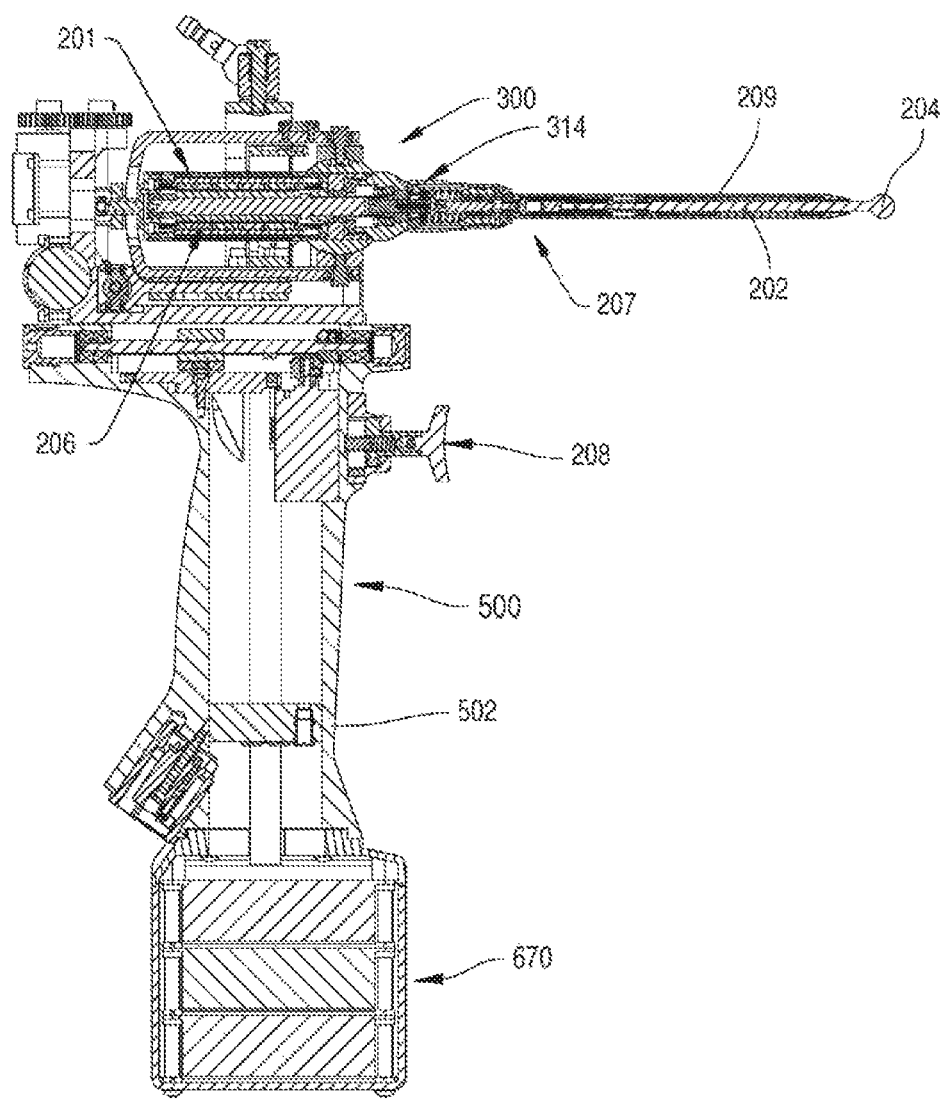
FIG. 8 is a cross-sectional view taken through the surgical instrument from FIG. 7.
Figure 9:
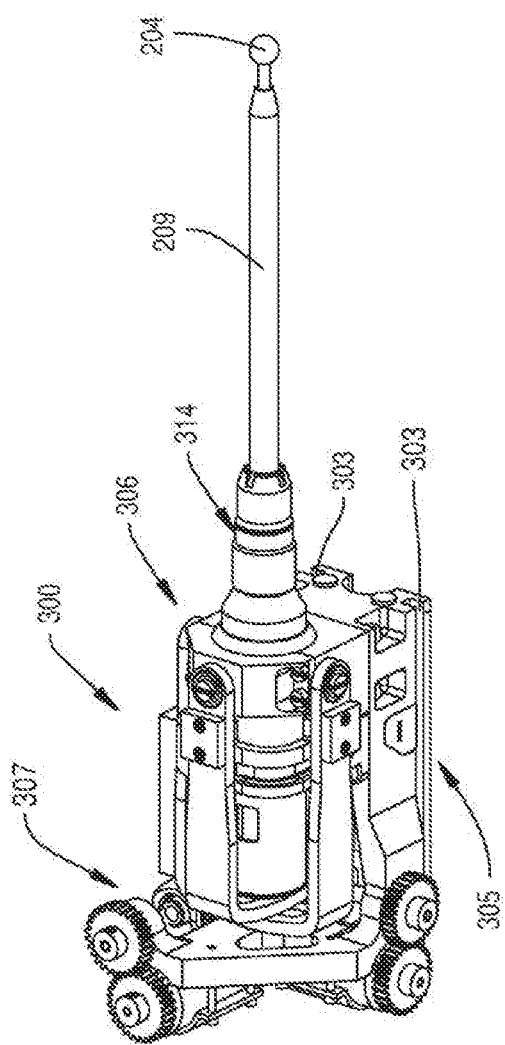
FIG. 9 is a top perspective view of an upper assembly of the surgical instrument of FIG. 6.
Figure 10:
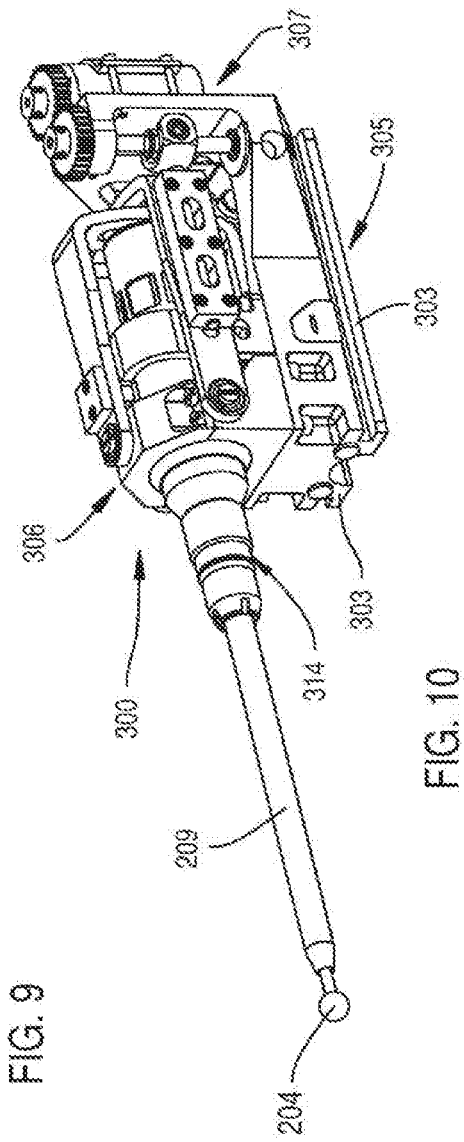
FIG. 10 is a perspective view of the upper assembly.
Figure 15:
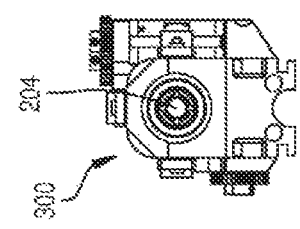
FIGS. 11-15 are front, top, bottom, left-side, and right-side views of the upper assembly.

Referring to FIGS. 2 through 8, various views of the surgical instrument 200 are shown. This includes views of the instrument 200 with protective covers 240a, 240b (FIGS. 2-5) and without protective covers 240a, 240b (FIGS. 6-8). The protective covers 240a, 240b are two halves of a housing for an upper assembly 300 of the instrument 200. The upper assembly 300 includes a drive assembly 314 that drives the cutting accessory 202. Covers 240a, 240b are placed on either side of the upper assembly 300 and fastened together by fasteners or the like. In other embodiments, the protective covers 240a, 240b may be replaced by a one-piece covering or housing (not shown).

In addition to the upper assembly 300, the instrument 200 includes the handle assembly 500, a shell 670, and a bracket assembly 700. The drive assembly 314 is coupled to the hand-held portion, e.g., handle assembly 500. The drive assembly 314 is slidably coupled to the handle assembly 500. Bracket assembly 700 and shell 670 are fixed to the handle assembly 500. Cutting accessory 202 extends distally forward from upper assembly 300. The handle assembly 500 includes a pistol-grip style handle 502 for being manually handled by a user and the trigger 208. Other embodiments have alternative handles with differing grip styles, such as a pencil grip.

B. Upper Assembly

Referring to FIGS. 9-17, 24 and 41, various views of the upper assembly 300, of the instrument 200 are shown. The upper assembly 300, and more specifically the drive assembly 314, supports the working portion, e.g., the cutting accessory 202. As set forth further below, the upper assembly 300 and the cutting accessory 202 move relative to the hand-held portion, e.g., the handle assembly 500, in a plurality of degrees of freedom.

The drive mechanism 201 moves in at least one degree of freedom relative to the hand-held portion, e.g., handle assembly 500. Specifically, the drive motor 206 moves in at least two degrees of freedom relative to the hand-held portion and, more specifically, moves in at least three degrees of freedom relative to the hand-held portion. At least one of the actuators moves the drive mechanism 201 and the drive motor 206 in pitch, yaw, and translation along the axis Z relative to the hand-held portion. Specifically, the motors 220, 222, and 224 move the drive mechanism 201 and the drive motor 206 in pitch, yaw, and translation along the axis Z, respectively, relative to the hand-held portion.

Figure 56:
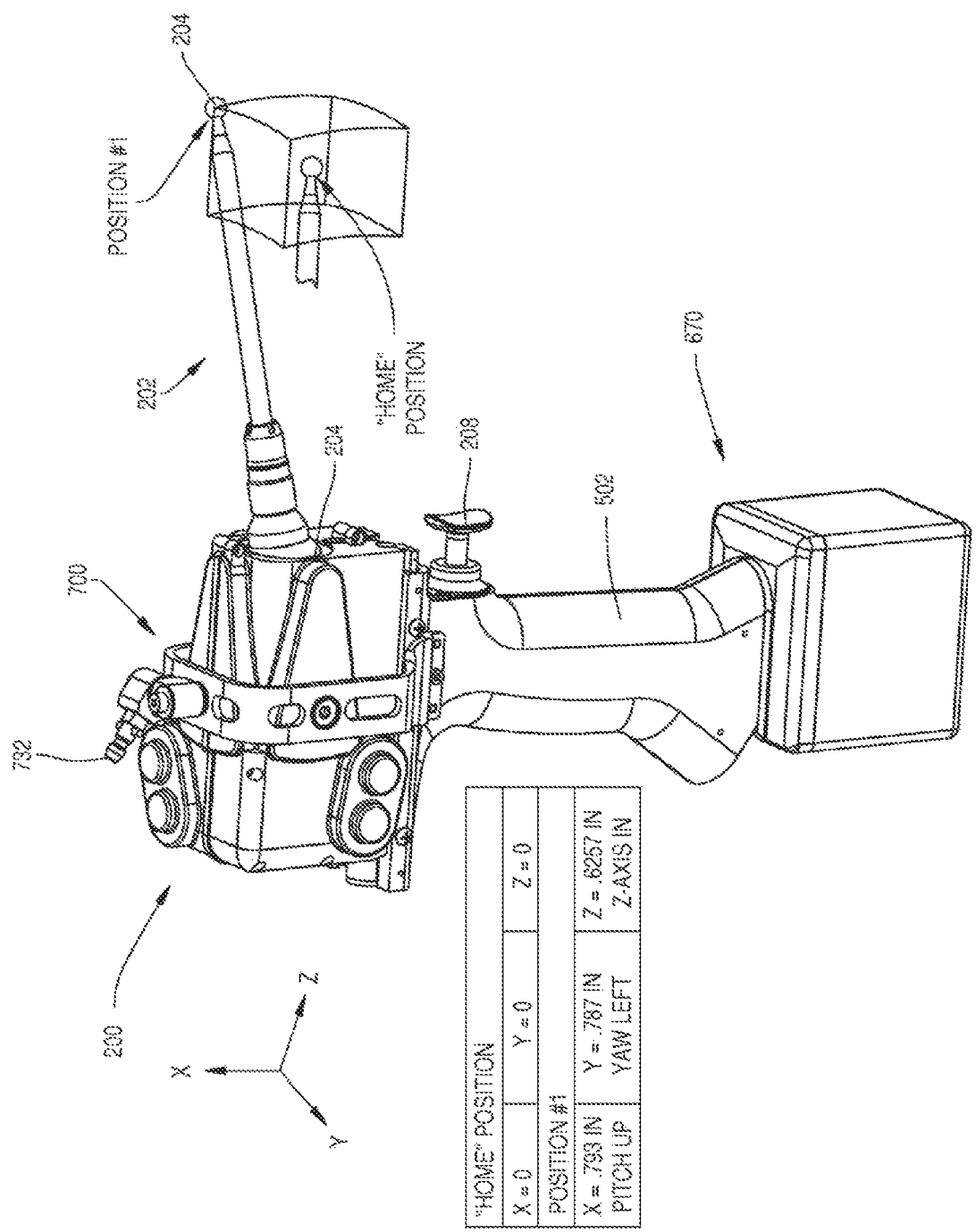
FIG. 56 is a top and front perspective view of the instrument illustrating the range of motion of the end effector.

As best shown in FIGS. 18-27 and 56, the plurality of actuators, e.g., motors 220, 222, and 224, are capable of moving the working portion relative to the hand-held portion in at least three degrees of freedom including pitch, yaw, and translation along the axis Z. These individual degrees of freedom are best shown in FIGS. 18-20 (pitch), FIGS. 21-23 (yaw), and FIGS. 37-39 (z-axis). FIGS. 24-27 show a sample of possible positions for pitch and yaw, and FIG. 56 shows the resulting range of motion when all three degrees of freedom are expressed. Further, in an embodiment where the working portion, i.e., the cutting accessory 202, comprises a bur head 204, the drive motor 206 moves in four degrees of freedom relative to the hand-held portion, i.e., the drive motor 206 rotates the bur head 204.

The upper assembly 300 includes a carrier 302, as identified in FIG. 17, for example. Carrier 302 is slidably mounted to handle assembly 500. The carrier 302 is in the form of a single piece metal structure that is often formed from aluminum. Carrier 302 is shaped to have a base 305 that is in the form of a rectangular frame. A riser 307, also part of the carrier 302, extends vertically upwardly from the proximal end of the base. Flanges 303 extend outwardly along the opposed outer side edges of the base 305. The flanges 303 ride in channels 504 formed in handle assembly 500. As seen in FIG. 43, the carrier 302 is further formed to have an elongated slot 317 that extends upwardly from the downwardly directed face of carriage base 305. Slot 317 is semi-circular in cross sectional shape and extends the length of the base 305. Slot 317 is centered on the longitudinal axis that extends along the downwardly directed face of the slot base 305.

With reference to FIG. 17, a gimbal housing 306 is mounted to carrier base 305. Gimbal housing 306 holds a gimbal 304 disposed around motor 206 to pivotally secure the motor 206 to the carrier 302. Working portion, e.g., cutting accessory 202, moves about gimbal 304 in at least two degrees of freedom relative to the hand-held portion, e.g., handle assembly 500. Specifically, the working portion is adjustable in pitch and yaw about the gimbal 304. The gimbal 304 is movable along the axis Z relative to the hand-held portion, e.g., handle assembly 500.

Gimbal 304 is a ring shaped structure that has an outer shape of sphere the opposed ends of which have been removed. Gimbal 304 holds the cutting accessory 202 to the upper assembly 300 so the cutting accessory 202 is able to pivot around two axes. More particularly, motor 206 and coupling assembly 207 are the components of the instrument 200 securely attached to the gimbal 304. Gimbal 304 is located around the center of gravity of a sub-assembly consisting of the cutting accessory 202, motor 206 and coupling assembly 207. This minimizes the mass moment of inertia of the sub assembly as it is pivoted and maximizes the angular acceleration for a given supplied torque.

With continued reference to FIG. 17, the gimbal housing 306 includes an upper collar 308 and a lower collar 310. Collars 308 and 310 are both generally U-shaped. Upper collar 308 is mounted to a lower collar 310 by fasteners 301. Fasteners 309 mount the lower collar 310 to the carrier base 305. The opposed inner faces of collars 308 and 310 have surfaces that conform to slice sections through a sphere. Gimbal 304 is sandwiched between the collars 308 and 310. Gimbal housing 306 and gimbal 304 are collectively shaped to both prohibit lateral and longitudinal movement of the gimbal yet allow the pivoting of the motor 206 and cutting accessory 202 in two degrees of freedom relative to the longitudinal axis extending through the gimbal housing 306.

A fastener 424 prevents rotation of the gimbal 304 relative to the gimbal housing 306 in the roll direction, around the longitudinal axis through the housing 306. Fastener 424 has a distal protrusion, that when installed in the upper collar 308, mates in a slot 425 in the gimbal 304. The slot 425 extends longitudinally along the gimbal 304. The seating of stem of the fastener 424 in slot 425 inhibits rotation of the gimbal 304 and, by extension the cutting accessory 202 while allowing pitch and yaw adjustment of the cutting accessory 202.

With continued reference to FIG. 17, upper assembly 300 includes a pitch adjustment mechanism 312 that sets the pitch of the cutting accessory 202. Here the "pitch" is the up-down angular orientation of a longitudinal axis or rotational axis R of the cutting accessory 202 relative to a horizontal plane through the center of the gimbal housing 306. A yaw adjustment mechanism 412 sets the yaw of the cutting accessory 202. "Yaw" is the right-left angular orientation of the longitudinal or rotational axis of the cutting accessory 202 relative to a vertical plane through the center of the gimbal housing 306. Pitch and yaw adjustment mechanisms 312 and 412, respectively, are actuated to simultaneously adjust the pitch and yaw of the cutting accessory 202. The pitch adjustment mechanism 312 and the yaw adjustment mechanism 412 are also capable of independent adjustment.

The pitch adjustment mechanism 312 includes a link 316, sometimes called a swing arm, that is a three-sided structure. Link 316 includes a base 319 from which a pair of parallel arms 318 extends distally outwardly. Link 316 is positioned so that the base 319 is located proximal to the carrier riser 307 and the free ends of the arms 318 are disposed against opposed sides of the lower collar 310. The outer end of each arm 318 has a bore 320 with a counterbore 321. A flanged bearing 322 is seated in each bore 320 and counterbore 321. A screw 324 extends through each bearing 322. The screw 324 has a head 326 that holds the flanged bearing 322 to the arm 318. Each screw 324 also has a threaded shaft 328 that engages a corresponding threaded bore 330 formed in the adjacent side of the lower collar 310. Link 316 pivots relative to the gimbal housing 306 about the axis through the coaxial screws 324. This axis extends through the center of the gimbal 304.

Link base 319 is formed to have an elongated slot 332. Slot 332 receives a guide post 334 extending from a proximal end of motor 206. The guide post 334 rides in the slot 332 when the yaw of the cutting accessory 202 is being adjusted. When the pitch is being adjusted, the guide post 334 is moved by the link 316 to place the bur head 204 in the desired pitch position. The slot 332 is dimensioned with a relatively tight tolerance to the guide post 334 across its width, while still allowing the guide post 334 to freely slide in the slot 332 as the yaw of the cutting accessory 202 is changed. In one version of the invention guide post 334 has a diameter of 0.4 cm and, the width across the slot 334 is approximately 0.01 to 0.05 mm wider. The length across the slot 334 is approximately 2.1 cm.

Pitch adjustment mechanism 312 includes a lead screw 336 that is driven by motor 220. The lead screw 336 has opposed first and second stems, 338 and 340, respectively, that are cylindrical in shape. Stems 338 and 340 are located on opposing sides of a screw body 339 formed with threading (threading not illustrated). Each screw stem 338 and 340 is seated in a separate bearing 342. Bearing 342 are located in opposed coaxial bores 344, 345 formed in the carrier 302. One bore, bore 344, is formed in a portion of the riser 307. The second bore, bore 345, is formed in the carrier base 305. An end plug 346 is threaded into a matching internal thread 347 formed in the riser 307 around bore 344 to secure the bearings 342 and lead screw 336 to the carrier 302.

A spur gear 348 is fit over the upper of the two screw stems, stem 338. Set screws, (not identified) hold the spur gear 348 to the stem 338 so that the gear rotates in unison with the stem 338. Spur gear 348 has teeth that mate with teeth on a spur gear 352. Spur gear 352 is fixed to the output shaft 354 of the pitch motor 220 by set screws (not identified). FIG. 17A shows a cross-section through the lead screw 336. A mounting bracket 358 secures the motor 220 to the proximally directed face of the carrier riser 307 with fasteners 360. Specifically, the carrier riser 307 is formed to have an arcuate recess 362 that extends inwardly from the proximally directed face of the riser 307. Recess 362 is shaped to receive a section of the cylindrically shaped motor 220. Mounting bracket 358 is arcuate in shape so as to seat around the portion of the motor 220 that extends outward of the carrier riser 307.

Pitch adjustment mechanism 312 further includes a yoke assembly 364. The yoke assembly 364 includes a rectangular bar 366. Bar 366 is formed so as to have an elongated bore 372, only the openings of which are seen, that extends longitudinally through the bar 366. Threaded fasteners 374 secure bar 366 to the outer face of the arm 318 of link 316 adjacent lead screw 336. While not illustrated, bar 366 may be formed with a rib that projects outwardly from the face of the bar 366 that is disposed against the adjacent arm 318. The rib has a width thereacross less than the width of the bar 366. The link arm 318 is formed with a groove having a width that allows the close seating of the rib. This rib-in-groove facilitates the securing of the bar 366 to the link. This rib also allows bore 372 to be positioned relatively close to the link arm 318.

Yoke assembly 364 further includes a three sided yoke 368. A rod 370 is integral with the yoke 368 and extends distally forward from the yoke 368. The rod 370 is cylindrical in shape. The rod 370 is slidably disposed in the bore 372 internal to bar 366. A nut 376 is pivotally mounted to the yoke 368. Nut 376 is formed to have opposed trunnions 377. Each trunnion 377 seats in a bearing assembly 379 mounted to a side section of the yoke 368 (see FIG. 17A). The nut 376 has internal threads that mate with the lead screw 336.

The cutting accessory 202 is pivoted up and down, along the Y-axis, by actuating motor 220. The resultant rotation of motor output shaft 354 is transferred through gears 352 and 348 to cause a like rotation of lead screw 336. Nut 376 is attached to yoke 368. Yoke 368 is, through rod 370 attached to link 316. As a consequence of the attachment of nut 376 to the link 316, the nut 376 is blocked from rotation. Consequently, the rotation of lead screw 336 results in the movement of the nut 376 up or down the lead screw 336. The displacement of the nut 376 results in a displacement of rod 370 that results in a like displacement of the link 316. During this displacement, the yoke 368 pivots around nut trunnions 377. Rod 370 freely slides in and out of bore 372 internal to plate 366. As a consequence of the up/down displacement of the portion of the bracket adjacent shaft, link 316 pivots about the axis through bearings 322. When the pitch adjuster 316 pivots, the guide post 334 is forced to undergo a like displacement. This displacement of the guide post forces the motor 206 and cutting accessory 202 to likewise pivot. It should be understood that the downward pivoting of link 316 and guide post 334 cause an upward pivoting of the bur head 204.

Lead screw body 339 has fine pitch and lead angle to prevent backdriving (i.e. it is self-locking). As a result, a load placed on the bur head 204 does not back drive the motor 220. In one embodiment, the lead screw body 339 has a diameter of 0.125 inches (0.318 cm) and has a lead of 0.024 inches/revolution (0.061 cm/revolution). One such lead screw is available from Haydon Kerk Motion Solutions, Inc. of Waterbury, Conn.

Magnets 380 are mounted in a pair of pockets (not identified) defined in an outside surface of one of the link arms 318. A plate 384 is mounted to the arm 318 by fasteners (not identified) to hold the magnets 380 in the pockets. Magnets 380 are mounted to the arm 318 so that the North pole of the first magnet and the South pole of the second magnet are adjacent the plate 384. The magnets 380 are used to establish the zeroed (or "home") position for the cutting accessory 202 on the X-axis.

Figure 12:
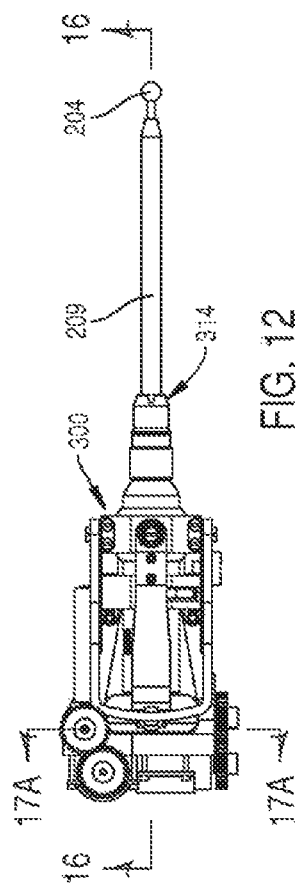
Figure 11:
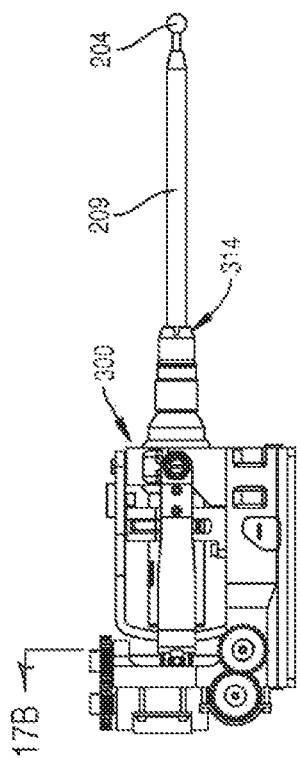
Figure 13:
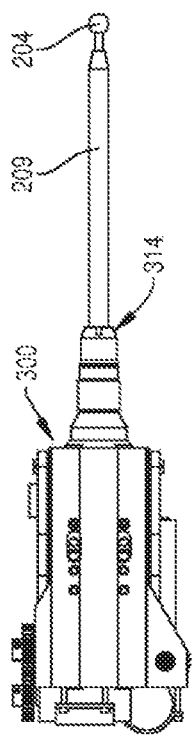
Figure 14:
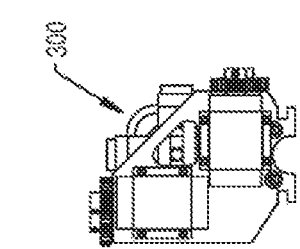

Yaw adjustment mechanism 412 includes a link 416 similar in shape to link 316. While not apparent from FIG. 17, as seen in FIGS. 11 and 12, link 416 is located distally forward of link 316. Link 416 includes a base 419 from which a pair of parallel arms 418 extends distally forward. A first end of each arm 418 has a bore 420 with a counterbore 421. A flanged bearing 422 is supported in each bore 420 and counterbore 421. Fastener 424, the fastener that seats in the flanged bearing 422, has a head 426 that holds the flanged bearing 422 to the top located arm 418. Fastener 424 also has a threaded shaft 428 that engages a corresponding threaded bore 430 formed in upper collar 308. A fastener 425, similar but not identical to fastener 424, holds the bottom located arm against lower collar 310. Fastener 425 extends into a bore formed in the lower collar 310 (bore not identified). Link 416 is able to freely pivot relative to the carrier 302 about an axis defined by the flanged bearings 422. This axis extends through the center of the gimbal 304.

An elongated slot 432 is formed in link base 419. Slot 432 is centered on and extends along the longitudinal axis of link base 419. Slot 432, like the slot 332 integral with link 316, receives the guide post 334 extending from the proximal end of motor 206. Slot 432 has a length of approximately 2.0 cm. Slot 432 is slightly smaller in end-to-end length than slot 332 integral with link 316 because the pitch of link 416 is greater than the yaw of link 316. Consequently to ensure the same up/down and right/left arc of the distal end of the cutting accessory 202, the movement of post 334 to the left and right of link 416 should be less than the movement of the post 334 up and down relative to link 316. The side-to-side width across slot 432 is approximately equal to the side-to-side width across slot 332. Guide post 334 freely moves up and down in the slot 432 when the pitch of the cutting accessory 202 is adjusted. When cutting accessory 202 yaw is adjusted, the guide post 334 is moved by the yaw adjustment mechanism 412 to place the bur head 204 in the desired position. The slot 432 is dimensioned with a relatively tight tolerance to the guide post 334 across its width, while still allowing the guide post 334 to freely slide in the slot 432 as the pitch of the cutting accessory 202 is changed by the instrument controller 120.

Figure 17B:
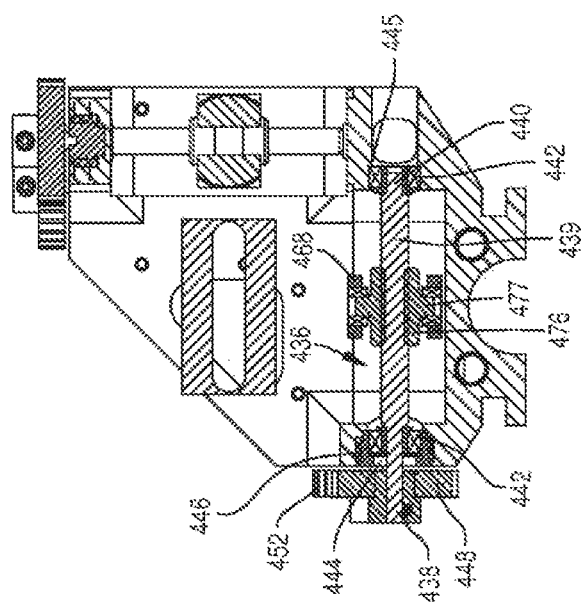
FIG. 17B is a cross-sectional view of the upper assembly taken generally along the line 17B-17B in FIG. 11.
Figure 21:
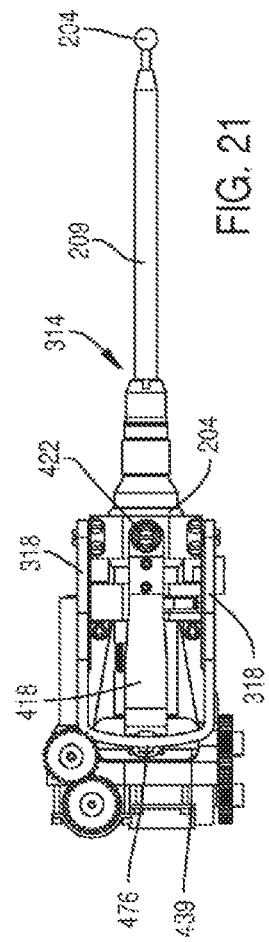
FIGS. 21-23 are top views of the upper assembly illustrating different yaw positions of the end effector.
Figure 22:
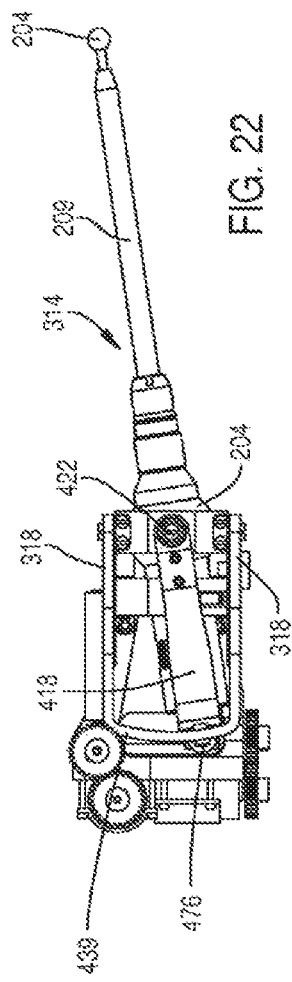
Figure 23:
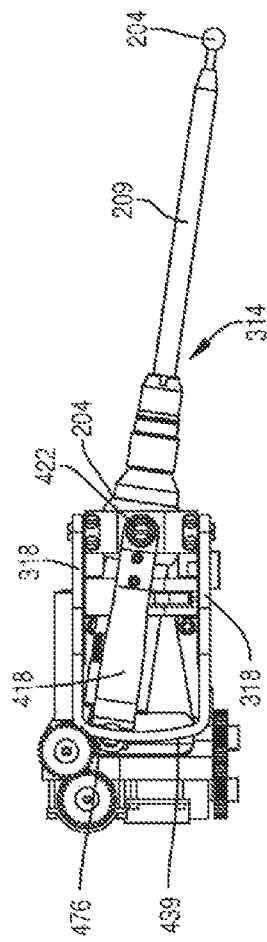
Figure 26:
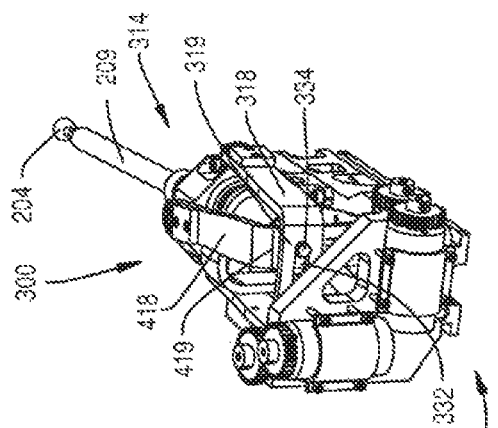
FIGS. 24-27 are rear perspective views of the upper assembly illustrating different yaw/pitch positions of the end effector.
Figure 27:
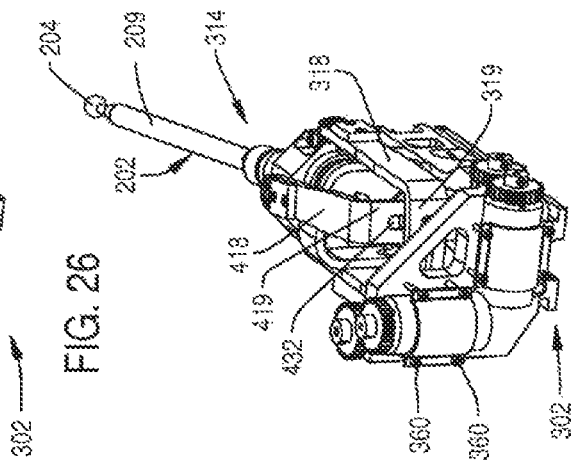
Figure 25:
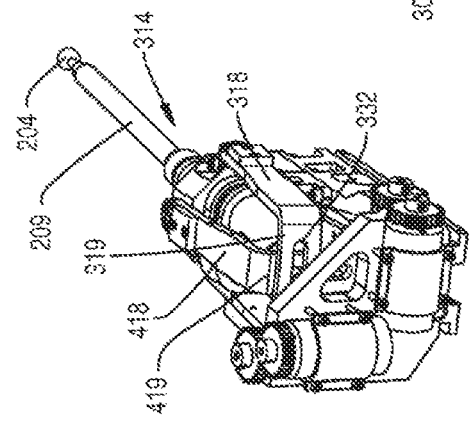
Figure 24:
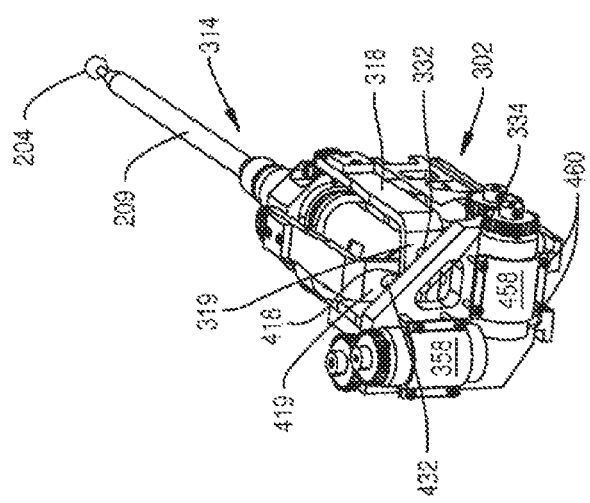
Figure 29:
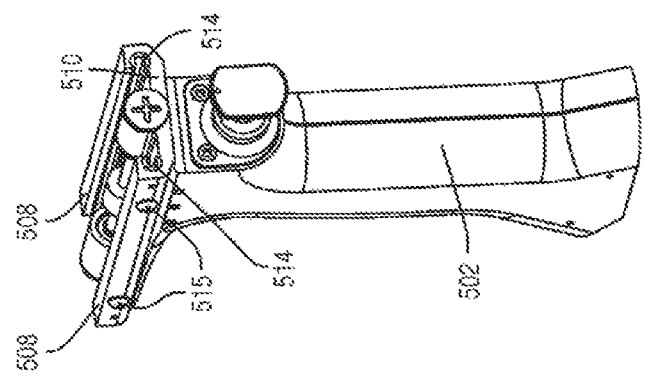
FIG. 29 is a front and right perspective view of the handle assembly.
Figure 28:
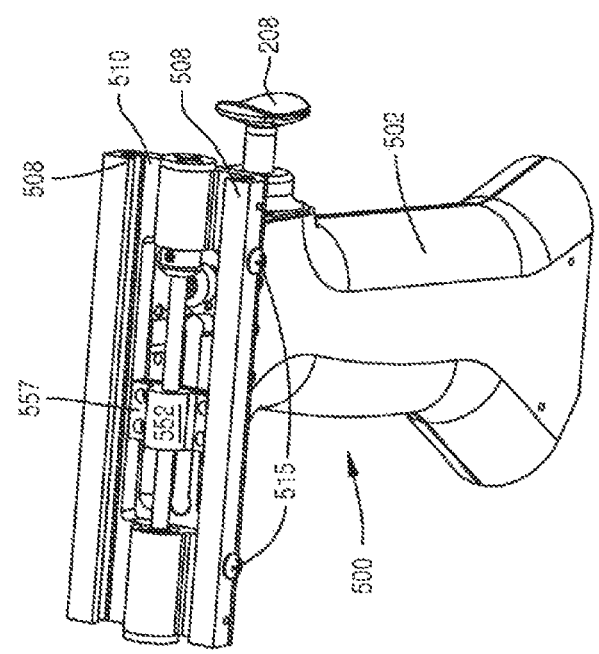
FIG. 28 is a top perspective view of a handle assembly of the surgical instrument of FIG. 6.

The yaw adjustment mechanism 412 includes a lead screw 436 that is rotated by the motor 222. The lead screw 436 has opposing first and second stems, 438 and 440, respectively. Stems 438 and 440 are cylindrical in shape. The lead screw 436 has a threaded portion 439 located between stems 438 and 440. Stems 438 and 440 are rotatably supported by two bearings 442 (with bushings (not numbered) in between). The bearings 442 are located in opposing bores 444, 445 formed in the carrier 302. An end plug 446 is threaded into a matching internal thread 447 in the carrier 302 to secure the bearings 442 and lead screw 436 to the carrier 302. The first stem 438 supports a spur gear 448 that is fixed to the screw 436 by set screws (not identified). The spur gear 448 has teeth that mate with teeth on a spur gear 452. The spur gear 452 is fixed to an output shaft 454 of yaw motor 222 by set screws (not identified). FIG. 17B shows a cross-section through lead screw 436.

A mounting bracket 458 secures motor 222 to the carrier 302 with fasteners (not identified). In particular, the proximal end of the carrier base 305 is formed with an arcuate recess 462 for receiving a section of the cylindrically shaped motor 222. Mounting bracket 458 has an arcuate shape to seat over the portion of the motor that extends beyond the carrier 302 to hold the motor 222 in position.

The yaw adjustment mechanism 412 further includes a yoke assembly 464 mounted to link 416. Yoke assembly 464 includes a rectangularly shaped bar 466. Bar 466 is formed to have a bore 472, only the opening of which is seen, that extends longitudinally through the bar 466. Bar 466 is secured to the outer face of the bottom of two arms 418 of link 416 by fasteners (not identified). The bar 466 is secured to the adjacent arm 418 so that the bore 472 is directed towards the arm 418. Bar 466 may be identical to bar 366. Accordingly, the adjacent link arm 418 may have a recess for receiving a rib integral with the bar 466.

The yoke assembly 464 includes a three sided yoke 468. A cylindrical rod 470, integral with the yoke 468 extends distally forward of the yoke 468. The rod 470 is slidably disposed in bore 472 between bar 466 and the adjacent link arm 418.

A nut 476, identical to nut 376, is pivotally mounted to the yoke 468 by trunnions 477. Each trunnion 477 is seated in a bearing assembly mounted to the side of yoke 468. The nut 476 has internal threads that mate with threads on the lead screw 436. The connection of nut 476 to link 416 by yoke 468 and rod 470 prevents the nut 476 from rotation. Consequently, the rotation of lead screw 436 results in the right/left movement of the nut 476 along the screw 436. Yoke 468 and, by extension, rod 470, move to the right/left with the movement of nut 476. The rod 470, being slidably coupled to the link 416 and bar 466, causes the link 416 to engage in the like displacement. During the movement of these components it should be appreciated that the yoke 468 pivots around the trunnions 477 and the rod 470 slides in and out of the bore 472. Since link 416 is pivotally mounted to the gimbal housing 306, the right/left displacement of the link 416 pivots the link 416 about the axis through bearings 422. This pivoting of the link 416 forces guide post 334 to engage in a like right/left movement. The displacement of the guide post 334 results in opposed left/right pivoting of the bur head 204.

The lead screw threaded portion 439 and complementary yoke nut 476 have a fine pitch and lead angle to prevent backdriving (i.e. it is self-locking). As a result, a large load placed on the bur head 204 does not result in undesired back driving of the yaw motor 222. In one embodiment of the invention, the lead screw 436 is identical to lead screw 336.

Magnets 480 are mounted in a pair of pockets (not identified) defined in an outside surface of one of the arms 418. A rectangular plate 484 is mounted to the arm 418 by a pair of fasteners (not identified). Plate 484 holds magnets 480 in the pockets. Magnets 480 are mounted to the arm 418 so that the north pole of one magnet 480 and the south pole of the second magnet 480 both face the plate 484. The magnets 480 are used to establish the home position for the cutting accessory 202 along the Y-axis.

A bracket 488 is fixed to the carrier 302 with fasteners 490. Bracket 488 is mounted to the top surface of the carrier base 305. The center of bracket 488 is open. The bracket 488 is formed to have two pockets, pocket 394 and pocket 494. Pocket 394 is located immediately above carrier base 305. Pocket 494 is spaced further above the carrier base 305. Upon assembly of surgical instrument 200, motor 206 is seated in and extends through bracket 488. The arms 318 and 418 of, respectively links 316 and 416, are both located outside of bracket 488. The link arm 318 that holds magnets 380 is located adjacent pocket 394. The link arm 418 that holds magnets 480 is located adjacent pocket 494. Hall-effect sensors 392 and 492 are mounted in pockets 394 and 494, respectively. The signal from Hall-effect sensor 394 varies as a function of the proximity of magnets 380. The signal from Hall-effect sensor 494 varies as a function of the proximity of magnets 490.

The analog signals output by Hall-effect sensors 392 and 492 are applied to, respectively, motor controller 230 and motor controller 232. Each motor controller 230 and 232 has an analogue to digital converter, (not illustrated) to which the associated analogue Hall sensor signal is applied. Motor controllers 230 and 232 forward the digitized representations of the signals from Hall-effect sensors 392 and 492, respectively, to controller 120.

FIGS. 18-27 show various pitch and yaw positions of the cutting accessory 202. From these Figures it can be appreciated that lead screw 336 is parallel with motor 220. Lead screw 436 is parallel with motor 222. This arrangement of the components of instrument 220 minimizes the overall size of the instrument 200.

C. Handle Assembly

Referring to FIGS. 28 through 37 the handle assembly 500 is now described. The handle assembly 500 slidably supports carrier 302. The sliding movement of the carrier 302 results in the linear adjustment of the cutting accessory 202 along the longitudinal axis Z (also referred to as a z-axis) of the instrument 200. Handle assembly 500 comprises the handle 502, a trigger assembly 506, and a linear adjustment mechanism 513.

The handle 502 is hollow and defines a cavity 503 in which motor 224 is disposed. At a top of the handle 502 is a wall 510. A hand-grip portion of the handle 502 descends downwardly from the wall 510. Wall 510 is formed with an opening 505 (identified in FIG. 37) that extends into cavity 503. Handle 502 is further formed to have two steps 509 and 511 (seen best in FIG. 50) that are located below opening 505 and that define portions of cavity 503. Step 509, the more proximal of the two steps, is closest to wall 510. Step 511 extends distally forward from and is located below step 509. A threaded bore 515 extends downwardly from the base of step 511.

As shown in FIG. 34, elongated rails 508 extend longitudinally along the opposed sides of the top of handle wall 510. Each rail 508 is shaped to define a groove 512. Handle 502 is formed so that grooves 512 face each other. Bearing strips or liners 514 fit inside the grooves 512. The bearing strips 514 are channel-shaped to define the channels 504 to receive the corresponding carrier flanges 303. The carrier flanges 303 are supported in the bearing liners 514 such that the weight of the carrier 302 is born by the bearing liners 514. The bearing liners 514 are preferably formed of a low friction material to facilitate sliding of the carrier flanges 303 in the bearing liners 514. Such materials may include high performance polymers such as iglide® J from Igus, Inc. of East Providence, R.I. Screws 517 hold the bearing liners 514 in position by engaging flats in the liners 514 at the screw locations (not shown).

Carrier 300, handle 502 and liners 514 are collectively designed so that while carrier flanges 303 are able to slide back and forth in the liners 514, there is ideally no up/down or right/left movement of the carrier 300 relative to the handle 502. Specifically the handle 502 and liners 514 are designed so that the outer diameter of the liners 514 is slightly less than the diameter of the rail grooves 512 in which the liners 514 are seated. In some versions of the invention, the diameter of rail grooves 512 is between approximately 0.02 to 0.12 mm more the diameter of liners 514. Liners 514 have an outer diameter of approximately 4.78 mm. The distance between the opposed faces of the liners 514 against which the carrier flanges 303 seat is also slightly less than distance between the opposed outer faces of the flanges 303. This difference may be between approximately 0.05 and 0.15 mm. These features collectively minimize the up/down and right/left play of the carrier flanges 303 in the liners 514.

Figure 36:
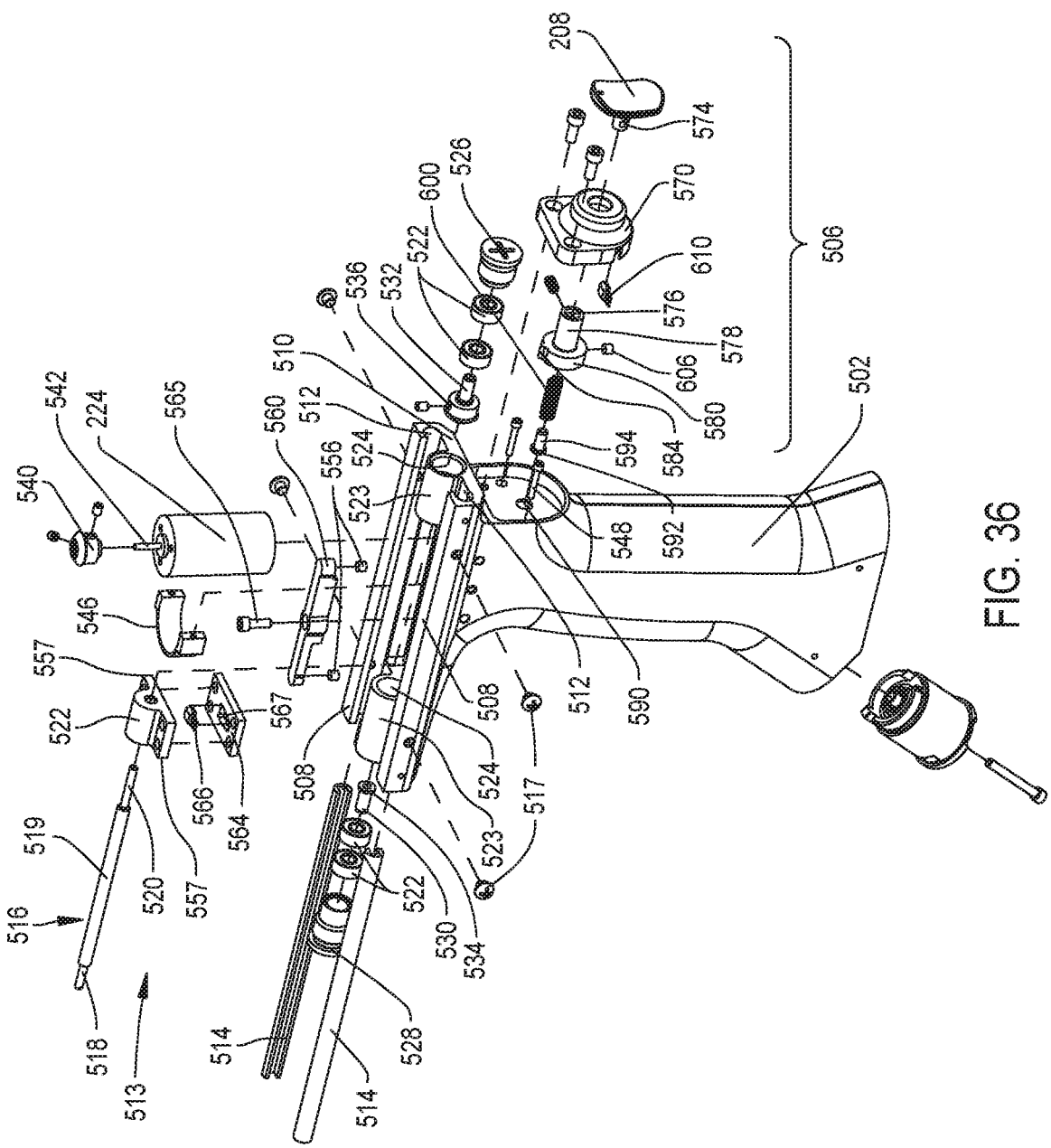
FIG. 36 is an exploded view of the handle assembly.

Handle 502 has two spaced apart coaxial sleeves 523, identified in FIG. 36, that are integral with and located above wall 510. One sleeve 523 extends forward from the proximal end of the wall 510. The second sleeve 523 extends proximally rearward from the distal end of the wall 510. Each sleeve 523 is formed to have a bore 524.

Referring to FIG. 36, the linear adjustment mechanism 513 includes a lead screw 516 that is rotated by motor 224. Screw 516 has opposing first and second stems 518 and 520, respectively that are cylindrical in shape. Screw 516 has a threaded body 519 located between stems 518 and 520. Bearings 522 rotatably hold lead screw 516 to sleeves 523.

Two bearings 522 are disposed over each screw stem section 518 and 520. Each pair of bearings 522 is located in one of the sleeve bores 524. End plugs 526 and 528 are threaded into internal threads in the bores 524 to secure the bearings 522 and lead screw 516 to the handle 502. (Bore threading not illustrated) End plug 526 is disposed in the distal end of distal most sleeve 523. End plug 528 is disposed in the proximal end of the proximal sleeve 523.

Inside bearings 522, bushings 530 and 532 are disposed about the screw stems 518 and 520, respectively. Bushing 530 has an annular, outwardly extending flange 534 that abuts an end of the threaded body 519 of the lead screw 516. Bushing 532 is integrally formed with a bevel gear 536 that is located on the proximal end of the bushing. The bevel gear 536 is fixed to the screw stem 520 by set screws (only one shown). The bevel gear 536 has teeth that mate with teeth on another complimentary bevel gear 540. The complimentary bevel gear 540 is fixed to an output shaft 542 of motor 224 by set screws, (not identified). The bevel gears 536, 540 are positioned such that their corresponding teeth mate to rotate lead screw 516 upon actuation of motor 224.

A mounting bracket 546 secures the motor 224 in the handle 502 with fasteners 548. In particular, the handle 502 has an arcuate recess 550 (as shown in FIG. 49) in the cavity 503 for receiving a portion of the cylindrically shaped outer wall of the motor 224. Mounting bracket 546 is arcuately shaped to seat over the portion of motor 224 that extends away from the adjacent internal surfaces of the handle 502.

Figure 35:
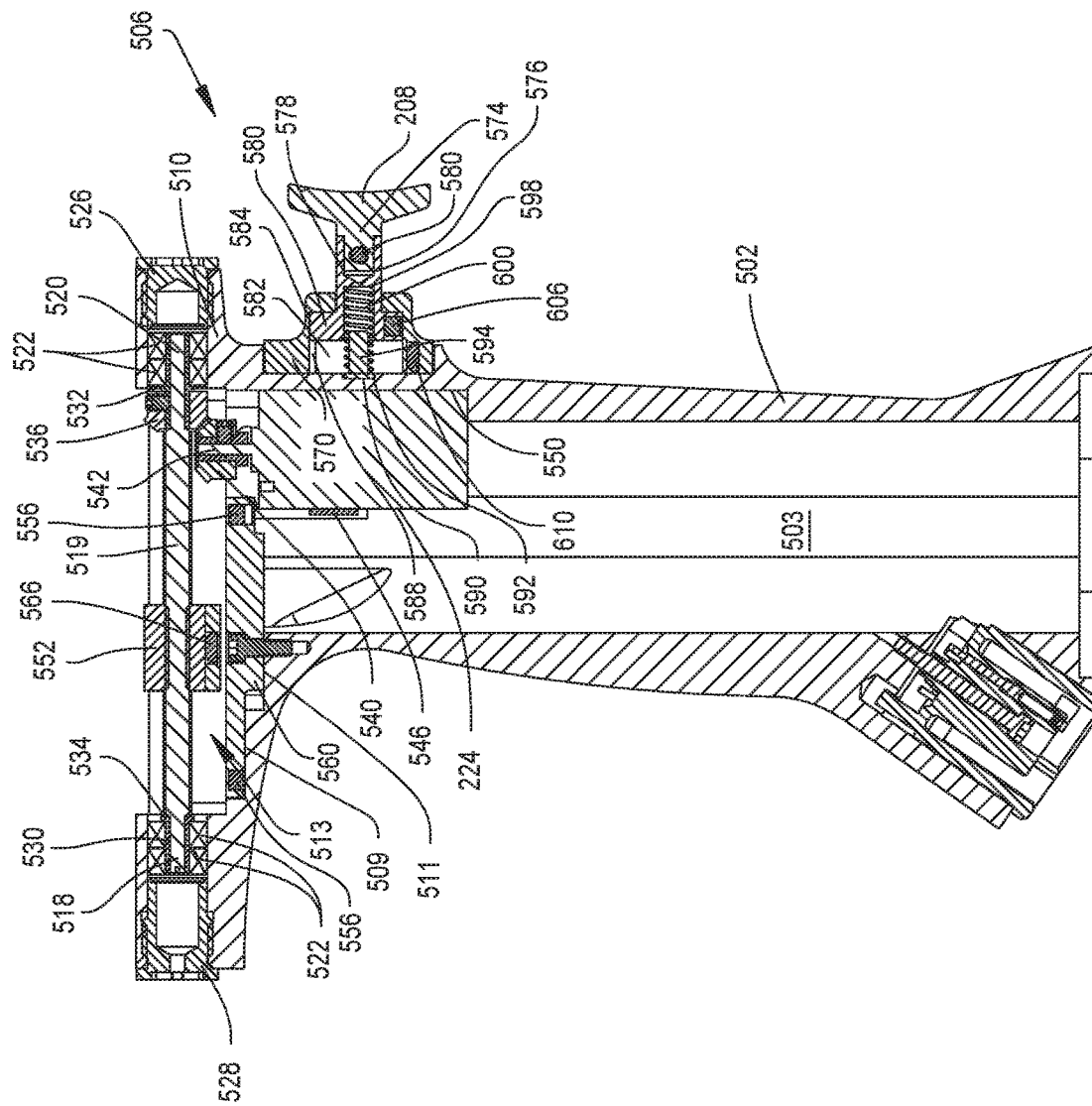
FIG. 35 is a cross-sectional view taken along the line 35-35 in FIG. 31.
Figure 35A:
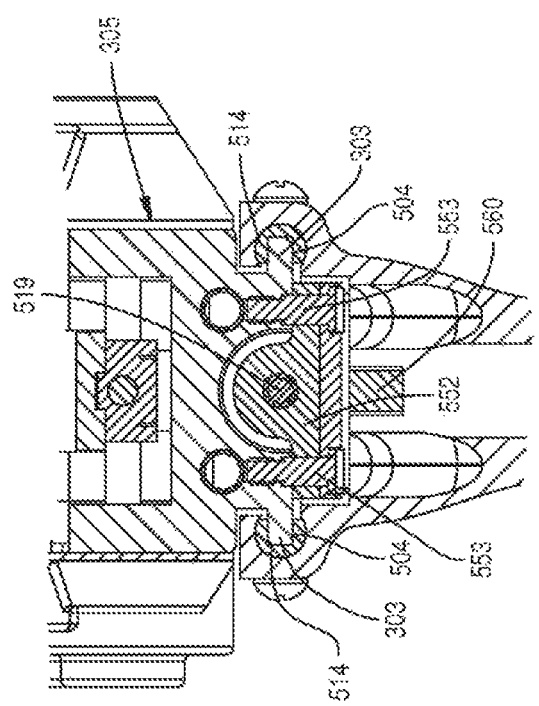
FIG. 35A is a cross-sectional view showing the sliding arrangement of the slider subassembly relative to the handle assembly.

A nut 552 is disposed in carrier slot 317, seen in FIG. 35A. Nut 552 has a center cylindrical body (not identified) from which two wings 557 (identified in FIG. 38) extend. The nut 552 is formed so that wings 557 have a coplanar face. A portion of this coplanar face extends across the body of the nut 552. The nut 552 is positioned so that the wings 557 are disposed against the face of the carrier base 502 on the opposed sides of slot 317. Fasteners 553 (FIG. 35B) extend through openings in wings 557 and complementary openings in the carrier base 305 to hold the nut 552 to the carrier 302 (nut and carrier openings not identified). The nut 552 has internal threads that mate with threads on the lead screw 516. Since nut 552 is firmly attached to the carrier 302 it should be appreciated that the nut 552 does not rotate. Consequently, the rotation of the lead screw 516 results in the movement of the nut 552 and, by extension, the carrier 302 and attached components, relative to handle 502.

As the nut 552 travels along the lead screw 516, the carrier flanges 303 are able to freely slide in the bearing liners 514. The entire mass of the upper assembly 300 moves relative to the handle 502 during displacement of nut 552 along the lead screw 516. The lead screw 516 has fine pitch and lead angle to prevent backdriving (i.e. it is self-locking). As a result, a large load placed on the bur head 204 will not result in undesired back driving of the axial motor 224. In one embodiment, the lead screw 516 is of the same diameter as and has the same lead as screws 336 and 436.

Figure 35B:
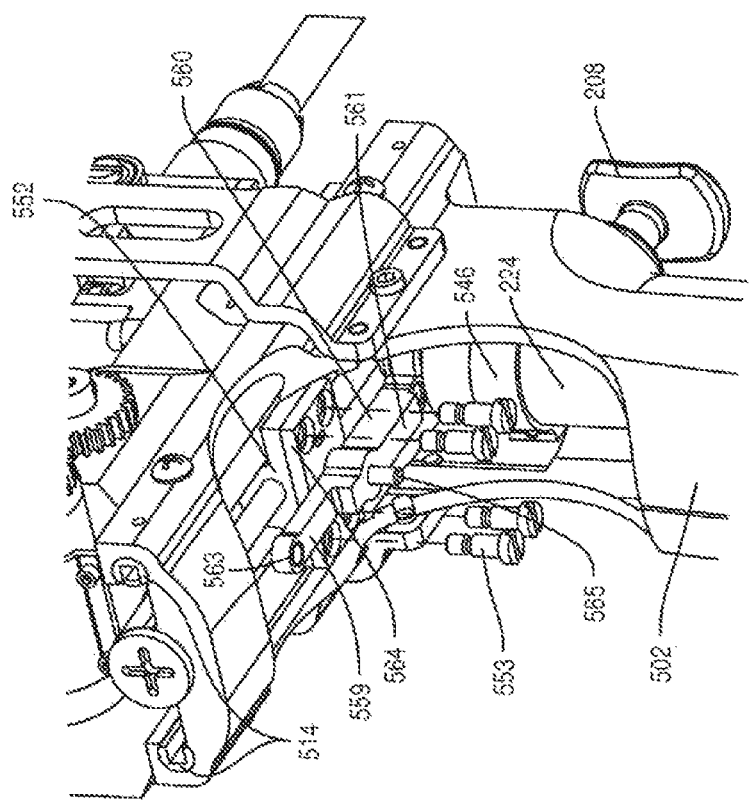
FIG. 35B is a partial rear perspective view of the instrument with a portion of the handle cut away to show a nut and lead screw.

A magnet holder 560, now described by reference to FIGS. 35 and 35B, is disposed in handle cavity 503. Magnet holder 560 is a single piece unit that includes a beam 559 and a foot 561 located below the beam. Foot 561 has a length relative to the beam 559 such that the proximal end of the foot 561 is located forward of the proximal end of the beam 559 and the distal end of the beam 559 is located rearward of the distal end of the beam 559. A closed end bore 563 (one identified) extends through each end of beam 559. Bores 563 open from the underside of beam 559 and have longitudinal axes that are perpendicular to the longitudinal axis of the beam 559. When instrument 200 is assembled, the proximal end of magnet holder beam 559 seats on handle step 509; foot 561 seats on step 511. A fastener 565 extends through the beam 559 and step 511 into handle bore 515 to secure magnet holder 560 to the handle 502. A magnet 556 is mounted in each holder bore 563. Magnets 556 are mounted to holder 560 so that the north pole of one magnet 556 and the south pole of the second magnet 556 are both directed to the carriage 302.

A plate 564 is fixed to the nut 552 with the same fasteners 553 that mount the nut 552 to the carrier 302. Plate 564 is disposed against the common planar outer face of nut wings 557. A Hall-effect sensor 566 is seated in a pocket 567 formed in plate 564. Sensor 566 outputs a signal that is function of the proximity of the sensor 566 to magnetic fields generated by magnets 556. The analog signal output by sensor 566 is applied to controller 234. Controller 234 digitizes this signal and forwards the digitized signal to the instrument controller 120.

The trigger assembly 506 includes the trigger 208. The trigger 208 slides in a trigger housing 570. The trigger housing 570 is mounted to the handle 502 with fasteners (not identified). The trigger 208 has a head (not identified) shaped to be pressed by a finger of the user. A stem 574 extends rearward from the trigger head.

Trigger stem 574 is located inside a bore 576 in a trigger shaft 578. A set screw holds the stem 574 inside the trigger shaft 578. The trigger shaft 578 has a generally cylindrical head 580 sized to slide within a larger bore 582 of a trigger housing 570. The head 580 has a rib 584 at a top thereof. The rib 584 is formed on a flat of the head 580. The rib 584 extends upwardly into a corresponding groove 588 defined inside the trigger housing 570 as an extension of the bore 582. The rib 584 slides in the groove 588 to prevent rotation of the trigger shaft 578 relative to the trigger housing 570.

A spring pin 594 is located in a cylindrically-shaped pocket 590 of the handle 502. In particular, the spring pin 594 has a head 592 located in the pocket 590. A pin shaft extends forward from the head 592 into a correspondingly shaped bore 598 in the trigger shaft 578. A spring 600 is at least partially positioned in the bore 598. The spring 600 is located between an internal end wall of the trigger shaft 578 and the head 592 of the spring pin 594. The spring 600 biases the trigger shaft 578 away from the handle 502.

The trigger shaft 578 further defines a magnet pocket on an underside thereof. A magnet 606 is secured in the magnet pocket preferably with adhesive. The trigger housing 570 also defines a sensor pocket opposite the groove 588.

A Hall-effect sensor 610 is secured in the sensor pocket preferably with adhesive. The Hall-effect sensor 610 transmits a variable signal back to the instrument controller 120 based on the distance of the magnet 606 from the Hall-effect sensor 610. Accordingly, the instrument controller 120 can determine the amount of depression of the trigger 208 by the user. The data connection 133 transmits not only power signals and control signals between the motor 206 and the instrument driver 130, but also transmits signals from the Hall-effect sensor 610 to the instrument console 130.

Figure 38:
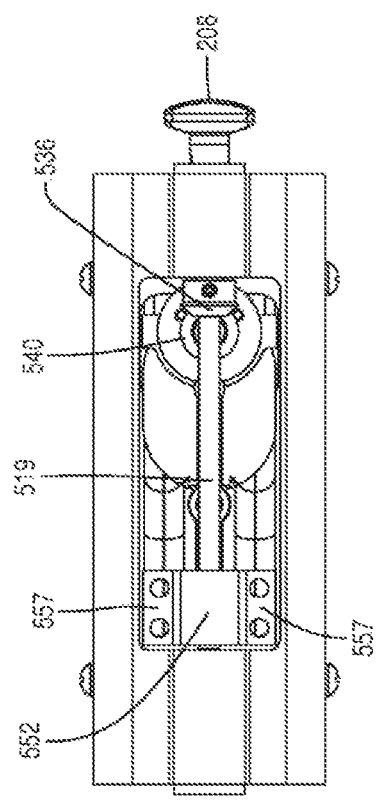
FIGS. 37-39 are top views of the handle assembly illustrating different z-axis positions of a linear nut that drives the upper assembly.
Figure 37:
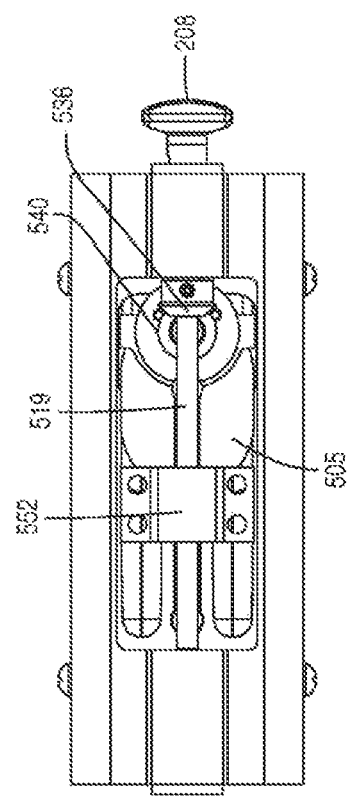
Figure 39:
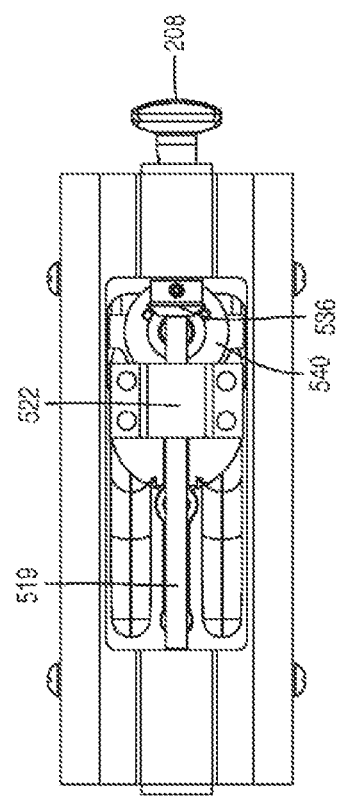

FIGS. 37-39 show various Z-axis positions of the nut 552 (and carrier 302) along the axis Z with respect to the handle 502.

D. Wire Fittings

Figures 44, 45:
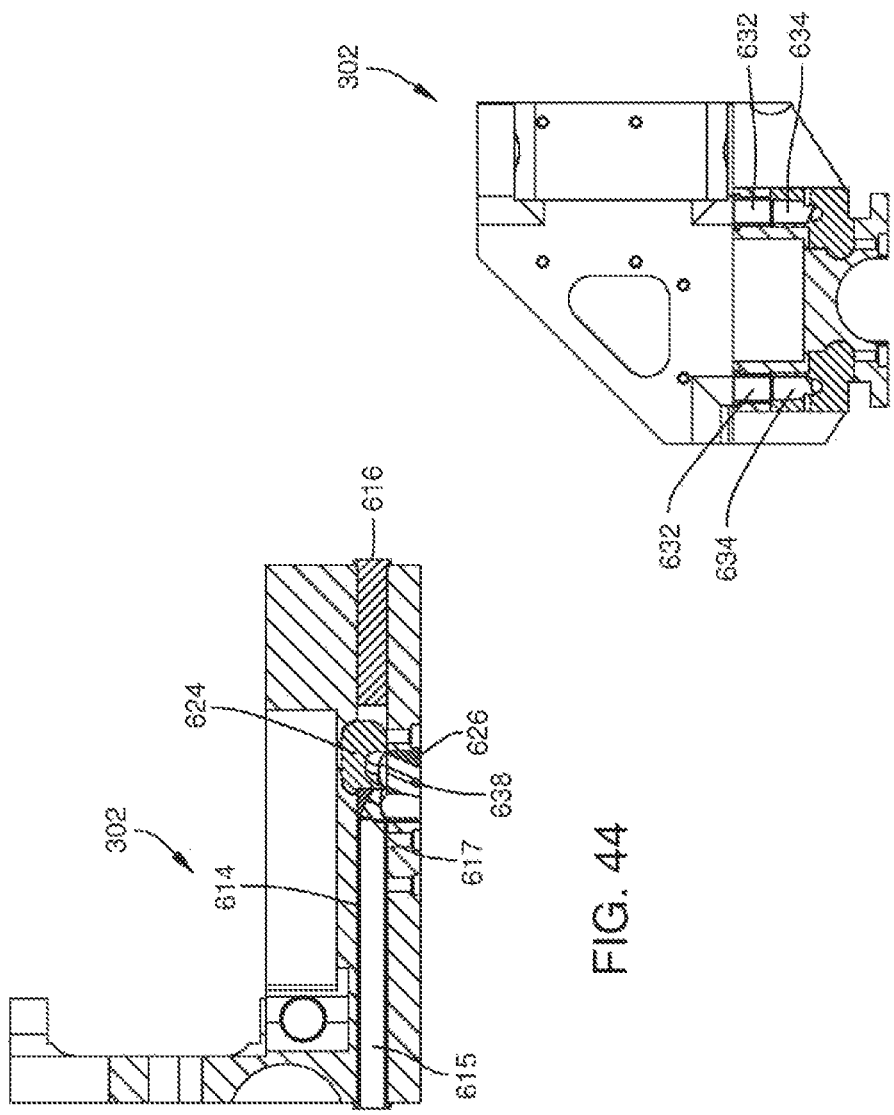
FIG. 44 is a cross-sectional view of the slider subassembly taken along the line 44-44 in FIG. 43A.
FIG. 45 is a cross-sectional view of the slider subassembly taken along the line 45-45 in FIG. 43A.

As now described by reference to FIGS. 40 through 45, carrier 302 includes a number of bores through which wires are routed. These wires (not illustrated) are the wires over which sensor signals are received from and power signals are applied to the various components mounted to the carrier 302. Carrier base 305 defines a pair of longitudinal through bores 612. Each through bore 612 is located above and inwardly of a separate one of the flanges 303. A guide tube 614, preferably formed of plastic, is located inside each through bore 612. The lumen 615 internal to one tube 614 functions as for the conduit for the eight wires that extend to motor 220. The lumen 615 through the second tube 614 functions as the lumen for the eight wires connected to motor 222. During assembly, the guide tubes 614 are inserted into one end of the bores 612. A plug tube 616 closes the opposed end of each bore 612. Each guide tube 614 has a first end disposed in the associated bore 612 and a second end with a head 618 that abuts the proximally directed face of carrier base 305. As seen in FIG. 44, each guide tube 614 is shaped so that at the distal end, the end disposed in carrier bore 612 there is a foot 617. The foot 617, which has the same arcuate dimensions as the body of the tube 614 has a surface coincident with the inner surface of the body of the tube 614 (surface not identified). Extending distally forward from the end of the tube body, this foot surface curves downwardly.

Two holes 620 extend downwardly from the top face 311 of carrier base 305. Holes 620 are oval in cross sectional shape. Each hole 620 is located inwardly of and does not intersect an adjacent bore 612. Carrier base 305 is further formed to have two opposed pockets 636. Each pocket 636 extends inwardly from a side face 313 of the carrier 302. Each pocket 636 intersects one of the through bores 612 and the adjacent hole 620. A plastic sleeve 622 is seated in each hole 620. Each sleeve 622 has a tubular body 630 dimensioned to slip fit in the hole 620. Sleeve body 630 has a through bore 632. A flange 628 extends radially outwardly from the upper end of the body 630. The flange 628 seats in a counterbore around hole 620 to hold the sleeve 622 flush with carrier base top face 311. A plug 624 is seated in each pocket 636. Each plug 624 is formed with a mid bore 634. When a sleeve 622 and adjacent plug 624 are fitted to the carrier base 305 the plug midbore 634 is aligned with the sleeve bore 632. A pair of sleeves 626 are also mounted to carrier 302. Each sleeve 626 is seated in a bore (not identified) that extends upwardly from one of the bottom face surfaces 315 of the carrier 302. Each sleeve 626 is adjacent and located inward of the associated carrier bore 620. Each sleeve 626 is also positioned to intersect the associated bore 612. The outer face of sleeve 626 is flush with the bottom face 315 of the carrier base 305. Each sleeve 626 is formed to have a bottom bore 638 aligned with the top bore 632 and the mid bore 634. The plugs 622, 624, 626 are held in position by adhesive and/or press fit. All of the plugs 622, 624, 626 are preferably made from plastic.

FIGS. 46-50 illustrate the void spaces internal to the handle 502 through which the wires are routed through the handle 502. These void spaces include a pair of wire troughs 640. Troughs 640 are parallel recesses that extend inwardly from wall 510 in the top of the handle 502. Each trough 640 holds a bundle of wires that extend to the carrier 302 (wire bundles not illustrated). The wire bundles include the wires that extend to the instrument motor 206, the motors 220 and 224 that pivot the cutting accessory 202 and the Hall effect sensors 392, 492, and 566.

Figure 52:
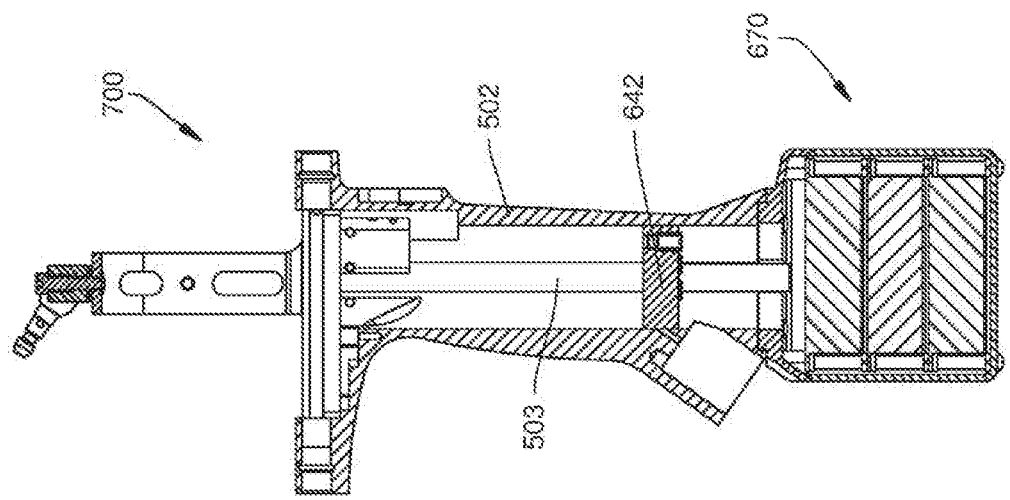
FIG. 52 is a cross-sectional view taken along the line 52-52 in FIG. 51.
Figure 51:
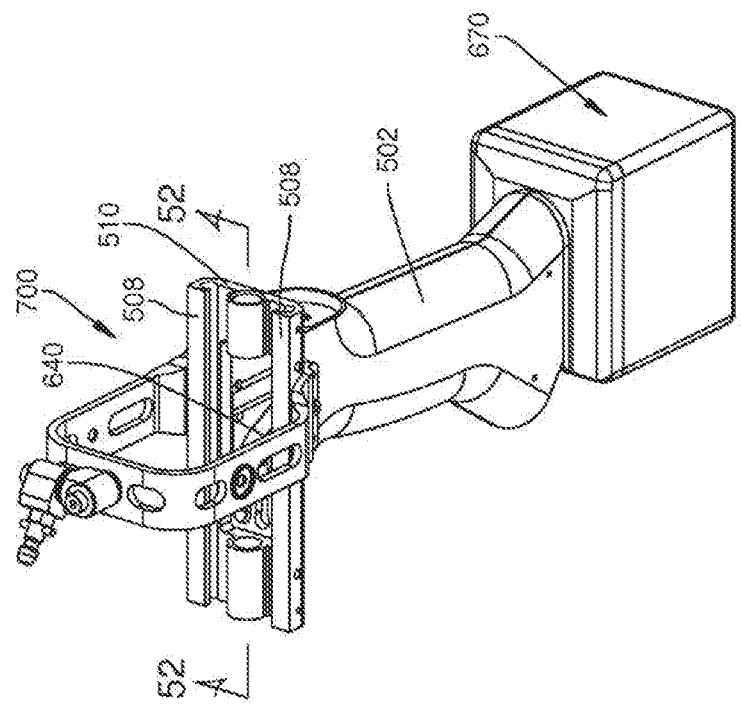
FIG. 51 is a perspective view of the handle assembly with a navigation bracket, drive enclosure, and wire sorter attached thereto.
Figure 53A:
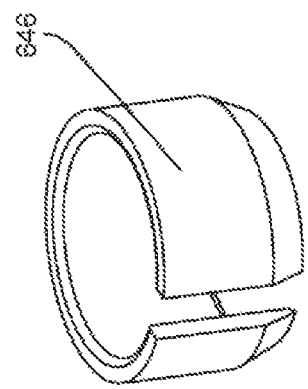
FIG. 53A is a perspective view of a ferrule.
Figure 53:
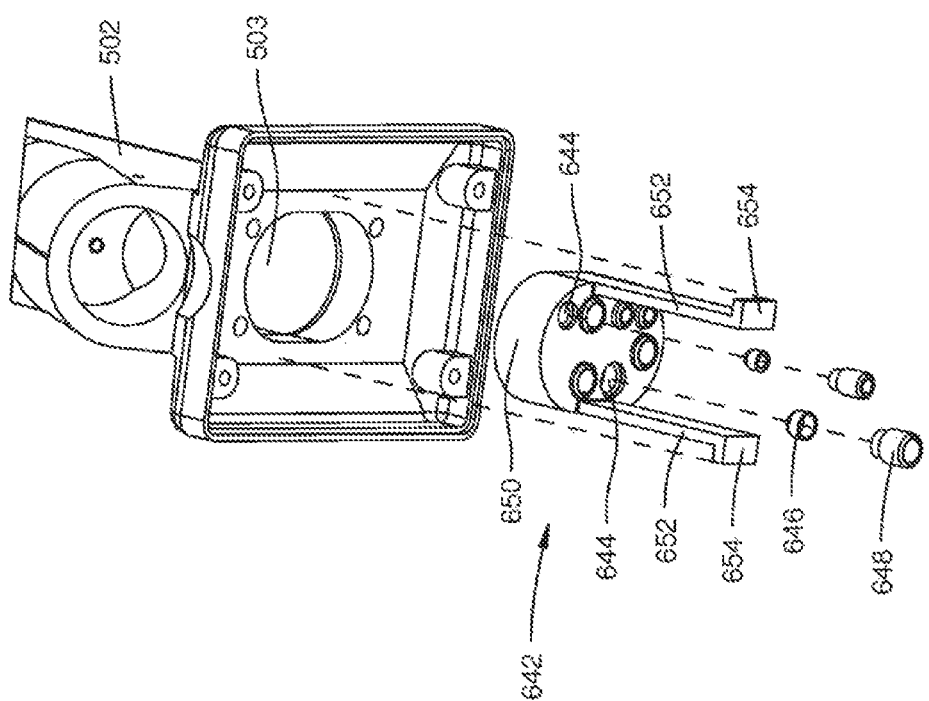
FIG. 53 is an exploded view of the wire sorter.

The wires that extend through to the carrier 302 as well as the wires associated with trigger 208 and motor 226, extend through handle cavity 503. A wire sorter 642, now described with reference to FIGS. 52, and 53, disposed in the cavity 503 holds the wires static. Referring to FIG. 53, the wire sorter 642 has a head 650 dimensioned to slip fit in the handle cavity 503. Head 650 is disposed on a plane that is perpendicular to the longitudinal axis through the cavity

503. A number of openings 644 extend top to bottom through the head 650. Openings 644 function as conduits through which individual wires and wire bundles pass through the cavity 503. A threaded retainer 648 and ferrule 646 are positioned in each opening 644. Legs 652 extend downwardly from the head 650. In the depicted version of the invention, in the plane perpendicular to the top-to-bottom axis through the head 650, the head 650 is oval in shape. The legs 652 extend downwardly from the opposed parallel sides of the head 650. A foot 654 extends outwardly from the free end of each of the legs 652. Wire sorter feet 654 are adhesively secured to an inner step around the bottom end shell lid 674 (FIG. 54) so as to set the position of the sorter head 650 in the handle cavity 503.

Wire Sorter 642 provides strain relief for the wire bundles running through the handle 502. The ferrules 646, which are formed of plastic, hold the wire bundles in place. The ferrules 646, best seen in FIG. 53A, are compressed inside the sorter openings 644 via a tapered front and the thrust provided on the tapered front by the threaded retainers 648. Each ferrule 646 is slotted along its entire length such that it compresses diametrically as the threaded retainer 648 forces the ferrule's tapered tip into its tapered hole. While not called out in drawings, the diameter of each ferrule 646 is proportional to the diameter of the opening in which the ferrule 646 is seated.

E. Shell

Figure 54:
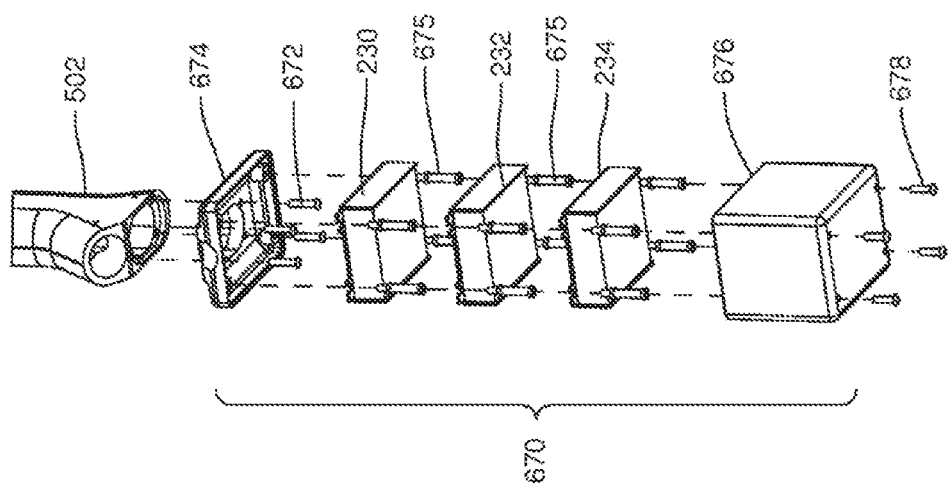
FIG. 54 is an exploded view of the contents of the shell in which the motor controllers are housed.

Referring to FIG. 54, the shell 670 is mounted to a bottom of the handle 502. The shell 670 houses the controllers 230, 232, 234. Shell 670 includes a rectangular case 676 in which the controllers 230, 232 and 234 are disposed. Case 676 is open at the top. A lid 674 is secured over the open top end of the case 676. Lid 674 is mounted to the bottom of the handle 502 with fasteners 672. Internal to the case are standoffs 675 that are post-like in shape. Controllers 230, 232 and 234 are stacked one on top of the other in the case 676. One set of standoffs 675 hold the bottommost controller away from the bottom of the case 676. A second set of standoffs hold the middle controller away from the bottommost controller. A third set of standoffs 675 hold the topmost controller away from the middle controller. The wires from the motors 220, 222, 224 and Hall effect sensors 392, 492, 566 terminate at the controllers 230, 232 and 234.

In alternative embodiments, the controllers 230, 232, 234 are mounted in the control unit 120 and not on the instrument 200. These embodiments of the invention do not include shell 670.

F. Tracker Bracket

Figure 55:
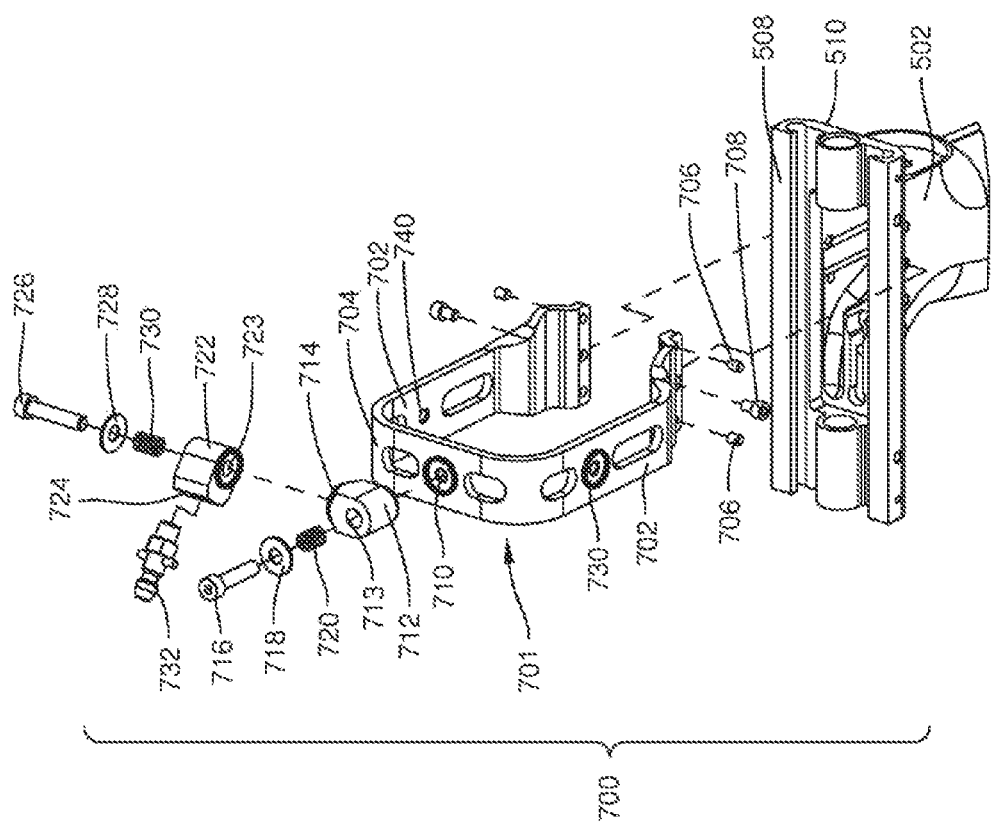
FIG. 55 is an exploded view of the navigation bracket.

Referring to FIG. 55, the bracket assembly 700 is mounted to the handle 502 to hold the tracking device 114 if needed. In alternative embodiments, the LEDs of the tracking device 114 are built into the instrument 200 eliminating the need for the bracket assembly 700.

Bracket assembly 700 includes a generally U-shaped bracket 701. Bracket 701 has a pair of parallel mounting arms 702 that extend downwardly from a web 704. An end of each mounting arm 702 is aligned with the handle 502 by alignment pins 706. Fasteners 708 hold the mounting arms 702 to the handle 502. The tracking device 114 is designed to be fixed to the handle 502.

Bracket web 704 is formed with a threaded bore 710. A block 712 is disposed over web 704. A threaded fastener 716 extends through a bore 713 in block 712 and into web bore 710. Fastener 716 holds block 712 to bracket 701 so that the block 712 is able to rotate around the axis through web bore 710. Fastener 716 is longer in length than block 712. A washer 718 is located immediately below the head of fastener 716 (fastener head not identified). To lock block 712 in a fixed orientation, fastener 716 is tightened down so that the block 712 is clamped between bracket web 704 and washer 718.

To adjust the orientation of block 712, fastener 716 is loosened. A spring 720 extends around fastener 716 below washer 718. The opposed end of the spring 720 seats against a step (not illustrated) internal to block 721 that is inside the block bore 713. When fastener 716 is loosened to adjust the rotational orientation of block 712, spring 720 is in a compressed state between washer 718 and the step internal to the block 712. This compressive force inhibits the free rotation of block 712 when fastener 716 is loosened.

While not illustrated, in some versions of the invention, bracket web 704 is formed with arcuately spaced apart teeth that radiate outwardly from bore 710. The adjacent bottom surface of the block 712 is formed with complementary teeth. As part of the position of setting the rotational position of the block 712, the block 712 is set so that the block teeth are interleaved between the complementary teeth in the bracket web 704. This tooth-against-tooth engagement serves to further prevent rotational movement of the block 712 when in the locked state.

A second block, block 722 is rotatably attached to block 712. Block 722 is positioned to abut a side face, face 714 of block 712. Block 722 is formed with a through bore 723 that extends axially through the block 722. Block 712 is formed with a second bore, (not illustrated) that extends inwardly from the center of face 714. This second bore is perpendicular to block bore 713. A fastener 726, similar if not identical to fastener 716 extends through block bore 723 and into the second bore of block 712. Fastener 726 holds block 722 to block 712 so that block 722 can rotate around the fastener 716. A washer 728 is located between the head of the fastener 726 and block 722. The tightening of fastener 716 causes block 722 to be clamped between block 712 and washer 718.

While not illustrated, blocks 712 and 722 are formed with complementary teeth. The teeth integral with block 712 extend radially outwardly from the bore formed in block face 714. The teeth integral with block 722 are formed in the face of the block 722 that seats against block 712. As part of the process of fixing the rotational orientation of block 722, the block 722 is rotated so that the teeth integral with block 722 engage between the teeth formed in face 714 of block 712. This tooth-between-tooth engagement further locks block 722 to block 712.

A spring 730 is disposed around fastener 726. Spring 730 from washer 728 extends into block bore 723. Spring 730 seats against a step internal to block bore 723. When fastener 726 is loosened, spring 730 imposes a force on block 722 that inhibits the free rotation of block 722.

Block 722 is further formed with a second bore, bore 724. Bore 724 extends through one of the side faces of the block 722 toward bore 723. A fitting 732 is press fit into bore 724. Fitting 732 is provided with features not relevant to the current invention that facilitate the removable attachment of a tracker to the fitting 732.

Block 712 rotates around a longitudinal axis between bracket arms 702. Block 722 rotates around an axis perpendicular to the axis around which block 712 rotates. Thus this arrangement allows the position of tracker attached to fitting 732 to be selectively positioned around two rotational degrees of freedom. This facilitates the ability to orient the tracker to ensure good line-of-sight with the camera 110 of the navigation unit 108.

In the depicted version of the invention, one bracket arm 702 is provided with a threaded bore 730. The second arm 702 is provided with a threaded bore 740. Bores 730 and 740 are both designed to receive fastener 716. While not illustrated, the bracket arms 702 are provided with teeth around bores 730 and 740 similar to the teeth provided around web bore 710. Thus, these structural features make it possible to mount blocks 712 and 722 to either one of the bracket arms 702. This makes it possible to mount the tracker to either of the bracket arms 702 if such positioning facilitates the optimal positioning and orienting of the tracker to ensure a line of sight relationship with the localizer.

IV. Registration, Calibration and Homing

Figure 58:
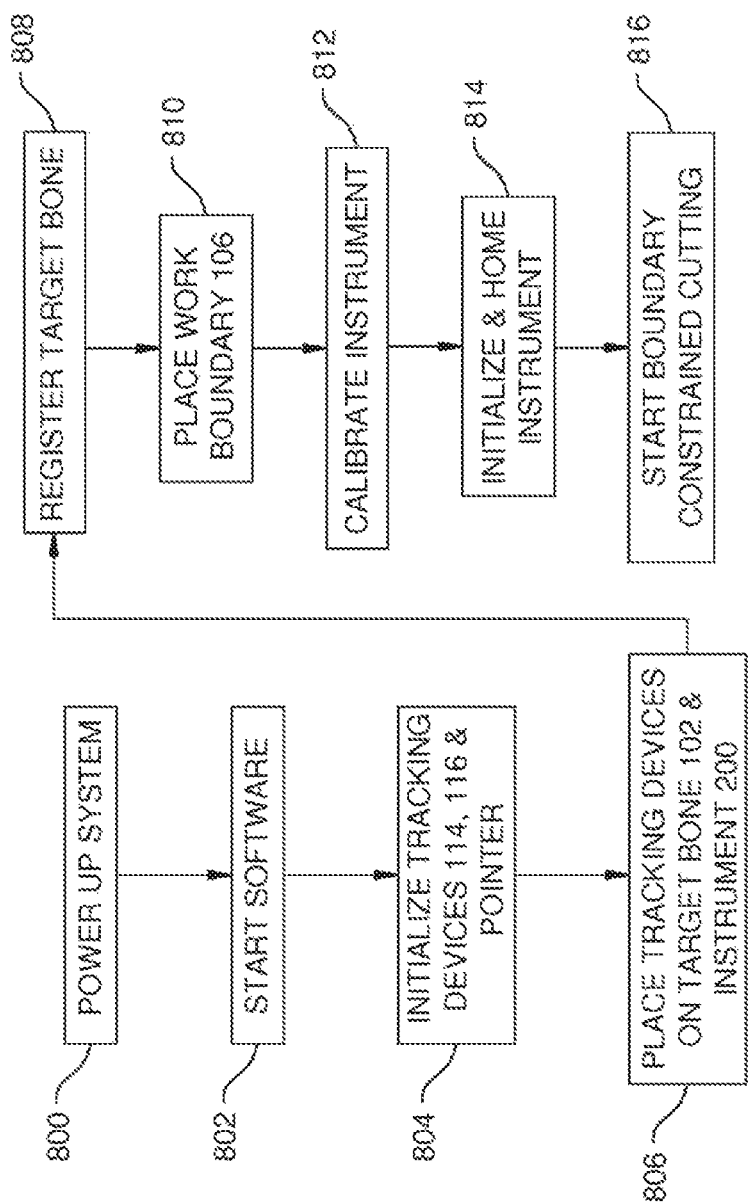
FIG. 58 is a flow chart showing the initialization steps of the system.

Referring to FIG. 58, the basic steps taken to prepare the system for operation are shown (the system is considered to be the tracking and control system 100 and instrument 200). In a first step 800, the system is powered up. The software application for operating the system is started in step 802. In steps 804 and 806, the trackers 114, 116 and the pointer (not shown) are initialized and the trackers 116, 114 are placed on the target bone (e.g., femur 102) and the instrument 200.

With the tracking device 116 mounted to the femur 102, the femur 102 (and any other bone or tissue) is registered in step 808 using registration techniques known to those having ordinary skill in the art. This may require the user to touch certain surfaces or landmarks on the femur 102 with a tracked pointer device. In some embodiments this requires the user to touch several points on the surface of the femur 102 while pressing a select button on a pointer device. This "paints" the points on the surface in the system for matching with a preoperative or an intraoperative image of the femur 102. The preoperative image or an intraoperative image of the femur 102 is loaded into the navigation computer. The tracked portion of the femur 102 is registered to the preoperative image. By extension, this allows the tracking and control system 100 to, as the femur 102 moves, present an image of the actual position and orientation of the bone based on the preoperative image on the display 113 (and/or display 1402).

In step 810 the work boundary 106 is defined. Software running on instrument controller 120 generates an initial definition of the work boundary 106. The user typically has the ability and option to adjust the placement of the work boundary 106 as may be necessary. In some embodiments, the work boundary 106 is defined before the operation such as after the preoperative image is taken and a 3-D model of the femur 102 or other tissue is generated, but before the patient is prepared for surgery. Thus, the work boundary 106 may be defined preoperatively or intraoperatively.

In the calibration procedure in step 812, the orientation and location of the tracking device 114 is calibrated relative to the handle 502 by reference to the fixed and known locations of divots 507 (FIG. 3). In the embodiments in which the tracking device 114 is integrated into the instrument 200, then such calibration would be unnecessary since the relative locations of the LEDs or other transmitters are known.

The pointer device is used to register the target bone 102 to tracking device 116.

Referring to FIGS. 56 and 58, a homing procedure of step 814 establishes the home position for the accessory distal end bur head 204, the distal end of the bur head. This process establishes the initial positions of the carriage 302 and links 316 and 416. Initially in this process, the counters internal to the controllers 230, 232 and 234 that store the cumulative counts representative of the angular positions of rotors internal to motors 220, 222 and 224 are set to zero.

The process by which carriage 302 is set in the home position along the axis Z is described first. At a beginning step of this process, controller 120 directs motor controller 234 to actuate the associated motor 224. First, motor 224 is actuated to rotate lead screw 519 so as to cause the forward, distal, displacement of carriage 302. During this time period, motor controller 234 monitors the signals from the Hall-effect sensors internal to the motor 224. The controller 234 maintains the count in the counter that is representative of the total degrees of rotation of output shaft 542. In some constructions of the invention, each incremental count associated the rotation of the motor rotor that results in the distal displacement of the motor rotor is a positive incremental count. Each incremental count associated with the rotation of the rotor resulting in the proximal movement of the carriage is a negative incremental count. As a result of the displacement of the carriage 302, sensor 566 is advanced towards the distal of the two magnets 556 mounted to the handle 502. As a result of the movement of the sensor 566 towards the distal magnet 566, the output signal from the sensor changes.

During this displacement of the carriage 302, controller 234 forwards to controller 120 the digitized representation of the signal output by Hall-effect sensor 566. Also forward from controller 234 to controller 120 during this process is the cumulative count data representative of the rotational position of the motor rotor.

Controller 120 compares the data from the counter integral with controller 234 to a first threshold value. This first threshold value is a signal level representative of the signal Hall-effect sensor 566 outputs when the sensor 566 is in a defined position along handle 502. This position of the carriage 302 can be considered the distal homing position. When the signal from sensor 566 reaches this first threshold level, controller 120 directs controller 234 to terminate the application of energization signals to the motor 224. This stops the distal advancement of the carriage 302. Controller 120 stores the current cumulative count value from the counter.

Controller 120 then directs motor controller 234 to apply energization signals are then applied to motor 224 to cause the motor to displace carriage 302, proximally. During this displacement of the carriage 302, controller 234 generates negative incremental counts representative of the degrees through which the rotor is rotated. These negative counts, when applied to the counter, cause the cumulative count to decrease. The cumulative count stored in the counter may decrease to zero or to a negative number. During this displacement of the carriage 302, motor controller 234 again forwards the digitized representations of the output signal from Hall-effect sensor 566 and the data in the counter to controller 120.

The motor 224 is actuated so as to cause carriage 302 to move along handle 502 to a proximal homing position. As a consequence of the displacement of carriage 302, the signal output by the Hall effect sensor 566 changes levels as it moves away from the distal magnet 556 and toward the proximal magnet 556. Controller 120 compares the signal from Hall-effect sensor 566 to a second threshold level. This second threshold level is the level of the signal sensor 566 outputs when the carriage 302 is in the proximal homing position. When the signal comparison indicates that the carriage 302 is in the proximal homing position, controller 120 instructs controller 234 to terminate actuation of the motor 224. At this time, controller 120 also stores the count data from the counter internal to the controller 234.

At this time, the controller 120 has stored as data the cumulative counts representative of the angular position of the motor rotor needed to displace the carriage 302 first to the distal homing position and then to the proximal homing position. The absolute difference between these two counts is calculated. This difference is divided by two. This value represents the number of counts, through which the rotor integral with motor 234 must be cycled from its current position in order to center carriage 302 to the home position on handle 502. For example, in this process, computer may receive indication that: when the carriage 302 was in the distal homing position, the count value was 250; and when in the proximal homing position, the count value was −148. The difference between these count values is 398. One half this difference is 199.

Once this displacement count is calculated, controller 120 adds the value to the current count value. In the present example −148+199=51. This number is referred to as a target position. During the homing process, this target position is a positive or negative number equal to the cumulative count representative of the angular position the rotor integral with motor 234 should rotate to cause the displacement of carriage 302 to the axis Z home position. Controller 120 forwards this target position to motor controller 120. The motor controller 234 in turn, applies energization signals to the motor 224 so as to cause the rotor to rotate towards this count represented by the target position. During the resultant rotation of the motor rotor, the changing values of the motor Hall-effect sensors result in the output of counts that result in the incremental increase of the count value stored in the controller counter.

During this step, motor controller 234 compares the cumulative count stored in the counter to the count represented by the target position. When these two values are equal, controller 234 terminates the application of energization signals to motor 224. It should be understood that this rotation of the motor rotor and, by extension, lead screw 516 results in the displacement of carriage nut 552 along the lead screw 516. This movement of nut 552 is what moved the carriage 302 and the cutting accessory 202 to their home positions along the axis Z.

Motors 220 and 222 are actuated in a like manner to position the cutting accessory 202 in the home positions along the X- and Y-axes. Specifically, motor 220 is actuated to pivot link 316 between opposed upper and lower homing positions. During this process, the signal from Hall-effect sensor 392 varies as a result of the displacement of magnets 380. The digitized representation of this Hall signal as well as the count value from controller 230 is output to controller 120. The signal from Hall-effect sensor 392 is compared between two threshold signal levels to determine when the link 316 reaches the threshold positions. The differences in the cumulative counts from the motor rotor when the link 316 is in these two positions is determined. The difference in cumulative counts is divided in two. The resultant quotient is added to the current count value to produce a target position. This target position is a positive or negative number equal to a targeted cumulative count. This targeted cumulative count is proportional to the angular position to which the motor rotor needs to be rotated to in order cause the movement of link 316 to its home position.

The target position is output from controller 120 to controller 230. Controller 230 applies energization signals to the motor 220 that results in the rotation of the motor rotor. This rotation of the rotor results in the count maintained by the counter internal to the controller 230 reaching the cumulative count of the target position. Once the controller 230 determines the cumulative count and equals the target position, the controller 230 terminates the application of energization signals to the motor 220. The rotation of the lead screw 336 and resultant displacement of nut 376 cause link 316 to pivot to its home position. This pivoting of the link 316 to the home position, in turn, causes the like pivoting of the cutting accessory 202 to its home position along the X-axis.

To move cutting accessory 202 to its home position on the Y-axis, motor 222 is actuated to pivot link 416 between opposed right and left homing positions. During this process, the signal from Hall-effect sensor 492 varies as a function of the movement of magnets 480 to/from the sensor 492. During this homing process, controller 232 provides controller 120 with: the digitized representation of the output signal from Hall-effect sensor 492; and the count value maintained by the controller 232 as a result of the rotation of the motor rotor. By way of example, motor 222 is initially actuated to cause link 416 to pivot to first pivot to the left homing position. Controller 120 compares the signal from Hall-effect sensor 492 to a first threshold level. This comparison is performed to determine when link 416 reaches the left homing position. Motor 222 is then actuated to pivot the link 416 towards the right homing position. Controller 120 recognizes that the link 416 is in this second homing position when the signal from Hall-effect sensor 492 reaches a second threshold level.

Controller 120 then computes the difference in count values from when the link 416 was in the right and left homing positions. This difference in count values is divided by two. The resultant quotient is added to the present cumulative count. This sum is a count value representative of the angular position to which the rotor integral with motor 222 needs to rotated to center link 416 in its home position. This count value is added to the current count value associated with the rotor integral with motor 222. Controller 120 outputs this target position to controller 232.

In response to receipt of this target position, controller 232 applies energization signals to the motor 222 that result in the rotation of the rotor. More specifically, the rotor is rotated so that the Hall-effect sensors integral with motor 222 output counts that result in the incrementing or decrementing of the cumulative count to the target position. Once controller 232 determines that the cumulative count equals the target position, the computer terminates the application of energization signals to motor 222. During this process, the rotation of the motor rotor and lead screw 436 resulted in the displacement of nut 476 and the pivoting of link 416. The link 416 is pivoted to its home position which results in a like pivoting of the cutting accessory 202 to the cutting accessory home position along the Y-axis.

Each controller 230, 232 and 234 informs controller 120 of when the count of the rotor associated with the controller reaches the target position. Controller 120 accepts these state data as an indication that the cutting accessory 202 is in the home position. Once the cutting accessory 202 is centered on the X-, Y- and Z-axes, controller 120 zeros out the counters internal to the motor controllers 230, 232 and 234 that maintain the rotor count values.

Once the cutting accessory 202 is in the home position, a navigation pointer may be used to determine the location of the distal end of the cutting accessory 202, bur head 204. Thus, the system 100 knows the position of the bur head 204 in the home position and its relation to the position and orientation of the hand-held portion. Accordingly, when the hand-held portion is moved by the user and its position and orientation is tracked using tracker 114, the system 100 also tracks the position of the bur head 204. In other versions of the invention, as a result of prior calibration processes, the position of the distal end of the cutting accessory 202 relative to the instrument 200 is assumed to be known.

Once registration, calibration, and homing (if used) are complete, the navigation unit 108 is able to determine the spatial position of the bur head 204 with respect to the target bone 102 and the target volume 104. The instrument 200 is ready for boundary constrained cutting of the target volume of material 104 in step 816.

V. Instrument Control

After the homing process, control by controller 120 of the instrument 200 are based on (1) the position and orientation data from the navigation computer 112; (2) the cumulative count data from controllers 230, 232, 234; and three signals indicating the extent to which trigger 208 is actuated.

As represented by FIG. 56, surgical instrument 200 is designed to allow the displacement of the cutting accessory 202 that results in the displacement of bur head 204 in each of the X-(pitch), Y-(yaw) and Z-axes by at least +/−0.2 inches (+/−0.508 cm). Said differently, the distal tip or bur head 204 of the working portion is capable of a total displacement of at least 0.4 inches(1.016 cm) in each of the plurality of degrees of freedom. In another embodiment, for example, the distal tip 204 of the working portion, e.g., the bur head 204, is capable of a total displacement of at least 0.2 inches (0.508 cm), i.e., +/−0.1 inches (+/−0.254 cm) in each of the plurality of degrees of freedom. In other embodiments, for example, the distal tip of the working portion is capable of total displacement of at least 0.5 inches (1.27 cm), i.e., +/−0.25 inches (+/−0.635 cm); at least 1.0 inches (2.54 cm), i.e., +/−0.5 inches (+/−1.27 cm); at least 1.5 inches (3.81 cm), i.e., +/−0.75 inches (+/−1.905 cm); at least 2.0 inches (5.08 cm), i.e., +/−1.0 (+/−2.54 cm); at least 2.4 inches (6.096 cm), i.e., +/−1.2 inches (+/−3.048), or at least 3.0 inches (7.62 cm), i.e., +/−1.5 inches (+/−3.81), or more. In many versions of the invention, the displacement of the bur head 204 along the X axis is equal to the displacement along the Y axis which is equal to the displacement along the Z axis.

The normal operating position of the cutting accessory 202 is the home position. The range-of-motion data provided above is given with respect to the bur's center. In many versions of the invention, when the bur head 204 is in the home position, the bur head 204 is able to travel an equal distance, up/down, right/left, proximal/distal along axis, respectively the X-, Y- and Z axis. If the potential displacement of the bur head 204 is equal along each axis, the bur head 204, when in the home position can be considered to be in the center of the sphere that represents the range of motion defined by the control system 100. The outer perimeter of the sphere is the outer perimeter of the potential movement of the bur head 204 away from the home position. As discussed below instrument controller 120 moves the bur head 204 away from the constraint boundary 111 when the bur head 204 intersects or crosses the boundary 111. This deflection could be along any one, two or three of the axes along which the cutting accessory 202 can be displaced.

Figure 59:
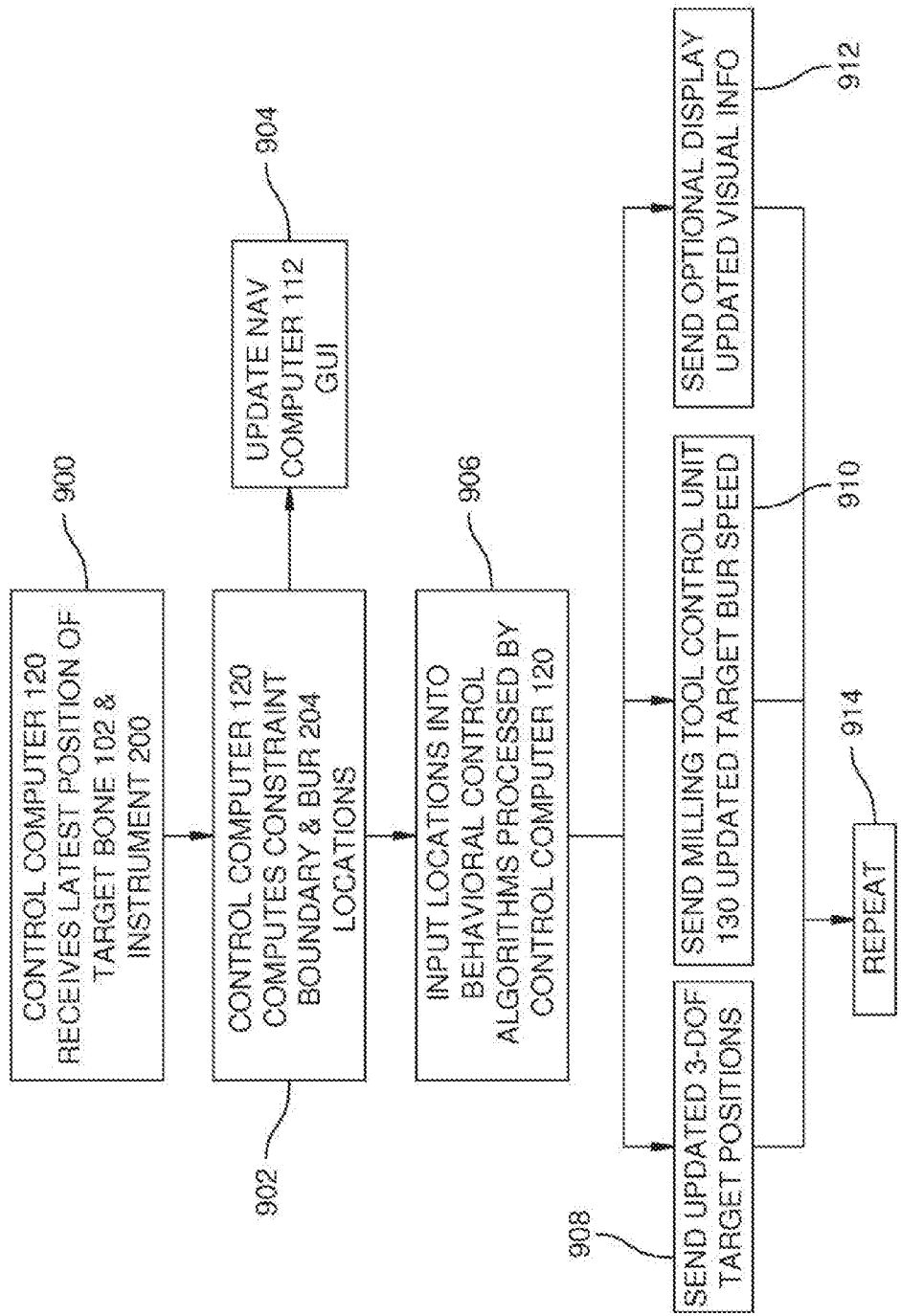
FIG. 59 is a flow chart showing the operational steps taken during use of the system.

Referring to FIG. 59, a sample flow chart of steps taken by the instrument controller 120 to control the instrument 200 is shown. In step 900, the latest positions of the target bone 102 and the instrument 200 are transmitted from the navigation computer 112 to the instrument controller 120 over the data connection 121. Using these data, the instrument controller 120 determines the locations of the working boundary, the constraint boundary 111 and bur head 204 in free space, step 902. As part of step 902, the relative location of the bur head 204 to the constraint boundary 111 is also computed. In step 904 the instrument controller 120 updates the navigation GUI (display 113) with the position of the bur head 204 relative to the tissue to which the bur head 204 is applied. An indication of the location of the working boundary 106 may also be presented.

Regardless of the location of the bur head 204 to the constraint boundary 111, when the bur head 204 is pressed against tissue, the bur head 204 is exposed to the resistance of the tissue. This resistance is in opposition to the force the practitioner places on the bur head 204 as a result of the practitioner moving the instrument 200 forward. The resistance of the tissue essentially is a force imposed on the cutting accessory 202 in opposition to the forward force placed on the cutting accessory 202 by the practitioner. This force is significant when the tissue is a hard unyielding tissue such as bone.

As discussed above, lead screws 336, 436 and 516 and complementary nuts 376, 476, and 552, respectively, are finely threaded. This fine threading prevents the displacement of the associated nut 376, 476 or 552 when force is placed on the nut that is parallel to the longitudinal axis of the lead screw. By way of example, if the bur head 204 is pressed against a bone face so that the longitudinal axis of the cutting accessory 202 is normal to the bone face, the resistance of the bone becomes a back force against the cutting accessory 202. This back force is transferred through coupling assembly 207 and gimbal 304 to the carriage 302. By extension, this back force attempts to push carriage nut 552 proximally rearwardly. However, the fine pitch engagement of nut 552 over lead screw 516 inhibits, locks out, this proximal displacement of nut 552. This locking out of nut 552 from rearward movement results in a like locking out of rearward movement by carriage 302 and, therefore, the cutting accessory 202. It should likewise be appreciated that this locking out of the movement of lead screw 516, likewise inhibits back driving of the output shaft 542 or rotor of motor 224.

Similarly, the fine pitch engagement of nut 376 over lead screw 336 locks out unintended displacement of cutting accessory 202 along the X-axis. The fine pitch engagement of nut 476 over lead screw 436 locks out unintended displacement of cutting accessory 202 along the Y-axis. Again this locking out of the lead screws 376 and 476 prevents the back driving of, respectively, motors 220 and 222.

In step 906, the relative location of the centroid of the bur head 204 to constraint boundary 111 is evaluated by the controller 120 to determine if action needs to be taken, i.e., moving the bur head 204, changing the rotational speed of the bur head 204, stopping the bur head 204, etc. Display 1402 (see below) can also be updated by the instrument controller 120.

As depicted by step 908, instrument controller 120 sends instructional data packets to the motor controllers 230, 232 and 234. These instructional data packets include the target position for the rotor of the motor 220, 222 and 224 with which the controller is associated. Here, each target position is positive or negative number representative of a targeted cumulative count for the associated motor rotor. This targeted cumulative count is proportional to a target angular position for the motor rotor from the home position for the rotor integral with the motor 220, 222, or 224 controlled by the controller.

Instrument controller 120 generates and sends these instructional data packets to each motor controller 230, 232 or 234 at the rate one packet every 0.5 to 4 milliseconds. In many versions of the invention, each controller 230 and 232 and 234 receives an instruction packet at least once every 2 milliseconds.

As represented by step 910, instrument controller 120 also selectively regulates the speed of the instrument based on the relative location of the bur head 204 to the constraint boundary 111.

In step 912, visual feedback is provided to surgeon by a display located on the instrument 200 and separately wired to the instrument controller 120 with data connection 1002 to transmit and receive data to and from the instrument controller 120.

The steps are repeated at step 914.

Figure 60:
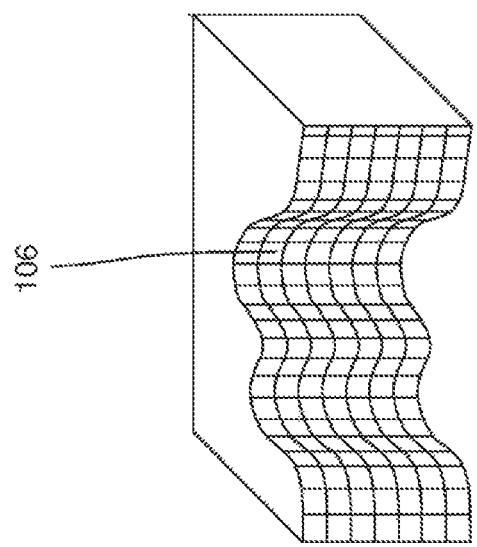
FIG. 60 is a perspective view of a surface model of a work boundary.
Figure 61:
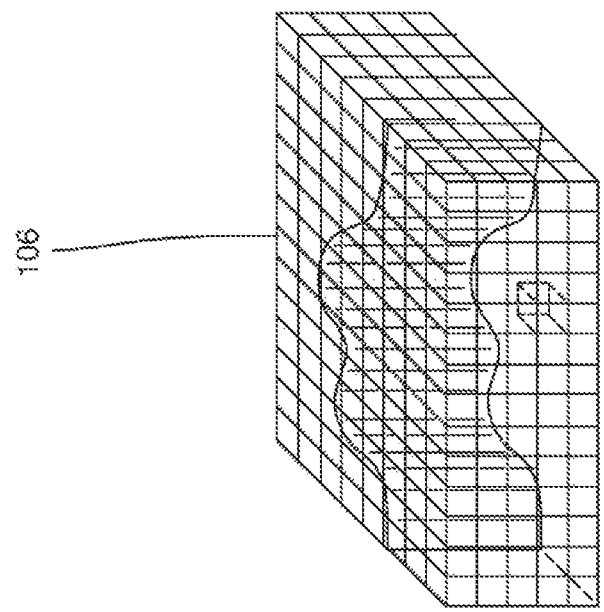
FIG. 61 is a perspective view of a volume model of a work boundary.

Referring to FIGS. 60 and 61, the work boundary 106 can be modeled as surfaces (FIG. 60) or volumes (FIG. 61). When surfaces are used to model the work boundary 106, the surfaces can be tessellated into triangles, quadrilaterals, NURBS, etc. On the other hand, when the work boundary 106 is modeled as volumes, the volumes can be represented by cubical voxels or other parallelepiped-shaped voxels.

Figure 62:
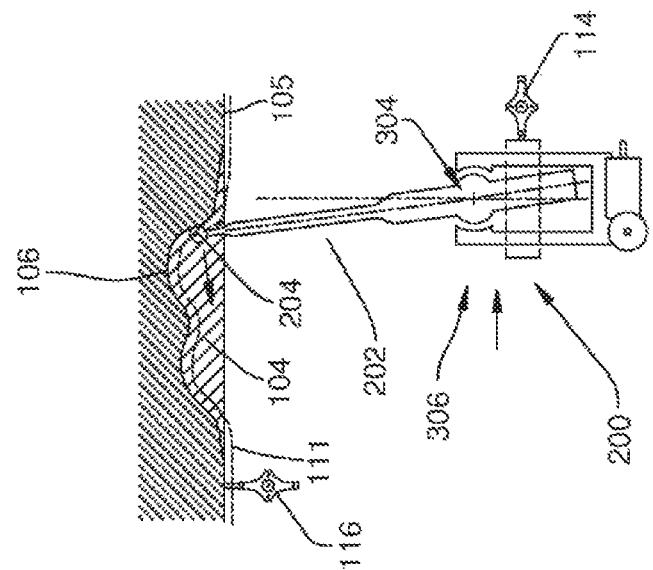
FIG. 62 is an illustration showing a bur head outside of the work boundary.
Figure 63:
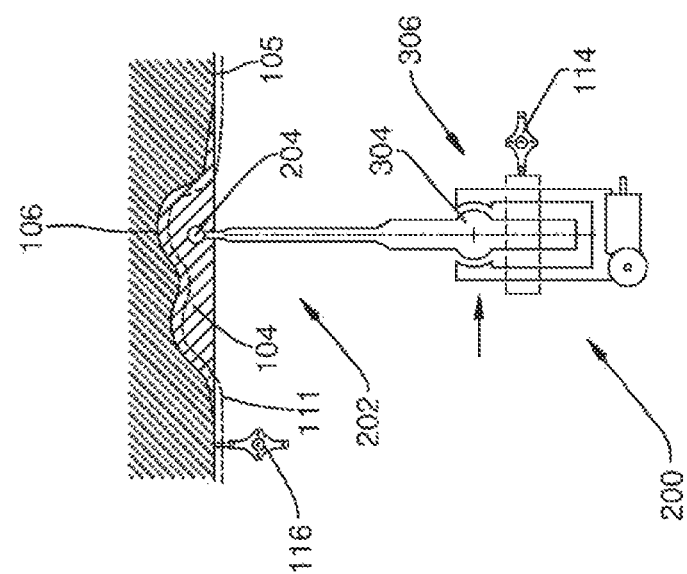
FIG. 63 is an illustration showing the bur head at the work boundary.

Referring to FIGS. 62-63, operation of the instrument 200 with respect to the work boundary 106 and constraint boundary 111 is shown. Here, surgical instrument 200 is operated in what is referred to as a passive mode. In the passive mode, system 100 monitors the position of the bur head 204 relative to the working boundary 106. When the bur head 204 approaches or intersects this boundary 106 system 100 deflects the position of the cutting accessory 202 and/or attenuates the speed of the motor 206.

In FIG. 62, bur head 204 is spaced away from the constraint boundary 111. At this time controller 120 maintains the bur head 204 in the home position. When the surgical instrument 200 is in this state, instrument controller 120 continually sends data packets indicating target positions of zero to the motor controllers 230, 232 and 234. Assuming the cutting accessory 202 is already in the home position, the current cumulative counts maintained by the controllers 230, 232 and 234 are already zero. Given that the target positions equal the current zero value cumulative counts, controllers 230, 232 and 234 do not actuate motors 220, 222 and 224, respectively. Cutting accessory 202 is thus held in the home position.

As the bur head 204 advances against the tissue, the head 204 eventually contacts the working boundary 106 as represented by FIG. 63. Instrument controller 120, through connection to the navigation system 108, recognizes that the bur head 204 is in this position as a consequence of the determination that the centroid of the bur head 204 has intersected the constraint boundary 111. As a consequence of the bur head 204 being in this position, the instrument controller 120 calculates a new position, a deflected position, for the bur head 204 that is normal to the constraint boundary 111. This deflected position is spaced from the home position. Specifically, using algorithms and other processes, the instrument controller 120 calculates the deflected position for the bur head 204. This deflected position is calculated with reference to the reference frame of the instrument 200. This deflected position is quantified as a set of distances along the X-, Y- and Z-axes relative to the home position.

Instrument controller 120 then generates a set of target position counts to which the rotors integral to the motors 220, 222 and 224 must rotate to reposition the cutting accessory 202 at the deflected position. The target motor rotor angular positions are determined based on the following relationships:

1) During the up/down and right/left pivoting of the cutting accessory 202, the cutting accessory 202 functions as a lever pivoting about the center of gimbal 304. One end of this lever is bur head 204. The opposed end of this lever is the nut 376 or 476. This is because the displacement of the nut 376 or 476 is responsible for, respectively, the up/down or right/left pivoting of the cutting accessory 202. There is approximately a first order relationship between the extent to which each nut 376 and 476 needs to be displaced from the home position of the nut in order to pivot the bur head 204 in the X- or Y-axes from its home position. In order to displace the cutting accessory 202 along the axis Z, carriage 302 and by extension carriage nut 552 must be displaced forwardly or rearwardly by the same distance. Accordingly, there is a linear relationship between the displacement of nut 552 from its home position and the displacement of the bur head 204 along the axis Z. (As a consequence of the pivoting of the cutting accessory 202, in either the X- or Y-axis, there is some displacement of the bur head 204 from the home position in the axis Z. This displacement is accounted for in the algorithms that are used to determine the individual X-, Y- and Z-axes displacements of the bur head 204 in order to position the bur head 204 in the deflected position)

2) There is a first order relationship between the degrees of rotation of each lead screw 336, 436 and 516 the linear displacement of the nut, respectively, nuts 376, 476, and 552, fitted to the lead screw.

3) There is a first order relationship between the degrees of rotation of the rotor of each motor 220, 222 and 224, and the lead screw, respectively, lead screw 336, 436 and 516 and geared to the rotor.

4) There is first order relationship between the degrees through which the rotor of each motor 220, 222 and 224 rotates and the cumulative count representative of that position that is maintained by the associated controller 230, 232 and 234, respectively.

Based on the above relationships, once controller 120 determines the deflected positions for the bur head 204 on the X-, Y- and Z-axes, the computer determines the target position for each motor rotor. Controller 120 transmits packets to the motor controllers 230, 232 and 234 containing these target positions. Based on these targets position, each motor controller 230, 232 and 234 applies the appropriate energization signals to the associated motor 220, 222 and 224, respectively. These energization signals cause the rotation of the rotor that results in the repositioning of the carriage 302, link 316, and link 416 that displaces the bur head 204 into the intended deflected position.

In terms of time, it typically takes approximately 40 ms to displace the bur head 204 from the home position that to a deflected position that is approximately 2 cm away from the home position. During this time period the practitioner is still applying a forward force on the handpiece 200. Thus, often, rather than the bur head 204 being totally withdrawn away from the surface of the bone to which the bur head 204 is applied, the bur head 204 remains pressed against the bone. However, as a result of the deflection of the bur head 204, the bur head 204 only minimally, if any, crosses the working boundary 106. If the bur head 204 does cross the working boundary 106, it only goes beyond the boundary 106 by a distance that is within acceptable tolerance levels for the shape to which the tissue is being formed. Instead, as a result of the deflection of the bur head 204 along a line perpendicular to the constraint boundary 111, the bur head 204 remains in contact with bone at the working boundary 106. Thus, while the bur head 204 continues to remove tissue, the tissue removed is in the section of the bone from which the practitioner wants to remove tissue.

When the system 100 is operated in the passive mode, the application of energization signals to the motor 206 is jointly regulated by the controller 120 and instrument driver 130. Initially, by setting controls on the instrument driver 130, the surgeon establishes a maximum speed for the motor 206. Throughout the time the system 100 operates in the passive mode, controller 120 sends instruction packets to the instrument driver 130, the process of step 908. These packets indicate the percentage of the surgeon-established maximum speed at which the motor 206 should run. As long as controller 120 determines there is no need to deflect the cutting accessory 202, these instruction packets indicate that the motor should run at 100% of the established maximum speed.

As long as these instruction packets are received, whenever instrument driver 130 receives an indication there has been depression of the trigger 208, the driver outputs energization signals to cause the motor 206 to run at the maximum speed. Instrument driver 130 takes this action even if the depression of the trigger is such that, if the system was operated in the below-discussed manual mode, the driver would output energization signals that would cause the motor 206 to run at a speed below the maximum speed.

Figure 64:
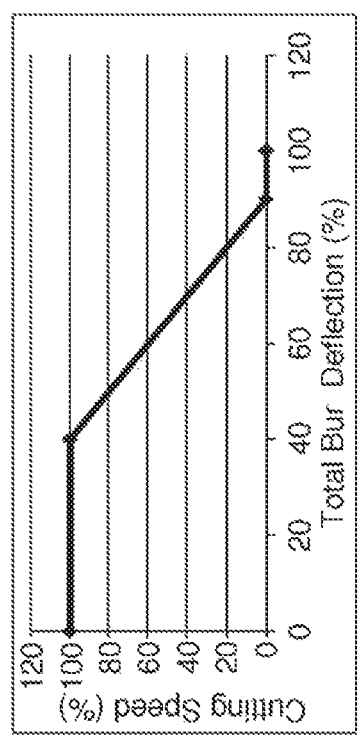
FIG. 64 is a chart of a speed profile of the bur with respect to bur deflection.

In the version of the invention illustrated by FIG. 64, controller 120 causes the speed of the motor 206 to be selectively attenuated as a function of the extent to which bur head 204 is deflected away from the home position, i.e., the control system 100 tracks deviation of the working portion from the home position during the medical procedure. Here, controller 120 does not generate instructions to attenuate the motor speed as long as the computer determines there is no need to deflect the bur head 204 from the home position. In other words, the working portion is capable of operating at the maximum cutting speed when the working portion is in the home position and the control system 100 attenuates the cutting speed of the working portion when the working portion deviates from the home position. Specifically, as discussed further below, when the working portion crosses a virtual boundary, e.g., work boundary 106 defined in control system 100, the working portion deviates from the home position to deflect the working portion away from the virtual boundary. Said differently, the working portion deflects away from the work boundary 106 of the tissue to prevent removal of tissue beyond the work boundary 106.

The control system 100 attenuates the cutting speed of the working portion based on this deviation. Speed control of the motor 206 is based on several factors including 1) the maximum speed set by the practitioner, 2) the depression of trigger 208 by the practitioner, 3) the percentage of total deflection, and 4) the shape of the speed profile, i.e., FIG. 64. When it is necessary for the computer to determine a deflected position for the bur head 204, controller 120 determines the percentage of the deflection of the bur head 204. This deflection is based on a proportional comparison of the necessary diversion to the maximum possible diversion of the bur head 204. In one version of the invention, the maximum possible diversion is the distance from the home position to the outer range of the total possible deflection of the cutting accessory 202. Along any one of the individual X-, Y- and Z-axes, this distance may be less than the actual possible maximum diversion of the cutting accessory 202 along that axis.

As long as the calculated necessary diversions of the bur head 204 are below a set percentage of the maximum possible deflection, controller 120 continues to not generate any instructions to attenuate the motor speed. Once the calculated deflection of the bur head 204 is above a threshold percentage of the maximum deflection, controller 120 starts to attenuate motor speed. In the example of FIG. 64, the threshold percentage is 40% of the maximum deflection. When the system 100 is in this state, controller 120 transmits instruction packets to driver 130 that indicate the motor 206 is to be driven at less than 100% of the established maximum speed. These instruction packets direct console 130 to cause energization signals to be applied to the motor 206 that result in the motor 206 running at a speed that is less than 100% of the user-set speed for the motor 206. Controller 120 determines the percentage of the user-set speed the motor 206 should operate at as a function of the percentage of the calculated deflection of the bur head 204 relative to the maximum possible deflection. In the speed profile of FIG. 64, when the calculated deflection reaches 90% of the maximum possible deflection, controller 120 instructs the console 130 to turn off the motor 206. As the deflection increases from 40% to 90% of the maximum possible deflection, controller 120 sends instruction packets to the console 130 indicating that the motor speed should be decreased linearly from the 100% of the user-set speed to the motor off state.

In some versions of the invention console 130 asserts signals to the instrument motor 206 that results in the active braking, active deceleration of the motor 206 to the attenuated speed. This braking is the primary force that decelerates the cutting accessory 202. A secondary force that decelerates the cutting accessory 202 is the resistance of the bur head 204 against the tissue being cut.

In one version of the invention, controller 120 sends instruction packets to console 130 indicating the extent to which the motor speed should be attenuated at a frequency of between 500 and 2,000 Hz. These instruction packets are sent even when the bur head 204 is in position in which it is not necessary to slow the speed of the motor 204.

The disclosed navigation system that determines the relative position of the instrument 200 to the working boundary 106 is exemplary, not limiting. For example, some navigation systems have trackers that reflect light. Still other navigation systems include trackers with sensors that monitor light or electromagnetic fields emitted by fixed sources.

Controller 120 determines the relative position of the bur head 204 to the constraint boundary 111. In one version of the invention, instrument controller 120 performs this evaluation at a frequency of 1000 Hz. Many navigation systems do not provide navigation data indicating the relative position of the instrument 200 to the bone to which the instrument is applied at this frequency. Controller 120, compensates for the relative slow updating of data from the navigation system. One method of performing this compensation is to first use the data from the navigation system to determine the positions of the trackers. These positions are determined for at a number of times in order to determine averaged positions. Based on these averaged tracker positions, the relative position of the distal end of the cutting accessory 202 to the working boundary is determined. These averaging processes make it possible to generate averaged indications of the position of the cutting accessory 202 relative to the working boundary 106 at times between the times of actual tracker positions are measured.

Each time controller 120 makes the above evaluation, the evaluation is made based on the assumption that the bur head 204 is in the home position. Thus, in this evaluation, the fact that the bur head 204 may be actually be in a deflected position is disregarded. Instrument controller 120 determines, based on each of these evaluations, what, if any, the appropriate deflected position is for the bur head 204. Thus, if, as a result of one these evaluations, it is determined that the bur head 204 has crossed the constraint boundary 111, controller 120 may determine that the deflected position for the bur head 204 is even further spaced from the home position than the current deflected position. Alternatively, instrument controller 120 may determine that, owing to the current relative position of the bur head 204 to the constraint boundary 111, the appropriate deflected position for the bur head 204 is closer to the home position than the current deflected position. At the end of either determination, controller 120 generates target positions for the rotors integral to motors 220, 222 and 224. These target positions are transmitted to the motor controllers 230, 232, 234. If the new target positions are different from the previous target positions, motor controllers 230, 232, 234 apply energization signals to the motors 220, 222, and 224, respectively, in order to force displacement of the bur head 204 to the newly-determined target position.

As mentioned above, once instrument controller 120 determines it is appropriate to reposition the bur head 204 in a deflected position that is a defined distance away from the home position, the controller causes the speed of the motor 206 to be attenuated. As a consequence the drop off of motor speed, the pitch of the noises generated by the instrument 200 changes. One reason is that the fall off in motor speed invariably results in a change of characteristics of the noise emitted by the motor 206. Should the bur head 204 be pressed against the bone, the pitch of the noise generated as a consequence of this metal-against-bone contact also changes. These changes in sound provide the practitioner feedback that the bur head 204 is approaching or at the working boundary 106.

The above aural feedback the practitioner receives from the motor 206 is the reason in one embodiment system 100 is configured so that the user may not attenuate the motor 206 from the initially set maximum speed. If the practitioner is, during the procedure, allowed to so reduce the speed of the motor 206, it may be difficult for the practitioner to aurally perceive an attenuation in motor speed as a consequence of the cutting accessory 202 approaching or breaching the working boundary 106.

Another source of feedback to the practitioner is that, as a result of the slowing of the instrument the vibration of the instrument in the practitioner's hand changes. As a result of this feedback, the practitioner is placed on notice that, to avoid having the bur head 204 remove tissue beyond the working boundary 106, it is necessary to reposition the bur head 204 and/or adjust the force applied to the instrument to press the bur head 204 against the bone.

Another feedback source the practitioner has regarding the position of the bur head 204 relative to the working boundary 106 is the relative position of the cutting accessory 202 to the rest of the handpiece. Visually moderate to large displacement of the cutting accessory 202 from the home position is readily apparent. The movement of the cutting accessory 202 to one of these displaced positions therefore serves as a visual cue to the practitioner that the bur head 204 is at or approaching the working boundary 106.

There may be circumstances in which it appears that the position of the instrument is not being reset sufficiently to avoid having the bur head 204 remove tissue from beyond the working boundary 106. It should be understood that when the instrument is in this position, it is already in the state in which the cutting accessory 202 is deflected from the home position. In this state though, the diversion of the cutting accessory 202 is less than the maximum possible diversion. In this case, the further necessary diversion of the cutting accessory 202 would exceed the maximum allowed diversion. In the example depicted in FIG. 64, the maximum allowed diversion is 90% of the total diversion. If controller 120 determines it is necessary to so reposition the bur head 204 in order to avoid having the bur head 204 move beyond the working boundary 106, the controller 120 sends an instructional packet to console 130 directing the console 130 to terminate the application of energization signals to the motor 206.

The stopping of the instrument motor 206 has two end effects. First, the stopping of the motor 206 prevents the bur head 204 from cutting tissue beyond the working boundary 106. Secondly, the stopping of the motor 206 provides the practitioner notice that, to avoid, cutting tissue outside of the working boundary 106, it is necessary to reposition the instrument 200. Repositioning of the instrument 200 away from the working boundary 106 results in the continued application of energization signals to the motor 206.

After the bur head 204 is deflected, the practitioner continues to reposition the surgical instrument. As a consequence of this repositioning, controller 120 often determines that the instrument is positioned so that, if the bur head 204 is in the home position, the bur head 204 will be spaced from the constraint boundary 111. When this condition occurs, controller 120 sends instruction packets to the motor controllers 230, 232 and 234, with target positions that indicate that the motor rotors should be in the home angular positions. The count values in these instruction packets are zero. In response to the receipt of these instruction packets, the motor controllers 230, 232 and 234 selectively actuate motors 220, 222 and 224, respectively. The motors 220, 222, and 224 are actuated to return carriage 302 and links 316 and 416 back to their home positions. This displacement of the carriage 302 and the links 316 and 416 results in a like return of the bur head 204 to the home position.

System 100 can also control the position of the cutting accessory 202 in what is referred to as an "active" mode. In the active mode, controller 120 does not deflect the cutting accessory 202 away from a constraint boundary 111. Instead, the controller 120 actively directs the cutting accessory 202 to a path along which tissue is to be removed. For example, the system may be operated in the active mode to cut a bore or other void space in the bone that is located along a specific longitudinal axis.

To form a void space in the active mode, the longitudinal axis of the void space is initially defined and loaded into the controller 120. An extension of this axis is plotted to extend out of the bone. The practitioner, holding the instrument so that the bur head 204 is just above the location for the opening into the void space, brings the instrument into approximate alignment with this axis. This task is performed by reference to the image presented on the surgical navigation display. This image includes a depiction of the axis along which the void space is to be formed.

Initially, the controller 120 determines if the distal end of the cutting accessory 202 is within a set space above the surface of the bone in which the opening is to be cut. In some applications of this invention, this distance is approximately 0.5 to 1.5 cm. Controller 120 then determines if the cutting accessory 202 is within a given radius, a snapping radius of the location where the void is to be formed. This radius is typically less than the maximum deflection radius of the cutting accessory 202. If the instrument 200 is not so positioned, the controller 120 causes a message to be presented on the navigation display that it is necessary for the practitioner to reposition the instrument. If controller 120 determines that the cutting accessory 202 is within the snapping radius, the computer deflects, snaps, the cutting accessory 202. Specifically, controller 120 instructs the motor controllers 230, 232, 234 to actuate the instrument motors 220, 222 and 224, so that the distal end of the cutting accessory 202 is positioned immediately above the location at which the void space is to be formed. During these steps of the process, controller 120 sends instruction packets to console 130 that prevent the operation of the instrument motor 206.

The practitioner's continued movement of the instrument thus results in the distal end of the cutting accessory 202 being pressed against the surface of the tissue at the location in which the void is to be formed. Again, at this time, the practitioner is not able to actuate the instrument motor 206. Also, images are presented on the navigation display that indicate the relative location of the instrument to the axis along which the void space is to be formed.

Once the instrument 200 is so positioned, the practitioner, based on the images of the instrument relative to the target axis, orientates the instrument. As a consequence of the initial orienting of the instrument, controller 120 returns cutting accessory 202 to the home position. The practitioner continues to orient the instrument. Specifically, based on the images indicating the orientation of the cutting accessory 202 relative to the target axis, continues to orient the accessory until it is in registration over this axis.

As a consequence of the monitoring of the information on the navigation screen, the practitioner becomes aware of the fact that the cutting accessory 202 is aligned on the axis along which the void space is to be formed. Once the controller 120 determines that the instrument 120 is in this state, the controller starts to send instruction packets to console 130 indicating that the instrument motor 206 can be actuated. The practitioner at this time depresses trigger 208 to actuate motor 206. The cutting accessory 202 is therefore energized so as to cause the formation in the tissue of the intended void space at both the target location and along the target axis.

Once the practitioner starts to form the void, controller 120 appreciably restricts the practitioner's ability to apply the cutting accessory 202 off the target axis. For example, in some implementations of the invention, as soon as the navigation system provides any indication that the cutting accessory 202 is moving off axis, controller 120 immediately instructs the console 130 to terminate the application of energization signals to the instrument motor 206. Controller 120 takes this action without performing any deflection of the cutting accessory 202. This reduces the likelihood that, as the depth of the void space increases, the void space is formed along an axis that is off axis with the target axis. In some implementations of this feature of the invention, the acceptable variation of the misalignment of the cutting accessory 202 with the target axis may vary inversely as the depth of the void space being formed increases.

Controller 120 monitors the depth of the cut. In some versions of the invention, when it is determined that that the depth of the void space is between 0.1 and 2.0 mm of the target depth, controller 120 starts to deflect the cutting accessory 202. This particular type of deflection may just be the rearward retraction of the cutting accessory 202. As the carrier is deflected, controller 120 sends instruction packets to console 130 that causes for the slowing and then the stopping of motor 206. These process steps thus cause the resultant void space to be formed to the target depth.

In an alternative use of system 100 in the active mode, the system 100 displays prompts that direct the practitioner to position the handpiece so that bur head 204 is adjacent the surface of the tissue to be removed. This distance is less than maximum distance the bur head 204 can be deflected to from the home position. Typically, this distance is less than 20 to 80% of the total distance which the bur head 204 can be deflected.

Once the instrument 200 is so positioned, the instrument controller 120 sends instructions to the motor controllers 230, 232 and 234 that result in the diversion of the bur head 204 from the home position towards the tissue that is to be cut. The bur head 204 removes the tissue. During this process, the instructions controller 120 generates instructions regarding the displacement of the bur head 204, only result in the displacement of the bur head 204 towards the working boundary 106. Controller 120 does not send instructions that would result in the repositioning of the bur head 204 beyond the working boundary 106. Thus, in this process, the controller 120 sends the instructions that direct the bur head 204 to sculpt the bone into the desired shape.

In this process, the practitioner may move the instrument closer towards the bone being cut. In response to the controller 120 determining that the instrument is being so repositioned, the computer adjusts the extent to which the bur head 204 needs to be deflected to perform the desired tissue removal. In this readjustment of the position of the bur head 204, the bur head 204 may be reset to the home position. In situations where the instrument 200 is moved even closer to bone, controller 120 may then determine it is necessary to start deflecting the bur head 204 away the tissue being cut. Thus, an aspect of this active mode operation of the instrument may include the passive mode diversion of the bur head 24 in order to avoid removing tissue beyond the working boundary.

The above described operation of the system 100 alternating between the active and passive modes can be considered a hybrid mode operation of the system 100. The operation may be useful to form surfaces of the bone. These surfaces include surfaces located inwardly from the exposed face of the bone that define void spaces located within the bone.

The system 100 can also be operated in a manual override mode. In this mode the user overrides the ability of the motors 220, 222, 224 to re-position the bur head 204. In this mode the instrument 200 defaults to the home position and essentially become a fixed, stiff, burring tool. Elements of controlling the rotational speed of the burhead 204 could be maintained if desired (for example: cutting outside of the constraint boundary 111 could still be disallowed). A complete override would allow the user to use the trigger 208 to vary the rotational speed of the bur head 204 (in the active and passive modes, the trigger 208 is simply an on/off safety feature). This would essentially make the instrument 200 a conventional instrument because it would no longer be guided by the navigation unit 108.

It should be understood that when the instrument is operated in the above-described modes, the self locking features of the nuts on the lead screws prevent the unintended displacement, backdriving, of the bur head 204 from the home position.

The passive and active modes can be thought of as the two ends of a spectrum of possible operating modes (for surface machining), but variants are possible. For instance, the system 100 could operate in a passive mode with bur tip prediction. In this mode, the bur head 204 starts accelerating away from the work boundary 106 prior to actually reaching the work boundary 106. To do this, estimates of future positions of the bur head 204 are needed. In addition to positions, the speeds of both the target bone 102 and instrument 200 are outputted from the navigation unit 108 to the instrument controller 120 to predict the future positions of the bur head 204 relative to the bone 102 and instrument 200 and react accordingly. This mode utilizes knowledge of each motor's performance specifications (akin to knowing a motor's speed-torque curve). This variant of the passive mode increases the instrument's performance envelope (re-activity) and overall accuracy.

Another hybrid mode is adding a longer "sticking" time. In such a mode, the control system 100 is configured to control the actuators, e.g., motors 220, 222, and 224, to actively position the working portion at the boundary while the user moves the hand-held portion relative to the boundary such that the working portion is substantially maintained at the boundary independent of the movement of the hand-held portion. In essence, the bur head 204 acts like a magnet to a boundary only after the bur head 204 has begun "riding" on that boundary. This is accomplished by allowing the bur head 204 to travel beyond the "Home" position while the bur head 204 is pulled away from the boundary. This feature may be adjustable as a user preference.

Still another hybrid mode of operation is semi-autonomous cutting. In this mode, the control system 100 is configured to control the actuators to move the working portion relative to the hand-held portion such that the working portion autonomously follows a path defined in the control system 100 to remove the target volume of the material while the user substantially maintains the hand-held portion in a gross position relative to the target volume during the medical procedure. Here, the user grossly positions the bur head 204 and then holds the instrument 200 in a region of interest. The bur head 204 is then guided and moved based on signals from the instrument controller 120 to the controllers 230, 232, 234 to cut out the target volume of material 104 defined by the work boundary 106. The instrument 200, much like a CNC mill, would then execute a semi-autonomous run by following a prescribed path calculated by the instrument controller 120 or the user (or a path generated on-the-fly). The instrument path's coverage would be limited by the available range of motion (and the user's ability to hold the instrument 200 still).

Another hybrid mode of operation involves dithering in which the cutting accessory 202 is moved in controlled pattern. This pattern may be one that results in the bur head shaping the bone 102 so as to result the finished surface having a specific degree of smoothness. In a dithering operation, the cutting accessory 202 may be moved from the home position so as to cause the bur head 204 to: move in an orbital pattern; move in a figure-eight pattern; and/or oscillate along a defined arc. This dithering is performed parallel to the surface of the local boundary.

VI. Applications

Figure 65:
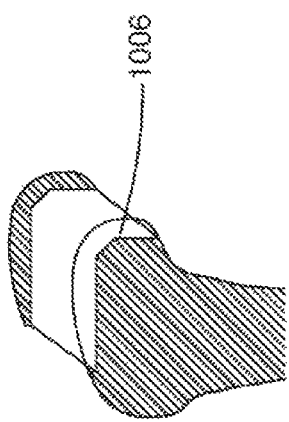
FIG. 65 is an illustration of an application of the invention for use in bone sculpting.

Referring to FIG. 65, one possible application for the system is for bone sculpting as described above. In essence, the removed bone provides a "negative" cavity 1006 for an implant (e.g., knee implant). The instrument 200 could also cut complex 3-D shapes (i.e. mirror symmetric features). Likewise, the instrument 200 could be used to shave/smooth-out jagged bone and deformities.

Figure 66:
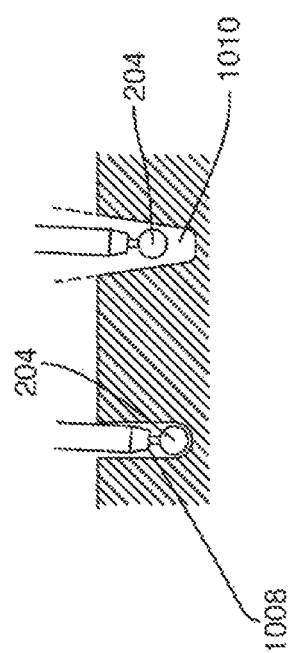
FIG. 66 is an illustration of an application of the invention for use in bore tunneling.

Referring to FIG. 66, the system 100 could be used for tunneling into bone, other tissue, or other materials. The instrument 200 can be configured to bore a straight hole 1008 that equals (or is slightly larger) than a diameter of the bur head 204. As FIG. 66 shows inverted cone constraint geometry 1010 could be defined for accessing various parts of the body (e.g., spine).

Figure 67B:
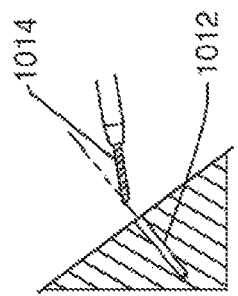
FIGS. 67A-67C are illustrations of an application of the invention for use in targeting/alignment.
Figure 67C:
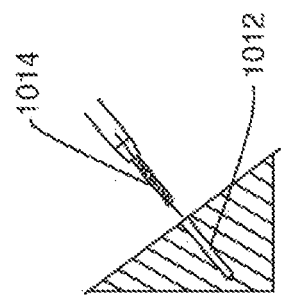
Figure 67A:
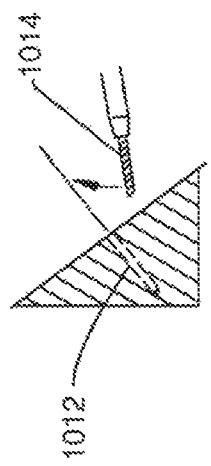

Referring to FIG. 67A-67C, use of the system 100 for targeting/alignment is shown. This allows a user (e.g., surgeon) to quickly locate a pre-planned or predefined location of a hole 1012 by "snapping" the tip of a drill bit 1014 to the hole's centerline (e.g., pre-drilling for pedicle screws). Once located, the display 1402, could then be used to properly align the axis of the drill bit 1014 (or other cutting accessory) to the axis of the desired hole 1012. With reference to screen shot of the display 1402 shown in FIG. 68, the display shows dots 1016 that indicate the alignment is off-axis 1018 and needs to be moved. The instrument 200 corrects for deviations in alignment as drilling is underway by changing the pitch, yaw, or translation along the axis Z of the drill bit 1014.

Referring to FIG. 69, the instrument 200 may be used for cutting, ablating, or other surgical procedure near soft tissues and nerves 1020 with the ability to avoid these delicate areas. In this application, pre-op imaging and pre-planning to create constraint boundaries to avoid these sensitive areas. In some embodiments, the instrument 200 can be combined with a nerve monitor to prevent damaging nerves. This mapping can be performed during the procedure as the need arises.

Referring to FIG. 70, the instrument 200 can be depth controlled. This allows the user to cut or drill to a specified depth (e.g., pedicle screws). The user, however, prevented from cutting too deeply or breaking thru other side of bone (e.g., bi-cortical screw). In this application, the work boundary is the depth surface of the bore.

Figure 71:
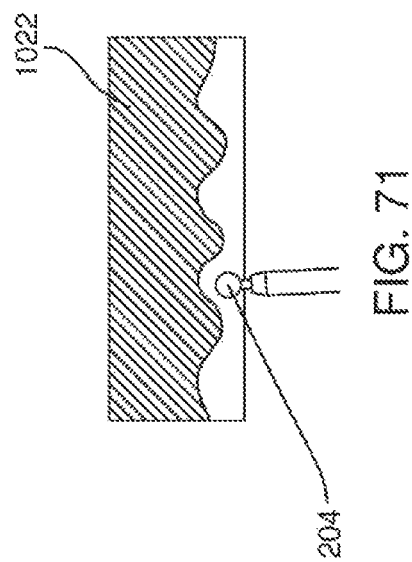
FIG. 71 is an illustration of an application of the invention for use in shaping implants.

Referring to FIG. 71, the instrument 200 can also be used for custom implant shaping. In this application, a bur or other shaping tool can cut non-bone objects 1022 to a specified shape (e.g., plastic implants). The system could also be configured to modify objects to conform and match surfaces previously created while sculpting or manually cutting with the instrument 200.

The system 100 and instrument 200 described herein are merely exemplary of the present invention. The invention could be utilized on several tissue types, including hard and soft tissues, for materials like plastic and metal, and for many different procedures, including, but not limited to cutting, ablating, drilling, general collision avoidance, and the like.

VII. Alternative Embodiments

The foregoing is directed to one specific version of system. Alternative versions of the system of this invention are possible. For example, instrument 200 can have a mechanism that vibrates (like an eccentric motor) while near a boundary, on boundary, or after exceeding a certain amount of deflection. This provides the user with further feedback that the distal end tip of the cutting accessory is approaching the boundary. Lights (e.g., LEDs) could be provided on the instrument 200, such as the handle 502 to provide visual indication of the proximity of the cutting accessory to the working boundary. For instance, a green signal=good, yellow=on boundary, red=problem/stop.

Features may be provided on the instrument 200 to show the extent to which the bur head 204 is deflected from its home position. These features may be incorporated in the display 1402 on the instrument 200 (see FIG. 1 and FIG. 68). The display 1402 is preferably mounted to the handle 502 to remain fixed relative to the handle 502 during use. In alternative embodiments, the display 1402 is attached to the upper assembly 300 to move with the upper assembly 300. A driver (not shown) for the display 1402 is installed in the instrument controller 120.

Surgical instrument 200 of this invention may be used with navigation systems other than the described system. For example, the instrument can be used with an image-less navigation system.

For bone sculpting applications, the display 1402 would give the status of the current amount of deflection of the cutting accessory 202/bur head 204 or whether it is in the "Home" position. For Targeting/Alignment applications, the display 1402 would direct the user to align a cutting accessory's axis with a target axis. During the semi-autonomous cutting mode, the display 1402 could give visual instructions to inform the user where best to grossly position the bur head 204 or instrument 200. In addition, the display 1402 could display navigation information (i.e. blocked LEDs for tracking purposes, percentage of cut completed, where additional material needs to be removed, etc.).

Data connection 1002 may be an IEEE 1394 interface, which is a serial bus interface standard for high-speed communications and isochronous real-time data transfer between the instrument controller 120 and the display 1402. Data connection 1002 could use a company specific protocol.

Alternative assemblies may be provided for moving the cutting accessory to/from the home position. For example, mechanical assemblies that transfer power from the motors may include assemblies other than nuts disposed on lead screws. One such assembly could have a drive plate that is attached to the motor. The plate includes a pin that engages a link connected to the cutting accessory in order to displace the cutting accessory. Also, in some versions of the invention, belt drives may be employed to displace the cutting accessory. Still in another version of the invention the actuation of a motor may displace a rack. The rack is linked to the cutting accessory to displace the cutting accessory.

In another alternative version of the invention, the gimbal to which the cutting accessory is mounted is itself pivotally mounted to the body of the instrument. Thus the gimbal still provides the X- and Y-axes deflection of the cutting accessory. In these versions of the invention, the mechanism that holds the cutting accessory to the gimbal is moveably mounted to the gimbal. For example either the motor and coupling assembly or just the coupling assembly may be mounted to the gimbal so as to be able to move proximally or distally. In these versions of the invention, the motor that moves the cutting accessory distally and proximally may itself also be mounted to the gimbal to pivot with the gimbal. This displacement of the cutting accessory is, it should be appreciated, the displacement of the cutting accessory along axis Z.

Similarly, there is no requirement that, in all versions of the invention, mechanical energy be the source of power that positions the cutting accessory. For example the cutting accessory may be electromagnetically selectively displaced to/from the home position. In one version of this embodiment of the invention, instrument 200 may include solenoids. These solenoids are selectively actuated to retract/extend pins that are attached to the cutting accessory. The pins are selectively extended/retracted to cause the displacement of the cutting accessory to/from the home position. Alternatively, there may be other coils mounted internal to the instrument. These coils generate localized magnetic fields. The coils in each set of coils selectively attract or repel a set of magnets on the cutting accessory. The movement of the magnets results in the movement of the cutting accessory. In this version of the invention, the energization of a particular set of coils may selectively reply/attract a set of magnets that results in the simultaneous displacement of the cutting accessory on two or three axes.

Assemblies other than the fine pitched lead screws may function as the self locking feature of the instrument that blocks unintended back movement of the cutting accessory when the accessory is exposed to resistance. The exact structure of the self locking assembly is a function of the structure of the actuators that displace the cutting accessory. For example, if electromagnetic actuators are employed, the actuators serve as the self locking mechanism. Specifically, currents are applied to the coils to prevent resistive forces applied to the cutting accessory from preventing the unintended displacement of the cutting accessory. In some versions springs may also apply forces that inhibit the unintended movement of the cutting accessory. A cam assembly may also be used to lock the cutting accessory from unintended movement.

Instrument 200 may include components other than the described Hall-effect sensors internal to the motors to determine and control the position of the cutting accessory 202. For example in some versions of the invention, absolute rotary position encoders or absolute angular position encoders may be used to monitor the rotational positions of the components that displace the cutting accessory. For monitoring some types of motion, for example, motion of the carriage along the axis Z, absolute linear position encoders may be incorporated into the instrument of this invention. In these versions of the invention, there may not be a need to provide supplemental position encoders to facilitate the zero state or home centering of the cutting accessory.

There is no requirement that in all versions of the invention the motor or other component that provides energy to the cutting accessory 202 be rigidly connected to the cutting accessory 202. Thus in some versions of the invention, the energy output component may be flexibly linked to the cutting accessory 202. If, for example, the cutting accessory 202 is a mechanically driven device, some type of drive cable or flexible joint may transfer the motive power to the cutting accessory 202. For example the motor could be fixedly secured to the moveable carrier 305 while the cutting accessory 202 is pivotally connected to the carrier 305. An advantage of this structure is that it reduces the mass of the component of the instrument 200 that needs to be moved towards/away from the home position.

In some versions of the invention, instrument 200 may be designed so that the extent to which the cutting accessory 202 may be displaced upon each of the X-, Y- and Z-axes is not equal to each other.

Also, there may be variations in the processes used to position the cutting accessory 202 in the home position. For example, typically, if the cutting accessory 202 is to be displaced along the axis Z, the accessory 202 is more often than not, moved rearward, proximally. Controller 120 therefore establishes a Z-axis home position for the carriage 302 that is typically forward of, distal to, the home position initially established during the homing process. This offsetting of the home position increases the extent to which, during the procedure, the cutting accessory 202 can be retracted proximally.

One means of so resetting the home position of the carrier 302 is to initially actuate the motor 224 so as to cause the carrier 302 to move to home position using the above-described homing process. Controller 120 then adds an offset count to the previously calculated target position count upon which the carrier 302 was moved to the displaced home position. This offset count is based on data previously stored in the controller 120. This offset target position count is then forwarded to the motor controller 234. Controller 234 actuates the motor 224 to cause the carrier 302 to move distally. The carrier 302 is moved until the cumulative count from the motor equals the offset target position count. Once the carrier 302 is so repositioned in the offset home position, the controller 120 zeros out the cumulative count.

When the Z-axis home position of the cutting accessory 202 is so offset, the range of motion of the accessory tip or bur head 204 along the axis Z does not equal the range of motion of the tip or bur head 204 along the X- and Y-axes. Thus, in these implementations of the invention, the boundary of the spaced volume through which the accessory tip or bur head 204 moves when displaced to its maximum deflected positions is not spherical.

Likewise, it should be understood that in other versions of the invention, the full range of deflection of the cutting accessory tip or bur head 204 in the X- and Y-axes may not be equal.

The extent to which the speed of the instrument motor 206 is attenuated may also vary from what was described with respect to FIG. 64. For example, in some versions of the invention as soon as there is any deflection of the cutting accessory 202 from the home position, the controller 120 causes some attenuation of the motor speed. This provides the practitioner some immediate aural and tactile feedback that the bur head 204 is at the working boundary 106. The level of this speed attenuation remains constant as long as the deflection is within a set percentage of the maximum cumulative deflection. Once the deflection exceeds this threshold percentage, the controller 120 asserts instruction packets to the console 130 that serve to increase the extent to which the motor speed is attenuated. This provides a second set of aural and tactile feedback signals to the practitioner that it may be appropriate to further adjust the position of and force applied to the cutting accessory 202.

Further in some versions of the invention, the controller 120 may cause the speed of the instrument motor 206 to be attenuated as a function of the proximity of the accessory tip or bur head 204 to the working boundary 106. Specifically, there may be instrument packets sent to the console 130 that result in a first level of speed attenuation when it is determined that the accessory tip or bur head 204 is a first distance from the working boundary 106. Once the accessory tip or bur head 204 intersects or crosses the working boundary 106, the controller 120 causes the motor speed to be attenuated to a second level. Then, as the extent to which the bur head 204 is diverted from the home position increases beyond a threshold level, the controller 120 increases the attenuation of the motor speed. This stepped attenuation of motor speed provides the practitioner with a stepped indication of the proximity of the accessory tip or bur head 204 to the working boundary 106.

Also, the processes by which the controller 120 determines the relative position of the distal end tip of the cutting accessory 202 relative to the working boundary 106 may differ from what has been described. Ideally, the navigation unit 108 should be able to provide data from which this position can be determined at a frequency equal to the frequency with which the computer recalculates the extent to which the cutting accessory 202 is to be moved from the home position. In actuality, navigation systems are typically not able to perform measurements at these frequencies. One potential solution is to have the controller 120 use the last few frames of data from the navigation unit 108 to determine the velocity of the direction of the instrument 200 towards/away from the bone. Based on this determination, the controller 120 generates extrapolated estimations of the relative location of the instrument 200 to the bone after the last true position information received from the navigation unit 108. Based on these predictions of instrument position, the controller 120 determines whether or not and the extent to which cutting accessory 202 should be diverted from the home position.

Still other means of providing measured or arcuate estimates of the relative position and orientation of the distal end of the cutting accessory 202 relative to the working boundary 106 are associated with features of the navigation unit 108 that are not within the scope of the current invention.

Likewise, depending on the processing speed and/or the ability to transmit data to/from the controller 120, it may not always be necessary to determine the relative position of the cutting accessory 202 based on the assumption that the accessory 202 is in the home position. It is within the scope of this invention that this determination be made based not only on the relative position of the trackers 114, 116. This additional data includes data defining the extent to which the distal end of the cutting accessory 202 is diverted from the home position.

Likewise there is no requirement that all components be in all versions of the invention. For example, it may be that in some versions of the system 100 that a single set of sensors provide the signals used to both initially center or home the cutting accessory 202 and then to monitor the extent to which the cutting accessory 202 is displaced from the home position.

Also, the degree of required alignment should be understood to be a function of the type of cutting accessory 202 fitted to the instrument 200. For example, when forming a bore hole in the active mode, it is often necessary to more precisely position the cutting accessory 202 when the accessory 202 is a drill bit as opposed to a bur head 204.

In alternative embodiments, the controllers 230, 232 and 234 that regulate the actuators that set the position of the cutting accessory 202 are mounted in the control unit 120. This eliminates the need to provide the instrument 200 with a structure like shell 670.

It should likewise be appreciated that precision of the operation of instrument 200 can be enhanced by increasing the frequency with which the accessory to boundary determination and subsequent instrument control cycles are preformed. For example, it may be desirable to provide the instrument controller 120 with hardware and software capable of executing these cycles at a frequencies of 2 kHz and higher, 4 kHz and higher and 8 kHz and higher.

In some embodiments the tracking devices 114, 116 attached to the instrument 200 and the anatomy may be non-optically based trackers such as tracking devices that transmit or receive electromagnetic waves, ultrasonic waves, RF signals, or other tracking devices known to those having ordinary skill in the art.

VIII. Pencil Grip Embodiment

In addition to the alternative embodiments described in the section above, FIGS. 72-111 show another embodiment of the surgical instrument, hereinafter numbered 1200, that has a pencil grip configuration. Surgical instrument 1200 can be used in the tracking and control system 100 shown in FIG. 1 and described above. As set forth above, the tracking and control system 100 tracks the positions and orientations of the target volume 104 and the surgical instrument 1200 to keep the tip or bur head 204 of the cutting accessory 202 at the target volume 104. Surgical instrument 1200 can be used in the same applications as surgical instrument 200 discussed above. Surgical instrument 1200 typically includes a cord 1203 for connection to the tracking and control system 100, and specifically to the instrument controller 120.

Figure 72:
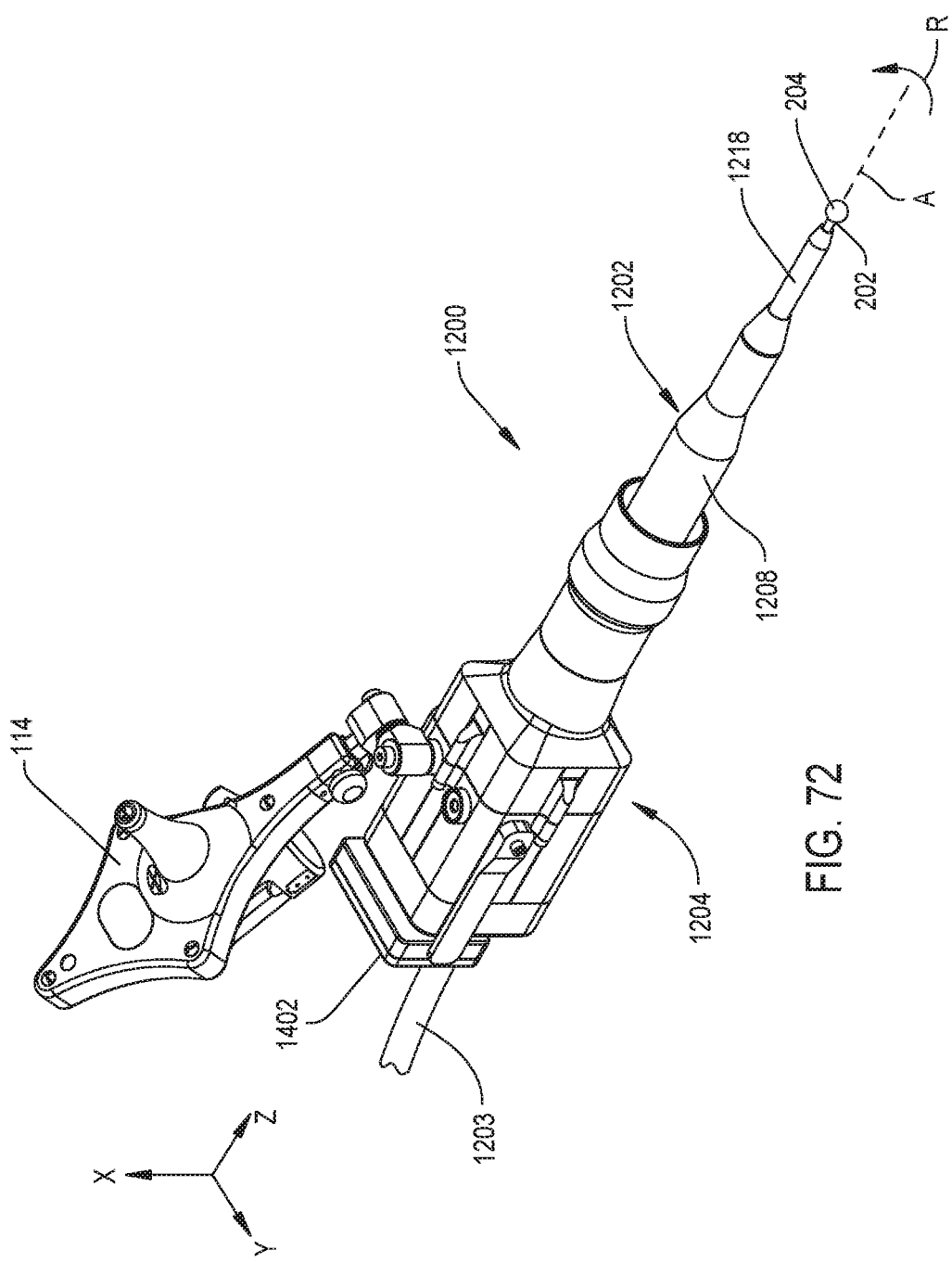
FIG. 72 is a perspective view of a pencil-grip embodiment of the instrument including a proximal assembly and a distal assembly.
Figure 73:
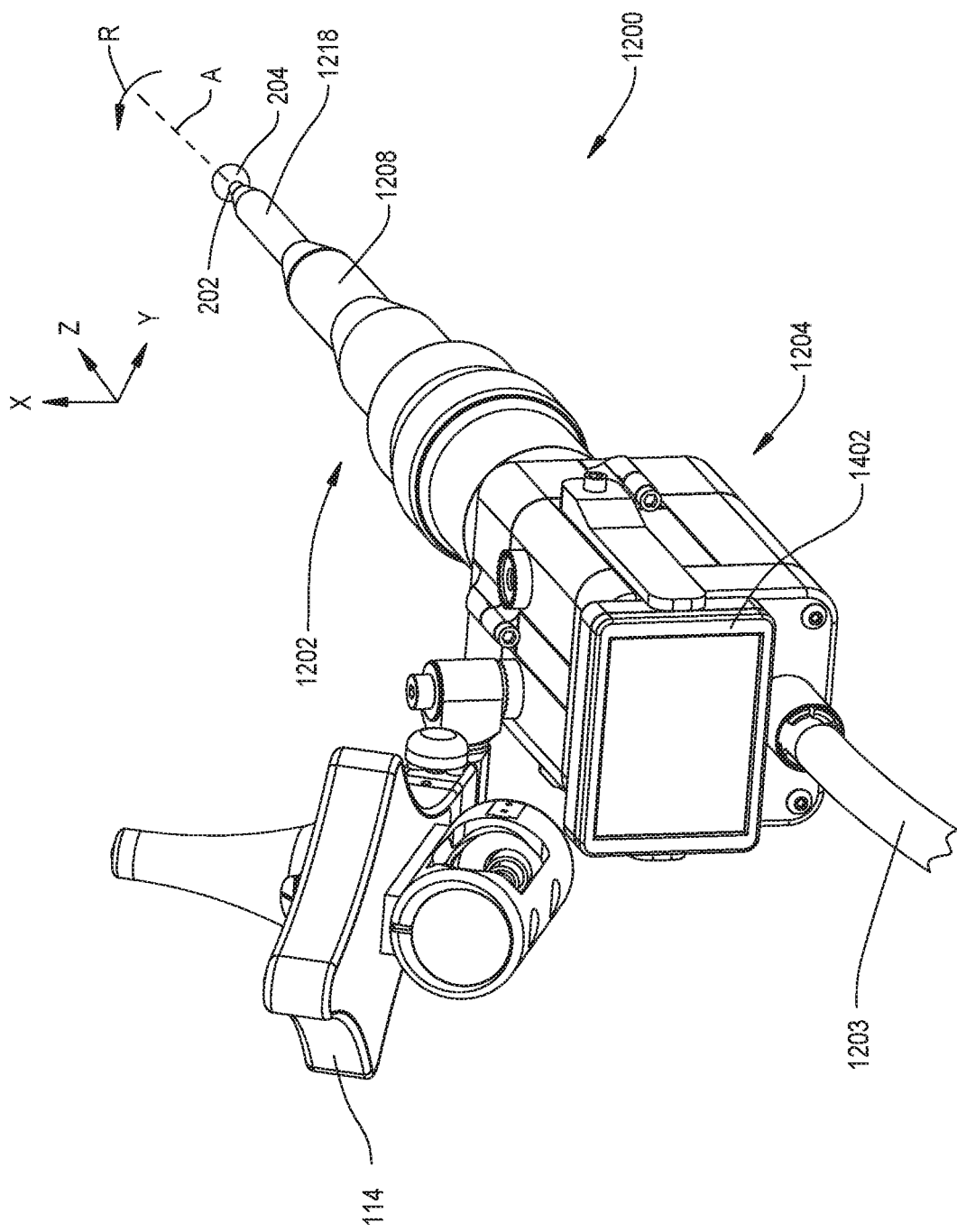
FIG. 73 is another perspective view of the instrument of FIG. 72.
Figure 74:
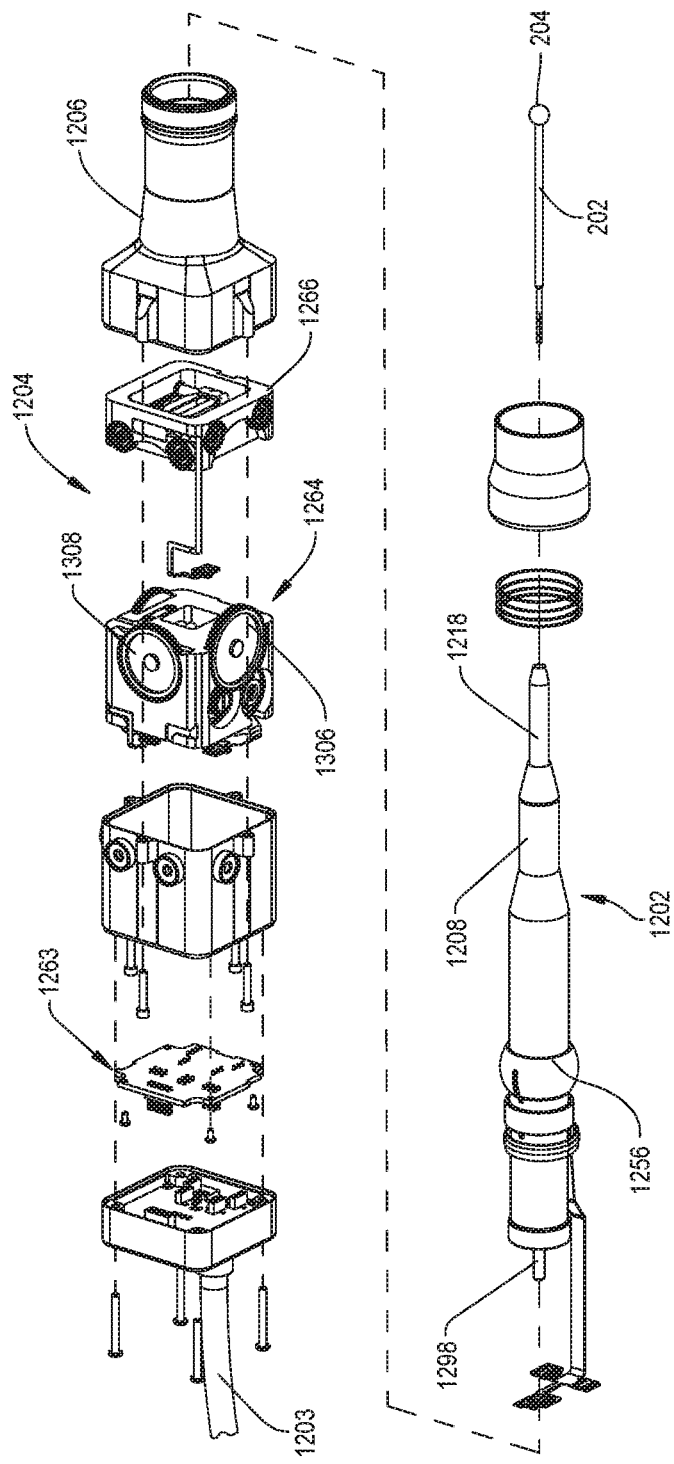
FIG. 74 is an exploded view of a portion of the instrument of FIG. 72.

With reference to FIGS. 72-74, the surgical instrument 1200 includes a distal assembly 1202, also referred to as a drive assembly 1202, and a proximal assembly 1204, also referred to as the hand-held portion 1204. The hand-held portion 1204 is manually supported and moved by a user. The user operates the instrument 1200 by grasping and supporting hand-held portion 1204 and the instrument 1200 is unsupported by other mechanical arms, frames, etc. As set forth with the embodiments described above, the tracking device 114 is attached to the hand-held portion 1204 for tracking the instrument 1200.

The working portion, e.g., the cutting accessory 202, is movably coupled to the hand-held portion 1204. As set forth in greater detail below, the distal assembly 1202 releasably holds the working portion, e.g., the cutting accessory 202, drives the working portion to perform the medical/surgical task on the tissue of the patient, and moves the working portion in the axis Z, as identified in FIGS. 72 and 73, to prevent the distal tip or bur head 204 of the accessory 202 from colliding with or breaching the work boundary 106 of the target volume 104 to which the cutting accessory 202 is being applied.

The proximal assembly 1204 engages the distal assembly 1202 and moves the distal assembly 1202 to adjust the pitch and yaw of the cutting accessory 202 to prevent the distal tip or bur head 204 of the accessory 202 from colliding with or breaching the work boundary 106 of the target volume 104. As set forth above, "pitch" is the up-down angular orientation (i.e., the X-axis shown in the Figures) of the longitudinal axis A of the distal assembly 1202 and the cutting accessory 202 relative to a horizontal plane through the center of a gimbal bushing 1256 and "yaw" is the right-left angular orientation (i.e., the Y-axis shown in the Figures) of the longitudinal axis A of the distal assembly 1202 and the cutting accessory 202 relative to a vertical plane through the center of the gimbal bushing 1256. FIGS. 75A-C, for example, show three different positions of adjustment in the pitch of the distal assembly 1202 relative to the proximal assembly 1204. The range of motion of the tip 204 of the cutting accessory 202 relative to the distal assembly 1202 as defined by the control system 100 is shown as a circle C in FIGS. 75A-C and 85-87. Various views of the distal assembly 1202, or portions thereof, are shown in FIGS. 74-106. With reference to FIGS. 75A-C, the proximal assembly 1204 includes an outer casing 1206 and the distal assembly 1202 includes a casing 1208 that remains rotationally fixed about the longitudinal axis A relative to the outer casing 1206 of the proximal assembly 1204. Proximal assembly 1204 engages the distal assembly 1202 and adjusts the pitch and yaw of the distal assembly 1202 relative to the proximal assembly 1204, as set forth further below.

Figure 76:
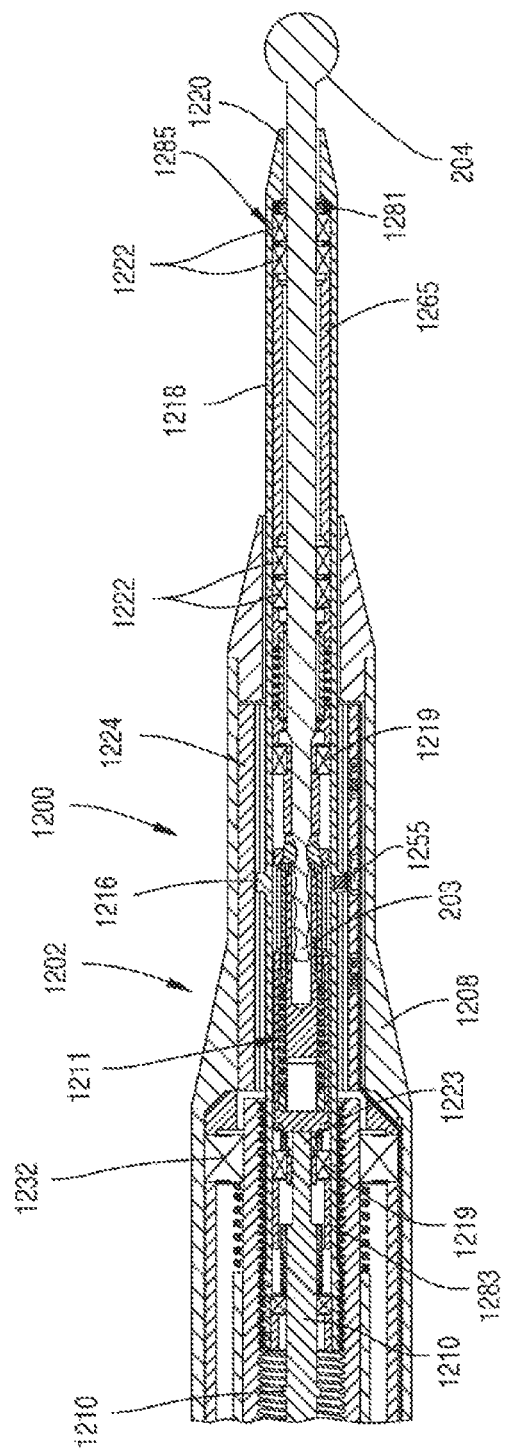
FIG. 76 is a cross-sectional view of a portion of the instrument of FIG. 72.
Figure 77:
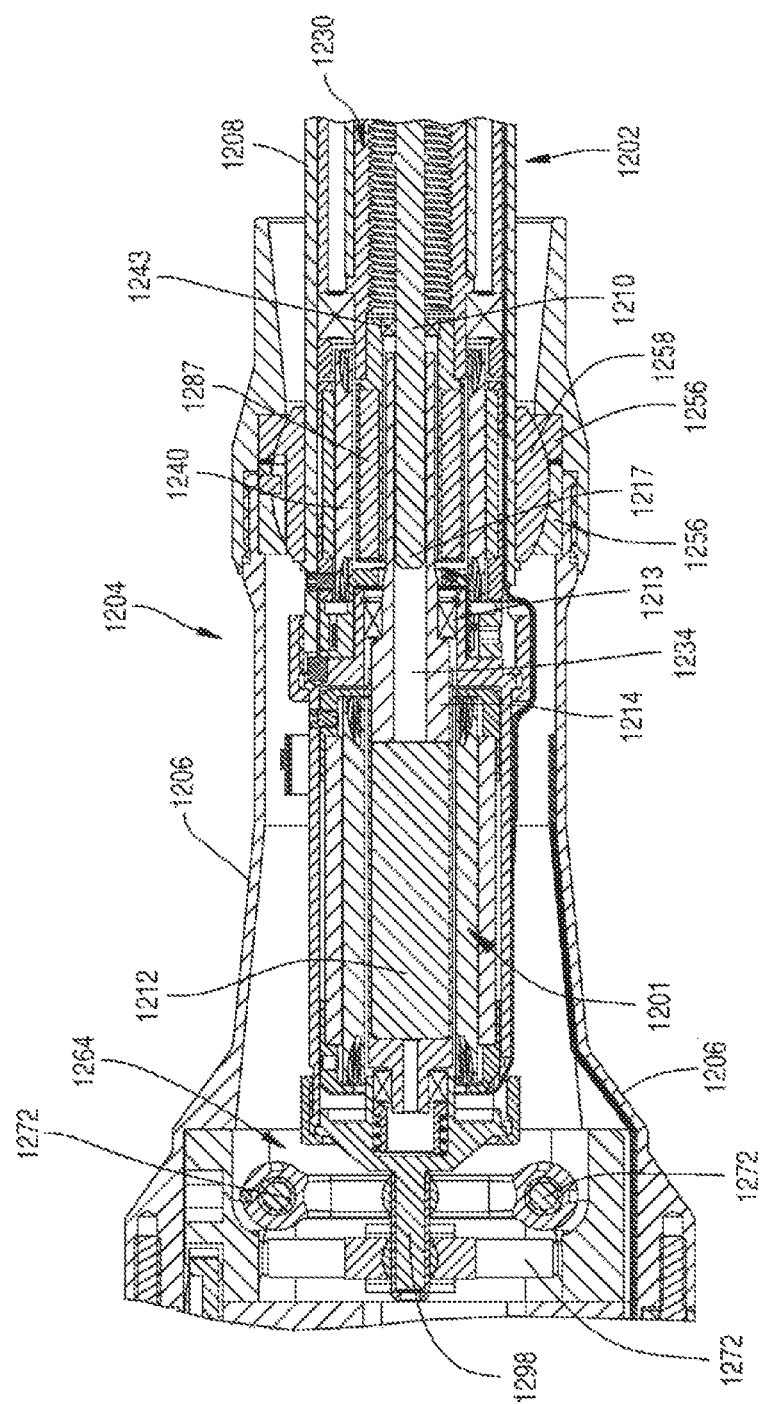
FIG. 77 is a cross-sectional view of another portion of the instrument of FIG. 72.
Figure 80:
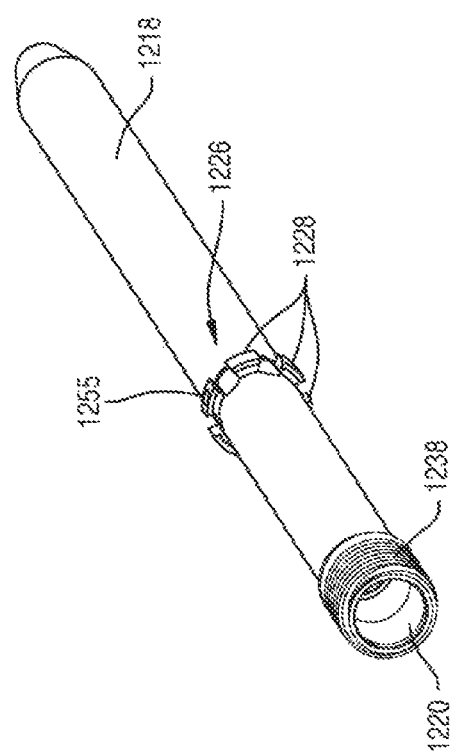
FIG. 80 is a perspective view of a nose tube.

With reference to FIGS. 75A-C, a nose tube 1218 extends from the casing 1208 and supports the cutting accessory 202. The nose tube 1218 defines a nose tube bore 1220 (as best shown in FIGS. 76 and 80). A collet assembly 1211 (shown in isolation in FIGS. 81-84) is rotatably disposed in the nose tube bore 1220 for releasably engaging the cutting accessory 202 in the nose tube bore 1220, as set forth further below.

A drive mechanism 1201 is coupled to the working portion for rotating the working portion about the longitudinal axis A as indicated by arc R. The drive mechanism 1201 includes a drive motor 1212, also referred to as an accessory motor 1212, disposed in the casing 1208 for driving the collet assembly 1211 and the cutting accessory 202, e.g., for rotating the cutting accessory 202.

As set forth further below, the drive assembly 1202 and the cutting accessory 202 move relative to the hand-held portion 1204 in a plurality of degrees of freedom. A plurality of actuators, e.g., lead screw motor 1240, yaw motor 1302, and pitch motor 1304, are operatively coupled to the working portion for moving the working portion in a plurality of degrees of freedom relative to the hand-held portion 1204.

The drive mechanism 1201 moves in at least one degree of freedom relative to the hand-held portion 1204 and, more specifically, the drive motor 1212 moves in at least two degrees of freedom relative to the hand-held portion 1204 relative to the hand-held portion 1204. At least one of the actuators, and more specifically, the yaw motor 1302 and the pitch motor 1304, move the drive mechanism 1201 and the drive motor 1212 in pitch and yaw relative to the hand-held portion 1204. Specifically, the casing 1208 is movable by at least one of the actuators, e.g., the yaw motor 1302 and the pitch motor 1304 in pitch and yaw relative to the hand-held portion 1204. The drive mechanism 1201 and the drive motor 1212 are fixed along the longitudinal axis A relative to the hand-held portion 1204. In this embodiment, the longitudinal axis A moves in pitch and yaw relative to the hand-held portion 1204.

As best shown in FIGS. 75A-C and 85-87, the plurality of actuators, e.g., lead screw motor 1240, yaw motor 1302, and pitch motor 1304, are capable of moving the working portion relative to the hand-held portion 1204 in at least three degrees of freedom including pitch, yaw, and translation along the longitudinal axis A. In an embodiment where the working portion, i.e., the cutting accessory 202, comprises a bur head 204, the drive motor 1212 moves in four degrees of freedom relative to the hand-held portion 1204, i.e., the drive motor 1212 rotates the bur head 204.

The drive assembly 1202 supports the working portion and one of the actuators and is movable by at least another of the actuators. Specifically the drive assembly 1202, and more specifically, the casing 1208, supports the lead screw motor 1240, also referred to as axial motor 1240, and the drive motor 1212. The lead screw motor 1240 translates the working portion along the longitudinal axis A. The drive assembly 1202 is movable by the yaw motor 1302 and the pitch motor 1304. The yaw motor 1302 and pitch motor 1304 move the drive motor 1212, the working portion, and the lead screw motor 1240 in pitch and yaw relative to the hand-held portion 1204.

The drive motor 1212 can be controlled by instrument driver 130 in the same manner as motor 206 is controlled in the prior described embodiments. A shaft 1210, as discussed further below, is disposed in the casing 1208 and extends from the drive motor 1212 to the collet assembly 1211 for transmitting rotation from the drive motor 1212 to the collet assembly 1211 for driving the cutting accessory 202.

Figure 84:
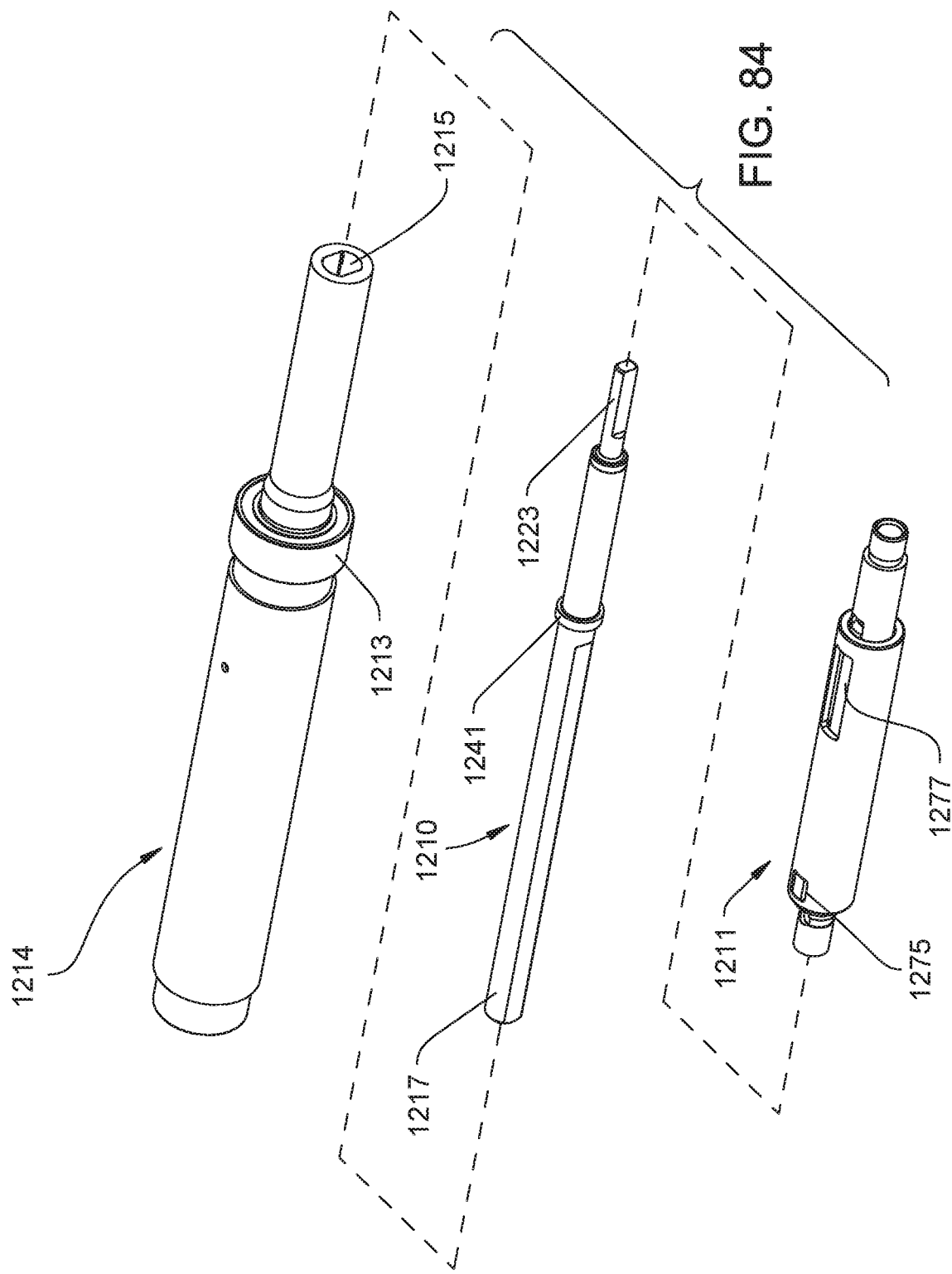
FIG. 84 is a partially exploded view of a shaft between a collar and the collet assembly.

The drive motor 1212 includes a rotor 1214, as shown for example in FIG. 84, that is rotatably coupled to the casing 1208 to drive the cutting accessory 202. The rotor 1214 can include at least one bearing 1213 engaging the casing 1208 to rotatably couple the rotor 1214 to the casing 1208 and allow rotation of the rotor 1214 relative to the casing 1208.

The rotor 1214 includes a keyed bore 1215. The shaft 1210, which is shown for example in FIG. 84, includes a first end 1217 configured to engage the keyed bore 1215 of the rotor 1214 such that rotation of the rotor 1214 is transmitted to the shaft 1210. The cross-sectional shape of the keyed bore 1215 and the first end 1217 are double-D shaped as shown in FIG. 84 but, alternatively, can be any suitable shape without departing from the nature of the present invention.

The collet assembly 1211 rotatably couples the drive shaft 1210 to the cutting accessory 202 so that the cutting accessory 202 rotates in direction R about the longitudinal axis A upon rotation of the drive shaft 1210. The collet assembly 1211, which is shown in isolation in FIGS. 81-84, is rotatably coupled to the nose tube 1218 in the nose tube bore 1220. With reference to FIG. 76, a stack-up 1285 of various components is disposed in the nose tube bore 1220 between the collet assembly 1211 and a lip 1281. A ring 1283, as best shown in FIG. 76, is fixed in the nose tube bore 1220, typically by press fit, adjacent the collet assembly 1211 to retain the collet assembly 1211 and the stack-up 1285 in the nose tube bore 1220.

The collet assembly 1211 can include at least one bearing 1219 (e.g., shown in FIG. 76) engaging the nose tube 1218 to rotatably couple the collet assembly 1211 to the nose tube 1218 and allow rotation of the collet assembly 1211 relative to the nose tube 1208.

The collet assembly 1211 includes a keyed end 1221 and the shaft 1210 includes a second end 1223 configured to engage the keyed end 1221 such that rotation of the shaft 1210 is transmitted to the collet assembly 1211. The second end 1223 and the keyed end 1221 are moveable relative to each other. Under normal operating conditions, the collet assembly 1211 and the shaft 1210 move together as a unit and, when the collet assembly 1211 is moved to lock and unlock the cutting accessory 202, as set forth further below, the keyed end 1221 and the second end 1223 of the shaft 1210 slide relative to each other. The cross-sectional shape of the keyed end 1221 and the second end 1223 of the shaft 1210 are double-D shaped as shown in FIG. 84 but, alternatively can be any suitable shape without departing from the nature of the present invention.

With reference to FIG. 76, the nose tube 1218 supports the working portion, e.g., cutting accessory 202, and is movable relative to the casing 1208 in translation in the Z direction along the longitudinal axis A, i.e., the nose tube 1218, which is typically cylindrical, adjusts the position of the cutting accessory 202 along the longitudinal axis A.

Figure 88:
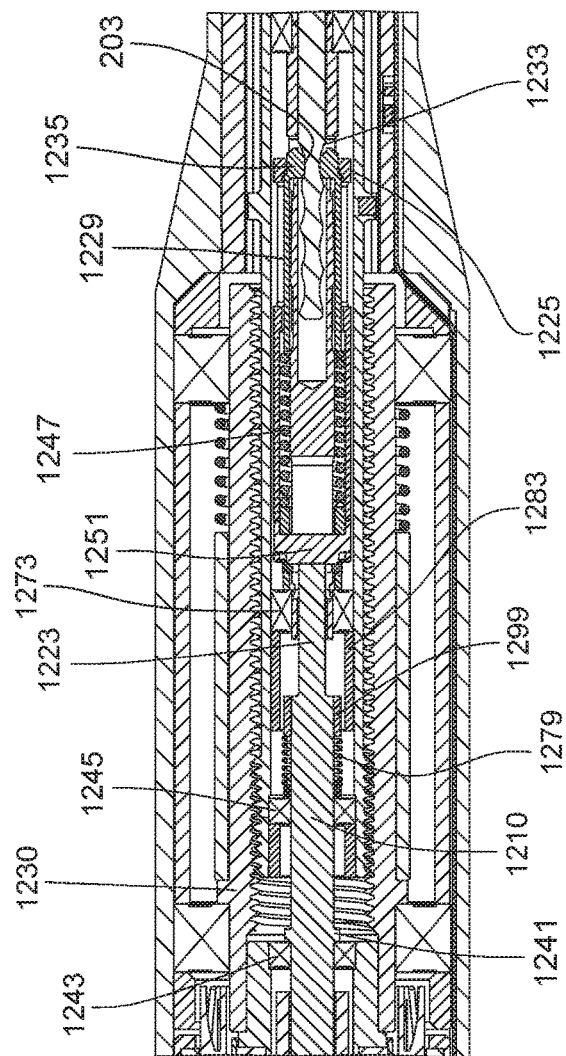
FIG. 88 is a cross-sectional view of a portion of the instrument with the shaft positioned such that the cutting accessory can be removed upon further retraction of the nose tube.
Figure 89:
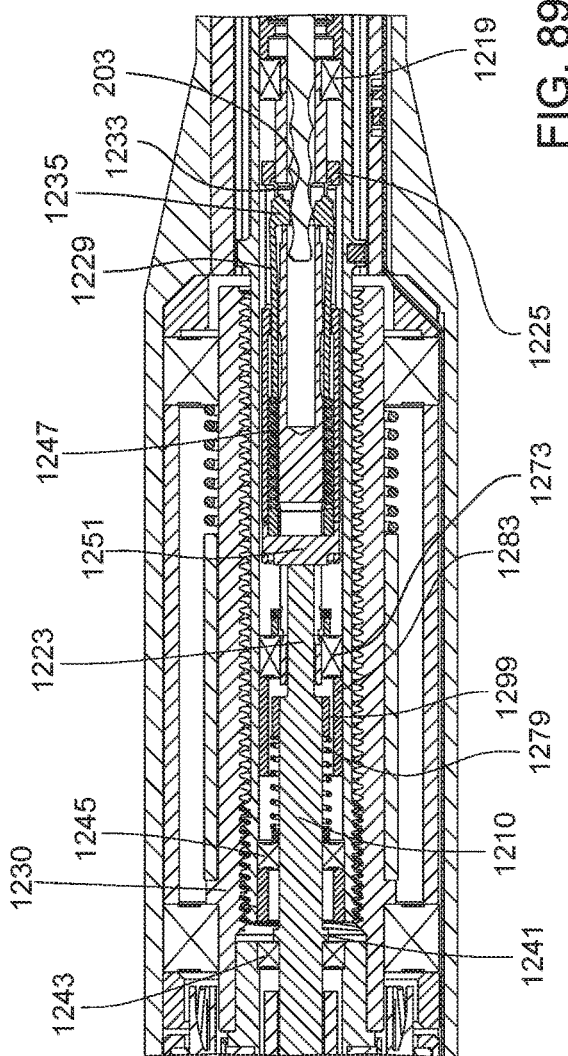
FIG. 89 is a cross-sectional view of a portion of the instrument with the collet assembly in an unlocked position.

With reference to FIG. 85-89, during normal operation, the nose tube 1218 is axially fixed relative to the shaft 1210 along the longitudinal axis A. As such, as the nose tube 1218 moves axially along the longitudinal axis A, the nose tube 1218 moves the shaft 1210 along the longitudinal axis A, as shown in FIGS. 85-87. When the collet assembly 1221 is moved to lock and unlock the cutting accessory 202, the nose tube 1218 and the shaft 1210 move relative to each other, as shown in FIGS. 88 and 89 and as set forth further below.

Figure 78:
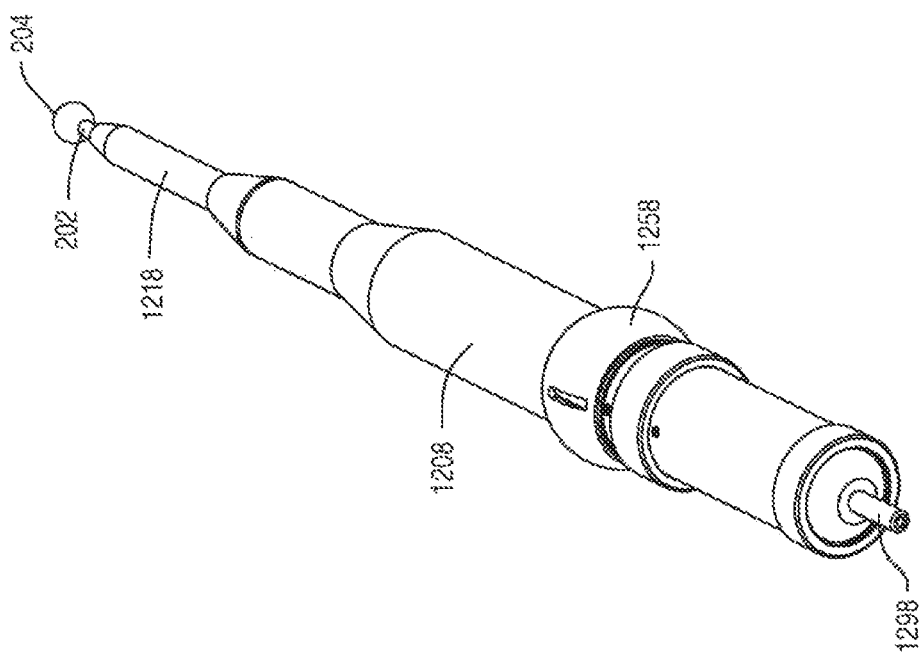
FIG. 78 is a perspective view of a distal portion of the instrument of FIG. 72.
Figure 79:
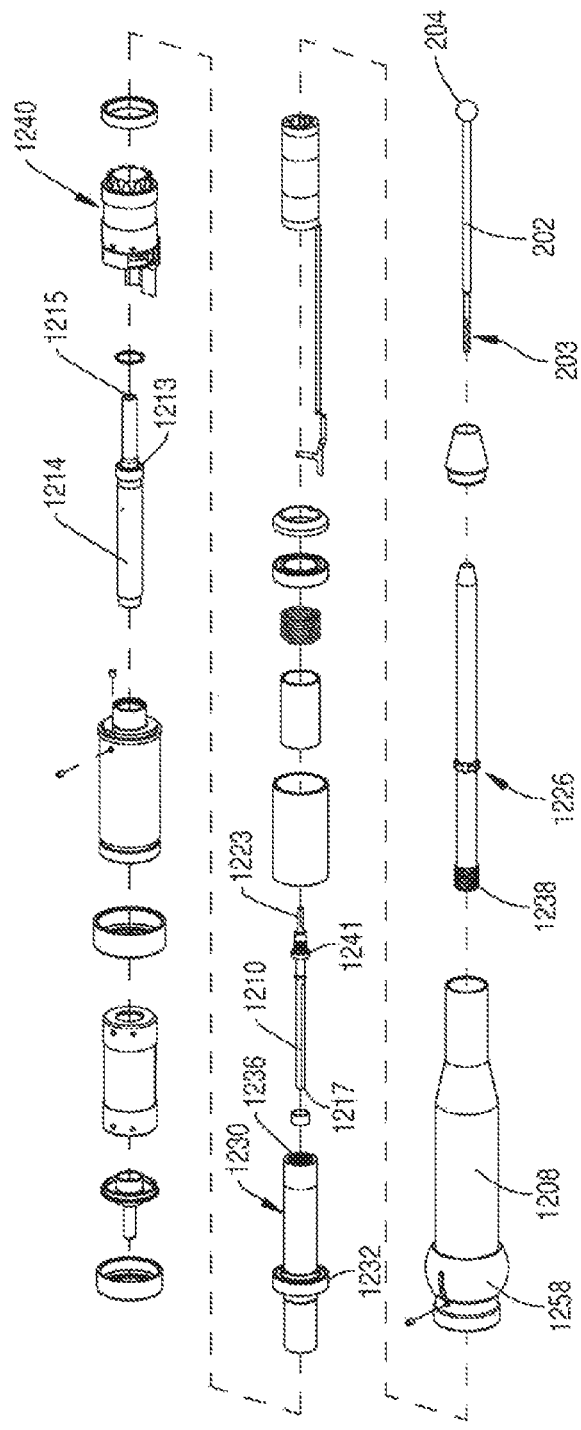
FIG. 79 is an exploded view of the distal portion.

With reference to FIGS. 78 and 79, nose tube bore 1220 rotatably receives the shaft 1210 and the cutting accessory 202. As best shown in FIG. 76, bearings 1222 are disposed in the nose tube bore 1220 for rotatably supporting the cutting accessory 202 in the nose tube bore 1220.

Figure 90:
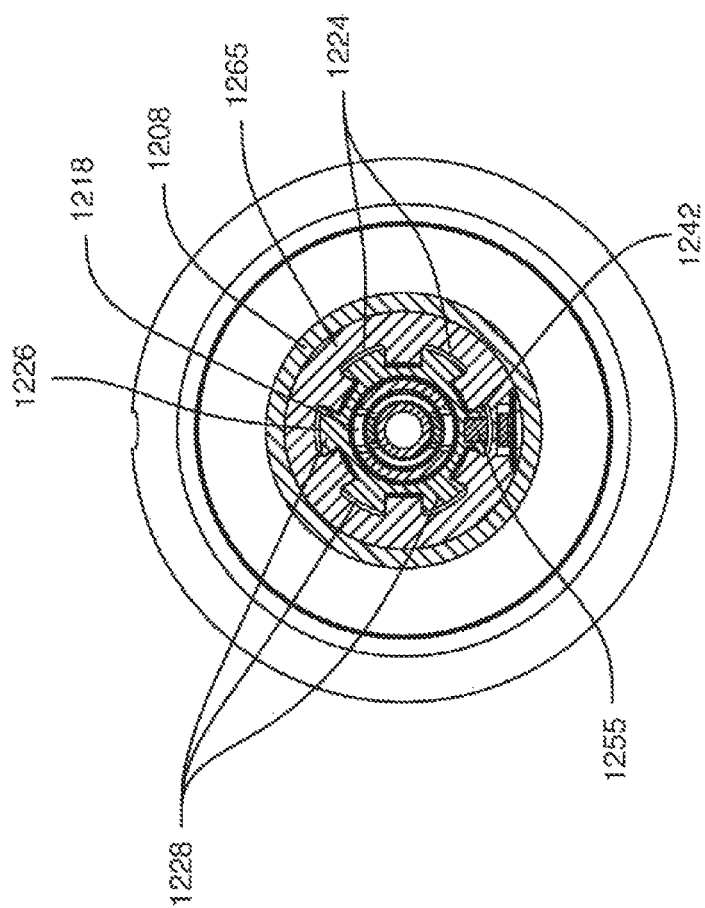
FIG. 90 is a cross-sectional view of the nose tube.

With reference to FIGS. 85-87, the casing 1208 telescopically receives the nose tube 1218. As best shown in FIG. 90, the casing 1208 defines channels 1224. As best shown in FIGS. 79 and 80, the nose tube 1218 includes a flange 1226 including protrusions 1228 engaging the channels 1224. Channels 1224 are circumferentially spaced from one another about the casing 1208. The protrusions 1228 are circumferentially spaced from one another about the nose tube 1218 to mate with the channels 1224. Channels 1224 extend parallel to the longitudinal axis A and are sized and shaped to restrain the protrusions 1228 to movement along the longitudinal axis A. It is appreciated that the protrusions 1228 and channels 1224 can be defined on either of the casing 1208 and the nose tube 1218, and the casing 1208 and the nose tube 1218 can include any number of corresponding protrusions 1228 and channels 1224 without departing from the nature of the present invention. The casing 1208 can, for example, include a bushing 1265 that is fixed to the rest of the casing 1208 and defines the channels 1224. The bushing 1265 is typically formed from a different type of material than the casing 1208. The bushing 1265 is typically formed of a material that provides a low-friction interface with the nose tube 1218 and is typically formed of a non-magnetic material to allow for position sensing.

As best shown in FIGS. 85-89 and 91-92, distal assembly 1202 includes a lead screw 1230 rotatably mounted in the casing 1208. The lead screw 1230 is typically cylindrical. Bearings 1232 are disposed in the casing 1208 between the casing 1208 and the lead screw 1230.

With reference to FIGS. 85-89, the lead screw 1230 threadably engages the nose tube 1218. The nose tube 1218 telescopically extends from the lead screw 1230 along the longitudinal axis A and is telescopically adjustable along the longitudinal axis A relative to the lead screw 1230. Specifically, lead screw 1230 defines a lead screw bore 1234 and interior threads 1236 in the lead screw bore 1234. Nose tube 1218 defines exterior threads 1238. Lead screw 1230 telescopically receives the nose tube 1218 in the lead screw bore 1234. The exterior threads 1238 of the nose tube 1218 threadedly engage the interior threads 1236 in the lead screw bore 1234. The interior threads 1236 and the exterior threads 1238 have a fine pitch and lead angle to prevent back driving, i.e., to encourage self-locking.

As set forth above, the actuators include the lead screw motor 1240. The lead screw motor 1240 includes a hollow rotor 1287, as identified in FIGS. 75A-C and 77, that rotatably receives the drive shaft 1210 therein such that the drive shaft 1210 rotates within the hollow rotor 1287 and relative to the hollow rotor 1287 so as to rotatably drive the working portion.

The nose tube 1218 is threadedly coupled to the hollow rotor 1287. Specifically, lead screw motor 1240, as best shown in FIGS. 85-87, is engaged with the lead screw 1230 to rotate the lead screw 1230 and the nose tube 1218 is threadedly engaged with the lead screw 1230.

The nose tube 1218 is rotationally constrained in the casing 1208 such that the rotation of the hollow rotor 1287 telescopes the nose tube 1218 relative to the casing 1208. In other words, since the engagement of the corresponding protrusions 1228 and channels 1224 prevents rotation of the nose tube 1218 relative to the casing 1208 and allows translation of the nose tube 1218 relative to the casing 1208 along the longitudinal axis A, the nose tube 1218 remains rotationally fixed relative to the casing 1208 as the lead screw motor 1240 rotates the interior threads 1236 of the lead screw 1230 relative to the exterior threads 1238 of the nose tube 1218. This relative rotation of the interior threads 1236 and the exterior threads 1238 moves the nose tube 1218 along the longitudinal axis A relative to the casing 1208. The protrusions 1228 slide in the channels 1224, respectively, as the nose tube 1218 moves along the longitudinal axis A. As a result, the cutting accessory 202, which is carried by the nose tube 1218 during operation, is translated along the longitudinal axis A in response to rotation of the lead screw 1230.

FIGS. 85-87, for example, show the nose tube 1218 moved to different locations relative to the casing 1208 along the longitudinal axis A. Specifically, in FIG. 85 the nose tube 1218 is nearly fully extended and in FIG. 87 the nose tube 1218 is nearly fully retracted. FIG. 86 shows a position between those shown in FIGS. 85 and 87. Specifically, FIG. 86 shows the nose tube 1218 in a "home" position. When the nose tube 1218 moves relative to the casing 1208, the collet assembly 1211, the cutting accessory 202, and all other components housed in the nose tube 1218 move with the nose tube 1218.

As shown in FIGS. 85-87, the keyed bore 1215 telescopically receives the shaft 1210. The shaft 1210 slides along the keyed bore 1215 as the shaft 1210 is moved into and out of the keyed bore 1215 as the nose tube 1218 is extended and retracted along the longitudinal axis A. As set forth above, the first end 1217 of the shaft 1210 is configured to engage the keyed bore 1215 such that rotation is transmitted from the rotor 1214 to the shaft 1210. As also set forth above, the second end 1223 is rotationally locked to the keyed end 1221 of the collet assembly 1211. As such, when the nose tube 1218 is retracted or extended, the shaft 1210 slides in the keyed bore 1215 and transmits rotation to the collet assembly 1211 regardless of the position of the shaft 1210 in the keyed bore 1215.

With continued reference to FIGS. 85-87, bearing 1243 rotatably supports the shaft 1210 in the keyed bore 1215. Bearing 1243 is disposed between a rotor of lead screw motor 1240 and shaft 1210. Rotor of drive motor 1212 rotates concentrically within lead screw motor 1240, while rotor of lead screw motor 1240 rotates about rotor of drive motor 1212. Shaft 1210 is longitudinally slideable relative to bearing 1243 during retraction and extension of the nose tube 1218.

Bearing 1245 rotatably supports the shaft 1210 in the nose tube 1218. Shaft 1210 is longitudinally slideable relative to bearing 1245 when the collet assembly 1221 is moved to lock and unlock the cutting accessory 202.

With reference to FIGS. 76 and 90, the flange 1226 can define a cavity 1242 for receiving a position identifier such as magnet 1255. In such an embodiment, the casing 1208 or the bushing 1265 supports one or more position sensors, e.g., magnetic sensors (not shown), such as a Hall-effect sensor, that measures the proximity of the magnet 1255 to track the location of the nose tube 1218 along the longitudinal axis A. The position sensor communicates with the control system 100.

As set forth above, the collet assembly 1211 releasably engages the cutting accessory 202. The collet assembly 1211 is configured to release the cutting accessory 202 in response to actuation of the lead screw motor 1240 beyond a predefined limit of actuation. The collet assembly 1211 engages the cutting accessory 202 to transmit movement, e.g., torque, from the shaft 1210 to the cutting accessory 202. Specifically, the collet assembly 1211 rotationally fixes the cutting accessory 202 to the shaft 1210. The collet assembly 1211, for example, could be of the type shown in U.S. Pat. No. 5,888,200 to Walen, which is hereby incorporated by reference, or the type shown in U.S. Pat. No. 6,562,055 to Walen, which is hereby incorporated by reference.

Figure 81:
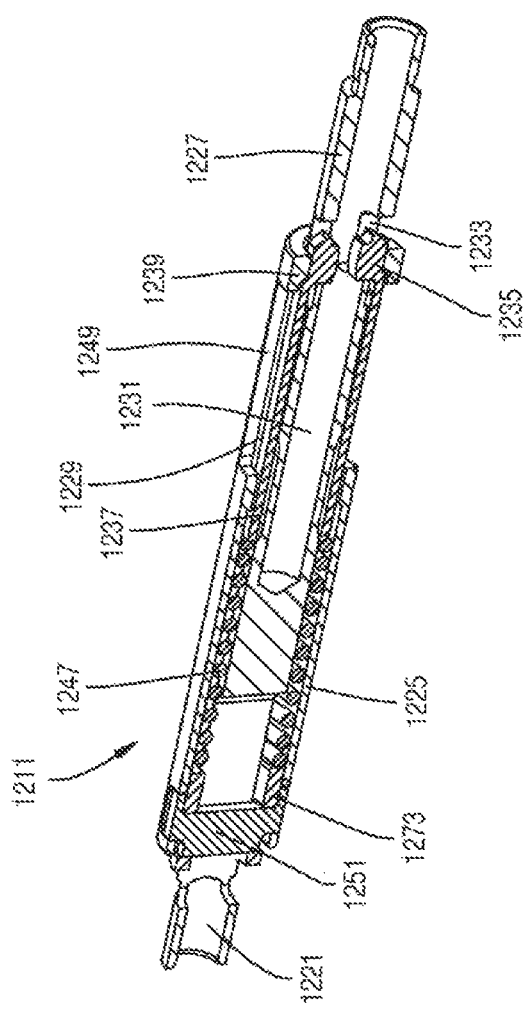
FIG. 81 is a cross-sectional view of a collet assembly.
Figure 82:
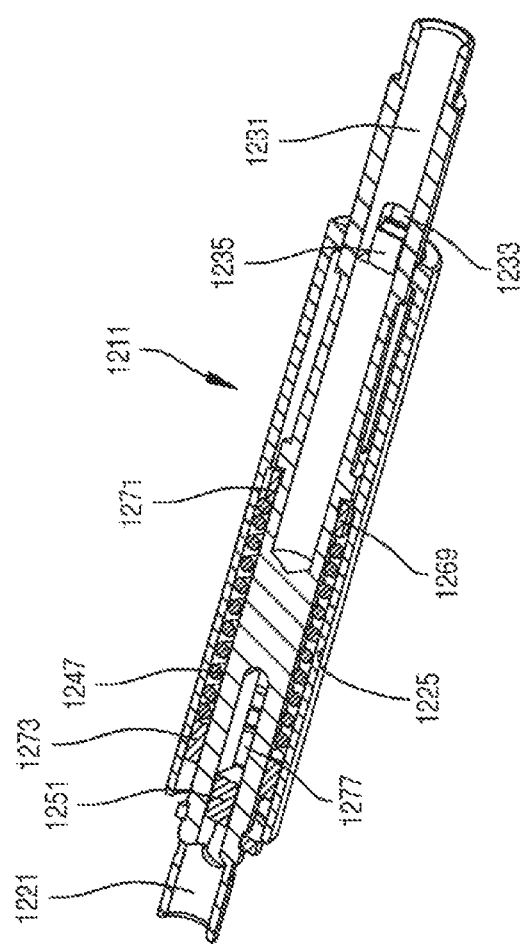
FIG. 82 is another cross-sectional view of the collet assembly.
Figure 83:
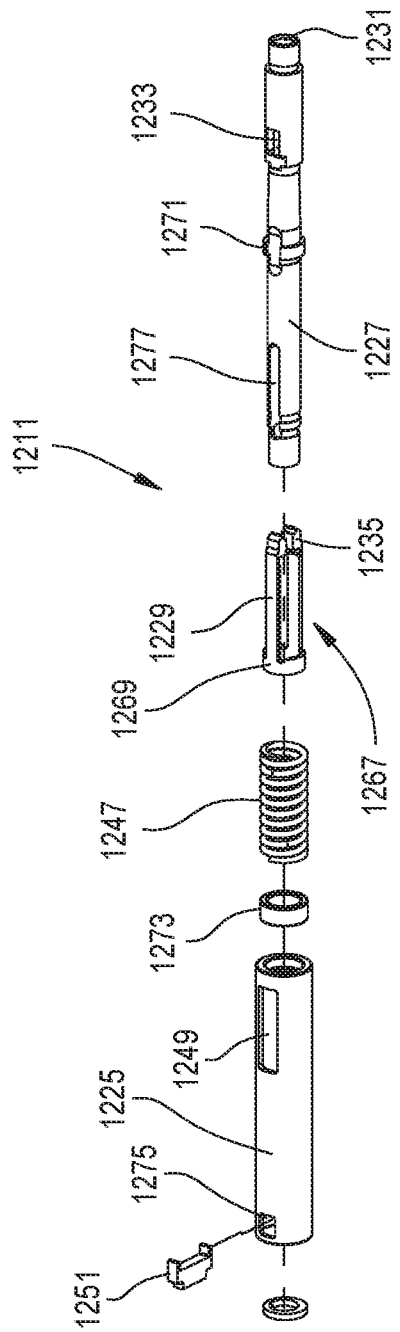
FIG. 83 is an exploded view of the collet assembly.

With reference to FIGS. 81-84, the collet assembly 1211 includes an outer sleeve 1225 and an inner member 1227 telescopically received in the outer sleeve 1225. A clamping member 1267, i.e., a collet, as shown in FIG. 83, is sandwiched between the inner member 1227 and the outer sleeve 1225. As set forth further below, the inner member 1227 selectively biases the clamping member 1267 into engagement with the cutting accessory 202.

The clamping member 1267 includes a ring 1269 and at least one arm 1229 extending from the ring 1269. FIG. 85 shows two arms 1229. It should be appreciated that the clamping member 1267 can include any number of arms 1229 without departing from the nature of the present invention.

With reference to FIGS. 81 and 82, the inner member 1227 defines a bore 1231 for receiving the cutting accessory 202. The inner member 1227 defines at least one opening 1233, also shown in FIG. 84, in communication with the bore 1231. Each arm 1229 includes a foot 1235 that can extend through the opening 1233 and into the bore 1231 to engage the cutting accessory 202, as set forth further below.

The inner member 1227 is slideable longitudinally relative to the outer sleeve 1225 and the arms 1229 between a locked position (shown in FIG. 88) and an unlocked position (shown in FIG. 89). Specifically, in the locked position, the outer sleeve 1225 provides a retention force on the arms 1229 to retain the feet 1235 in the opening 1233. In the unlocked position, the outer sleeve 1225 is moved relative to the arms 1229 to eliminate the retention force and the feet 1235 are free to move out of the opening 1233. Specifically, when the outer sleeve 1225 is in the unlocked position, the feet 1235 naturally remain in the opening 1233, however, the arms 1229 are free to bend allowing the feet 1235 to move out of the opening 1233. As such, when the cutting accessory 202 is inserted into the bore 1231, the cutting accessory 202 moves the feet 1235 outwardly.

The collet assembly 1211 includes a pin 1251 that abuts the shaft 1210, as best shown in FIG. 88. A spring 1279 pre-loads the shaft 1210 into engagement with the pin 1251. In particular, a collar 1299 is fixed to shaft 1210 and spring 1279 acts against bearing 1245, which is axially fixed to nose tube 1218, to urge collar 1299 distally. As set forth above, the shaft 1210 is longitudinally slideable relative to the bearing 1245 when the collet assembly 1211 is moved to lock and unlock the cutting accessory 202, and the spring 1279 urges the shaft 1210 to move distally with the nose tube 1218 during normal operation of the nose tube 1218.

The outer sleeve 1225 defines a hole 1275, shown in FIGS. 83 and 84, that receives the pin 1251 such that the outer sleeve 1225 and the pin 1251 move together as a unit relative to the inner member 1227. The inner member 1227 defines a slot 1277 that receives the pin 1251.

When the outer sleeve 1225 and the inner member 1227 move relative to each other, the shaft 1210 slides longitudinally in the keyed end 1221 of the inner member 1227 and the pin 1251 slides along the slot 1277. In other words, the inner member 1227 moves relative to the outer sleeve 1225, the pin 1251, and the shaft 1210. As set forth further below, to move to the unlocked position, the shaft 1210 exerts force on the pin 1251 to hold the outer sleeve 1225 in place relative to the casing 1208 and the nose tube 1218 exerts force on the inner member 1227 to move the inner member 1227 relative to the outer sleeve 1225.

The outer sleeve 1225 includes a boss 1239 that rides along the arms 1229. In the locked position, the boss 1239 of the outer sleeve 1225 retains the feet 1235 in the slots 1233 and in the bore 1231 as shown in FIG. 88. The outer sleeve 1225 defines holes 1249 through which the arms 1229/feet 1235 can extend in the unlocked position.

A spring 1247 is disposed between the outer sleeve 1225 and the inner member 1227. The spring 1247 biases the outer sleeve 1225 and the inner member 1227 toward the locked position. The spring 1247 abuts the ring 1269 of the clamping member 1267 and abuts a washer 1273. The spring 1247 biases the ring 1269 against a flange 1271 of the inner member 1227 and biases the washer 1273 against the pin 1251, which is fixed relative to the outer sleeve 1225.

As best shown in FIGS. 88 and 89, the cutting accessory 202 defines flats 203. To engage the cutting accessory 202 with the collet assembly 1211, the outer sleeve 1225 and inner member 1227 are moved to the unlocked position such that the boss 1239 moves along the arms 1229 away from the feet 1235. The cutting accessory 202 is then inserted into the bore 1231 and bias the feet 1235 out of the bore 1231 until the flats 203 are aligned with the feet 1235. Feet 1235 spring back into the bore 1231 when the flats 203 are aligned with the feet 1235 such that the feet 1235 engage one of the flats 203. The inner member 1227 is then moved relative to the outer sleeve 1225 to the locked position to lock the feet 1235 in engagement with the flat 203 to rotationally and translationally lock the cutting accessory 202 to the collet assembly 1211.

The outer sleeve 1225 and inner member 1227 can be moved between the locked position and the unlocked position by selective movement of the lead screw 1230. As set forth above, various positions within the normal operating range of the nose tube 1218 are generally shown in FIGS. 85-87. The shaft 1210 includes a flange 1241. As the nose tube 1218 is extended and retracted, the flange 1241 moves relative to the bearing 1243. As shown in FIG. 87, the flange 1241 is near the bearing 1243 when the nose tube 1218 is nearly fully retracted. When the nose tube 1218 is fully retracted, the flange 1241 is slightly spaced from, or alternatively, in contact with, the bearing 1243.

The outer sleeve 1225 and inner member 1227 can be moved to the unlocked position by retracting the nose tube 1218 beyond the near retracted position of FIG. 88, i.e., beyond the predefined limit of actuation for normal operation. When the nose tube 1218 is retracted beyond the retracted position, the flange 1241 of the shaft 1210 abuts the bearing 1243 and prevents further movement of the shaft 1210 into the keyed bore 1215, as shown in FIGS. 88 and 89.

As set forth above, the inner member 1227 and the nose tube 1218 are translationally fixed to each other and the inner member 1227 is telescopically received in the outer sleeve 1225. Spring 1247 urges the outer sleeve 1225 and the inner member 1227 such that the arms 1229 are in the locked position. When the flange 1241 abuts the bearing 1243 and the nose tube 1218 is further retracted, the shaft 1210 prevents further movement of the pin 1251 and thus the outer sleeve 1225 and, as such, further retraction of the nose tube 1218 moves the inner member 1227 relative to the outer sleeve 1225 thereby compressing the spring 1247, as shown in FIG. 89. In other words, the shaft 1210 abuts the pin 1251, which is fixed to the outer sleeve 1225, to prevent further movement of the outer sleeve 1225 while the inner member 1227 continues to move and compress the spring 1247. As such, the inner member 1227 is moved relative to the outer sleeve 1225 to move the arms 1229 to the unlocked position, as set forth above, in response to actuation of the lead screw motor 1240 beyond the predefined limit of actuation.

During normal operation, e.g., during use for a navigated surgical procedure, the nose tube 1218 can travel between the extended and retracted positions and does not retract beyond the retracted position. An additional step outside of the normal operation is required to engage the cutting accessory 202 with the nose tube 1218 or disengage the cutting accessory 202 from the nose tube 1218. For example, an input device (not shown) such as a button, switch, etc., can be mounted to the outer casing 1206 to provide input that allows for the nose tube 1218 to be retracted beyond the retracted position, as set forth above, to move the arms 1229 to the unlocked position. Alternatively, movement of the nose tube 1218 beyond the retracted position can be controlled with software.

It should be appreciated that the collet assembly 1211 shown in FIGS. 81-84 is shown merely for exemplary purposes and the shaft 1210 can engage the cutting accessory 202 in any suitable manner without departing from the nature of the present invention.

Figure 93:
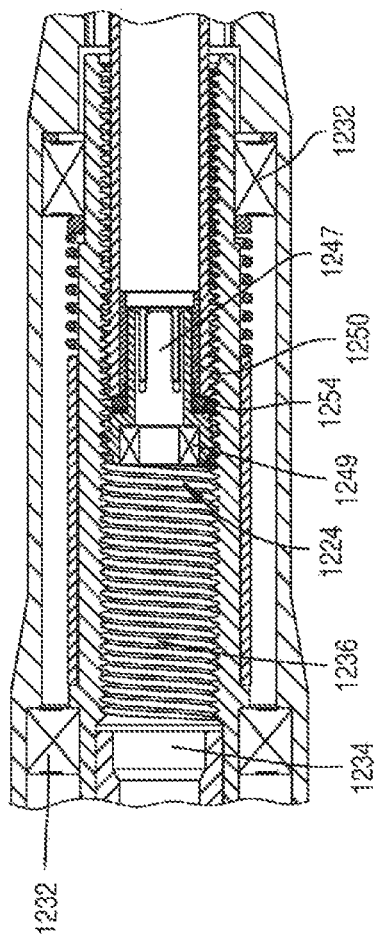
FIG. 93 is a cross-sectional view of an embodiment of the nose tube including an anti-backlash device.
Figure 94:
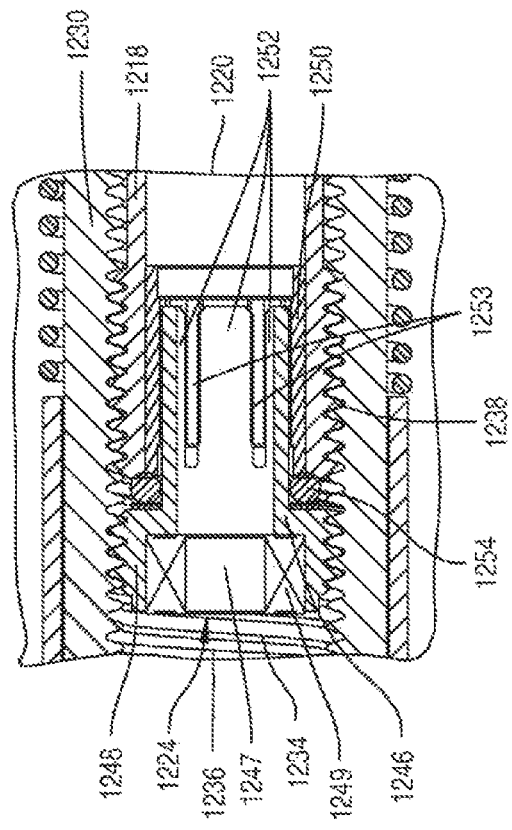
FIG. 94 is another cross-sectional view of the anti-backlash device.

In another embodiment shown in FIGS. 93 and 94, the nose tube 1218 can include an anti-backlash device 1224 that engages the lead screw 1230 and the nose tube 1218. The anti-backlash device 1224 includes an insert 1246 with a threaded shoulder 1248 that threadedly engages the interior threads 1236 of the lead screw 1230. A coupling 1250 is fixed to the nose tube 1218 in the nose tube bore 1220. The coupling 1250 is typically fixed in the nose tube bore 1220 by press fit engagement, however, the coupling 1250 can be fixed in the nose tube bore 1220 in any suitable fashion without departing from the nature of the present invention. The insert 1246 and the coupling 1250 define a bore 1247 that rotatably receives the shaft 1210. A bearing 1249 can be disposed between the insert 1246 and the shaft 1210.

Insert 1246 includes circumferentially spaced fingers 1252 and the coupling 1250 includes slots 1253. The fingers 1252 and the slots 1253 are engaged in alternating arrangement circumferentially about the longitudinal axis A. The fingers 1252 of the insert 1246 and the slots 1253 of the coupling 1250 interlock with each other circumferentially about the longitudinal axis A to prevent relative rotation and slidingly engage each other along the longitudinal axis A to allow for relative translation along the longitudinal axis A during assembly of the anti-backlash device 1224. As such, the insert 1246 can slide along the longitudinal axis A relative to the nose tube 1218.

A spring element 1254 is disposed between the insert 1246 and the nose tube 1218 and extends along the longitudinal axis A between the insert 1246 and the nose tube 1218. The spring element 1254 can be an O-ring of elastomeric material, but alternatively can be any type of suitable spring element without departing from the nature of the present invention. The spring element 1254 exerts axial pressure on the nose tube 1218 along the longitudinal axis A to bias the exterior threads 1238 of the nose tube 1218 against the interior threads 1236 of the lead screw 1230, which eliminates play between the exterior threads 1238 and interior threads 1236 to eliminates backlash during changes in rotational direction of the lead screw 1230 relative to the nose tube 1218.

As best shown in FIG. 78, the casing 1208 supports and at least partially encloses the rest of the distal assembly 1202 such as the nose tube 1218, lead screw 1230, lead screw motor 1240, etc. As such, adjustment of the yaw and pitch of the casing 1208, as set forth further below, also adjusts pitch and yaw of the rest of the distal assembly 1202 and the cutting accessory 202 held by the distal assembly 1202.

Figure 95:
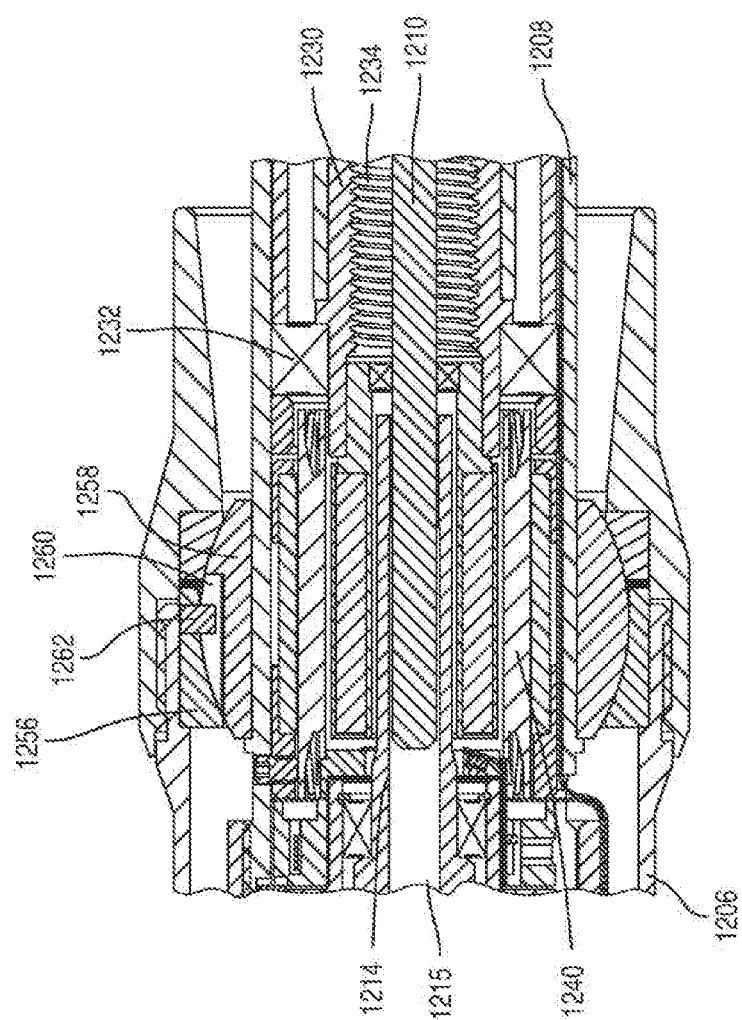
FIG. 95 is a cross-sectional view of a portion of the instrument of FIG. 72 including a gimbal.

With reference to FIG. 95, the working portion, e.g., cutting accessory 202, moves about the gimbal 1258 in at least two degrees of freedom relative to the hand-held portion 1204. Specifically, the working portion is adjustable in pitch and yaw about the gimbal 1258. The gimbal 1258 is fixed along the longitudinal axis A relative to the hand-held portion 1204. The nose tube 1218 translates relative to the gimbal 1258 along longitudinal axis A.

The gimbal bushing 1256 is connected to the outer casing 1206. The gimbal 1258 is attached to the casing 1208 of the distal assembly 1202 and the gimbal bushing 1256 holds the gimbal 1258 to pivotally secure the casing 1208 of the distal assembly 1202 to the outer casing 1206 of the proximal assembly 1204. The gimbal bushing 1256 and the gimbal 1258 typically have matching inner and outer surfaces so that gimbal 1258 can pivot relative to gimbal bushing 1256. The gimbal bushing 1256 shown for example in the Figures is split, i.e., includes two portions. The gimbal bushing 1256 is formed of a low friction material such as, for example, brass or bronze.

Gimbal 1258 is a ring shaped structure that has a frusto-spherical shape, i.e., an outer shape of a sphere the opposed ends of which have been removed. The gimbal 1258 is attached to the casing 1208 of the distal assembly 1202 so the distal assembly 1202 and the cutting accessory 202 are able to pivot relative to the proximal assembly 1204. The gimbal 1258 is located around the center of gravity G of distal assembly 1202 to minimize the mass moment of inertia of the distal assembly 1202 as the distal assembly 1202 is pivoted to maximize the angular acceleration for a given supplied torque.

With continued reference to FIG. 95, the gimbal 1258 defines a slot 1260 and the proximal assembly 1204 includes a peg 1262 fixed to and extending from the gimbal bushing 1256 into the slot 1260. The slot 1260 extends longitudinally along the gimbal 1258. The peg 1262 and the slot 1260 are sized and shaped to prevent rotation of the distal assembly 1202 about the longitudinal axis A relative to the proximal assembly 1204 while allowing pitch and yaw adjustment of the distal assembly 1202 relative to the proximal assembly 1204.

The proximal assembly 1204 includes an adjustment assembly 1264 for adjusting the pitch and yaw of the distal assembly 1202 relative to the proximal assembly 1204. The proximal assembly, e.g., outer casing 1206, is held and gripped by the user. As shown in FIGS. 74-75C, the outer casing 1206 of the proximal assembly 1204 houses the adjustment assembly 1264. Various views of the adjustment assembly 1264, or portions thereof, are shown in FIGS. 97-106.

Figure 101:
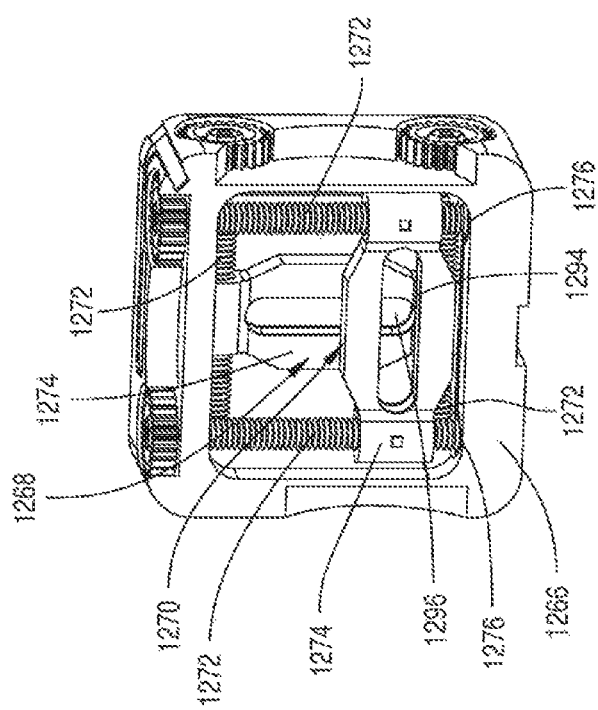
FIG. 101 is a perspective view of a portion of the adjustment assembly.

With reference to FIG. 101, adjustment assembly 1264 includes a frame 1266 that houses a yaw adjustment device 1268, i.e., a yaw adjustment mechanism 1268, and a pitch adjustment device 1270, i.e., a pitch adjustment mechanism 1270. The frame 1266 is fixed within the outer casing 1206 of the proximal assembly 1204. The yaw adjustment device 1268 and the pitch adjustment device 1270 move relative to the frame 1266 and engage the distal assembly 1202 to move the distal assembly 1202 relative to the frame 1266 and the outer casing 1206 to adjust the yaw and pitch, respectively, of the distal assembly 1202 relative to the proximal assembly 1204.

With continued reference to FIG. 101, yaw adjustment device 1268 and the pitch adjustment device 1270 each include a pair of lead screws 1272, which are threaded, and a carriage 1274 that threadedly engages the lead screws 1272. The lead screws 1272 typically include a fine pitched thread to prevent backdrive (see above). The components of the yaw adjustment device 1268 and the pitch adjustment device 1270, e.g., the pair of lead screws 1272 and the carriage 1274, are identical to each other and are arranged in the frame 1266. Specifically, the frame 1266 extends about an axis, and the yaw adjustment device 1268 and the pitch adjustment device 1270 are spaced from each other along the axis and are rotated 90° relative to each other about the axis.

With reference to FIG. 101, lead screws 1272 of the yaw adjustment device 1268 and the pitch adjustment device 1270 are rotatably engaged with the frame 1266. Bearings 1276 are disposed between the lead screws 1272 and the frame 1266 to rotatably retain the lead screws 1272 in the frame 1266. With reference to FIG. 101, lead screws 1272 each define a threaded surface 1278 and the carriage 1274 defines a pair of threaded bores 1280 for threadedly receiving the lead screws 1272. As set forth further below, simultaneous rotation of the pair of lead screws 1272 moves the carriage 1274 along the lead screws 1272. The carriage 1272 includes pockets (not numbered) for receipt of position identifiers, e.g., magnets, that communicate with position sensors, e.g., Hall-effect sensors. Such position sensors can be fixed, for example, to the frame 1266. The position sensors communicate with the control system 100.

Figure 105:
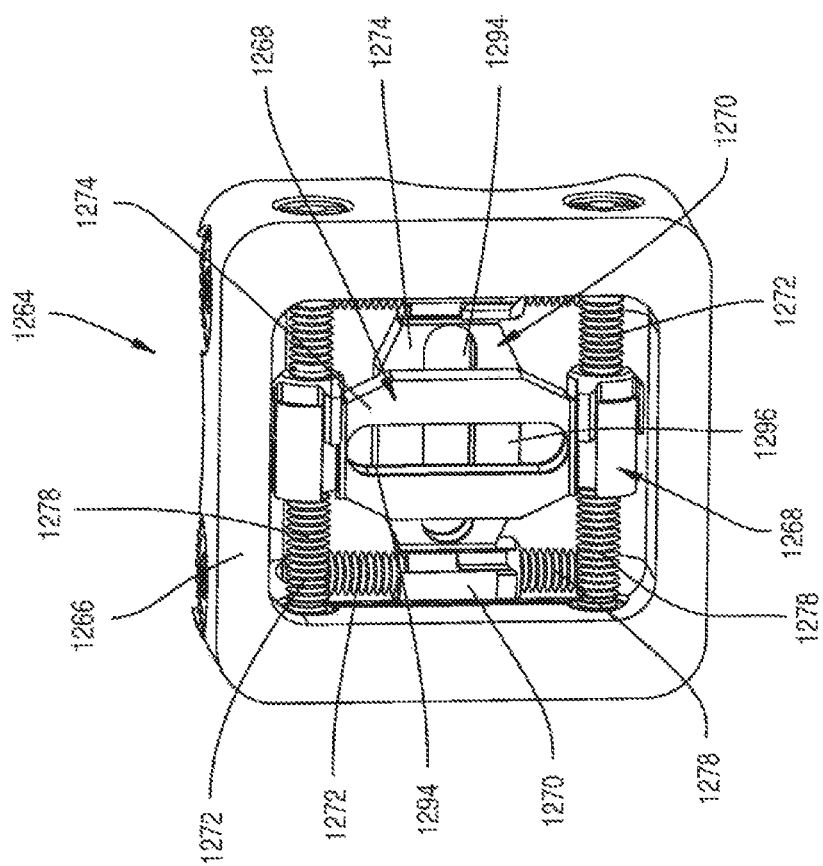
FIG. 105 is another embodiment of the adjustment assembly including an anti-backlash device.
Figure 106:
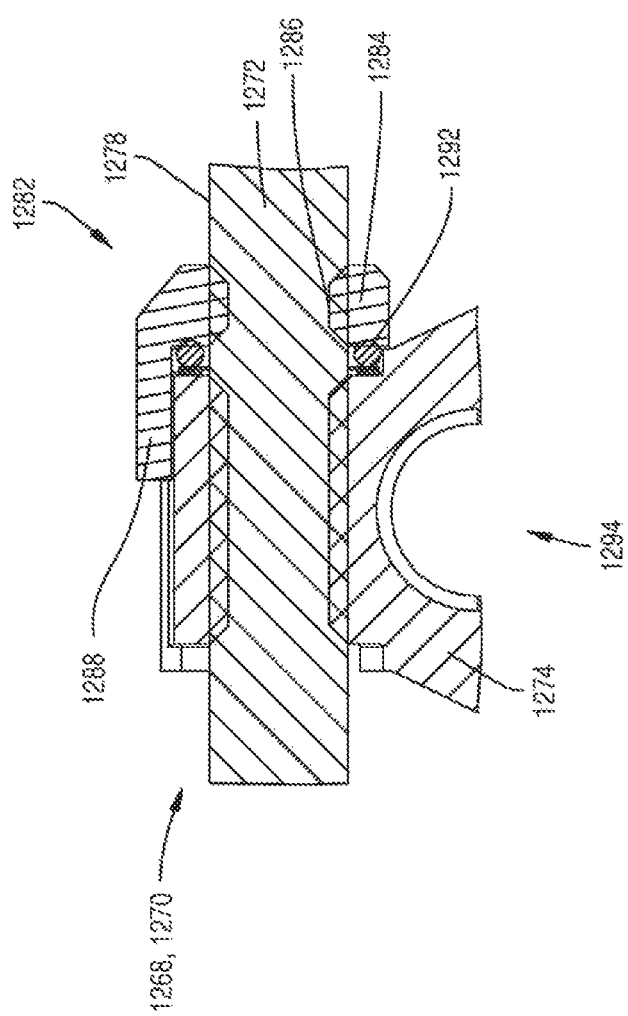
FIG. 106 is a perspective view of a portion of the adjustment assembly of FIG. 105.

In another embodiment shown in FIGS. 105 and 106, the carriages 1274 can each include an anti-backlash device 1282 disposed on each of the lead screws 1272. Each anti-backlash device 1282 includes a cap 1284 that defines a threaded bore 1286 that threadedly engages the lead screw 1272.

Cap 1284 is coupled to the lead screw 1272. The cap 1284 includes circumferentially spaced fingers 1288 spaced about the threaded bore 1286. With reference to FIG. 105, the carriage 1274 defines circumferentially spaced slots 1290. The fingers 1288 and the slots 1290 are engaged in alternating arrangement circumferentially about the lead screw 1272. The fingers 1288 of the cap 1284 engage the slots 1290 circumferentially about the lead screw 1272 to prevent relative rotation and slidingly engage each other axially along the lead screw 1272 to allow for relative translation along the lead screw 1272. As such, the cap 1284 can slide along and relative to the carriage 1274 axially along the lead screw 1272.

A spring element 1292 is disposed between the cap 1284 and the lead screw 1272. Spring element 1292 extends axially along the lead screw 1272 between the cap 1284 and the lead screw 1272. The spring element 1292 can be an O-ring of elastomeric material but alternatively can be any type of suitable spring element without departing from the nature of the present invention. The spring element 1292 exerts pressure on the carriage 1274 axially along the lead screw 1272 to bias the threads of the threaded bores 1280 of the carriage 1274 against the threads of the threaded surface 1278 of the lead screw 1272, which limits backlash during changes in rotational direction of the lead screws 1272 relative to the carriage 1274.

Figure 96:
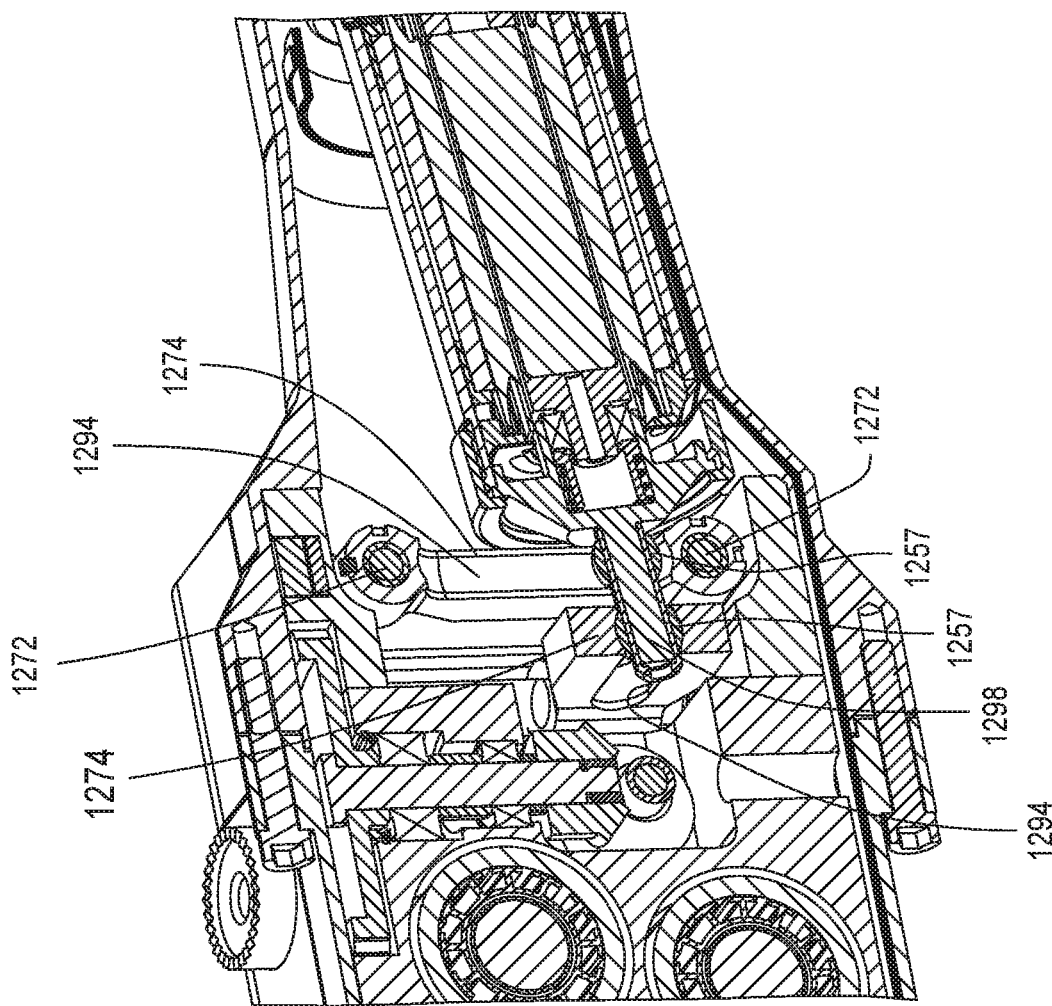
FIG. 96 is a cross-sectional view of an adjustment assembly.
Figure 97:
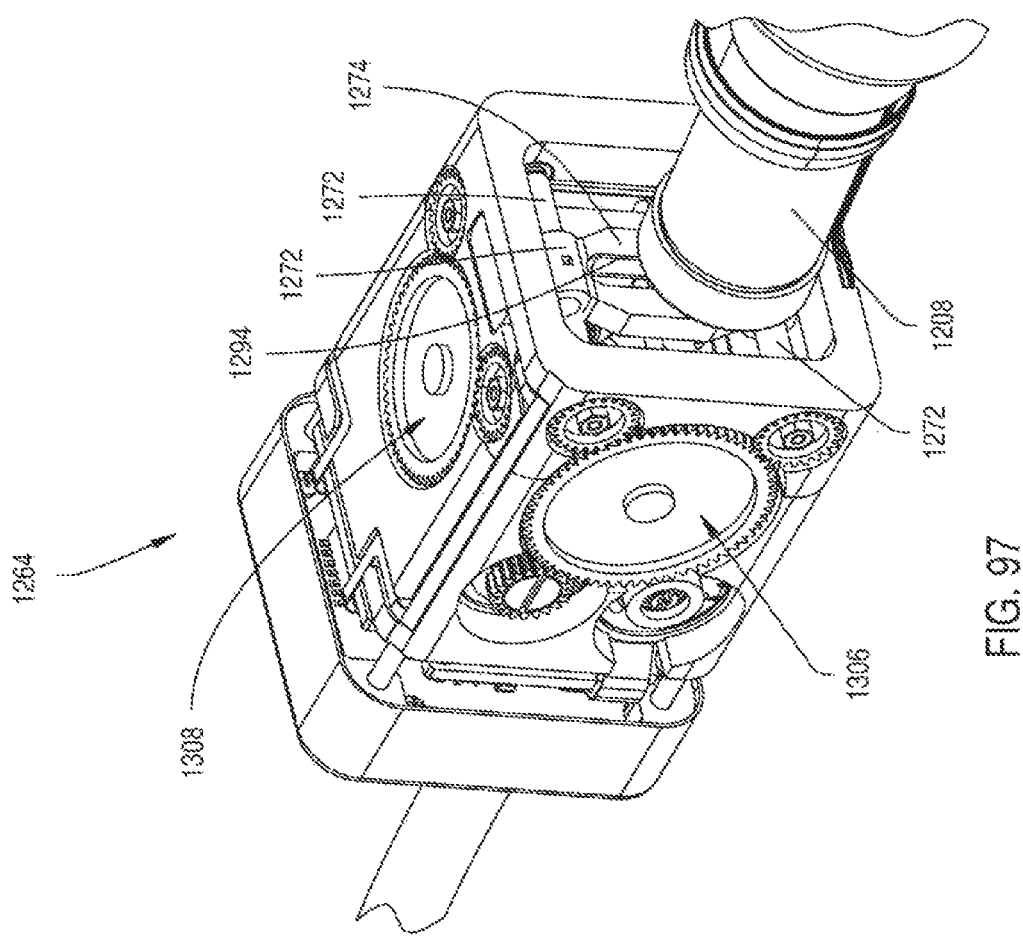
FIG. 97 is a perspective view of the adjustment assembly.
Figure 98:
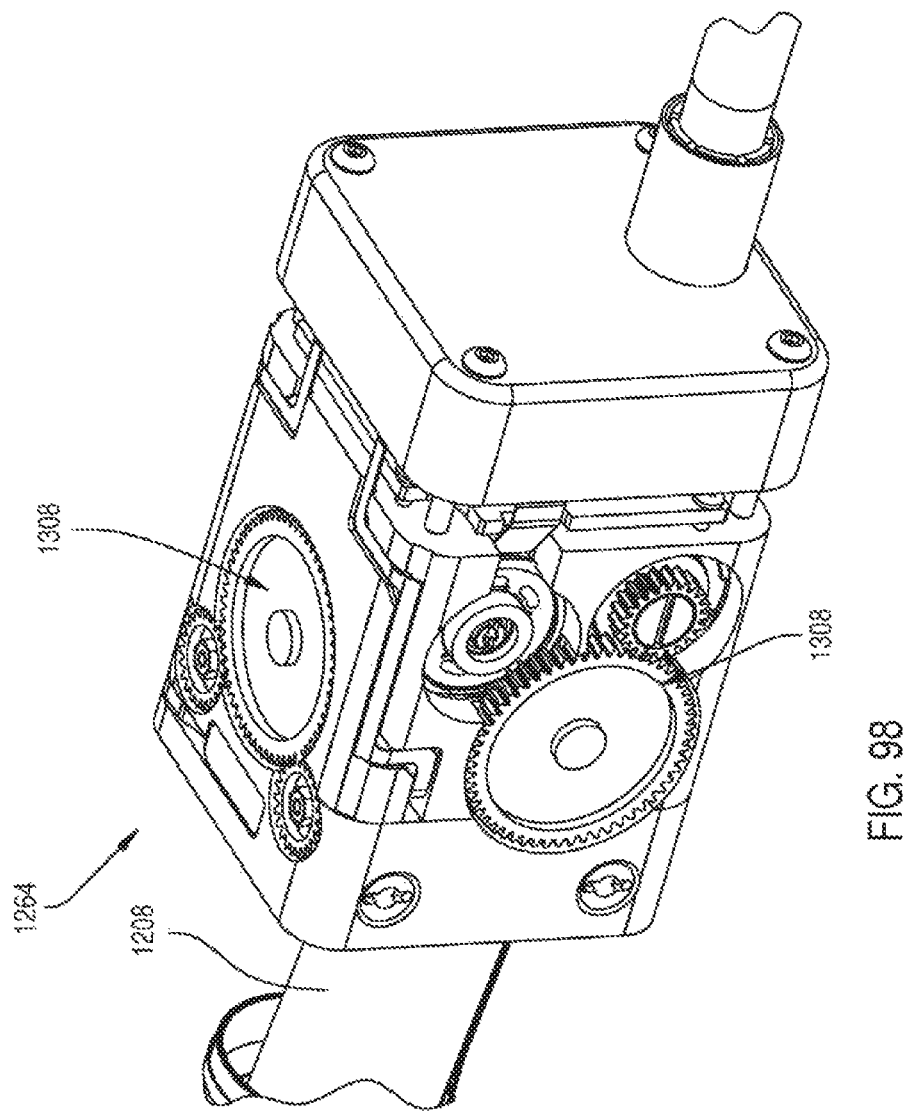
FIG. 98 is another perspective view of the adjustment assembly.
Figure 99:
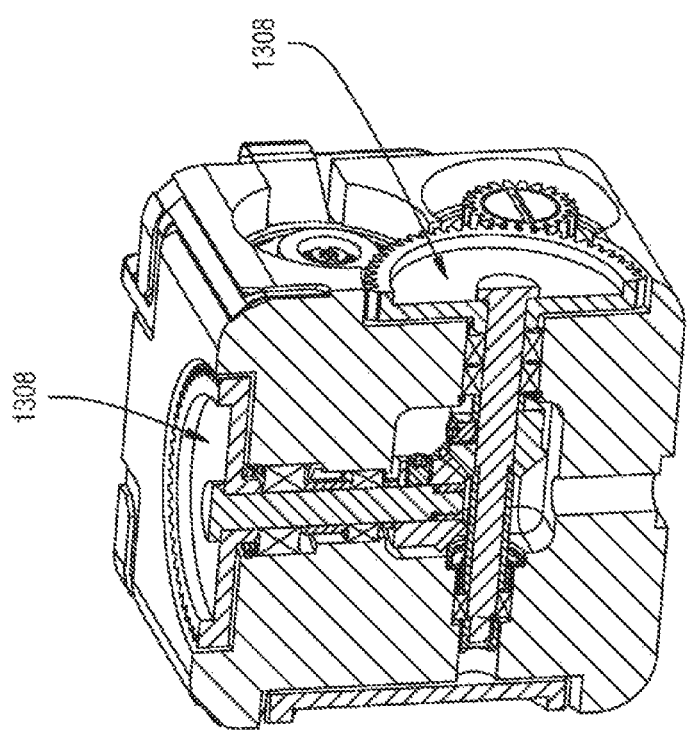
FIG. 99 is a cross-sectional view of the adjustment assembly.

With reference to FIG. 101, the carriages 1274 of the yaw adjustment device 1268 and the pitch adjustment device 1270 each define a slot 1294. The slots 1294 extend in perpendicular directions and intersect at a pocket 1296. As best shown in FIG. 96, the casing 1208 of the distal assembly 1202 includes a post 1298 that extends into the pocket 1296.

Figure 102:
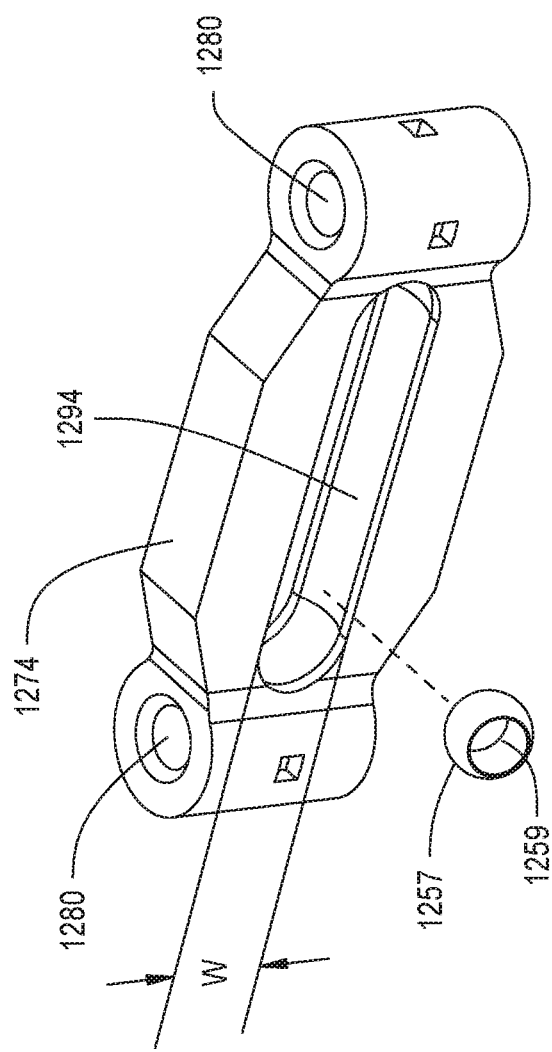
FIG. 102 is a perspective view of a carriage and a connecting member of the adjustment assembly.
Figure 104:
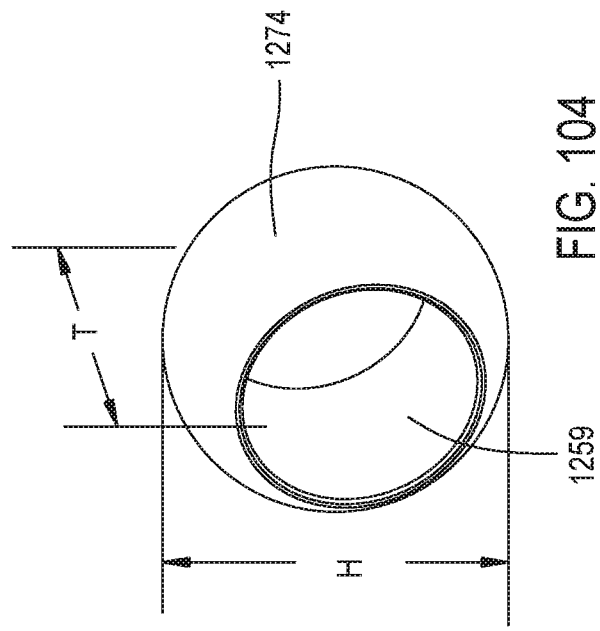
FIG. 104 is a perspective view of the connecting member.
Figure 103:
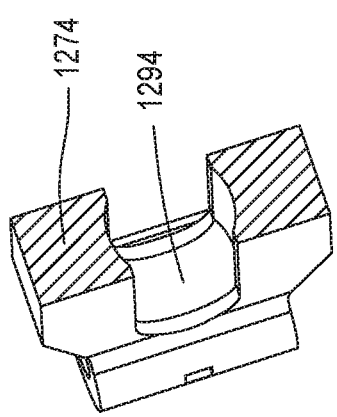
FIG. 103 is a cross-sectional view of the carriage.

With reference to FIGS. 102 and 103, the slots 1294 are rounded or arcuate in cross-section. As best shown in FIGS. 96, 102, and 104, a connecting member 1257 is engaged with each slot 1294 and the post 1298. Specifically, each connecting member 1257 is shaped like gimbal 1258 and defines an opening 1259 receiving the post 1298. The post 1298, the slots 1294, and the opening 1259 of the connecting member 1257 each typically include a surface formed of a low friction material such as, for example, stainless steel, brass, or bronze, and is typically highly polished. The outer surface of connecting member 1257 can pivot relative to the arcuate inner surface of slots 1294.

With reference to FIGS. 102 and 104, the connecting members 1257 each have a thickness T that is less than a width W of the slots 1294 and the connecting members 1257 each have a height H greater than the width W of the slots 1294. As such, the connecting members 1257 are introduced to the slots 1294 in an orientation such that the thickness T of the connecting member 1257 fits within the width W of the slot 1294. The connecting member 1257 is then rotated to the position shown in FIGS. 96 and 97 to engage the connecting member 1257 in the slot 1294. When engaged in the opening 1259, the post 1298 prevents rotation of the connecting member 1257 to a position of disengagement from the slots 1294.

Figure 100:
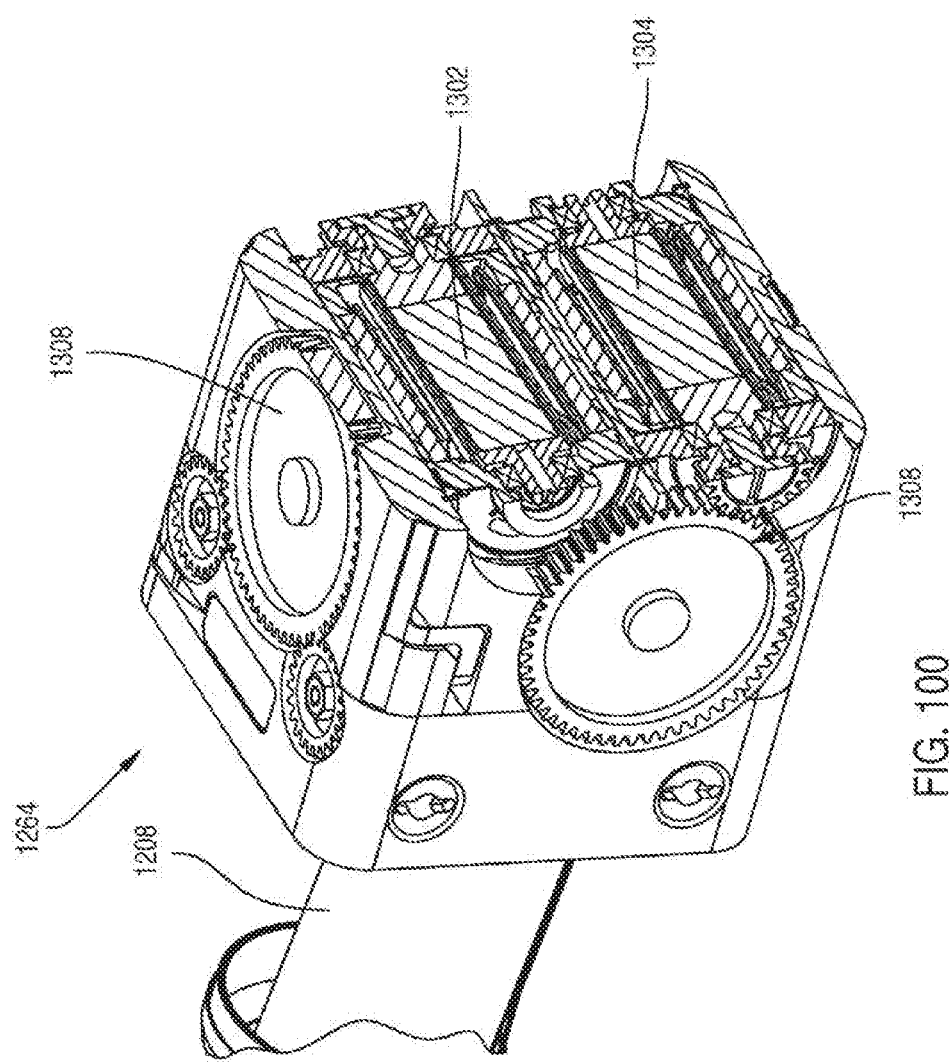
FIG. 100 is another cross-sectional view of the adjustment assembly.

With reference to FIG. 100, a yaw motor 1302 is engaged with the lead screws 1272 of the yaw adjustment device 1268 and a pitch motor 1304 is engaged with the lead screws 1272 of the pitch adjustment device 1270. The yaw motor 1302 and the pitch motor 1304 are connected to respective motor controllers 232, 234, which are connected to the power source 140 shown in FIG. 1 and described above. The motor controllers 232, 234 are typically disposed remotely from the instrument 1200.

A yaw gear set 1306 engages the yaw motor 1302 and the lead screws 1272 of the yaw adjustment device 1268. A pitch gear set 1308 engages the pitch motor 1304 and the lead screws 1272 of the pitch adjustment device 1270. The lead screws 1272 of the yaw adjustment device 1268 and the pitch adjustment device 1270 engages gears (not individually numbered) of the gear sets 1306, 1308, respectively, with a press-fit engagement and/or by engagement with keyed ends, e.g., hexagonally shaped ends. The outer casing 1206 of the proximal assembly 1204 houses the yaw motor 1302 and yaw gear set 1306 and houses the pitch motor 1304 and the pitch gear set 1308.

Yaw gear set 1306 is arranged to simultaneously rotate both lead screws 1272 of the yaw adjustment device 1268 at the same speed and angle upon actuation of the yaw motor 1302. Pitch gear set 1308 is arranged to simultaneously rotate both lead screws 1272 of the pitch adjustment device 1270 at the same speed and angle upon actuation of the pitch motor 1304. As such, the carriage 1274 for each respective adjustment device smoothly moves along the lead screws 1272 as the lead screws 1272 are rotated.

To adjust the yaw of the distal assembly 1202 relative to the proximal assembly 1204, the yaw motor 1302 rotates the yaw gear set 1306, which in turn rotates the lead screws 1272 and moves the carriage 1274 of the yaw adjustment device 1268 relative to the frame 1266 of the adjustment assembly 1264. As the carriage 1274 of the yaw adjustment device 1268 moves relative to the frame 1266, the carriage 1274 moves the post 1298, which pivots the casing 1208 about the gimbal 1258 to adjust the yaw of the distal assembly 1202 and the cutting accessory 202 mounted to the distal assembly 1202.

To adjust the pitch of the distal assembly 1202 relative to the proximal assembly 1204, the pitch motor 1304 rotates the pitch gear set 1308, which in turn rotates the lead screws 1272 and moves the carriage 1274 of the pitch adjustment device 1270 relative to the frame 1266 of the adjustment assembly 1264. As the carriage 1274 of the pitch adjustment device 1270 moves relative to the frame 1266, the carriage 1274 moves the post 1298, which pivots the casing 1208 about the gimbal 1258 to adjust the pitch of the distal assembly 1202 and the cutting accessory 202 mounted to the distal assembly 1202. The connecting member 1257 move along the slot 1294 when the carriage 1274 moves the post 1298.

Yaw motor 1302 and the pitch motor 1304 can be operated simultaneously and/or independently to adjust the yaw and the pitch of the distal assembly 1202 relative to the proximal assembly 1204. The lead screw motor 1240, as discussed above, can be operated simultaneously with the yaw motor 1302 and/or the pitch motor 1304 to simultaneously move the cutting accessory along the longitudinal axis A and adjust the yaw and/or pitch of the distal assembly 1202 relative to the proximal assembly 1204. The lead screw motor 1240 can also be operated independently from the yaw motor 1302 and the pitch motor 1304.

As shown in FIG. 74, at least one circuit board 1263 is mounted in the outer casing 1206. Position sensors for the longitudinal axis A position (e.g., magnet 1255 and magnet sensor), yaw position, and pitch position of the cutting accessory 202 are in communication with the circuit board 1263. For example, flex circuits connect the position sensors to the circuit board 1263.

In one embodiment, a trigger or foot pedal, or alternatively a button, (not shown) can be supported by the outer casing 1206 of the proximal assembly 1204 to power the accessory motor, i.e., to selectively supply power to or not supply power to the cutting accessory 202. As set forth above with respect to instrument 200, the instrument 1200 can include a sensor (not identified) disposed inside the instrument 1200. The sensor generates a signal if the trigger is actuated and/or not actuated. The output signals from the sensor are forwarded by the data connection 133 to the instrument driver 130. Based on the state of this sensor signal, the instrument driver 130 applies energization signals to the drive motor 1212 when the tip or bur head 204 of the cutting accessory 202 is in the boundary 106 of target volume 104. In the alternative to, or in addition to the trigger or button, a foot pedal (not shown) can be in communication with the instrument 1200 to control the drive motor 1212 by providing on/off instructions to the drive motor 1212. As set forth above, the rotational speed of the accessory 202 is also dependent upon the position of the tip or bur head 204 of the accessory 202 relative to the "home" position.

Figure 2:
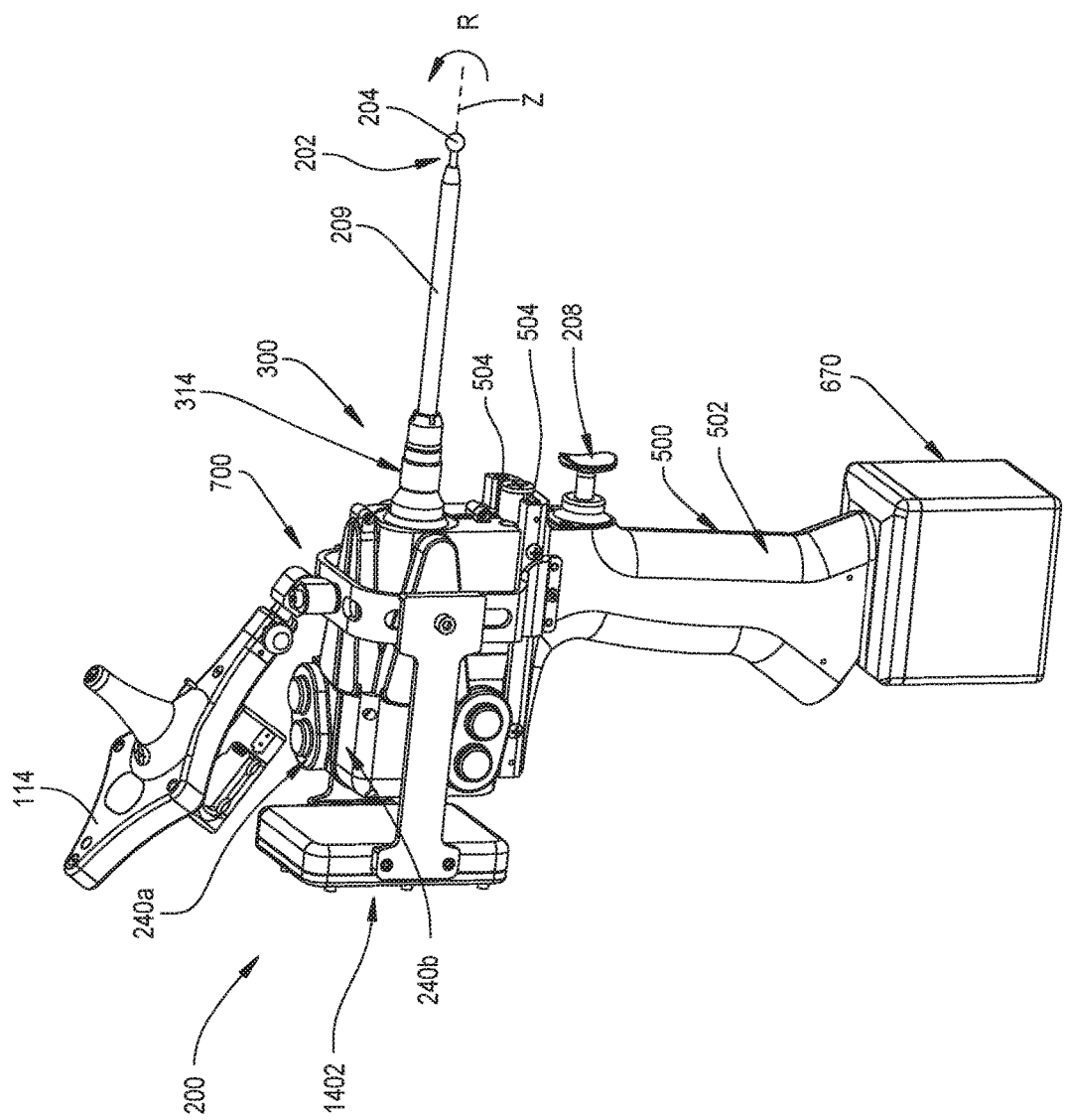
FIG. 2 is a perspective view of a surgical instrument used in the tracking and control system of FIG. 1.
Figure 2A:
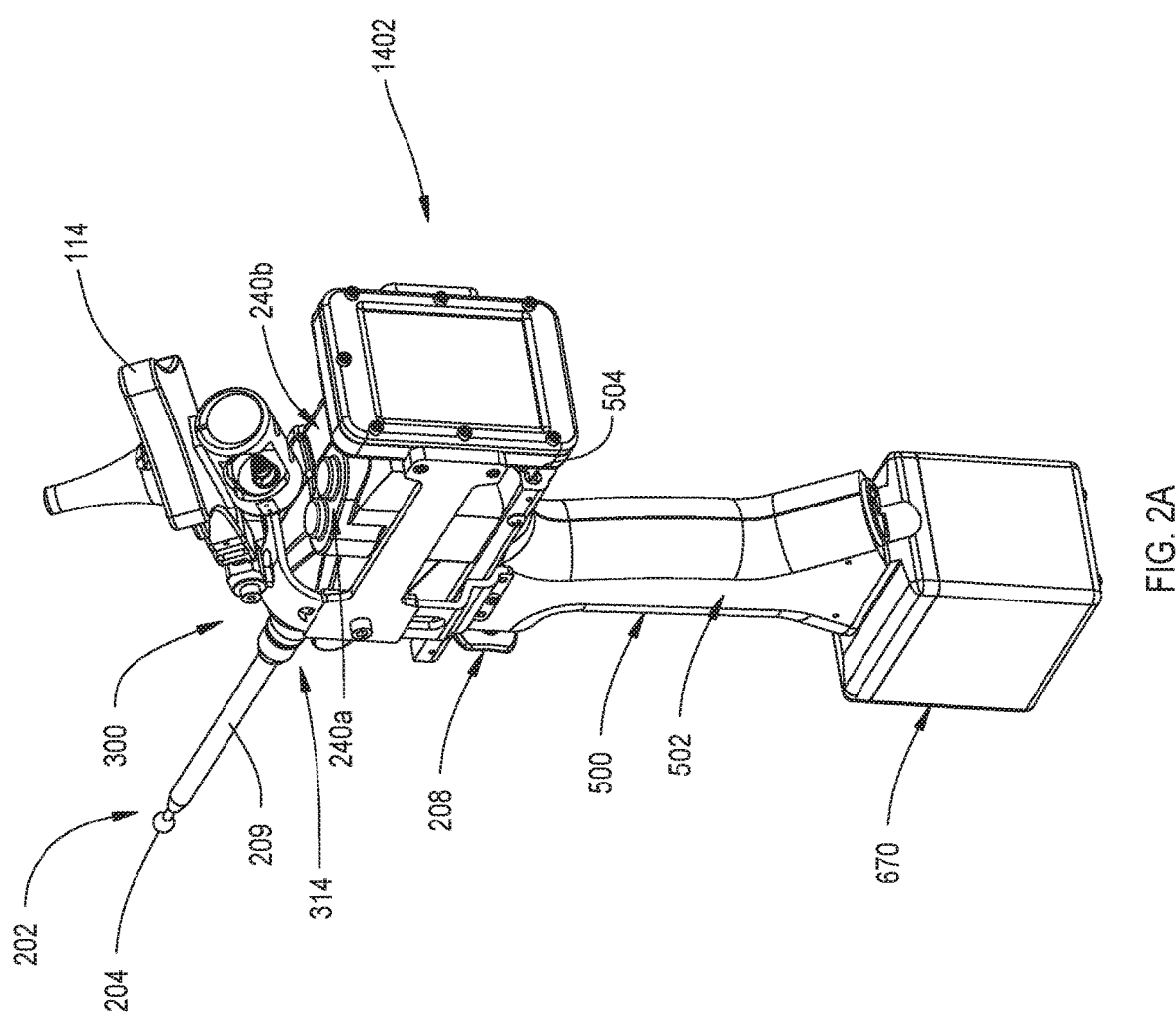
FIG. 2A is a rear perspective view of the surgical instrument used in the tracking and control system of FIG. 1.

As set forth above, when the tip or bur head 204 of the cutting accessory 202 is outside of the boundary 106 of the target volume 104, the instrument driver 130 does not apply an energization signal to the drive motor 1212 even if the trigger is actuated. The tracking and control system 100 can be configured such that the instrument driver 130 applies an energization signal to reduce the speed of the cutting accessory 202 when the tip or bur head 204 of the cutting accessory 202 enters the buffer 105 of the target volume 104, which is best shown in FIG. 2.

IX. Display Screen

A display screen 1402, also referred to as display 1402, is in communication with the surgical instrument 200, 1200 and provides instructions to the user for proper location and orientation of the surgical instrument 200, 1200 to locate and orientate the cutting accessory 202 in the work boundary 106. As set forth above, the display 1402 is in communication with the navigation system for indicating the position of the working portion relative to the work boundary 106.

As set forth above, the surgical instrument 200, 1200 adjusts the accessory 202 about three degrees of freedom within an adjustment range (not identified in the Figures) to orientate the accessory 202 in the work boundary 106. The display screen 1402 can be selectively used by the user. For example, the use of the display screen 1402 may be required for applications requiring more than three degrees of freedom of tip positioning and can be optional for applications requiring three or less degrees of freedom of tip positioning.

As set forth above, the tracking and control system 100 tracks the positions and orientations of the anatomy and the surgical instrument 1200 to keep the tip or bur head 204 of the cutting accessory 202 within the target volume 104. Based on the tracking of the positions and orientations of the anatomy and the surgical instrument 1200 by the tracking and control system 100, the display screen 1402 indicates adjustments, if any, that are required to locate and orientate the handle assembly 500 of the surgical instrument 200 or the outer casing 1206 of the surgical instrument 1200 such that the work boundary 106 is within the adjustment range of the surgical instrument 200, 1200, i.e., such that the surgical instrument is capable of adjusting to locate and orientate the cutting accessory 202 in the work boundary 106.

Display screen 1402 can, for example, be a liquid crystal display (LCD) monitor, a light emitting diode (LED) monitor, an organic light emitting diode (OLED) monitor, etc., however, it is appreciated that the display screen 1402 can be any type of digital or analog display without departing from the nature of the present invention. The display screen 1402 can be mounted to the surgical instrument 200, 1200 and, more specifically, can be mounted to be generally along the line of vision of the user when viewing the cutting accessory 202, as shown in FIGS. 72 and 73, for example. Alternatively, the display screen 1402 can be spaced from and independently movable relative to the surgical instrument 200, 1200.

Various embodiments of visual content of the display screen 1402 are shown in FIGS. 107-111. The display screen 1402 can display a target reticle 1404 including cross-hairs 1406 and concentric circles 1408. The intersection 1414 of the cross-hairs identifies the desired location and/or orientation of the handle assembly 500 of surgical instrument 200 or the outer casing 1206 of surgical instrument 1200.

Figure 108:
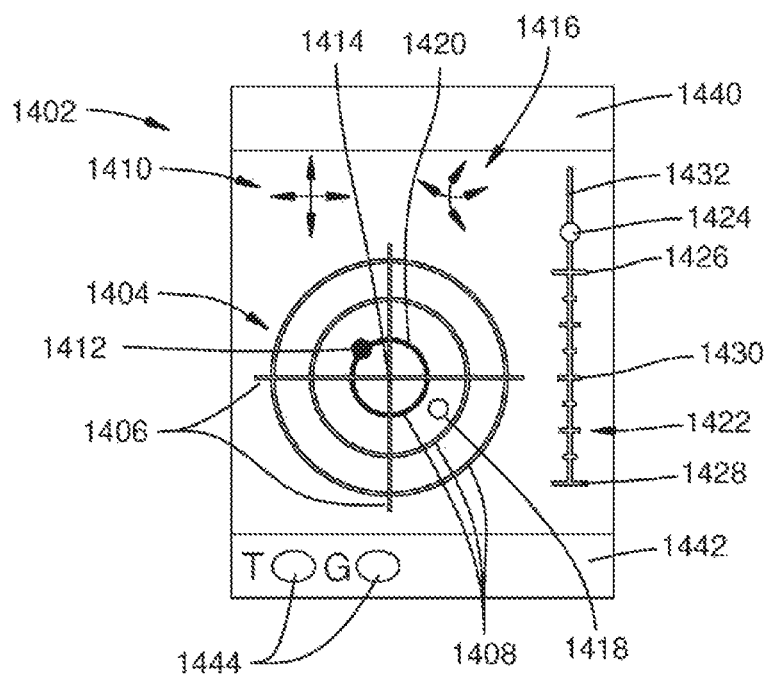
FIG. 108 is a view of a display screen including a target reticle, a depth legend, an extension extending from the depth legend, an acceptance circle, an orientation legend, and a translation legend.
Figure 110:
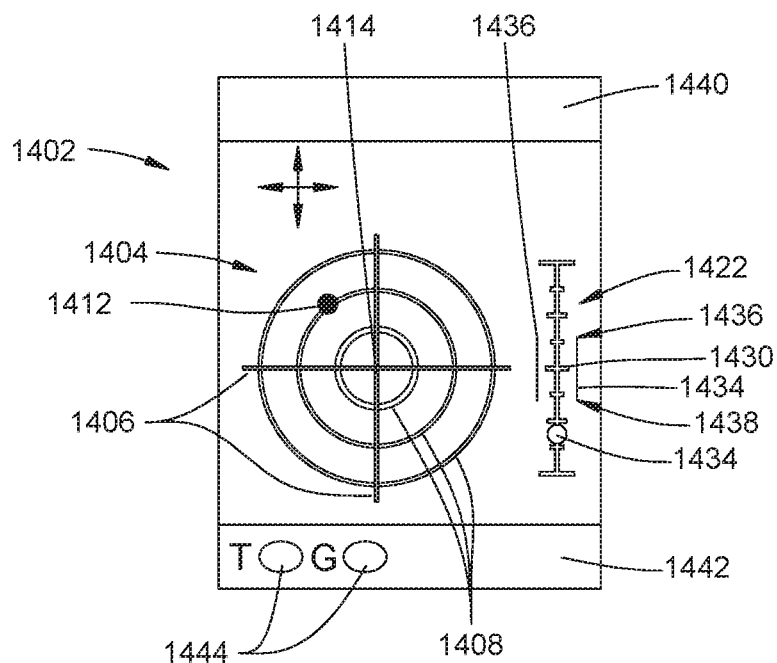
FIG. 110 is a view of a display screen including a target reticle, a depth legend, an acceptance bar, and a translation legend.
Figure 111:
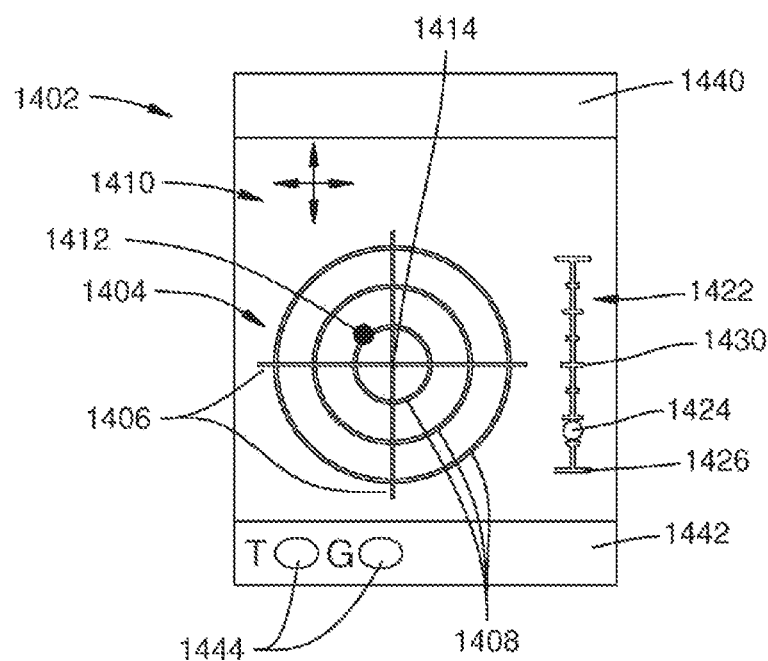
FIG. 111 is a view of the display screen including a target reticle, a depth legend, and a translation legend.

As shown in FIGS. 108, 110, and 111, display screen 1402 can display a translation legend 1410 and an associated translation marker 1412. Translation of the handle assembly 500 of the surgical instrument 200 or the outer casing 1206 of surgical instrument 1200 relative to the target volume 104 can be mirrored by movement of the translation marker 1412 on the display screen 1402. In other words, the translation marker 1412 moves to the left on the display screen 1402 in response to translation of the handle assembly 500 or the outer casing 1206 to the right, and the translation marker 1412 moves to the right on the display screen 1402 in response to translation of the handle assembly 500 or the outer casing 1206 the left. Similarly, the translation marker 1412 moves up or down on the display screen 1402 in response to translation of the handle assembly 500 or the outer casing 1206 down or up, respectively. As such, to properly locate the cutting accessory 202 relative to the target volume 104, the user translates the handle assembly 500 or the outer casing 1206 such that the intersection 1414 of the cross-hairs moves toward the translation marker 1412. It is appreciated that the scale on the display screen 1402 can be increased or decreased. In other words, translation of the translation marker 1412 on the display screen 1402 can be a different scale in comparison to actual translation of the handle assembly 500 or outer casing 1206.

When used with the target reticle 1404, for example, the user initially translates the handle assembly 500 or the outer casing 1206 left/right and/or up/down to locate the intersection 1414 of the cross-hairs 1406 at the translation marker 1412, which locates the cutting accessory 202 within the work boundary 106. Depending upon the surgical procedure, the cutting accessory 202 may be powered when the handle assembly 500 or outer casing 1206 is moved such that the translation marker 1412 moves away from the intersection 1414 of the cross-hairs 1406 but remains in the boundary 106. Alternatively, in other surgical procedures, such as drilling in preparation for insertion of a screw or pin, the cutting accessory 202 may only be powered when the intersection 1414 of the cross-hairs 1406 is aligned with the translation marker 1412 or the inner circle of the concentric circles 1408.

In some embodiments, the display screen 1402 indicates the deviation of the working portion relative to the home position. The translation marker 1412 indicates the deviation of the accessory distal tip or bur head 204 from home position. In this embodiment, the user can adjust the pitch, yaw, and translation along the longitudinal axis A to keep the cutting tip 204 on a path or trajectory as long as the tip or bur head 204 is not beyond the adjustment envelope, i.e., not beyond the constraints of pitch/yaw/z-axis adjustment from home position. As a result, the user only needs to maintain the translation marker 1412 within a certain range from center, which is dependent on the extent of deviation from home to which the instrument is capable.

Figure 107:
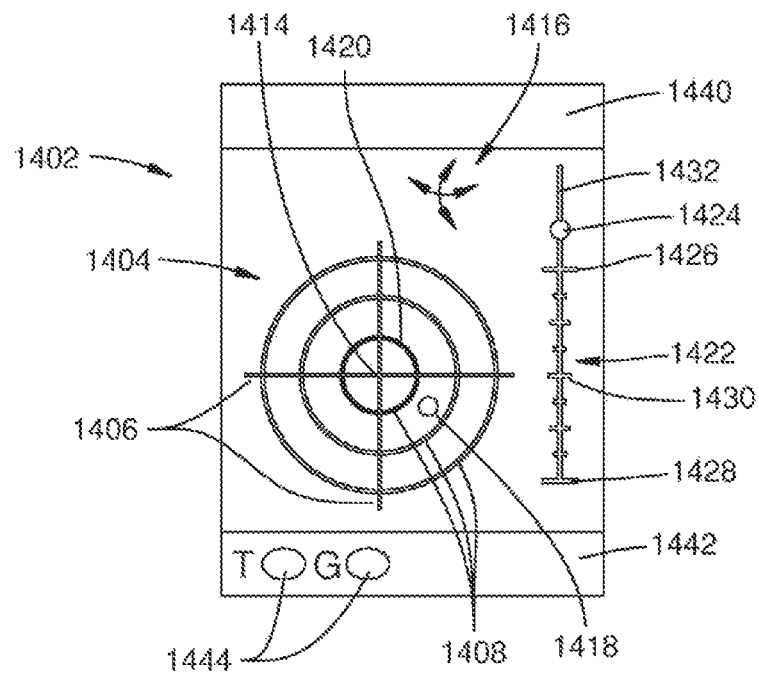
FIG. 107 is a view of a display screen including a target reticle, a depth legend, an extension extending from the depth legend, an acceptance circle, and an orientation legend.
Figure 109:
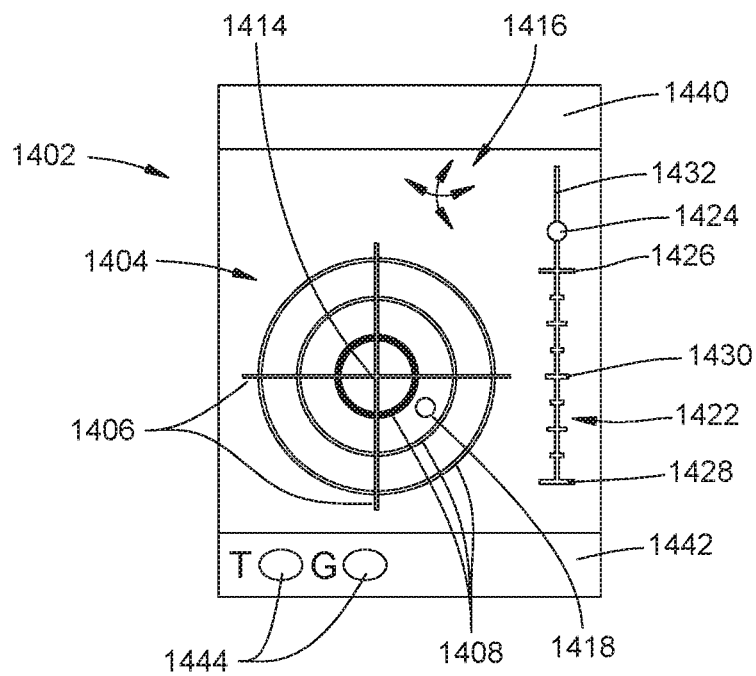
FIG. 109 is a view of a display screen including a target reticle, a depth legend, an extension extending from the depth legend, and an orientation legend.

As shown in FIGS. 107-109, the display screen 1402 can display an orientation legend 1416 and an associated orientation marker 1418. The orientation legend 1416 and orientation marker 1418 display the orientation, i.e., the pitch and yaw, of the handle assembly 500 or the outer casing 1206 relative to the target volume 104. Orientation of the handle assembly 500 or the outer casing 1206 can be schematically mirrored by movement of the orientation marker 1418 on the display screen 1402. Specifically, the orientation marker 1418 moves to the left or to the right on the display screen 1402 in response to yaw of the handle assembly 500 or the outer casing 1206 to the right or to the left, respectively, relative to the target volume 104. The orientation marker 1418 moves up or down on the display screen 1402 in response to pitch of the handle assembly 500 or the outer casing 1206 down or up, respectively, relative to the target volume 104. As such, to properly orientate the cutting accessory 202 relative to the target volume 104, the user moves the handle assembly 500 or the outer casing 1206 such that the intersection 1414 of the cross-hairs 1406 moves toward the orientation marker 1418.

The spacing between the circles 1408 can be a non-linear representation of the angular movement required to properly orientate the proximal assembly 1204 relative to the target volume 104. For example, when the orientation marker 1418 is on the innermost ring, the required movement of the handle assembly 500 or the outer casing 1206 is 1°, when the orientation marker 1418 is on the next ring, the required movement of the handle assembly 500 or the outer casing 1206 is 5°, and when the orientation marker 1418 is on the next ring, the required movement of the handle assembly 500 or the outer casing 1206 is 25°. The values associated with each ring can be adjusted.

When used with the target reticle 1404, for example, the user initially orientates the handle assembly 500 or the outer casing 1206 to locate the intersection 1414 of the cross-hairs 1406 at the orientation marker 1418, which orientates the cutting accessory 202 within the work boundary 106. Depending upon the surgical procedure, the cutting accessory 202 may be powered when the handle assembly 500 or outer casing 1206 is moved such that the orientation marker 1418 moves away from the intersection 1414 of the cross-hairs 1406 but the tip or bur head 204 remains in the work boundary 106 of the target volume 104 or within a predetermined deviation from the boundary 106, such as when the boundary 106 is a predefined trajectory. Alternatively, in other surgical procedures, such as drilling in preparation for insertion of a screw or pin, the cutting accessory 202 may only be powered when the intersection 1414 of the crosshairs 1406 is aligned with the orientation marker 1418 or the inner circle of the concentric circles 1408.

With reference to FIG. 109, the target reticle 1404 can include an acceptance ring 1420. The acceptance ring 1420, which can be the innermost of the concentric circles 1408 of the target reticle 1404, can be of a different color and/or thickness than the other concentric circles 1408 for identification purposes.

The acceptance ring 1420 can indicate the range of positions of the nose tube 1218 in which the cutting accessory 202 can be operated. The acceptance ring 1420 is typically used with the orientation marker 1418. In other words, the cutting accessory 202 can be operated when the orientation marker 1418 is in the acceptance ring 1420.

The control system 100 can be configured to control the display 1402 to change a resolution of the display 1402 as the working portion approaches the virtual boundary. In other words, the acceptance ring 1420 can, for example, change during a procedure. For example, during a drilling procedure to create a hole for a pedicle screw, the acceptable pitch and yaw position of the nose tube 1218 can change as the tip or bur head 204 of the cutting accessory 202 moves deeper into the bone, i.e., the acceptable pitch and yaw position decreases to avoid collision between the nose tube 1218 and the side of the hole as the hole gets deeper. In such a procedure, the acceptance ring 1420 can be configured to become smaller as the tip or bur head 202 moves deeper into the bone 102 to indicate that the amount of acceptable deviation in the pitch and yaw directions is decreasing.

Display screen 1402 can display a depth legend 1422 and an associated depth marker 1424. The depth legend 1422 and the depth marker 1424 display the depth of the tip or bur head 204 of the cutting accessory 202 relative to the target volume 104.

In one embodiment, the depth legend 1422 includes a top limit line 1426, a bottom limit line 1428, and a middle line 1430. The top limit line 1426, which is the top line on the depth legend 1422 in FIGS. 107-109, indicates the surface of the target volume 104 and the bottom limit line 1428, which is the bottom line on the depth legend 1422 in FIGS. 126-128 and 131, indicates the bottom of the target volume 104. In other words, the depth legend 1422 and the depth marker 1424 indicate that the tip or bur head 204 of the cutting accessory 202 is at the surface of the target volume 104 when the depth marker 1424 is located on the top limit line 1426. The depth legend 1422 and the depth marker 1424 indicate that the tip or bur head 204 of the cutting accessory 202 is at the bottom of the target volume 104 when the depth marker 1424 is located on the bottom limit line 1428.

In another embodiment, the middle line 1430 indicates a home position of the tip or bur head 204. To locate the bur head 204 of the cutting accessory 202 at the correct depth relative to the target volume 104, the user moves the handle assembly 500 or the outer casing 1206 such that the middle line 1430 of the depth legend 1422 is displayed about the depth marker 1424.

As shown in FIGS. 107-109, depth legend 1422 can display an extension 1432 that extends upwardly from the top limit line 1426. The extension 1432 indicates the area immediately adjacent the target volume 104.

As shown in FIG. 110, the display screen 1402 can display an acceptance bar 1434, which is shown adjacent the depth legend 1422 in FIG. 110. In the alternative in which the top limit line 1426 indicates the surface of the target volume 104 and the bottom limit line 1428 indicate the bottom of the target volume 104, the acceptance bar 1434 shown in FIG. 110 includes a top 1436 that indicates the surface of the target volume 104 and a bottom 1438 that indicates the bottom of the target volume 104.

The display screen 1402 displays a top banner 1440 and a bottom banner 1442, each of which can display selected information. For example, the top banner 1440 and/or the bottom banner 1442 can display the type of procedure being performed, patient information, etc. The top banner 1440 and/or the bottom banner 1442 can include indicators 1444 that indicate blocked visibility of the trackers 114, 116. The indicators 1444 can be color coded (e.g., red and green) to indicate whether visibility is established or not established.

Translation legend 1410/translation marker 1412, orientation legend 1416/orientation marker 1418, and depth legend 1422/depth marker 1424 can be independently displayed or hidden on the display screen 1402. The translation marker 1412, the orientation marker 1418, and the depth marker 1424 can each be of a different color for ease of differentiation. The translation legend 1410, the orientation legend 1416, and the depth legend 1422 can be colored the same color as the translation marker 1412, the orientation marker 1418, and the depth marker 1424, respectively, for easy identification. In addition to or in the alternative to color coding, the translation marker 1412, the orientation marker 1418, and the depth marker 1424 can each be a different symbol for ease of differentiation.

FIGS. 107-111 show various embodiments of visual content of the display screen 1402. The display screen 1402 shown in FIG. 109 displays the orientation legend 1416 and orientation marker 1418 and displays the depth legend 1422 and depth marker 1424. As set forth above, to properly orientate the cutting accessory 202 relative to the target volume 104, the user moves the handle assembly 500 or the outer casing 1206 such that the intersection 1414 of the cross-hairs 1406 moves toward the orientation marker 1418. As such, in the scenario shown in FIG. 107, the user adjusts the yaw of the handle assembly 500 or outer casing 1206 to the right and pitches the handle assembly 500 or outer casing 1206 downwardly to align the intersection 1414 with the orientation marker 1418. To locate the tip or bur head 204 of the cutting accessory 202 at the correct depth relative to the target volume 104, the user moves the handle assembly 500 or the outer casing 1206 such that the bottom line 1428 of the depth legend 1422 is disposed on the depth marker 1424. For example, the bottom line 1428 moves toward the depth marker 1424 when drilling into bone with a bur to create a bore for a pedicle screw or pin.

Display screen 1402 shown in FIG. 107 displays the acceptance ring 1420 and as such, the cutting accessory 202 can be powered when the acceptance ring 1420 is displayed about the orientation marker 1418. Alternatively, the display screen 1402 shown in FIG. 109 does not display an acceptance ring. Display screen 1402 shown in FIG. 108 displays the translation legend 1410 and translation marker 1412, the orientation axis and orientation marker 1418, and the depth legend 1422 and the depth marker 1424. In this scenario, the user adjusts the yaw of the handle assembly 500 or outer casing 1206 to the right and pitches the handle assembly 500 or outer casing 1206 downwardly to align the intersection 1414 with the orientation marker 1418. The user also translates the handle assembly 500 or outer casing 1206 upwardly and to the left to align the intersection 1414 with the translation marker 1412. To locate the tip or bur head 204 of the cutting accessory 202 at the correct depth relative to the target volume 104, the user moves the handle assembly 500 or the outer casing 1206. The display screen 1402 shown in FIG. 108 displays the acceptance ring 1420 and as such, the cutting accessory 202 can be powered when the acceptance ring 1420 is disposed about the orientation marker 1418.

Display screen 1402 shown in FIG. 108 displays the translation legend 1410 and translation marker 1412 and displays the depth legend 1422 and depth marker 1424. In this scenario, the user translates the handle assembly 500 or outer casing 1206 upwardly and to the left to align the intersection 1414 with the translation marker 1412, and more preferably align the intersection 1414 with the translation marker 1412. As set forth above, the display screen 1402 of FIG. 110 displays an acceptance bar 1434. In FIG. 110, the user locates the tip or bur head 204 of the cutting accessory 202 at the proper depth by moving the tip or bur head 204 deeper into the target volume 104 until the acceptance bar 1434 is displayed along the depth marker 1424.

Although not shown, it should be appreciated that display screen 1402 can be blank, i.e., does not display the target reticle 1404 and does not include any direction legends or markers. Such an embodiment can be used for cutting applications that do not require additional guidance from the display screen 1420.

The display screen 1402 shown in FIG. 111 displays the translation legend 1410 and translation marker 1412 and displays the depth legend 1422 and depth marker 1424. In this scenario, the user translates the handle assembly 500 or outer casing 1206 upwardly and to the left to align the intersection 1414 with the translation marker 1412. With continued reference to FIG. 111, the user locates the bur head 204 of the cutting accessory 202 at the proper depth by moving the bur head 204 out of the target volume 104 until the middle line 1430 is aligned with the depth marker 1424.

X. Surgical Procedures

Several surgical procedures can be carried out by the system 100 and instruments 200, 1200. Some of these procedures involve the removal of tissue such as bone. Removal of bone with the instruments 200, 1200 can include sculpting, shaving, coring, boring, or any other method of removing bone, depending on the procedure and the type of cutting accessory 202 attached to the instrument 200, 1200. The instrument 200, 1200 can be used to remove tissue in spine, knee, hip, cranium, and other procedures. These procedures may be open procedures or minimally invasive procedures.

During each surgical procedure, positions and/or orientations of the bur head 204 of the instrument 200, 1200 and the anatomy being treated are dynamically tracked. Representations of the bur head 204 and the anatomy are continuously shown on the displays 113, 1402 so that the surgeon is always aware of their relative position. The position of the bur head 204 is controlled by the system 100 based on the relationship of the bur head 204 to boundaries defined in the system 100, as previously described. In some cases, the boundaries define areas of the anatomy to avoid and in other cases, the boundaries define paths that the bur head 204 is specifically controlled by the system 100 to traverse.

Referring to FIGS. 112A through 112D, in one procedure, the instrument 200, 1200 is used to perform a spinal fusion. Spinal fusion procedures in which the instrument 200, 1200 can be employed to remove tissue include, but are not limited to, an ALIF (anterior lumbar interbody fusion), PLIF (posterior lumbar interbody fusion), TLIF (transforamenal lumbar interbody fusion), DLIF (direct lateral interbody fusion), or XLIF (extreme lateral interbody fusion).

Figure 112A:
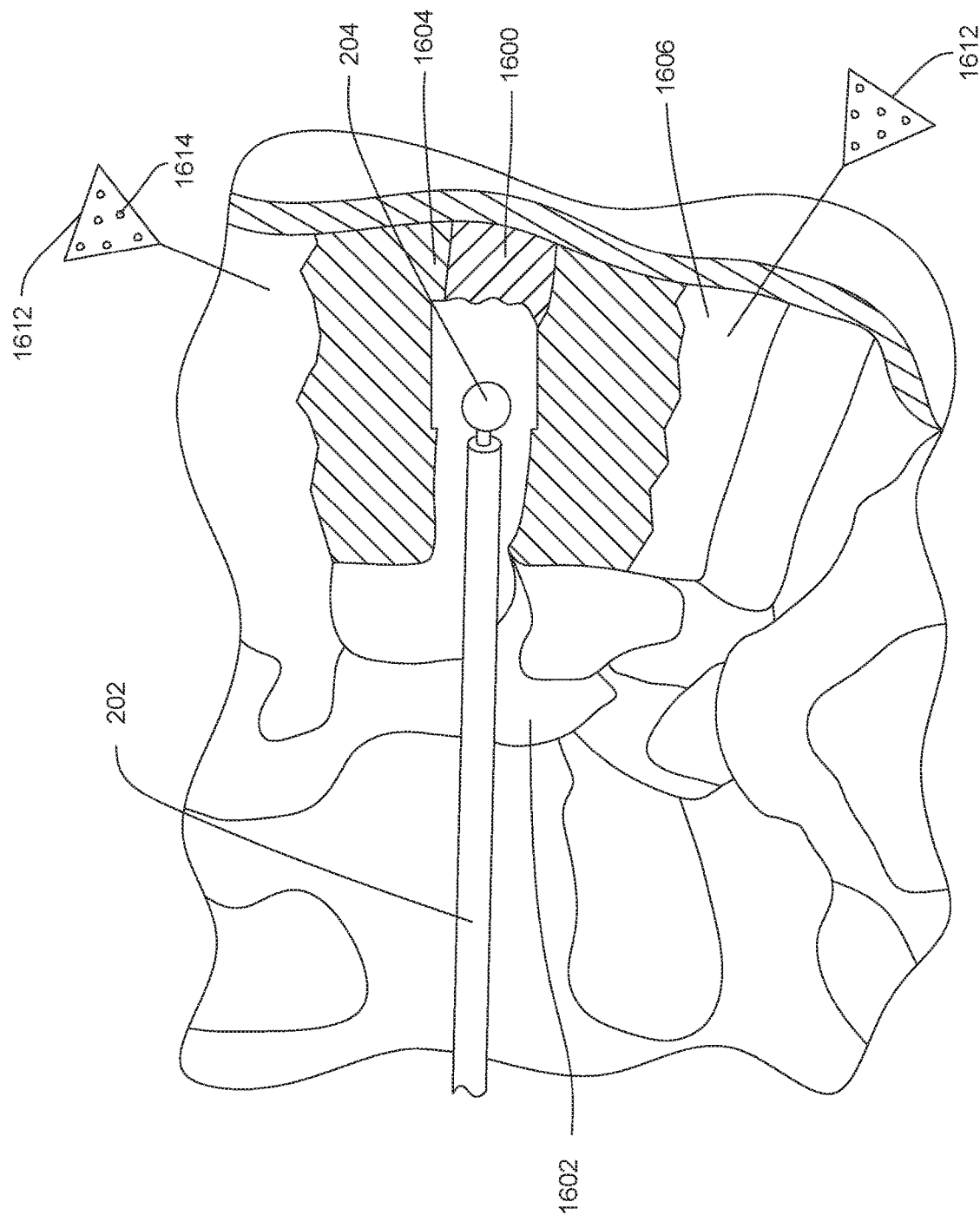
FIGS. 112A through 112D illustrate steps of performing a surgical fusion.

Referring to FIG. 112A, in some interbody spinal fusions, the instrument 200, 1200 may be used to first cut and penetrate through bone to access a patient's intervertebral disc 1600. For instance, posterior access to the disc 1600 may require penetration through the lamina 1602. Depending on the approach taken by the surgeon, total or partial removal of the lamina 1602 of a patient may be required to access the disc 1600. In these embodiments, the bur head 204 (e.g., tip) of the cutting accessory 202 penetrates into the patient's lamina 1602 to remove all or portions of the lamina 1602.

Still referring to FIG. 112A, once the bone has been cut away to gain access to the disc 1600, the instrument 200, 1200 can also perform a discectomy by cutting away all or part of the patient's disc 1600.

In some cases, it is not required to first remove bone to perform the discectomy. Whether bone is required to be cut to access the disc 1600 depends on the surgeon's entry decision for the procedure, e.g., whether ALIF, PLIF, TLIF, DLIF, etc. The portions of the lamina 1602 and the disc 1600 to be removed can be pre-operatively defined as boundaries stored in the system 100 to control movement of the bur head 204.

Positions and orientations of the vertebral bodies involved in the procedure, including their end plates 1604, 1606, and the disc 1600 are tracked using navigation by attaching a tracker 1612 to each of the vertebral bodies and then matching the vertebral bodies to pre-operative images so that the surgeon can visualize the material being removed on the display 113, 1402. The position and orientation of the disc 1600 can be inferred by tracking the position and orientation of the bone above and below the disc 1600. Portions of bone or disc to be removed can be displayed in one color, while the material to remain can be displayed in a different color. The display is updated as cutting progresses to show the material still to be removed while eliminating the material already removed. In some embodiments, each tracker includes three or more active or passive markers 1614 for tracking movement of the vertebral bodies.

Techniques for registering pre-operative images to a patient's anatomy are well known in the surgical navigation arts. In some embodiments, a tracked pointer, such as that shown in U.S. Pat. No. 7,725,162, entitled "Surgery System", the disclosure of which is hereby incorporated by reference, is used to identify anatomical landmarks on each vertebral body, which are then matched to the pre-operative image to register the pre-operative image to the anatomy.

Figure 112B:
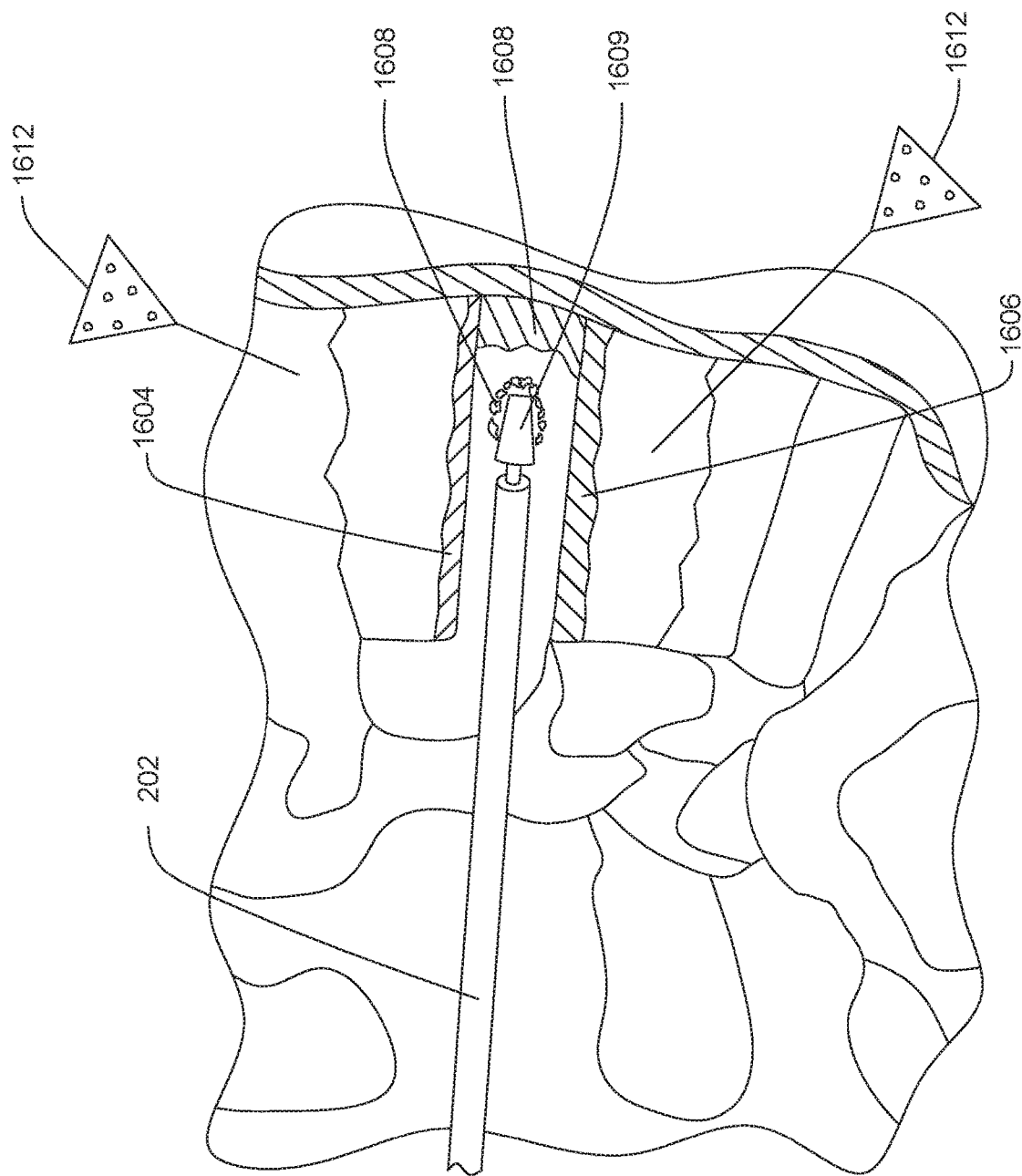

Referring to FIG. 112B, bone from bone plates 1604, 1606 can also be removed by the bur head 204 to expose bleeding spongy bone. The exposure of bleeding bone promotes bone ingrowth with bone matrix material 1608.

The surfaces of the end plates 1604, 1606 can be cut to a surgeon's shape preference. The end plates 1604, 1606 are shaped by the bur head 204 under the guidance of the tracking and control system 100 to create the desired shapes. The desired shape is predefined as a boundary in the system 100 so that the bur head 204 is controlled to stay within the boundary. In some cases, the desired shape is a planar surface milled into the end plates 1604, 1606, while in other cases, ribbed, undulating, rough, or other non-flat surfaces are preferred to further lock the implant 1610 (FIG. 112C) in position.

Figure 112C:
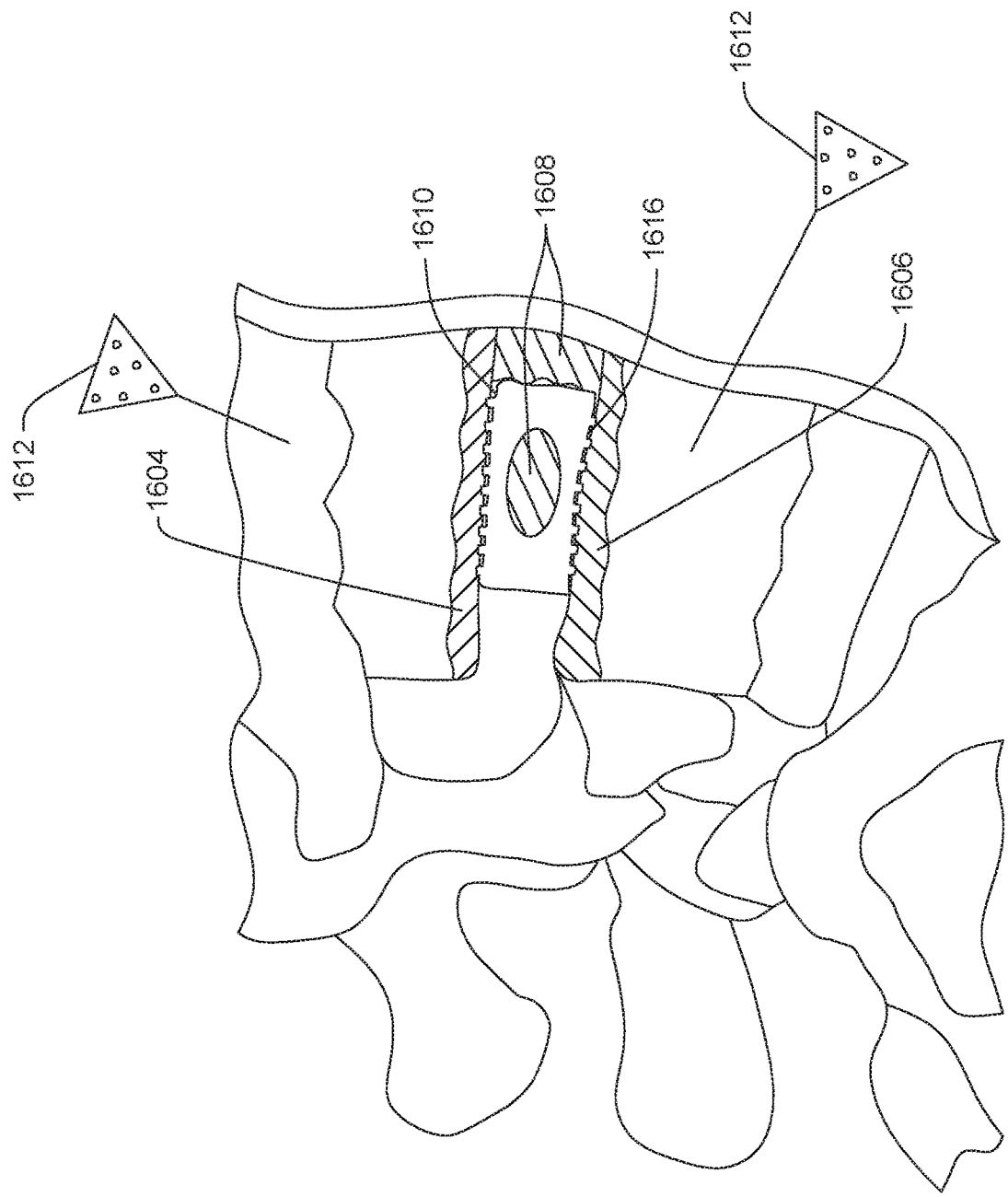

After preparing the end plates 1604, 1606, the implant 1610 is positioned between the end plates 1604, 1606. The bone matrix material 1608 can be placed in the disc space and inside the implant 1610 before and/or after placement of the implant 1610, depending on the type and size of implant being used and its location. The bone matrix material 1608 can include autograft or allograft materials with or without bone morphogenetic proteins (BMPs). The bone growth matrix 1608 could be placed into the disc space by forceps, cannula and plunger, or the like. FIG. 112C shows the implant 1610 in position with bone matrix material 1608 located in the disc space anterior to the implant 1610 and inside the implant 1610.

The implant 1610 shown has ribs 1616 defining upper and lower surfaces of the implant 1610. A boundary could be defined in the system 100 so that the end plates 1604, 1606 are milled to provide recesses (not numbered) to accommodate the ribs 1616 and further lock the implant 1610 in position.

Figure 112D:
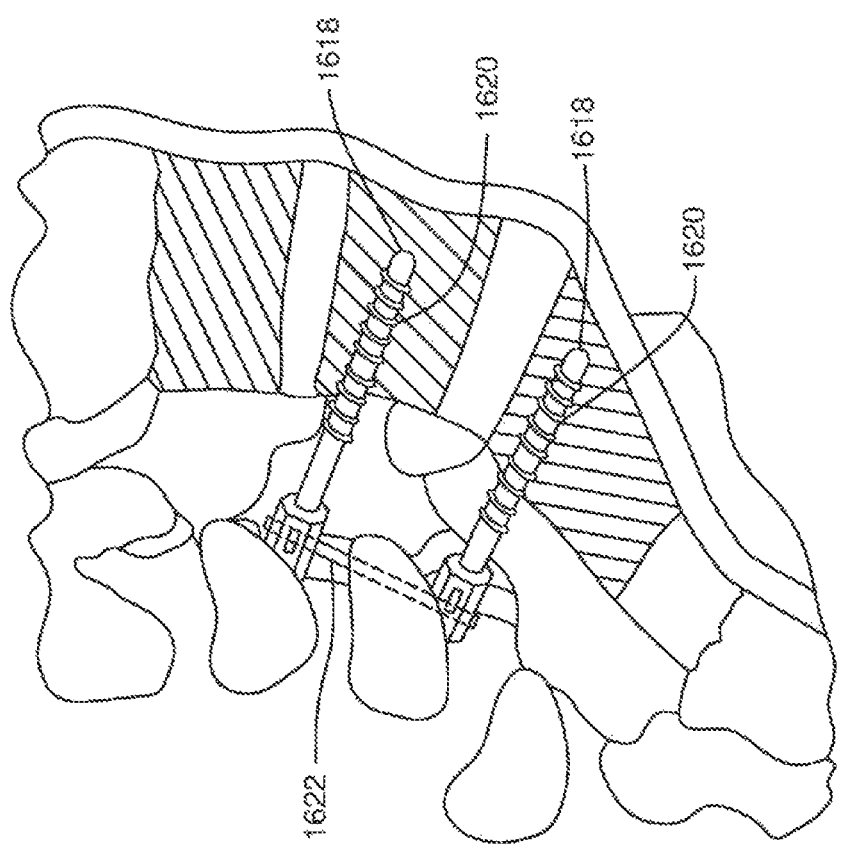

Referring to FIG. 112D, once the implant 1610 is positioned between the end plates 1604, 1606, the bur head 204 of the instrument 200, 1200 could be used to prepare pilot holes 1618 in the pedicles. The pilot holes 1618 are created to receive pedicle screws 1620 that form part of a screw/rod fixation system used to stabilize the implant 1610.

Separate boundaries define trajectories for the pilot holes. The system 100 controls the bur head 204 to stay along the trajectories as previously described to accurately cut the pilot holes 1618, including direction and depth. The screws 1620 are placed into the pilot holes 1618 with a screw driving tool (not shown). The screws 1620 are secured with an appropriate rod 1622.

In other embodiments, such as in anterior or lateral procedures, screws are used in conjunction with bone plates to provide fixation for the implants.

During spinal fusion procedures, additional boundaries (not shown) can be defined in the system 100 to indicate locations of sensitive anatomy that needs to be avoided by the bur head 204. By defining these boundaries in the system 100, they can be avoided by navigation of the instrument 200, 1200. When the bur head 204 approaches such boundaries, the bur head 204 can be diverted away in three degrees of freedom movement as described above. Additionally, the surgeon can visualize the boundaries defining the sensitive anatomy on the display 113, 1402. The sensitive anatomy may include the aorta and/or vena cava of the patient or any vasculature and/or nerves of the patient.

Other spine procedures in which the instrument 200, 1200 may be employed include any procedures involving stenosis, vertebral body replacement, or scar tissue removal. In the spinal procedures discussed, the bone of interest can be accessed either with an open procedure in which the tissue in cut and laid open, or in a minimally invasive procedure in which the bur head 204 is placed at the site in bone through a lumen of a guide tube, cannula or other access channel.

Referring to FIGS. 113A and 113B, another procedure that can be carried out by the instrument 200, 1200 is femoral acetabular impingement (FAI) surgery. FAI can occur when an excess amount of bone is present on the femoral head of a patient. The excess bone is usually located along an upper surface of the femoral head and creates a cam-shaped head. Due to its shape, i.e., non-spherical, rotation of the femoral head in a normally shaped socket results in impingement. See, for example, the impingement shown in FIG. 113A. To alleviate this impingement, the bur head 204 of the instrument 200, 1200 removes the excess bone to create a more uniform femoral head and relieve the area of impingement. The instrument 200, 1200 can also be used in some embodiments to shape bone of the acetabulum or labram attached to the acetabulum if desired.

Before the FAI procedure begins, planning involves pre-operative scans, e.g., MRI or CT scans, to provide 3-D images of the femur 1640 and hip 1642. These images are stored in the system 100. Boundaries defining the volume of excess bone 1641 to be removed and/or portions of anatomy to remain (such as the acetabulum) are then defined either automatically by the system 100 based on a dynamic simulation of hip movement or by the surgeon. The boundaries are stored in the system 100 and later used to control movement of the bur head 204 in three degrees of freedom to maintain the desired relationship between the bur head 204 and the boundaries.

Trackers 1644 with active or passive markers 1646 are mounted to the femur 1640 and hip 1642. The trackers 1644 may be fixed to the femur 1640 and hip 1642 using bone pins inserted into bone through the skin, or other methods known to those skilled in the art.

The pre-operative images are registered to the anatomy using the trackers 1644 and pointer as previously described so that the system 100 can track movement of the bur head 204 (e.g., tip) relative to the femur 1640 and the hip 1642. In particular, the position and orientation of the femoral head 1648 and acetabulum 1650 are tracked during the procedure.

In a next step of the procedure, two separate access paths are created through the patient's skin. One path is created for the bur head 204 of the instrument 200, 1200 and one path is created for an endoscope (not shown). These access paths can be provided by guide tube, cannula, or other access creation device. In certain embodiments, these access devices can be tracked with the system 100 by attaching a tracker (not shown) to the devices. This allows the system 100 or user to establish the correct path to the acetabulum/hip joint.

The instrument 200, 1200 is then placed through one access path. The instrument 200, 1200 is operated to remove away the desired volume of excess bone 1641 from the femoral head 1648. The trackers 1644 are used by the system 100 to monitor the location of the bur head 204 relative to the femoral head 1648, acetabulum, and any defined boundaries associated therewith. The instrument 200, 1200 is then controlled by the system 100 which moves the bur head 204, if necessary, to avoid tissue that is to remain and to ensure only the cutting of material that is to be removed. This ensures that only the desired volume of the material 1641 is removed from the femoral head 1648 to relieve the impingement.

In this procedure, when bone is being removed, the hip may need to be retracted to access difficult to reach areas of the femoral head 1648. In the autonomous mode the system 100 may first prompt for moving the patient and retracting the hip to access these other areas.

During the procedure, the surgeon can view the volume of bone on the femoral head 1648 to be removed, which can be indicated on the display 113, 1402 in a different color than the bone to remain. The display 113, 1402 can also show the bone remaining to be removed relative to the boundary defining the desired final shape of the femoral head 1648. By tracking the bur head 204, the femoral head 1648, and the acetabulum 1650, the position of the bur head 204 relative to the boundary and the anatomy can be shown on the display 113, 1402 thereby giving the surgeon confidence that a properly shaped femoral head 1648 remains after the procedure.

A representation of the bone on the femoral head 1648 remaining to be removed, as well as the desired final shape of the femoral head can be overlayed onto a viewing station associated with the endoscope (not shown). In this manner, the display for the endoscope also dynamically shows the bone being removed along with the endoscopic views of the bone and other tissues. In this embodiment, a tracking device (not shown) is also attached to the endoscope (not shown) so that the position and orientation of the endoscope can be determined in the same coordinate system as the anatomy and the instrument 200, 1200.

The system 100 can be programmed so that as bone is removed, the dynamic simulator of hip movement estimates the amount of impingement relieved or remaining. For instance, at the start of the procedure, the amount of free rotation (i.e., rotation with no impingement) of the femoral head 1648 in the acetabulum 1650 may be X degrees. As the procedure progresses the value of X increases. This value can be displayed on the display 113, 1402. The system 100 may alert the surgeon when the value of X reaches a predetermined threshold, indicating that enough bone material has been removed.

In some embodiments, other materials may be removed by the bur head 204. For example, the bur head 204 can be used to debride chondral lesions or labral, excise bony prominences and/or reshape the acetabular rim.

Referring to FIG. 114, another procedure performed by the system 100 and instrument 200, 1200 is anterior cruciate ligament (ACL) repair. In ACL repair, access to the knee is provided by an arthoscope (not shown) or other guide tube or cannula. The existing ACL is first removed using a shaver or other device. A graft 1651 is then created to replace the removed ACL. Suitable grafts include a semi-tendonosis/gracilis graft or bone-tendon-bone (BTB) graft.

Prior to the ACL repair, a pre-operative image, such as an MRI or CT scan can be used to create a three dimensional model of the knee joint, including femur 1656 and tibia 1658 and ACL. Tracking devices 1660 with active or passive markers 1662 are mounted to each of the femur 1656 and tibia 1658 using conventional methods, for purposes of tracking positions and orientations of the femur 1656 and tibia 1658 during the procedure and for registering the pre-operative image to the anatomy as previously described.

During the procedure, two tunnels or passages 1652, 1654 are made in the femur 1656 and tibia 1658, respectively, in which the graft 1651 is secured. Traditionally, the passages 1652, 1654 are made separately from different approaches to the femur 1656 and tibia 1658, thus requiring two separate cutting guides. For instance, in a typical procedure, the tibia 1658 is approached from beneath the joint and the tunnel is then drilled toward the joint. The femur 1656 is drilled by starting in the joint and then drilling away from the joint into the femur 1656. The instrument 200, 1200 can be used in the same traditional manner, without any cutting guides.

In the embodiment of FIG. 114, boundaries can be established in the system 100 that define the passages 1652, 1654. By tracking the positions of the bur head 204, femur 1656 and tibia 1658 the system 100 can control movement of the bur head 204 (e.g., tip) to stay within the boundaries. Since the boundaries are tied to the anatomy, tracking movement of the anatomy also tracks movement of the boundaries.

Using the tracking and control system 100, instead of two, separate, discontinuously-created paths in the femur 1656 and tibia 1658 as described above, continuously-formed passages can be created starting from outside of the knee joint, through the tibia 1658, into the knee joint, and then into the femur 1656. The passages can also be created starting from outside of the knee joint, through the femur 1656, into the knee joint, and then into the tibia 1658.

To facilitate continuously-formed passages, the virtual boundary defining the passage 1652 in the femur 1656 can be aligned with the virtual boundary defining the passage 1654 in the tibia 1658. For instance, the passage 1654 in the tibia 1658 can first be made and then, without removing the cutting accessory 202 from the tibia passage 1654, the virtual boundary defining the femur passage 1652 can be aligned with the tibia passage 1654 (or its virtual boundary). This can be done by tracking the femur 1656 and the tibia 1658 and providing an indication of the passage or boundary alignment (or misalignment) on the display 113, 1402. The value of alignment can be established as degrees from alignment or similar values that can also be displayed numerically or graphically on the display 113, 1402. The procedure can also be carried out by cutting first in the femur 1656 and then proceeding to the tibia 1658.

When the passages 1652, 1654 are aligned, the display 113, 1402 may provide an audible or visual indication so that the surgeon may operate the instrument 200, 1200 to further penetrate the bur head 204 into the femur 1656 to complete the cutting. The surgeon continues as long as the alignment is maintained. The result is forming the passages 1652, 1654 in one continuous direction without removing bur head tip 204 from the first formed passage and without any cutting guides.

Once the passages 1652, 1654 are created, the graft 1651 is passed through ACL placement instruments into the passages 1652, 1654. The graft 1651 is then fixed inside the passages 1652, 1654 with screws, pins, or the like.

Figure 115A:
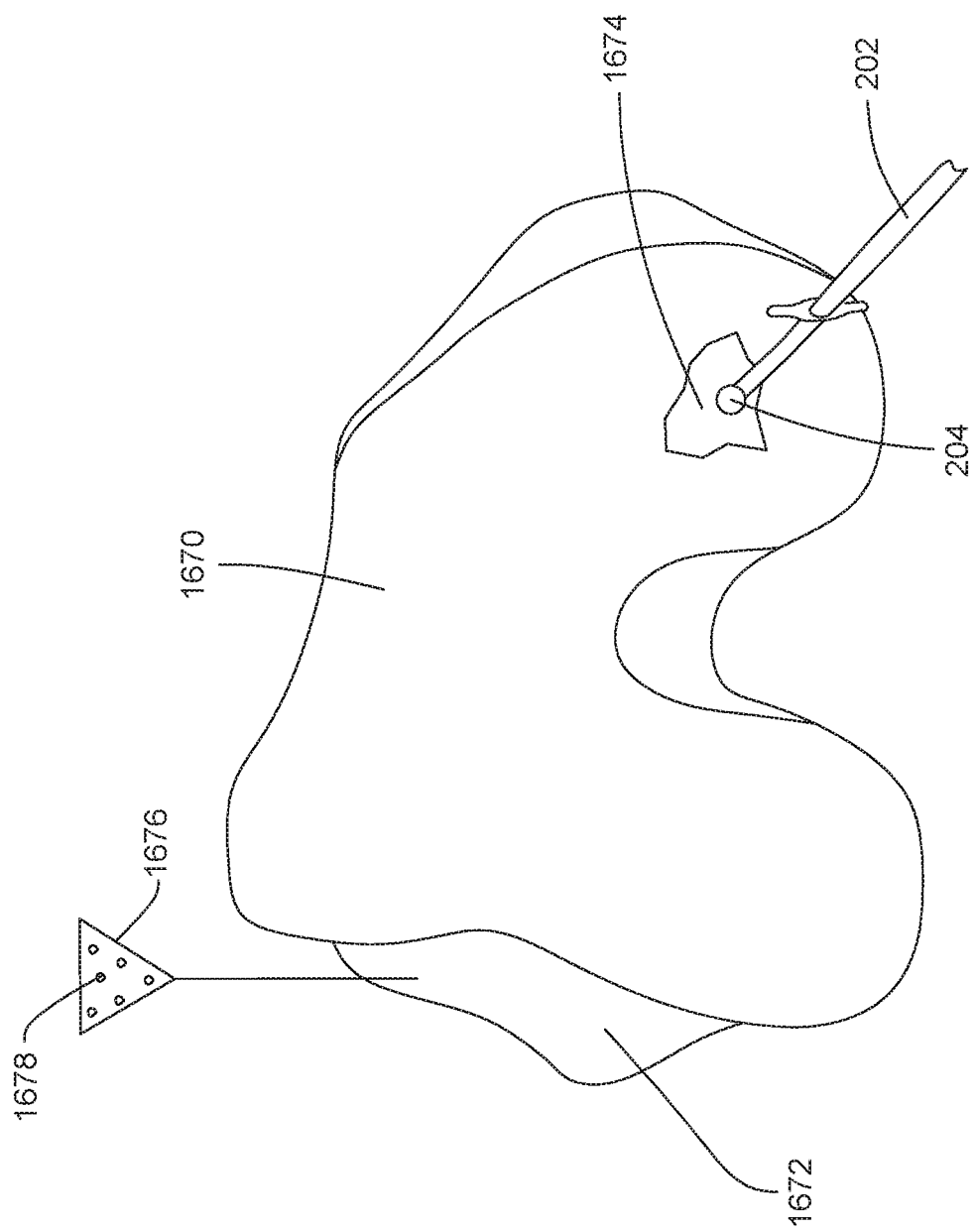
FIGS. 115A and 115B illustrate steps of repairing a focal cartilage defect.
Figure 115B:
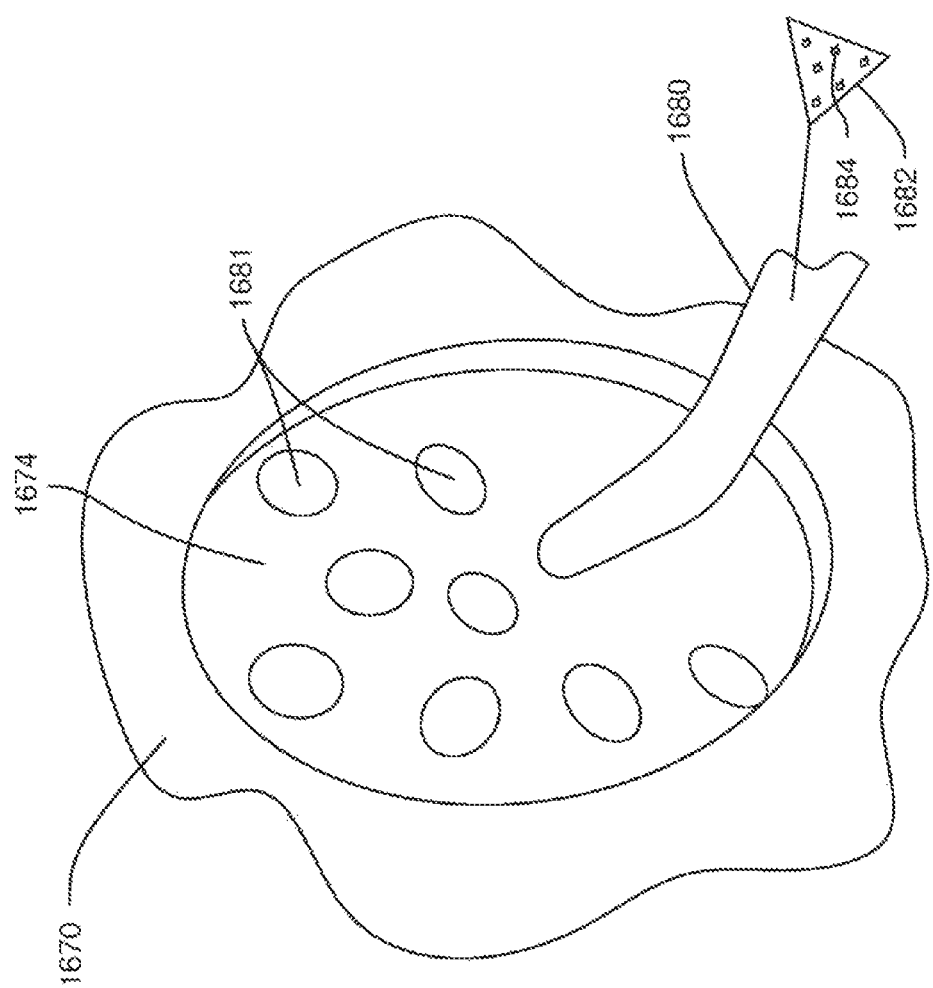

Referring to FIGS. 115A and 115B, another procedure in which the system 100 and instruments 200, 1200 can be employed is the repair of focal cartilage defects. One such procedure is arthroscopic microfracture surgery (AMS). AMS is used to repair cartilage 1670 on an articular surface that has worn away exposing bone 1674. The exposed bone, being on an articular surface, is often load bearing and can result in pain to the patient. Often AMS is employed on the articular surfaces of a knee joint, particularly, a femur 1672.

Prior to the AMS, a pre-operative image, such as an MRI or CT scan can be used to create a three dimensional model of the femur 1672 (and tibia if needed). Tracking devices 1676 with active or passive markers 1678 are mounted to each of the femur 1672 and tibia (if tracked) using conventional methods, for purposes of tracking the femur 1672 and tibia during the procedure and for registering the pre-operative image to the anatomy as previously described.

During the procedure, the worn away area of the bone 1674 and surrounding cartilage 1670 is accessed by an arthroscope, cannula, or other guide tube placed through the skin of the patient that provides an access path to the worn away area of the bone 1674. The bur head 204 of the instrument 200, 1200 is then placed through the created access path into proximity of the bone 1674. The worn away area of bone 1674 is then reshaped by the bur head 204 (e.g., tip) to smooth any rough edges of the remaining cartilage 1670 surrounding the bone 1674. The exposed bone 1674 is also smoothed by the bur head 204 to a contour resembling that of the original cartilage 1670 that was worn away.

A boundary can be established in the system 100 that defines the reshaped volume as shown in FIG. 115B. This volume is defined by a depth of cutting and a smooth outer edge. By tracking the positions and/or orientations of the bur head 204, femur 1672 and tibia (if tracked) during the procedure, the bur head 204 can be maintained within the boundary. Since the boundary is tied to the anatomy, tracking movement of the anatomy also tracks movement of the boundary.

Referring to FIG. 115B, once the worn away area of bone 1674 and cartilage 1670 is reshaped, an awl 1680 or other bone punching or penetrating instrument can be placed through the access path in proximity to the bone 1674. A tip of the awl 1680 is then poked into the bone 1674 in several spots to form microfractures 1681 in the bone 1674 and cause bleeding of the bone 1674. This bleeding facilitates the growth of a layer of material over the bone 1674 that replaces the missing cartilage to reduce pain. A separate tracking device 1682 with markers 1684 could be associated with the awl 1680 to track a position of the tip of the awl 1680. As a result, the microfractures 1681 can be placed at predefined depths in the bone 1674 and at predefined spatial locations in relation to one another to form a predefined pattern of the microfractures 1681. In some embodiments, as an alternative to the awl 1680, the bur head 204 could be replaced with a smaller diameter tip (e.g., smaller diameter bur head similar in diameter to awl tip) to drill a number of small holes instead of punching the holes with the awl 1680.

Other knee arthroplasty procedures in which the instrument 200, 1200 can be used includes mosaicplasty to treat focal cartilage defects, other ligament repair or reconstruction, removal of bone defects, and the like. A similar procedure employed for ACL repairs as described above could be employed for PCL repairs and repairs of other ligaments that stabilize joints.

In a mosaicplasty procedure, cartilage from an undamaged area of the joint is moved to the damaged area. So, in the focal defect described above, instead of AMS, the focal defect could be repaired by boring a small hole in the femur at the focal defect with the bur head 204 and then filling this hole with a plug of bone/cartilage from an undamaged area. The system 100 could be used to ensure that the depth of the hole is such that when the plug from the undamaged area is placed in the hole, the cartilage surface of the plug is flush with the cartilage surrounding the hole. The system 100 could also be used to ensure that the diameter of the hole is such that the plug has a predefined interference fit with the hole or a predefined tolerance to receive cement or other adhesive to secure the plug in position.

Figure 116:
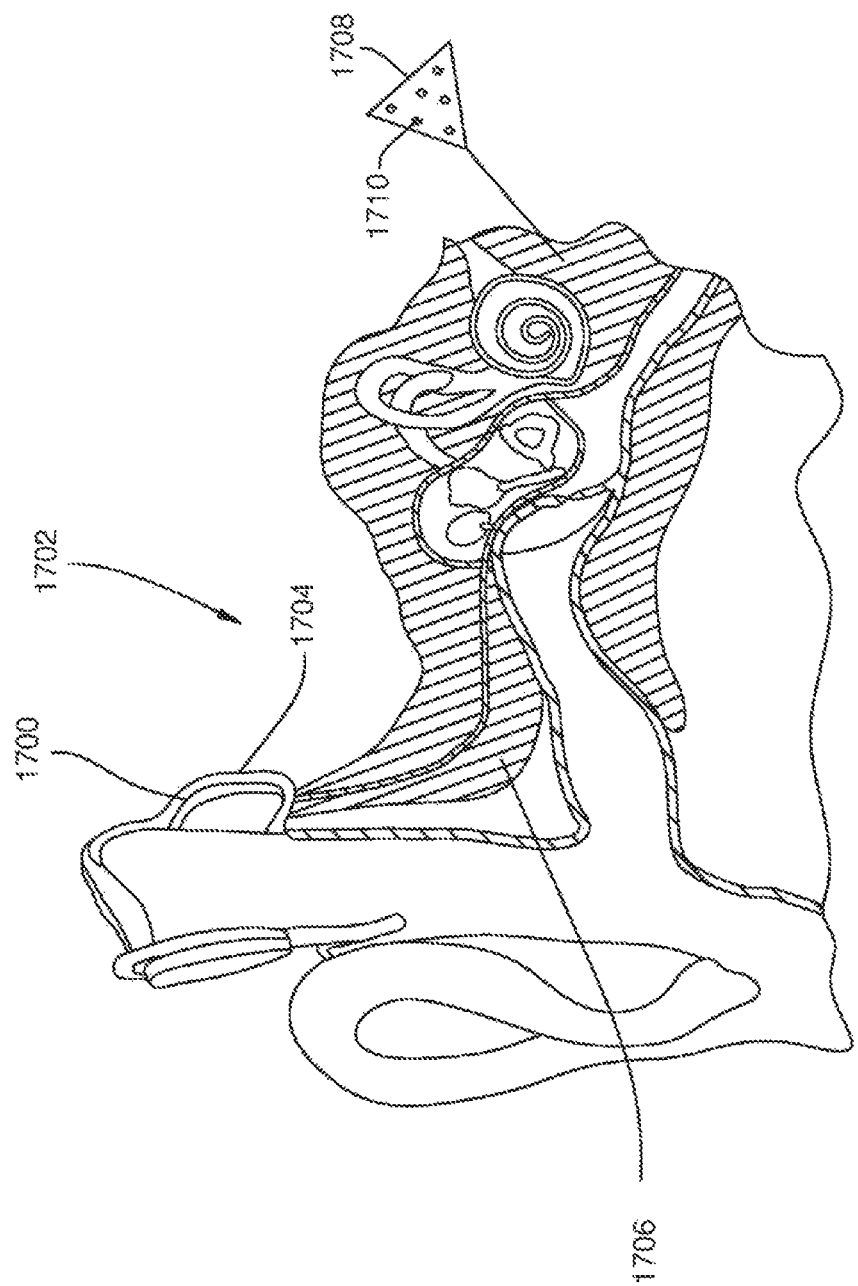
FIG. 116 illustrates formation of a pocket in bone to receive a cranial implant.

The system 100 and instrument 200, 1200 could also be used to mill pockets in bone for purposes of receiving an implant. As shown in FIG. 116, a receiver/stimulator 1700 of a cochlear implant 1702 can be placed in a pocket 1704 milled in skull bone 1706. As with the prior described embodiments, a boundary could be established in the system 100 that defines the pocket 1704. The bone 1706 could be tracked along with the bur head 204 so that the bur head 204 is maintained in the boundary to only cut the desired size and shape of pocket 1704 needed for the receiver/stimulator 1700.

A tracker 1708 with markers 1710 could be mounted to the bone 1706 for purposes of tracking the bone 1706 with the system 100 and for registering the bone 1706 to preoperative MRI or CT scans taken of the bone 1706. By tracking the positions of the bur head 204 and bone 1706 during the procedure, the bur head 204 can be maintained within the boundary. Since the boundary is tied to the anatomy, tracking movement of the anatomy also tracks movement of the boundary.

Pockets could also be created with the instrument 200, 1200 for other types of implants including neurostimulators, deep brain stimulators, and the like.

Rotating speed control of the bur head 204 may be employed in certain surgical procedures when cutting tissue such as bone. For instance, in the FAI procedure described above, the bur head 204 (e.g. bur head) may be controlled by the system 100 so that the speed of the bur head 204 is reduced as the bur head 204 approaches the acetabulum. Furthermore, the speed of the bur head 204 can be reduced as the bur head 204 approaches sensitive anatomical tissue.

In yet other embodiments, the rotating speed may not be affected until the bur head 204 deviates from the home position.

Therefore, it is an object of the intended claims to cover all such modifications and variations that come within the true spirit and scope of this invention.

The invention claimed is:

1. A control system for a hand-held instrument adapted to be freely held and moved by a user, the instrument including:
   a hand-held portion,
   a working portion movably coupled to the hand-held portion,
   a plurality of actuators operatively coupled to the working portion for moving the working portion in a plurality of degrees of freedom relative to the hand-held portion, at least one of the plurality of actuators includes a linear actuator, and
   a plurality of sensors for sensing positions of the working portion,
   the control system being configured to:
   control the actuators to move the working portion relative to the hand-held portion;
   maintain a desired relationship between the working portion and a virtual boundary;
   establish a home position of the working portion relative to the hand-held portion;
   track deflection of the working portion from the home position as the working portion moves in one or more of the plurality of degrees of freedom relative to the hand-held portion from the home position to a deflected position; and
   control a cutting speed of the working portion based on the deflection of the working portion into the deflected position.

2. The system of claim 1 wherein one of said actuators comprises a drive motor operatively coupled to said working portion to drive said working portion along a Z axis.

3. The system of claim 2 wherein said control system includes an instrument driver configured to apply energization signals to said drive motor when said working portion is within the virtual boundary.

4. The system of claim 1, wherein said working portion operates at a first cutting speed when said working portion is in the home position and at a second cutting speed when said working portion deflects from the home position, wherein said second cutting speed is attenuated relative to said first cutting speed.

5. A system comprising:
   a hand-held instrument adapted to be freely held and moved by a user, said hand-held instrument including;
   a hand-held portion configured to be grasped by the user;
   a working portion movably coupled to said hand-held portion,
   a plurality of actuators operatively coupled to said working portion for moving said working portion in a plurality of degrees of freedom relative to said hand-held portion, and
   a plurality of sensors for sensing positions of said working portion; and
   a control system coupled to said actuators to control said actuators to move said working portion relative to said hand-held portion, said control system being configured to establish a home position of said working portion relative to said hand-held portion;
   wherein said control system is configured to define a virtual boundary and control said working portion such that said working portion deviates from said home position to deflect away from the virtual boundary;

wherein said control system is configured to control a cutting speed of said working portion based on the deflection from the home position.

6. The system of claim 5, wherein said working portion operates at a first cutting speed when said working portion is in the home position and at a second cutting speed when said working portion deflects from the home position, wherein said second cutting speed is attenuated relative to said first cutting speed, indicating that said working portion has deflected from said home position.

7. A system comprising:
a hand-held instrument adapted to be freely held and moved by a user, said hand-held instrument including;
a hand-held portion configured to be grasped by the user;
a working portion movably coupled to said hand-held portion,
a plurality of actuators operatively coupled to said working portion for moving said working portion in a plurality of degrees of freedom relative to said hand-held portion, and
a plurality of sensors for sensing positions of said working portion; and
a control system coupled to said actuators to control said actuators to move said working portion relative to said hand-held portion, said control system being configured to establish a home position of said working portion relative to said hand-held portion and track deflection of said working portion from the home position into a deflected position as said working portion moves in one or more of the plurality of degrees of freedom relative to said hand-held portion in order to maintain a desired relationship to a virtual boundary;
wherein said control system is configured to control a cutting speed of said working portion based on the deflection from the home position, wherein said cutting speed of said working portion is greater than 0 when said deflection from said home position is less than 90% of a maximum deflection.

8. The system of claim 7, said working portion operates at a first cutting speed when said working portion is in the home position and at a second cutting speed when said working portion deflects from the home position, wherein said second cutting speed is less than said first cutting speed, indicating that said working portion has deflected from said home position.

9. A system comprising:
a hand-held instrument adapted to be freely held and moved by a user, said hand-held instrument including;
a hand-held portion configured to be grasped by the user;
a working portion movably coupled to said hand-held portion,
a plurality of actuators operatively coupled to said working portion for moving said working portion in a plurality of degrees of freedom relative to said hand-held portion, and
a control system coupled to said actuators to control said actuators to move said working portion relative to said hand-held portion, said control system being configured to establish a home position of said working portion relative to said hand-held portion and track a deflection of said working portion from the home position into a deflected position as said working portion moves in one or more of the plurality of degrees of freedom relative to said hand-held portion;
wherein said control system determines the deflection of the working portion from said home position, the deflection is based on comparison of a necessary deflection to a maximum possible deflection of said working portion;
wherein the maximum possible deflection is a distance from said home position to an outer range of a total possible deflection of said working portion; and
wherein said control system is configured to control a cutting speed of said working portion based on the deflection into said deflected position.

10. The system of claim 9 wherein said working portion operates at a first cutting speed when said working portion is in the home position and at a second cutting speed when said working portion deflects from the home position, wherein said second cutting speed is attenuated relative to said first cutting speed.

11. The system of claim 10, wherein said second cutting speed is less than said first cutting speed indicating that said working portion has deflected from said home position.

12. The system of claim 9 wherein said control system is configured to define a virtual boundary and when said working portion crosses the virtual boundary said working portion deviates from the home position to deflect away from the virtual boundary.

13. The system of claim 9 wherein said instrument includes a tracking device attached to said hand-held portion for tracking said instrument.

14. The system of claim 13 including a navigation system configured to determine a position of said working portion relative to a virtual boundary based on the tracking device.

15. The system of claim 14 including a display in coupled to said navigation system for indicating the position of said working portion relative to the virtual boundary.

16. The system of claim 9 wherein said working portion comprises a cutter.

17. The system of claim 9, wherein said working portion comprises a cutter further defined as a saw.

18. The system of claim 9, wherein the cutting speed of said working portion is greater than 0 when said necessary deflection is less than 90% of said maximum possible deflection.

19. The system of claim 9, wherein said necessary deflection is a first deflection and a second deflection, said first deflection corresponding to a first cutting speed of said working portion, and said second deflection corresponding to a second cutting speed of said working portion, said first cutting speed is greater than said second cutting speed.

20. The system of claim 19, wherein said first deflection is 40% of said maximum possible deflection and said first cutting speed is less than 100% of a maximum speed, and said second deflection is 50% of said maximum possible deflection and said second cutting speed is about 80% of said maximum cutting speed.

* * * * *